United States Patent
Vogel et al.

(10) Patent No.: US 7,087,722 B1
(45) Date of Patent: Aug. 8, 2006

(54) FIBRIN BINDING DOMAIN POLYPEPTIDES AND USES AND METHODS OF PRODUCING SAME

(75) Inventors: Tikva Vogel, Rehovot (IL); Avigdor Levanon, Rehovot (IL); Moshe Werber, Tel Aviv (IL); Rachel Guy, Rehovot (IL); Amos Panet, Jerusalem (IL)

(73) Assignee: Savient Pharmaceuticals, Inc., East Brunswick, NJ (US)

( * ) Notice: Subject to any disclaimer, the term of this patent is extended or adjusted under 35 U.S.C. 154(b) by 0 days.

(21) Appl. No.: 09/492,971

(22) Filed: Jan. 27, 2000

Related U.S. Application Data

(60) Continuation of application No. 08/909,140, filed on Aug. 11, 1997, now Pat. No. 6,121,426, which is a division of application No. 08/409,750, filed on Mar. 24, 1995, now Pat. No. 5,965,383, which is a continuation of application No. 08/058,241, filed on May 4, 1993, now Pat. No. 5,455,158, which is a division of application No. 07/526,397, filed on May 21, 1990, now Pat. No. 5,270,030, which is a continuation-in-part of application No. 07/345,952, filed on Apr. 28, 1989, now abandoned, which is a continuation-in-part of application No. 07/291,951, filed on Dec. 29, 1988, now abandoned.

(30) Foreign Application Priority Data

Dec. 29, 1989 (CA) .................................. 2006929

(51) Int. Cl.
*A61K 35/14* (2006.01)
*A61K 51/00* (2006.01)
*A61K 49/00* (2006.01)
*C07K 1/00* (2006.01)
*C12Q 1/56* (2006.01)

(52) U.S. Cl. ...................... 530/382; 530/381; 530/402; 424/1.69; 424/9.1; 424/9.3; 424/9.323; 424/9.34; 424/9.341; 424/9.4; 435/7.1; 435/13

(58) Field of Classification Search ................ 530/381, 530/382, 350, 300; 424/1.69, 9.1, 9.3, 9.323, 424/9.34, 9.341, 9.4; 435/7.1, 13
See application file for complete search history.

(56) References Cited

U.S. PATENT DOCUMENTS

| | | | |
|---|---|---|---|
| 4,315,906 A | 2/1982 | Gelder | 424/1 |
| 4,455,290 A | 6/1984 | Olexa et al. | 424/1.1 |
| 4,587,122 A | 5/1986 | Kagitani et al. | 424/101 |
| 4,663,146 A | 5/1987 | Morser et al. | 424/1.1 |
| 4,839,464 A | 6/1989 | McCarthy et al. | 530/326 |
| 5,026,537 A | 6/1991 | Daddona et al. | 424/1.1 |
| 5,270,030 A * | 12/1993 | Vogel et al. | 424/9 |
| 5,455,158 A | 10/1995 | Vogel et al. | 435/7.21 |
| 5,679,320 A | 10/1997 | Vogel et al. | 424/1.69 |
| 5,869,616 A | 2/1999 | Vogel et al. | 530/380 |
| 5,965,383 A * | 10/1999 | Vogel et al. | 435/69.1 |
| 6,121,426 A * | 9/2000 | Vogel et al. | 530/402 |

FOREIGN PATENT DOCUMENTS

| | | | |
|---|---|---|---|
| EP | 0207751 | * | 7/1987 |
| JP | 1261398 | | 10/1989 |
| WO | 8900051 | | 1/1989 |

OTHER PUBLICATIONS

Hynes et al., "Fibronectins: Multifunctional Modular Glycoproteins", J. Cell. Biol., vol. 95, pp. 369-377, 1982.*
Garcia-Pardo et al., *J. of Biol. Chem.*, 258:12670-12674 (1983).
Hynes and Yamada, *J. of Cell Biology*, 95:369-377 (1982).
Mosher and Procter, *Science*, 209:927-929 (1980).
Savill et al., *Anticancer Res.*, 6:315-320 (1986).
Uehara et al., *J. of Nuclear Medicine*, 29:1264-1267 (1988); and.
Wieiblen et al., *J. Immunol. Methods*, 58:73-81 (1983).

* cited by examiner

*Primary Examiner*—Jon Weber
*Assistant Examiner*—Rita Mitra
(74) *Attorney, Agent, or Firm*—John P. White, Esq.; Cooper & Dunham LLP

(57) ABSTRACT

This invention provides an imaging agent which comprises a polypeptide labeled with an imageable marker, such polypeptide having an amino acid sequence substantially present in the fibrin binding domain of naturally-occurring human fibronectin and being capable of binding to fibrin. The invention further provides a method wherein the imaging agent is used for imaging a fibrin-containing substance, i.e., a thrombus or atherosclerotic plaque. Further provided are plasmids for expression of polypeptides having an amino acid sequence substantially present in the fibrin binding domain of naturally-occurring human fibronectin and being capable of binding to fibrin, hosts containing these plasmids, methods of producing the polypeptides, methods of treatment using the polypeptides, and methods of recovering, refolding and reoxidizing the polypeptides. The invention also provides for purified polypeptides substantially free of other substances of human origin which have an amino acid sequence substantially present in the fibrin binding domain of naturally-occurring human fibronectin and which are capable of binding to fibrin.

4 Claims, 86 Drawing Sheets

FIGURE 1-1

```
  S    K    R    Q    A    Q    M    V    Q    P    Q    S    P    V
GAAG AGC AAG AGG CAG GCT CAG CAA ATG GTT CAG CCC CAG TCC CCG GTG         49
                         1                  5                      10                    15

A    V    S    Q    S    K    P    G    C    Y    D    N    G    K    H    Y
GCT GTC AGT CAA AGC AAG CCC GGT TGT TAT GAC AAT GGA AAA CAC TAT         97
                        20                              25                             30

Q    I    N    Q    W    E    R    T    Y    L    G    N    V    L    V
CAG ATA AAT CAA CAG TGG GAG CGG ACC TAC CTA GGT AAT GTG TTG GTT        145
                        35                              40                      45

C    T    C    Y    G    G    S    R    G    F    N    C    E    S    K    P
TGT ACT TGT TAT GGA GGA AGC CGA GGT TTT AAC TGC GAA AGT AAA CCT        193
                  50                              55                              60

E    A    E    T    C    F    D    K    Y    T    G    N    T    Y    R
GAA GCT GAA GAG ACT TGC TTT GAC AAG TAC ACT GGG AAC ACT TAC CGA        241
             65                              70                       75

V    G    D    T    Y    E    R    P    K    D    S    M    I    W    D    C
GTG GGT GAC ACT TAT GAG CGT CCT AAA GAC TCC ATG ATC TGG GAC TGT        289
       80                              85                       90                       95
```

FIGURE 1-2

```
    T   C   I   G   A   G   R   G   R   I   S   C   T   I   A   N
    ACC TGC ATC GGG GCT GGG CGA GGG AGA ATA AGC TGT ACC ATC GCA AAC    337
                    100                 105                 110

R   C   H   E   G   G   Q   S   Y   K   I   G   D   T   W   R
    CGC TGC CAT GAA GGG GGT CAG TCC TAC AAG ATT GGT GAC ACC TGG AGG    385
                    115                 120                 125

R   P   H   E   T   G   G   Y   M   L   E   C   V   C   L   G
    AGA CCA CAT GAG ACT GGT GGT TAC ATG TTA GAG TGT GTG TGT CTT GGT    433
                    130                 135                 140

N   G   K   G   E   W   T   C   K   P   I   A   E   K   C   F
    AAT GGA AAA GGA GAA TGG ACC TGC AAG CCC ATA GCT GAG AAG TGT TTT    481
                    145                 150                 155

D   H   A   A   G   T   S   Y   V   V   G   E   T   W   E   K
    GAT CAT GCT GCT GGG ACT CCC TAT GTG GTC GGA GAA ACG TGG GAG AAG    529
                    160                 165                 170                 175
```

FIGURE 1-3

```
    P   Y   Q   G   W   M   M   V   D   C   T   C   L   G   E   G
    CCC TAC CAA GGC TGG ATG ATG GTA GAT TGT ACT TGC CTG GGA GAA GGC    577
                    180                 185                 190

S   G   R   I   T   C   T   S   R   N   R   C   N   D   Q   D
    AGC GGA CGC ATC ACT TGC ACT TCT AGA AAT AGA TGC AAC GAT CAG GAC    625
                    195                 200                 205

T   R   T   S   Y   R   I   G   D   T   W   S   K   K   D   N
    ACA AGG ACA TCC TAT AGA ATT TGA GAC ACC TGG AGC AAG AAG GAT AAT    673
                    210                 215                 220

R   G   N   L   L   Q   C   I   C   T   G   N   S   S   G   E
    CGA GGA AAC CTG CTC CAG TGC ATC TGC ACA GGC AAC TCG AGC GGA GAG    721
                    225                 230                 235

W   K   C   E   R   H   T   S   V   Q   T   T   T   S   G   S
    TGG AAG TGT GAG AGG CAC ACC TCT GTG CAG ACC ACA TCG AGC GGA TCT    769
                    240                 245                 250                 255

G   P   F   T   D   V   R   A   A   V   Y   Q   P   Q   P   H
    GGC CCC TTC ACC GAT GTT CGT GCA GCT GTT TAC CAA CCG CAG CCT CAC    817
                    260                 265                 270
```

FIGURE 1-4

```
  P   Q   P   P   Y   G   H   C   V   T   D   S   G   V   V
CCC CAG CCT CCT CCC TAT GGC CAC TGT GTC ACA GAC AGT GGT GTG GTC    865
275                             280                 285

Y   S   V   G   M   Q   W   L   K   T   Q   G   N   K   Q   M
TAC TCT GTG GGG ATG CAG TGG TTG AAG ACA CAA GGA AAT AAG CAA ATG    913
        290                 295                 300

L   C   T   C   L   G   N   G   V   S   C   Q   E   T   A   V
CTT TGC ACG TGC CTG GGC AAC GGA GTC AGC TGC CAA GAG ACA GCT GTA    961
305                 310                 315

T   Q   T   Y   G   G   N   L   N   G   E   P   C   V   L   P
ACC CAG ACT TAC GGT GGC AAC TTA AAT GGA GAG CCA TGT GTC TTA CCA   1009
320                 325                 330                 335

F   T   Y   N   G   R   T   F   Y   S   C   T   T   E   G   R
TTC ACC TAC AAT GGC AGG ACG TTC TAC TCC TGC ACC ACG GAA GGG CGA   1057
                340                 345                 350
```

FIGURE 1-5

```
    Q    D    G    H    L    W    C    S    T    T    S    N    Y    E    Q    D
    CAG  GAC  GGA  CAT  CTT  TGG  TGC  AGC  ACA  ACT  TCG  AAT  TAT  GAG  CAG  GAC    1105
                        355                      360                      365

Q    K    Y    S    F    C    T    D    H    T    V    L    V    Q    T    Q
    CAG  AAA  TAC  TCT  TTC  TGC  ACA  GAC  CAC  ACT  GTT  TTG  GTT  CAG  ACT  CAA    1153
                        370                      375                      380

G    G    N    S    N    G    A    L    C    H    F    P    F    L    Y    N
    GGA  GGA  AAT  TCC  AAT  GGT  GCC  TTG  TGC  CAC  TTC  CCC  TTC  CTA  TAC  AAC    1201
                        385                      390                      395

N    H    N    Y    T    D    C    T    S    E    G    R    R    D    N    M
    AAC  CAC  AAT  TAC  ACT  GAT  TGC  ACT  TCT  GAG  GGC  AGA  AGA  GAC  AAC  ATG    1249
    400                      405                      410                      415

K    W    C    G    T    T    Q    N    Y    D    A    D    Q    K    F    G
    AAG  TGG  TGT  GGG  ACC  ACA  CAG  AAC  TAT  GAT  GCC  GAC  CAG  AAG  TTT  GGG    1297
                        420                      425                      430

F    C    P    M    A    A    H    E    E    I    C    T    T    N    E    G
    TTC  TGC  CCC  ATG  GCT  GCC  CAC  GAG  GAA  ATC  TGC  ACA  ACC  AAT  GAA  GGG    1345
                        435                      440                      445
```

FIGURE 1-6

```
     V   M   Y   R   I   G   D   Q   W   D   K   Q   H   D   M   G
     GTC ATG TAC CGC ATT GGA GAT CAG TGG GAT AAG CAG CAT GAC ATG GGT    1393
         450                 455                 460

H   M   M   R   C   T   C   V   G   N   G   R   G   E   W   T
     CAC ATG ATG AGG TGC ACG TGT GTT GGG AAT GGT CGT GGG GAA TGG ACA    1441
         465                 470                 475

C   I   A   Y   S   Q   L   R   D   Q   C   I   V   D   D   I
     TGC ATT GCC TAC TCG CAA CTT CGA GAT CAG TGC ATT GTT GAT GAC ATC    1489
         480                 485                 490                 495

T   Y   N   V   N   D   T   F   H   K   R   H   E   E   G   H
     ACT TAC AAT GTG AAC GAC ACA TTC CAC AAG CGT CAT GAA GAG GGG CAC    1537
         500                 505                 510

M   L   N   C   T   C   F   G   Q   G   R   G   R   W   K   C
     ATG CTG AAC TGT ACA TGC TTC GGT CAG GGT CGG GGC AGG TGG AAG TGT    1585
         515                 520                 525
```

FIGURE 1-7

```
  D   P   V   D   Q   C   Q   D   S   E   T   G   T   F   Y   Q
  GAT CCC GTC GAC CAA TGC CAG GAT TCA GAG ACT GGG ACG TTT TAT CAA   1633
              530             535             540

I   G   D   S   W   E   K   Y   V   H   G   V   R   Y   Q   C
  ATT GGA GAT TCA TGG GAG AAG TAT GTG CAT GGT GTC AGA TAC CAG TGC   1681
      545             550             555

Y   C   Y   G   R   G   I   G   E   W   H   C   Q   P   L   Q
  TAC TGC TAT GGC CGT GGC ATT GGG GAG TGG CAT TGC CAA CCT TTA CAG   1729
  560             565             570             575

T   Y   P   S   S   G   P   V   E   V   F   I   T   E   T
  ACC TAT CCA AGC TCA GGT CCT GTC GAA GTA TTT ATC ACT GAG ACT       1777
              580             585             590

P   S   Q   P   N   S   H   P   I   Q   W   N   A   P   Q   P
  CCG AGT CAG CCC AAC TCC CAC CCC ATC CAG TGG AAT GCA CCA CAG CCA   1825
          595             600             605

S   H   I   S   K   Y   I   L   R   W   R   P   K   N   S   V
  TCT CAC ATT TCC AAG TAC ATT CTC AGG TGG AGA CCT AAA AAT TCT GTA   1873
  610             615             620
```

FIGURE 1-8

```
      G   R   W   K   E   A   T   I   P   G   H   L   N   S   Y   T
     GGC CGT TGG AAG GAA GCT ACC ATA CCA GGC CAC TTA AAC TCC TAC ACC    1921
         625             630             635

I   K   G   L   K   P   G   V   V   Y   E   G   Q   L   I   S
     ATC AAA GGC CTG AAG CCT GGT GTG GTA TAC GAG GGC CAG CTC ATC AGC    1969
         640             645             650             655

I   Q   Q   Y   G   H   Q   E   V   T   R   F   D   F   T   T
     ATC CAG CAG TAC GGC CAC CAA GAA GTG ACT CGC TTT GAC TTC ACC ACC    2017
         660             665             670

T   S   T   S   T   P   V   T   S   N   T   V   T   G   E   T
     ACC AGC ACC AGC ACA CCT GTG ACC AGC AAC ACC GTG ACA GGA GAG ACG    2065
         675             680             685

T   P   F   S   P   L   V   A   T   S   E   S   V   T   E   I
     ACT CCC TTT TCT CCT CTT GTG GCC ACT TCT GAA TCT GTG ACC GAA ATC    2113
         690             695             700
```

FIGURE 1-9

```
    T   A   S   S   F   V   V   S   W   V   S   A   S   D   T   V
    ACA GCC AGT AGC TTT GTG GTC TCC TGG GTC TCA GCT TCC GAC ACC GTG    2161
        705             710             715             720

S   G   F   R   V   E   Y   E   L   S   E   E   G   D   E   P
    TCG GGA TTC CGG GTG GAA TAT GAG CTG AGT GAG GAG GGA GAT GAG CCA    2209
        720             725             730             735

Q   Y   L   D   L   P   S   T   A   T   S   V   N   I   P   D
    CAG TAC CTG GAT CTT CCA AGC ACA GCC ACT TCT GTG AAC ATC CCT GAC    2257
        740             745             750

L   L   P   G   R   K   Y   I   V   N   V   Y   Q   I   S   E
    CTG CTT CCT GGC CGA AAA TAC ATT GTA AAT GTC TAT CAG ATA TCT GAG    2305
        755             760             765

D   G   E   Q   S   L   I   L   S   T   S   Q   T   T   A   P
    GAT GGG GAG CAG AGT TTG ATC CTG TCT ACT TCA CAA ACA ACA GCG CCT    2353
        770             775             780

D   A   P   P   D   P   T   V   D   Q   V   D   D   T   S   I
    GAT GCC CCT CCT GAC CCG ACT GTG GAC CAA GTT GAT GAC ACC TCA ATT    2401
        785             790             795
```

FIGURE 1-10

```
  V   V   R   W   S   R   P   Q   A   P   I   T   G   Y   R   I
  GTT GTT CGC TGG AGC AGA CCC CAG GCT CCC ATC ACA GGG TAC AGA ATA    2449
  800             805             810             815

V   Y   S   P   S   V   E   G   S   S   T   E   L   N   L   P
  GTC TAT TCG CCA TCA GTA GAA GGT AGC AGC ACA GAA CTC AAC CTT CCT    2497
  820             825             830

E   T   A   N   S   V   T   L   S   D   L   Q   P   G   V   Q
  GAA ACT GCA AAC TCC GTC ACC CTC AGT GAC TTG CAA CCT GGT GTT CAG    2545
          835             840             845

Y   N   I   T   I   Y   A   V   E   E   N   Q   E   S   T   P
  TAT AAC ATC ACT ATC TAT GCT GTG GAA GAA AAT CAA GAA AGT ACA CCT    2593
          850             855             860

V   V   I   Q   Q   E   T   G   T   T   P   R   S   D   T   V
  GTT GTC ATT CAA CAA GAA ACC GGC ACT ACC CCA CGC TCA GAT ACA GTG    2641
          865             870             875
```

FIGURE 1-11

| P   | S   | P   | R   | D   | L   | Q   | F   | V   | E   | V   | T   | D   | V   | K   | V   |      |
|-----|-----|-----|-----|-----|-----|-----|-----|-----|-----|-----|-----|-----|-----|-----|-----|------|
| CCC | TCT | CCC | AGG | GAC | CTG | CAG | TTT | GTG | GAA | GTG | ACA | GAC | GTG | AAG | GTC | 2689 |
| 880 |     |     |     |     | 885 |     |     |     | 890 |     |     |     |     | 895 |     |      |

| T   | I   | M   | W   | T   | P   | P   | E   | S   | A   | V   | T   | G   | Y   | R   | V   |      |
|-----|-----|-----|-----|-----|-----|-----|-----|-----|-----|-----|-----|-----|-----|-----|-----|------|
| ACC | ATC | ATG | TGG | ACA | CCG | CCT | GAG | AGT | GCA | GTG | ACC | GGC | TAC | CGT | GTG | 2737 |
|     |     | 900 |     |     |     |     | 905 |     |     |     |     |     | 910 |     |     |      |

| D   | V   | I   | P   | V   | N   | L   | P   | G   | E   | H   | G   | Q   | R   | L   | P   |      |
|-----|-----|-----|-----|-----|-----|-----|-----|-----|-----|-----|-----|-----|-----|-----|-----|------|
| GAT | GTG | ATC | CCC | GTC | AAC | CTG | CCT | GGC | GAG | CAC | GGG | CAG | AGG | CTG | CCC | 2785 |
|     |     | 915 |     |     |     |     | 920 |     |     |     |     |     | 925 |     |     |      |

| I   | S   | R   | N   | T   | F   | A   | E   | V   | T   | G   | L   | S   | P   | G   | V   |      |
|-----|-----|-----|-----|-----|-----|-----|-----|-----|-----|-----|-----|-----|-----|-----|-----|------|
| ATC | AGC | AGG | AAC | ACC | TTT | GCA | GAA | GTC | ACC | GGG | CTG | TCC | CCT | GGG | GTC | 2833 |
|     |     | 930 |     |     |     |     | 935 |     |     |     |     |     | 940 |     |     |      |

| T   | Y   | Y   | F   | K   | V   | F   | A   | V   | S   | H   | G   | R   | E   | S   | K   |      |
|-----|-----|-----|-----|-----|-----|-----|-----|-----|-----|-----|-----|-----|-----|-----|-----|------|
| ACC | TAT | TAC | TTC | AAA | GTC | TTT | GCA | GTG | AGC | CAT | GGG | AGG | GAG | AGC | AAG | 2881 |
|     |     | 945 |     |     |     |     | 950 |     |     |     |     |     | 955 |     |     |      |

| P   | L   | T   | A   | Q   | Q   | T   | T   | K   | L   | D   | A   | P   | T   | N   | L   |      |
|-----|-----|-----|-----|-----|-----|-----|-----|-----|-----|-----|-----|-----|-----|-----|-----|------|
| CCT | CTG | ACT | GCT | CAA | CAG | ACA | ACC | AAA | CTG | GAT | GCT | CCC | ACT | AAC | CTC | 2929 |
| 960 |     |     |     |     | 965 |     |     |     | 970 |     |     |     |     | 975 |     |      |

FIGURE 1-12

```
      Q   F   V   N   E   T   D   S   T   V   L   V   R   W   T   P
      CAG TTT GTC AAT GAA ACT GAT TCT ACT GTC CTG GTG AGA TGG ACT CCA   2977
                              980             985             990

P   R   A   Q   I   T   G   Y   R   L   T   V   G   L   T   R
      CCT CGG GCC CAG ATA ACA GGA TAC CGA CTG ACC GTG GGC CTT ACC CGA   3025
                              995             1000            1005

R   G   Q   P   R   Q   Y   N   V   G   P   S   V   S   K   Y
      AGA GGC CAG CCC AGG CAG TAC AAT GTG GGT CCC TCT GTC TTC AAG TAC   3073
                              1010            1015            1020

P   L   R   N   L   Q   P   A   S   E   Y   T   V   S   L   V
      CCC CTG AGG AAT CTG CAG CCT GCA TCT GAG TAC ACC GTA TCC CTC GTG   3121
                              1025            1030            1035

A   I   K   G   N   Q   E   S   P   K   A   T   G   V   F   T
      GCC ATA AAG GGC AAC CAA GAG AGC CCC AAA GCC ACT GGA GTC TTT ACC   3169
      1040                    1045            1050            1055
```

FIGURE 1-13

```
      T   L   Q   P   G   S   S   I   P   P   Y   N   T   E   V   T
    ACA CTG CAG CCT GGG AGC TCT ATT CCA CCT TAC AAC ACC GAG GTG ACT    3217
                1060                1065                1070

E   T   T   I   V   I   T   W   T   P   A   P   R   I   G   F
    GAG ACC ACC ATC GTG ATC ACA TGG ACG CCT GCT CCA AGA ATT GGT TTT    3265
            1075                1080                1085

K   L   G   V   R   P   S   Q   G   G   E   A   P   R   E   V
    AAG CTG GGT GTA CGA CCA AGC CAG GGA GAG GCA CCA CGA GAA GTG        3313
                1090                1095                1100

T   S   D   S   G   S   S   I   V   V   S   G   L   T   P   G   V
    ACT TCA GAC TCA GGA AGC ATC GTT GTG TCC GGC TTG ACT CCA GGA GTA    3361
            1105                1110                1115

E   Y   V   Y   T   I   Q   V   L   R   D   G   Q   E   R   D
    GAA TAC GTC TAC ACC ATC CAA GTC CTG AGA GAT GGA CAG GAA AGA GAT    3409
                1120                1125                1130                1135

A   P   I   V   N   K   V   V   T   P   L   S   P   P   T   N
    GCG CCA ATT GTA AAC AAA GTG GTG ACA CCA TTG TCT CCA CCA ACA AAC    3457
            1140                1145                1150
```

FIGURE 1-14

```
      L   H   L   E   A   N   P   D   T   G   V   L   T   V   S   W
      TTG CAT CTG GAG GCA AAC CCT GAC ACT GGA GTG CTC ACA GTC TCC TGG    3505
                              1155                    1160                    1165

E   R   S   T   T   P   D   I   T   G   Y   R   I   T   T   T
      GAG AGG AGC ACC ACC CCA GAC ATT ACT GGT TAT AGA ATT ACC ACA ACC    3553
                              1170                    1175                    1180

P   T   N   G   Q   Q   Q   G   N   S   L   E   E   V   H   A
      CCT ACA AAC GGC CAG CAG CAG GGA AAT TCT TTG GAA GAA GTG GTC CAT GCT  3601
                              1185                    1190                    1195

D   Q   S   S   C   T   F   D   N   L   S   P   G   L   E   Y
      GAT CAG AGC TCC TGC ACT TTT GAT AAC CTG AGT CCC GGC CTG GAG TAC    3649
                              1200                    1205                    1210                    1215

N   V   S   V   Y   T   V   K   D   D   K   E   S   V   P   I
      AAT GTC AGT GTT TAC ACT GTC AAG GAT GAC AAG GAA AGT GTC CCT ATC    3697
                              1220                    1225                    1230
```

FIGURE 1-15

```
  S   D   T   I   I   P   A   V   P   P   T   D   L   R   F
TCT GAT ACC ATC ATC CCA GCT GTT CCT CCC ACT GAC CTG CGA TTC   3745
              1235                1240                1245

T   N   I   G   P   D   T   M   R   V   T   W   A   P   P
ACC AAC ATT GGT CCA GAC ACC ATG CGT GTC ACC TGG GCT CCA CCC CCA   3793
              1250                1255                1260

S   I   D   L   T   N   F   L   V   R   Y   S   P   V   K   N
TCC ATT GAT TTA ACC AAC TTC CTG GTG CGT TAC TCA CCT GTG AAA AAT   3841
              1265                1270                1275

E   E   D   V   A   E   L   S   I   S   P   S   D   N   A   V
GAG GAA GAT GTT GCA GAG TTG TCA ATT TCT CCT TCA GAC AAT GCA GTG   3889
1280                1285                1290                1295

V   L   T   N   L   L   P   G   T   E   Y   V   V   S   V   S
GTC TTA ACA AAT CTC CTG CCT GGT ACA GAA TAT GTA GTG AGT GTC TCC   3937
              1300                1305                1310

S   V   Y   E   Q   H   E   S   T   P   L   R   G   R   Q   K
AGT GTC TAC GAA CAA CAT GAG AGC ACA CCT CTT AGA GGA AGA CAG AAA   3985
              1315                1320                1325
```

FIGURE 1-16

```
   T   G   L   D   S   P   T   G   I   D   F   S   D   I   T   A
  ACA GGT CTT GAT TCC CCA ACT GGC ATT GAC TTT TCT GAT ATT ACT GCC   4033
                  1330            1335            1340

N   S   F   T   V   H   W   I   A   P   R   A   T   I   T   G
  AAC TCT TTT ACT GTG CAC TGG ATT GCT CCT CGA GCC ACC ATC ACT GGC   4081
              1345            1350            1355

Y   R   I   R   H   H   P   E   H   F   S   G   R   P   R   E
  TAC AGG ATC CGC CAT CAT CCC GAG CAC TTC AGT GGG AGA CCT CGA GAA   4129
          1360            1365            1370            1375

D   R   V   P   H   S   R   N   S   I   T   L   T   N   L   T
  GAT CGG GTG CCC CAC TCT CGG AAT TCC ATC ACC CTC ACC AAC CTC ACT   4177
                  1380            1385            1390

P   G   T   E   Y   V   V   S   I   V   A   L   N   G   R   E
  CCA GGC ACA GAG TAT GTG GTC AGC ATC GTT GCT CTT AAT GGC AGA GAG   4225
              1395            1400            1405
```

FIGURE 1-17

```
  E   S   P   L   L   I   G   Q   Q   S   T   V   S   D   V   P
GAA AGT CCC TTA TTG ATT GGC CAA CAA TCA ACA GTT TCT GAT GTT CCG    4273
                1410                1415                1420

R   D   L   E   V   V   A   A   T   P   T   S   L   L   I   S
AGG GAC CTG GAA GTT GTT GCT GCG ACC CCC ACC AGC CTA CTG ATC AGC    4321
                1425                1430                1435

W   D   A   P   A   V   T   V   R   Y   Y   R   I   T   Y   G
TGG GAT GCT CCT GCT GTC ACA GTG AGA TAT TAC AGG ATC ACT TAC GGA    4369
                1440                1445                1450                1455

E   T   G   G   N   S   P   V   Q   E   F   T   V   P   G   S
GAA ACA GGA GGA AAT AGC CCT GTC CAG GAG TTC ACT GTG CCT GGG AGC    4417
                1460                1465                1470

K   S   T   A   T   I   S   G   L   K   P   G   V   D   Y   T
AAG TCT ACA GCT ACC ATC AGC GGC CTT AAA CCT GGA GTT GAT TAT ACC    4465
                1475                1480                1485

I   T   V   Y   A   V   T   G   R   G   D   S   P   A   S   S
ATC ACT GTG TAT GCT GTC ACT GGC CGT GGA GAC AGC CCC GCA AGC AGC    4513
                1490                1495                1500
```

FIGURE 1-18

```
     K   P   I   S   I   N   Y   R   T   E   I   D   K   P   S   Q
     AAG CCA ATT TCC ATT AAT TAC CGA ACA GAA ATT GAC AAA CCA TCC CAG    4561
         1505                1510                1515

M   Q   V   T   D   V   Q   D   N   S   I   S   V   K   W   L
     ATG CAA GTG ACC GAT GTT CAG GAC AAC AGC ATT AGT GTC AAG TGG CTG    4609
     1520                1525                1530                1535

P   S   S   P   V   T   G   Y   R   V   T   T   T   P   K
     CCT TCA AGT TCC CCT GTT ACT GGT TAC AGA GTA ACC ACT CCC AAA        4657
                     1540                1545                1550

N   G   P   G   P   T   K   T   K   T   A   G   P   D   Q   T
     AAT GGA CCA GGA CCA ACA AAA ACT AAA ACT GCA GGT CCA GAT CAA ACA    4705
                         1555                1560                1565

E   M   T   I   E   G   L   Q   P   V   E   Y   V   V   S
     GAA ATG ACT ATT GAA GGC TTG CAG CCC ACA GTG GAG TAT GTG GTT AGT    4753
     1570                1575                1580
```

FIGURE 1-19

```
  V   Y   A   Q   N   P   S   G   E   S   Q   P   L   V   Q   T
GTC TAT GCT CAG AAT CCA AGC GGA GAG AGT CAG CCT CTG GTT CAG ACT      4801
1585                1590                1595

A   V   T   N   I   D   R   P   K   G   L   A   F   T   D   V
GCA GTA ACC AAC ATT GAT CGC CCT AAA GGA CTG GCA TTC ACT GAT GTG      4849
1600                1605                1610                1615

D   V   D   S   I   K   I   A   W   E   S   P   Q   G   Q   V
GAT GTC GAT TCC ATC AAA ATT GCT TGG GAA AGC CCA CAG GGG CAA GTT      4897
                1620                1625                1630

S   R   Y   R   V   T   Y   S   S   P   E   D   G   I   H   E
TCC AGG TAC AGG GTG ACC TAC TCG AGC CCT GAG GAT GGA ATC CAT GAG      4945
                1635                1640                1645

L   F   P   A   P   D   G   E   E   D   T   A   E   L   Q   G
CTA TTC CCT GCA CCT GAT GGT GAA GAA GAC ACT GCA GAG CTG CAA GGC      4993
                1650                1655                1660

L   R   P   G   S   E   Y   T   V   S   V   V   A   L   H   D
CTC AGA CCG GGT TCT GAG TAC ACA GTC AGT GTG GTT GCC TTG CAC GAT      5041
1665                1670                1675
```

FIGURE 1-20

```
   D   M   E   S   Q   P   L   I   G   T   Q   S   T   A   I   P
GAT ATG GAG AGC CAG CCC CTG ATT GGA ACC CAG TCC ACA GCT ATT CCT   5089
1680                    1685                1690                1695

A   P   T   D   L   K   F   T   Q   V   T   P   T   S   L   S
GCA CCA ACT GAC CTG AAG TTC ACT CAG GTC ACA CCC ACA AGC CTG AGC   5137
                1700                1705                1710

A   Q   W   T   P   P   N   V   Q   L   T   G   Y   R   V   R
GCC CAG TGG ACA CCA CCA AAT GTT CAG CTC ACT GGA TAT CGA GTG CGG   5185
                1715                1720                1725

V   T   P   K   E   K   T   G   P   M   K   E   I   N   L   A
GTG ACC CCC AAG GAG AAG ACC GGA CCA ATG AAA GAA ATC AAC CTT GCT   5233
                1730                1735                1740

P   D   S   S   V   V   S   G   L   M   V   A   T   K
CCT GAC AGC TCA GTT GTA TCA GGA CTT ATG GTG GCC ACC AAA           5281
                1745                1750                1755
```

FIGURE 1-21

```
  Y   E   V   S   V   Y   A   L   K   D   T   L   T   S   R   P
 TAT GAA GTG AGT GTC TAT GCT CTT AAG GAC ACT TTG ACA AGC AGA CCA    5329
 1760            1765            1770            1775

A   Q   G   V   V   T   T   L   E   N   V   S   P   P   R   R
 GCT CAG GGT GTT GTC ACC ACT CTG GAG AAT GTC AGC CCA CCA AGA AGG    5377
         1780            1785            1790

A   R   V   T   D   A   T   E   T   I   T   I   S   W   R
 GCT CGT GTG ACA GAT GCT ACT GAG ACC ACC ATC ACC ATT AGC TGG AGA    5425
 1795            1800            1805

T   K   T   E   T   G   F   Q   V   D   A   V   P   A
 ACC AAG ACT GAG ACT GGC TTC CAA GTT GAT GCC GTT CCA GCC            5473
         1810            1815            1820

N   G   Q   T   P   I   Q   R   T   I   K   P   D   V   R   S
 AAT GGC CAG ACT CCA ATC CAG AGA ACC ATC AAG CCA GAT GTC AGA AGC    5521
 1825            1830            1835

Y   T   I   T   G   L   Q   P   G   T   D   Y   K   I   Y   L
 TAC ACC ATC ACA GGT TTA CAA CCA GGC ACT GAC TAC AAG ATC TAC CTG    5569
 1840            1845            1850            1855
```

FIGURE 1-22

```
  Y   T   L   N   D   N   A   R   S   S   P   V   V   I   D   A
TAC ACC TTG AAT GAC AAT GCT CGG AGC TCC CCT GTG GTC ATC GAC GCC   5617
            1860            1865            1870

S   T   A   I   D   A   P   S   N   L   R   F   L   A   T   T
TCC ACT GCC ATT GAT GCA CCA TCC AAC CTG CGT TTC CTG GCC ACC ACA   5665
            1875            1880            1885

P   N   S   L   L   V   S   W   Q   P   P   R   A   R   I   T
CCC AAT TCC TTG CTG GTA TCA TGG CAG CCG CCA CGT GCC AGG ATT ACC   5713
            1890            1895            1900

G   Y   I   I   K   Y   E   K   P   G   S   P   P   R   E   V
GGC TAC ATC ATC AAG TAT GAG AAG CCT GGG TCT CCT CCC AGA GAA GTG   5761
            1905            1910            1915

V   P   R   P   R   P   G   V   T   E   A   T   I   T   G   L
GTC CCT CGG CCC CGC CCT GGT GTC ACA GAG GCT ACT ATT ACT GGC CTG   5809
            1920            1925            1930            1935
```

FIGURE 1-23

```
  E   P   G   T   E   Y   T   I   Y   V   I   A   L   K   N   N
GAA CCG GGA ACC GAA TAT ACA ATT TAT GTC ATT GCC CTG AAG AAT AAT         5857
                1940                1945                1950

Q   K   S   E   P   L   I   G   R   K   K   T   D   E   L   P
CAG AAG AGC GAG CCC CTG ATT GGA AGG AAA AAG ACA GAC GAG CTT CCC         5905
                1955                1960                1965

Q   L   V   T   L   P   H   P   N   L   H   G   P   E   I   L
CAA CTG GTA ACC CTT CCA CAC CCC AAT CTT CAT GGA CCA GAG ATC TTG         5953
                1970                1975                1980

D   V   P   S   T   V   Q   K   T   P   F   V   T   H   P   G
GAT GTT CCT TCC ACA GTT CAA AAG ACC CCT TTC GTC ACC CAC CCT GGG         6001
                1985                1990                1995

Y   D   T   G   N   G   I   Q   L   P   G   T   S   G   Q   Q
TAT GAC ACT GGA AAT GGT ATT CAG CTT CCT GGC ACT TCT GGT CAG CAA         6049
2000                2005                2010                2015

P   S   V   G   Q   Q   M   I   F   E   E   H   G   F   R   R
CCC AGT GTT GGG CAA CAA ATG ATC TTT GAG GAA CAT GGT TTT AGG CGG         6097
                2020                2025                2030
```

FIGURE 1-24

```
  T   T   P   P   T   T   A   T   P   I   R   H   R   P   R   P
ACC ACA CCG CCC ACA ACG GCC ACC CCC ATA AGG CAT AGG CCA AGA CCA    6145
                    2035                    2040                    2045

Y   P   P   N   V   G   Q   E   A   L   S   Q   T   T   I   S
TAC CCG CCG AAT GTA GGA CAA GAA GCT CTC TCT CAG ACA ACC ATC TCA    6193
                    2050                    2055                    2060

W   A   P   F   Q   D   T   S   E   Y   I   I   S   C   H   P
TGG GCC CCA TTC CAG GAC ACT TCT GAG TAC ATC ATT TCA TGT CAT CCT    6241
                    2065                    2070                    2075

V   G   T   D   E   E   E   P   L   Q   F   R   V   P   G   T   S
GTT GGC ACT GAT GAA GAA GAA CCC TTA CAG TTC AGG GTT CCT GGA ACT TCT  6289
2080                    2085                    2090                    2095

T   S   A   T   L   T   G   L   T   R   G   A   T   Y   N   I
ACC AGT GCC ACT CTG ACA GGC CTC ACC AGA GGT GCC ACC TAC AAC ATC    6337
                    2100                    2105                    2110
```

FIGURE 1-25

```
  I   V   E   A   L   K   D   Q   Q   R   H   K   V   R   E   E
ATA GTG GAG GCA CTG AAA GAC CAG CAG AGG CAT AAG GTT CGG GAA GAG      6385
                2115            2120            2125

V   V   T   V   G   N   S   V   N   E   G   L   N   Q   P   T
GTT GTT ACC GTG GGC AAC TCT GTC AAC GAA GGC TTG AAC CAA CCT ACG      6433
                2130            2135            2140

D   D   S   C   F   D   P   Y   T   V   S   H   Y   A   V   G
GAT GAC TCG TGC TTT GAC CCC TAC ACA GTT TCC CAT TAT GCC GTT GGA      6481
                2145            2150            2155

D   E   W   E   R   M   S   E   S   G   F   K   L   L   C   Q
GAT GAG TGG GAA CGA ATG TCT GAA TCA GGC TTT AAA CTG TTG TGC CAG      6529
        2160            2165            2170            2175

C   L   G   F   G   S   G   H   F   R   C   D   S   S   R   W
TGC TTA GGC TTT GGA AGT GGT CAT TTC AGA TGT GAT TCA TCT AGA TGG      6577
                2180            2185            2190

C   H   D   N   G   V   N   Y   K   I   G   E   K   W   D   R
TGC CAT GAC AAT GGT GTG AAC TAC AAG ATT GGA GAG AAG TGG GAC CGT      6625
        2195            2200            2205
```

FIGURE 1-26

```
  Q   G   E   N   G   Q   M   M   S   C   T   C   L   G   N   G
CAG GGA GAA AAT GGC CAG ATG ATG AGC TGC ACA TGT CTT GGG AAC GGA    6673
            2210                2215                2220

K   G   E   F   K   C   D   P   H   E   A   T   C   Y   D   D
AAA GGA GAA TTC AAG TGT GAC CCT CAT GAG GCA ACG TGT TAC GAT GAT    6721
        2225                2230                2235

G   K   T   Y   H   V   G   E   Q   W   Q   K   E   Y   L   G
GGG AAG ACA TAC CAC GTA GGA GAA CAG TGG CAG AAG GAA TAT CTC GGT    6769
2240                2245                2250                2255

A   I   C   S   C   T   C   F   G   G   Q   R   G   W   R   C
GCC ATT TGC TCC TGC ACA TGC TTT GGA GGC CAG CGG GGC TGG CGC TGT    6817
        2260                2265                2270

D   N   C   R   R   P   G   G   E   P   S   P   E   G   T   T
GAC AAC TGC CGC AGA CCT GGG GGT GAA CCC AGT CCC GAA GGC ACT ACT    6865
            2275                2280                2285
```

FIGURE 1-27

```
  G   Q   S   Y   N   Q   Y   S   Q   R   Y   H   Q   R   T   N
GGC CAG TCC TAC AAC CAG TAT TCT CAG AGA TAC CAT CAG AGA ACA AAC      6913
            2290            2295            2300

T   N   V   N   C   P   I   E   C   F   M   P   L   D   V   Q
ACT AAT GTT AAT TGC CCA ATT GAG TGC TTC ATG CCT TTA GAT GTA CAG      6961
            2305            2310            2315

A   D   R   E   D   S   R   E
GCT GAC AGA GAA GAT TCC CGA GAG TAA ATC TTT CCA ATC CAG AGG          7009
            2320            2325            2330            2335

AAC AAG CAT GTC TCT CTG CCA AGA TCC ATC TAA ACT GGA GTG ATG TTA      7057
            2340            2345            2350

GCA GAC CCA GCT TAG AGT TCT TCT TTC CTT AAG CCC TTT GCT CTG          7105
            2355            2360            2365

GAG GAA GTT CTC CAG CTT CAG CTC AAC TCA CAG CTT CTC CAA GCA TCA      7153
            2370            2375            2380
```

FIGURE 1-28

```
CCC TGG GAG TTT CCT GAG GGT TTT CTC ATA AAT GAG GGC TGC ACA TTG      7201
2385                          2390                     2395

CCT GTT CTG CTT CGA AGT ATT CAA TAC CGC TCA GTA TTT TAA ATG AAG      7249
2400                     2405                          2410     2415

TGA TTC TAA GAT TTG GTT TGG GAT CAA TAG GAA AGC ATA TGC AGC CAA      7297
          2420                          2425                2430

CCA AGA TGC AAA TGT TTT GAA ATG ATA TGA CCA AAA TTT TAA GTA GGA      7345
          2435                          2440                2445

AAG TCA CCC AAA CAC TTC TGC TTT CAC TTA AGT GTC TGG CCC GCA ATA      7393
2450                          2455                     2460

CTG TAG GAA CAA GCA TGA TCT TGT TAC TGT GAT ATT TTA AAT ATC CAC      7441
2465                     2470                          2475

AGT ACT CAC TTT TTC CAA ATG ATC CTA GTA ATT GCC TAG AAA TAT CTT      7489
2480                     2485                          2490     2495
```

FIGURE 1-29

```
TCT CTT ACC TGT TAT TTA TCA ATT TTT CCC AGT ATT TTT ATA CGG AAA    7537
                2500                      2505              2510

AAA TTG TAT TGA AAA CAC TTA GTA TGC AGT TGA TAA GAG GAA TTT GGT    7585
                2515                      2520              2525

ATA ATT ATG GTG GGT GAT TAT TTT TTA TAC TGT ATG TGC CAA AGC TTT    7633
                2530                      2535              2540

ACT GTG GAA AGA CAA CTG TTT TAA TAA AAG ATT TAC ATT CCA CAA        7681
                2545                      2550              2555

AAAAAAAA AAAAAAAA AAAA                                              7705
```

FIGURE 2A

PAIR 1
1 5'- AATTCATATGCAGGCACAGCAAATGGTTCAGCCCCAGTCCCCGGTGGCTGTCAGTCAAAGCAAGCCCGTT -3'
2 3'-    GTATACGTCCGTGTCGTTTACCAAGTCGGGGTCAGGGGCCACCGACAGTCAGTTCGTTCGGGCCAACAATA -5'

PAIR 2
3 5'- GTTATGACAATGGAAAACACTATCAGATAAATCAACAGTGGGAGCGGACCTACCTAGTTAATGTGTTG -3'
4 3'-    CTGTTACCTTTTGTGATAGTCTATTTAGTTGTCACCCTCGCCTGGATGGATCCATT -5'

PAIR 3
5 5'-        GTTTGTACTTGTTATGGAGGAAGCCCGAGTTTTAACTGCGAAAGTAAACCTGAAGCT -3'
6 3'- ACACAACCAAACATGAACAATACCCTCCTTCGGCTCAAAATTGACGCTTTCATTTGGACTTCGACTTCTCT -5'

PAIR 4
7 5'- GAAGAGACTGCTTTGACAAGTACACTGGGAACACTTACCGAGTGGCTGACACTTATGAGCGTCCTAAA -3'
8 3'-    GAACGAAACTGTTCATGTGACCCTTGTGAATGGCTCACCCACTGTGAATACTCGCAG -5'

FIGURE 2B

PAIR 5

9 5'-            GACTCCATGATCTGGGACTGTACCTGCATCGGGCTGGGCGAGGGAGAATAAGCTGTACC               -3'
10 GATTTCTGAGGTACTAGACCCTGACATGGACGTAGCCCGACCCTCCGCTCCTCTTATTC             -5'

PAIR 6

11 5-            ATCGCCAACGCTGCCATGAAGGGGTCAGTCCTACCAGATTGGTGACACCTGGAGGAGACCACATGAGACT       -3'
12 3'- GACATGGTAGCCGTTTGCGACGGTACTTCCCCCAGTCAGGATGGTCTAACCACTGTGGACCTCCTCCTGGTGTACTCTGACCACCAA -5'

PAIR 7

13 5'-   GGTGGTTACATGTTAGAGTGTGTGTGTCTTGGTAATGGAAAAGGAGAATGGACCTGCAAGCCCATAGCTGAG        -3'
14 3'-  TGTACAATCTCACACACAGAACCATTACCTTTTCCTCTTACCTGGACGTTCGGGTATCGACTCCTAG              -5'

FIGURE 5
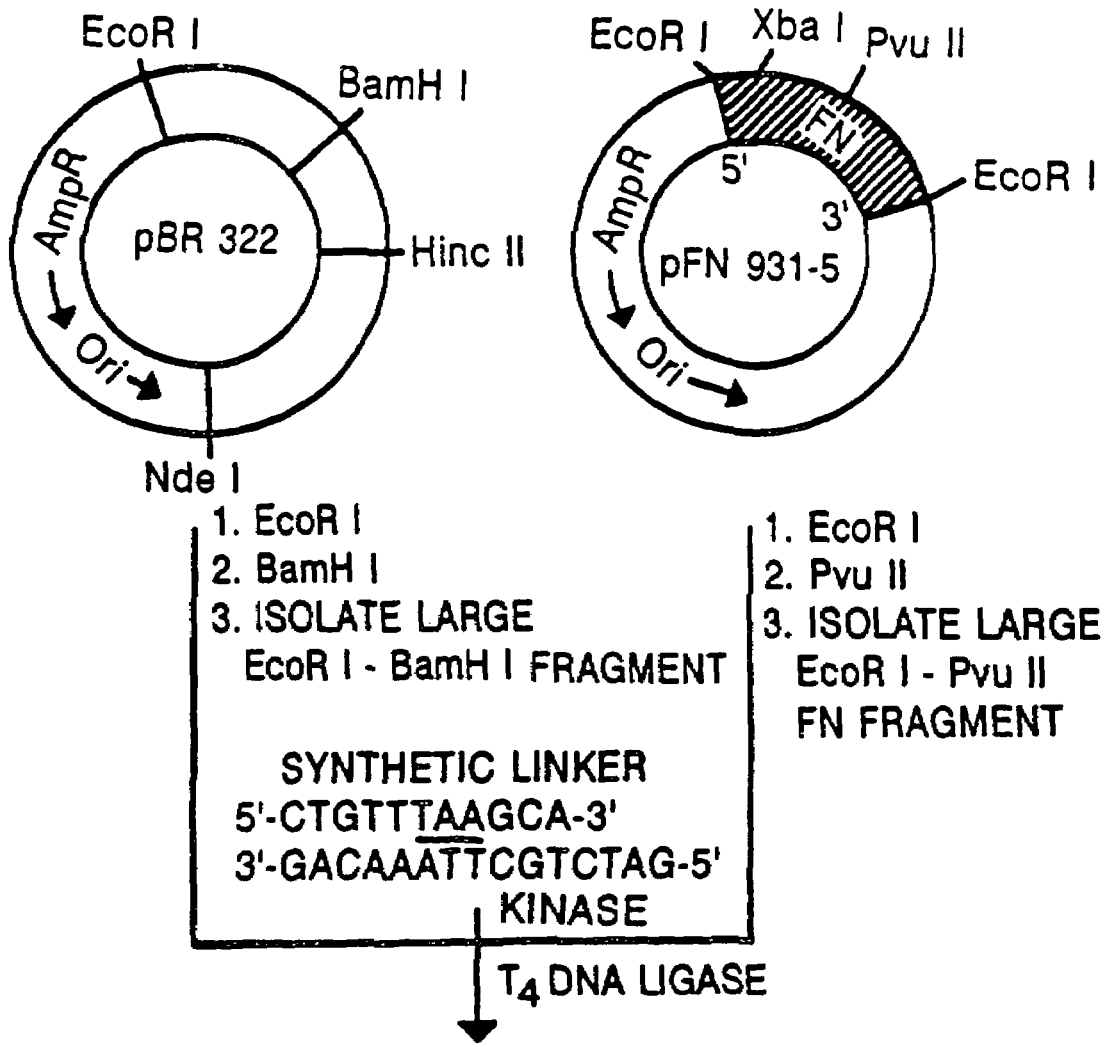
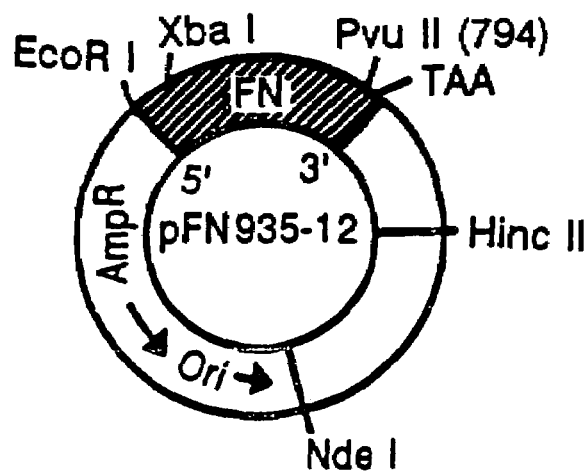

FIGURE 6
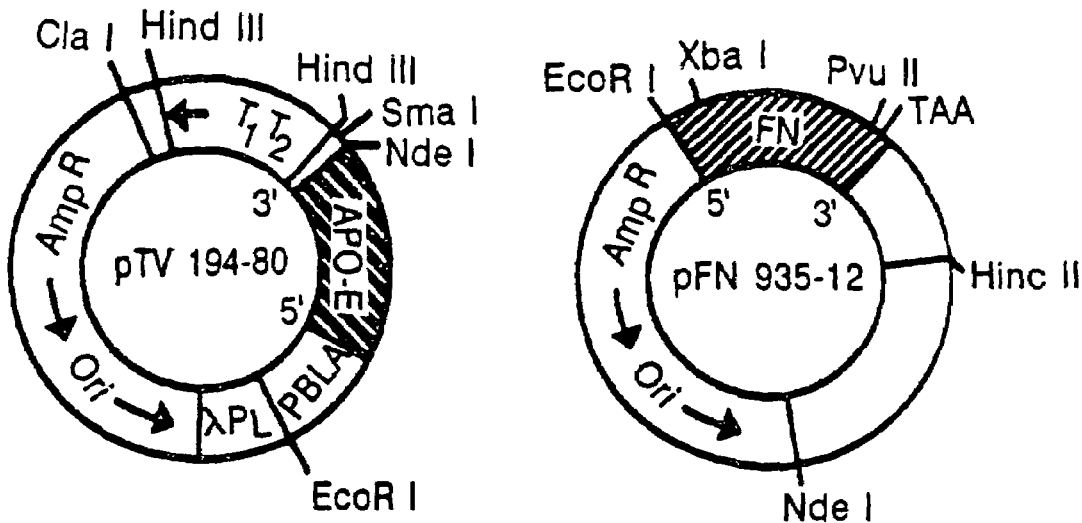
1. EcoR I
2. Sma I
3. ISOLATE LARGE
   EcoR I - Sma I FRAGMENT
1. EcoR I
2. Hinc II
3. ISOLATE
   EcoR I - Hinc II
   FN FRAGMENT
T₄ DNA LIGASE
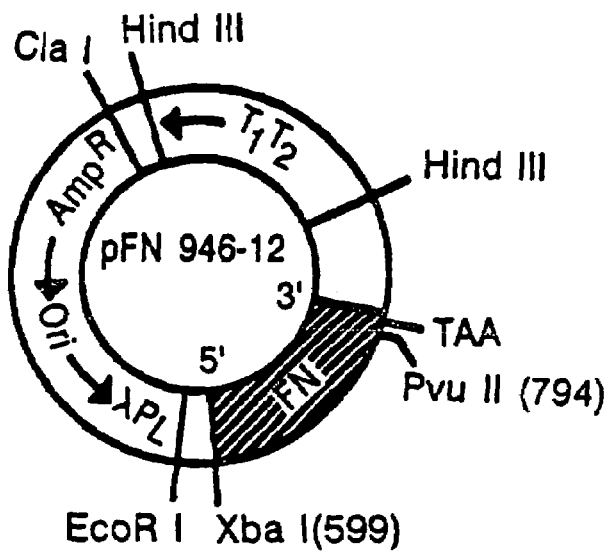

DISTRIBUTION OF RADIOACTIVITY IN RABBIT AORTA SEGMENTS AFTER 31kD FBD ADMINISTRATION

FIGURE 30
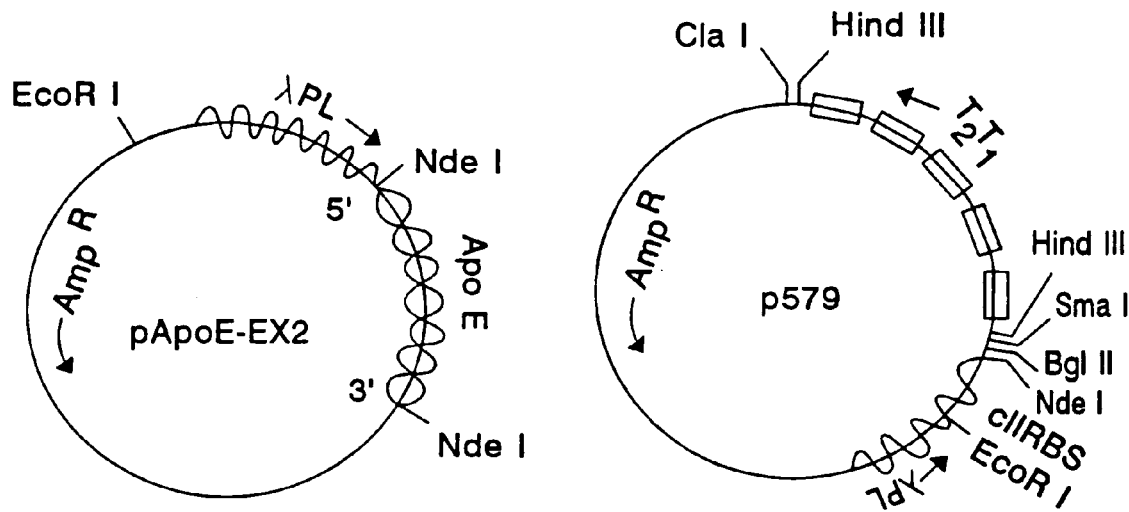
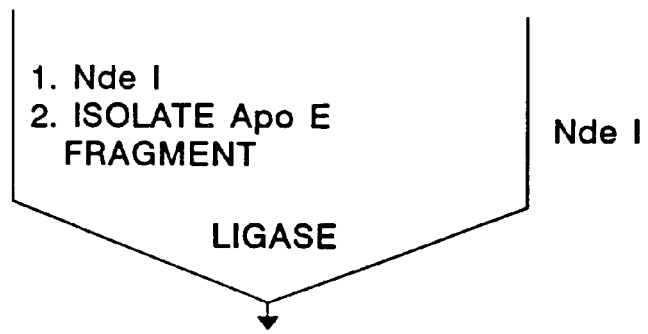
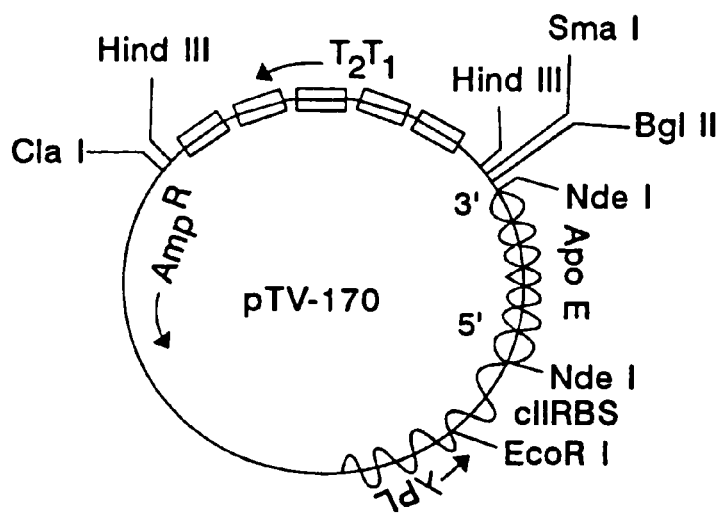

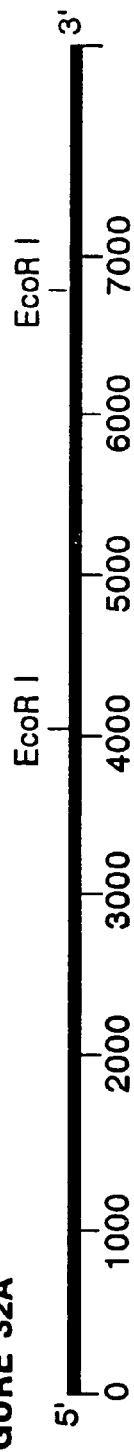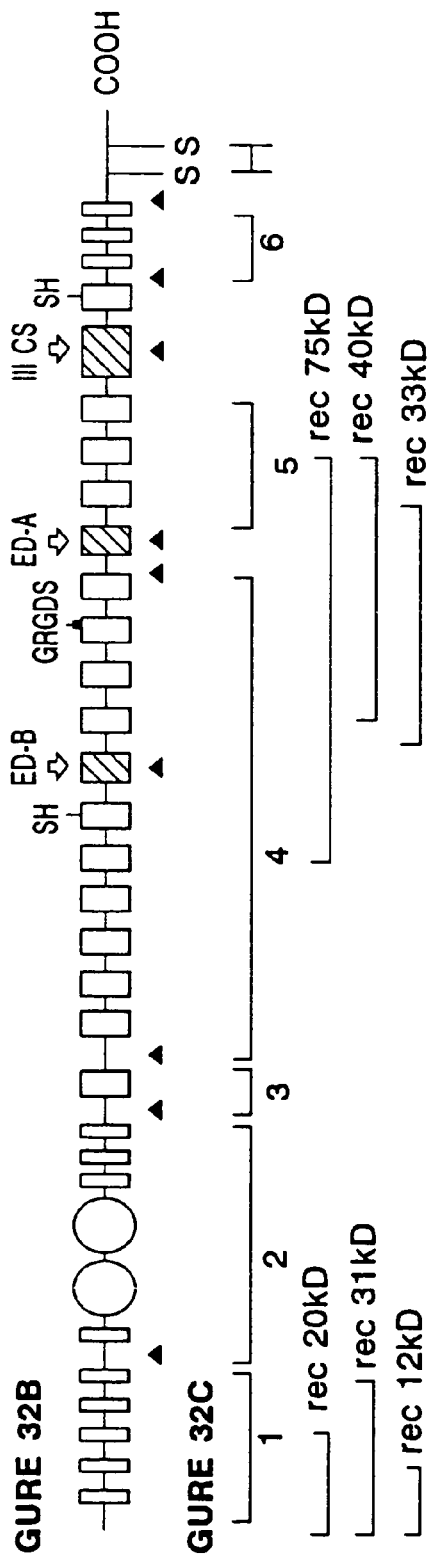
FIGURE 32A
FIGURE 32B
FIGURE 32C
FIGURE 32D
FIGURE 32E

FIGURE 34
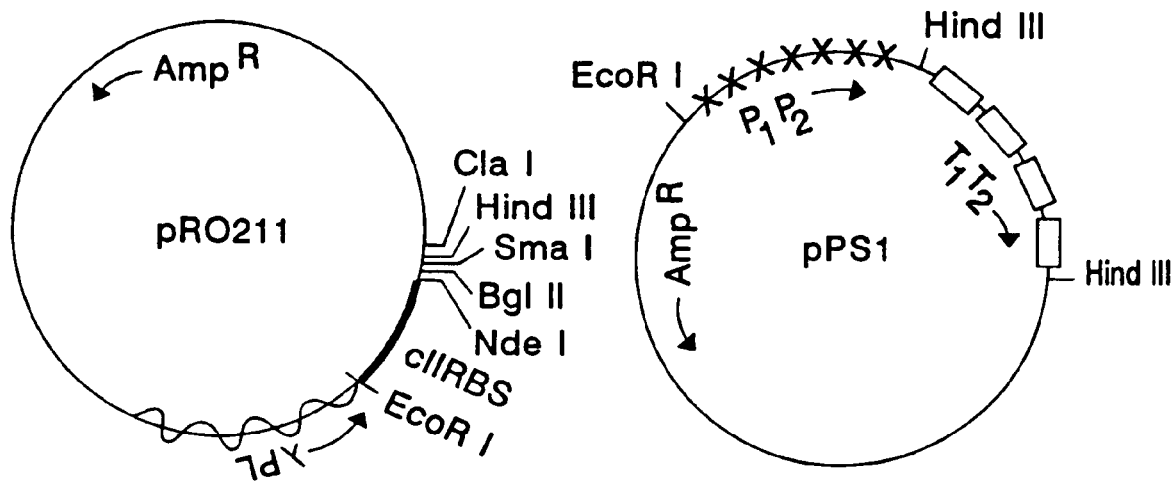
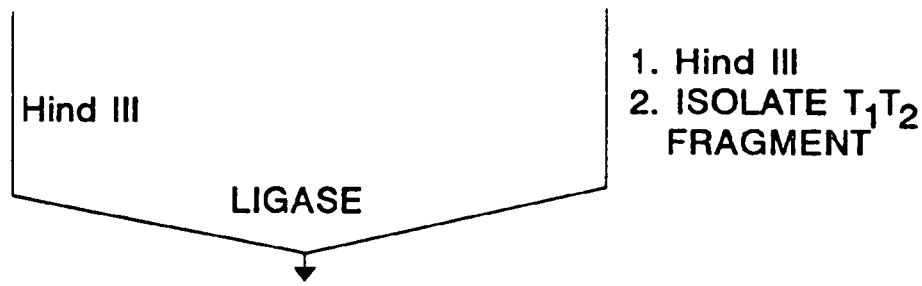
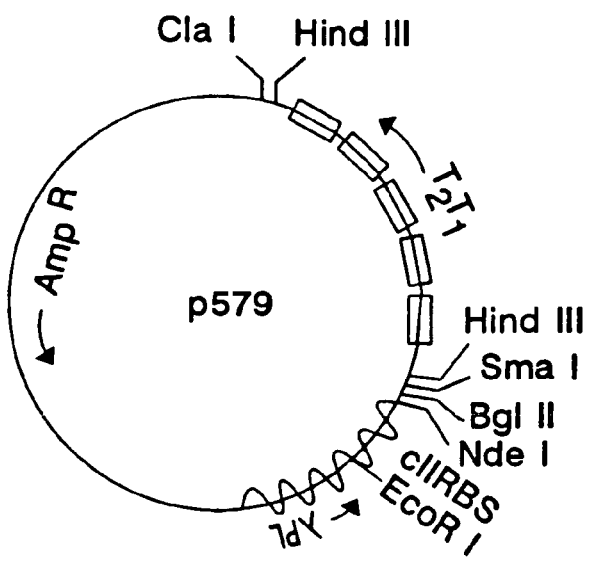

FIGURE 41

```
A   5'  GGGCTGGGCGAGGGAGAATAAGCTGTACCATGCGCAAACCGCTAACAGCTGA  3'
    3'        ACCCGCTCCCTCTTATTCGACATGGTAGCGTTTGGCGATTGTCGACTTCGA  5'

B   5'  GGGCTGGGCGAGGGAGAATAAGCTGTACCATCGCAAACCGCCATATGTAAA  3'
    3'        ACCCGCTCCCTCTTATTCGACATGGTAGCGTTTGGCGGTATACATTTCGA  5'

C   5'  ATGGCCGTGGAGACAGCTAACAGCTGA  3'
    3'  TACCGGCACCTCTGTCGATTGTCGACTTCGA  5'

D   5'  CTGTATACCAACC  3'
    3'  GACATATGGTTGGAT  5'
```

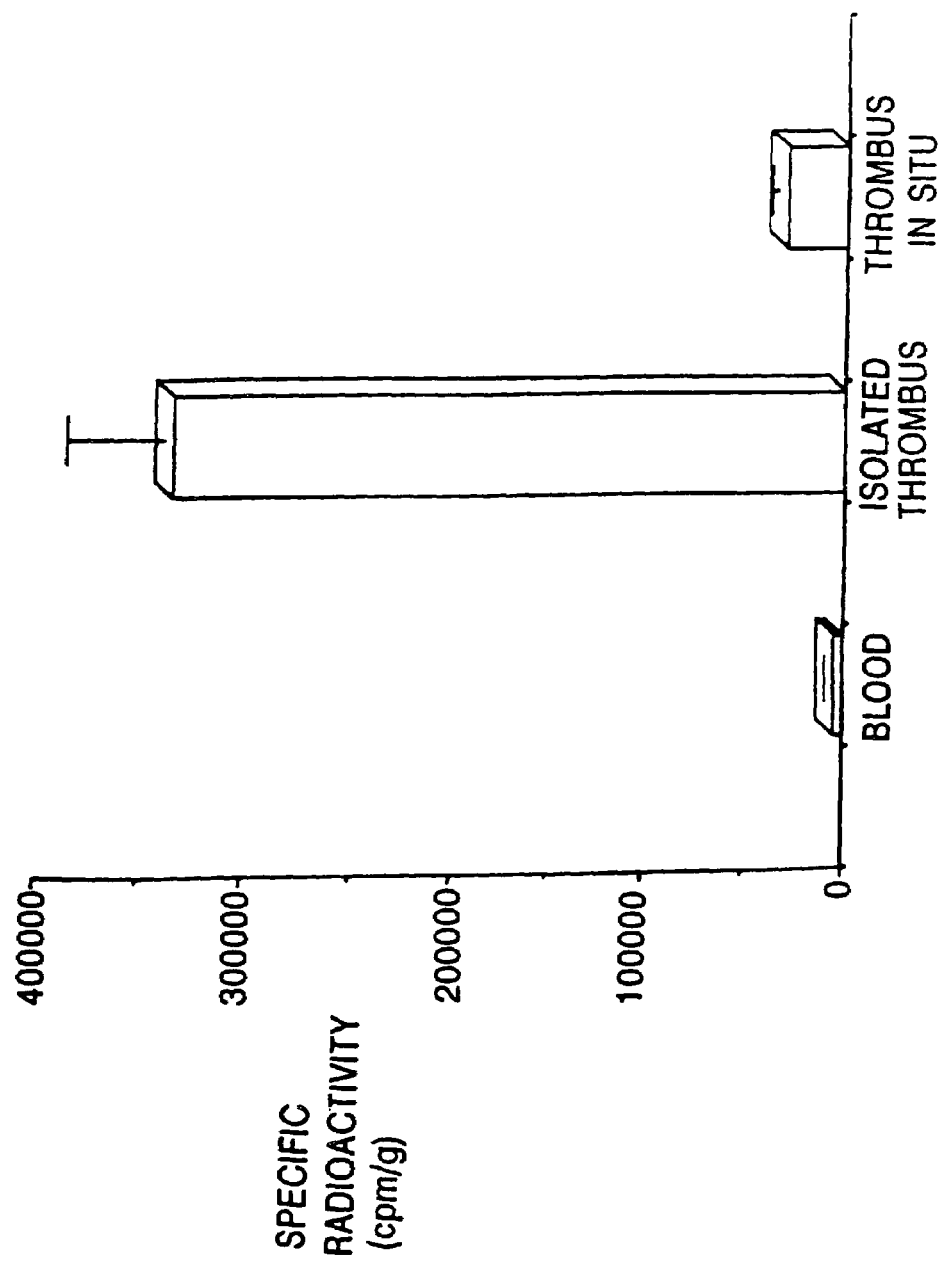

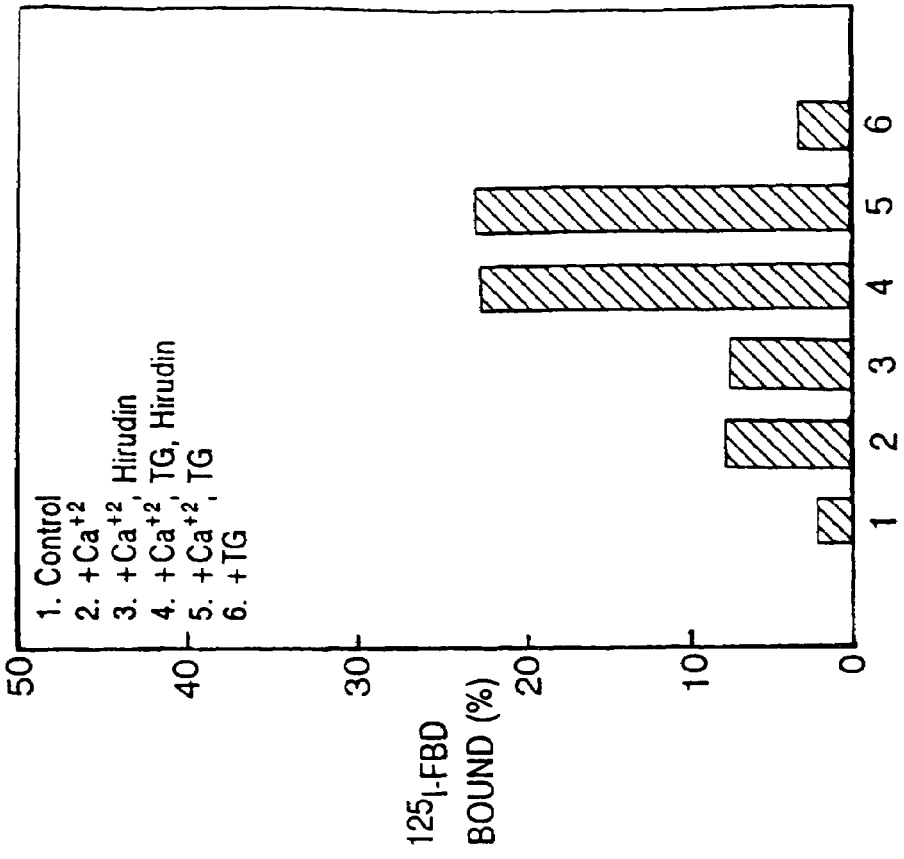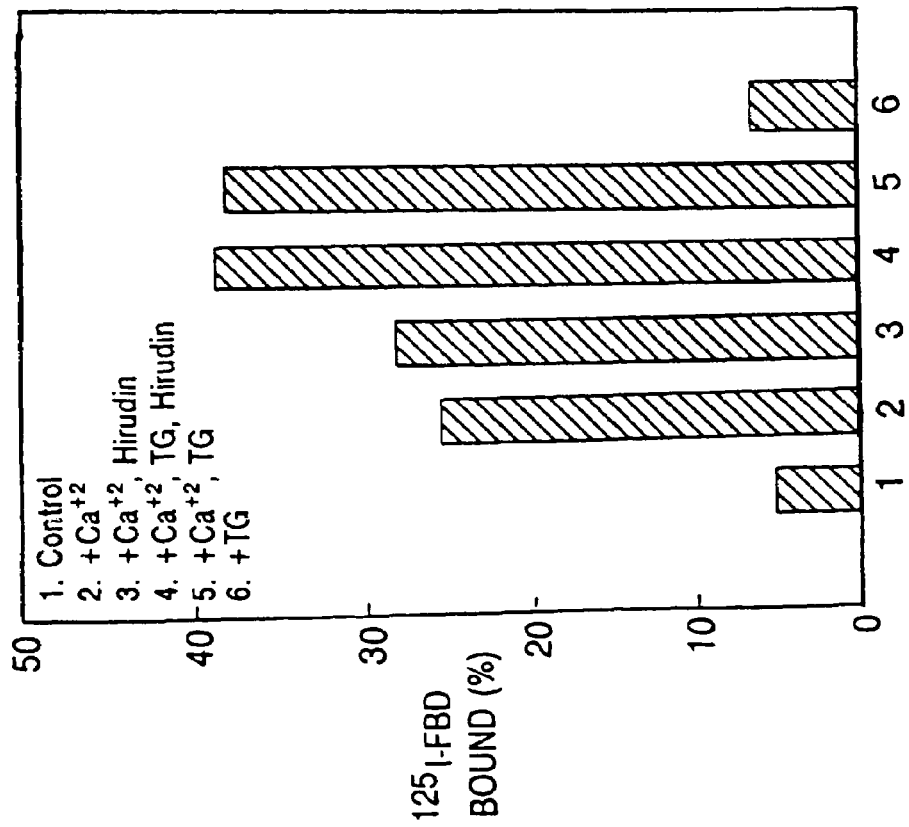

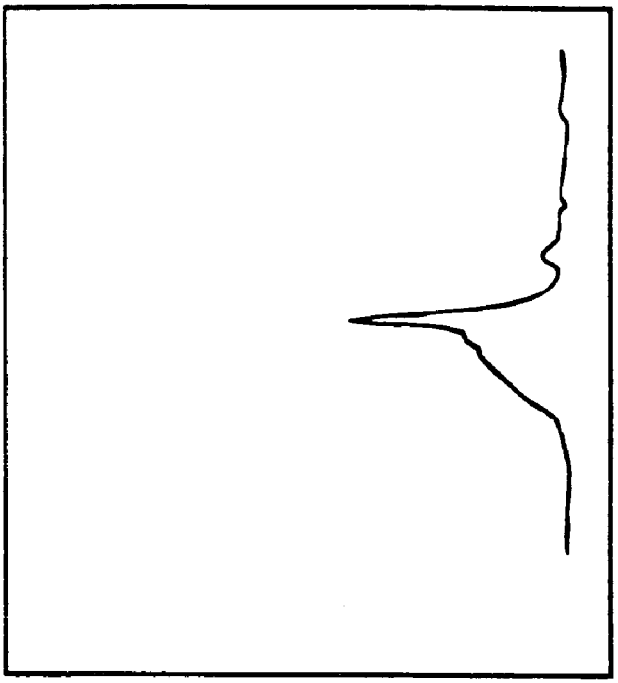
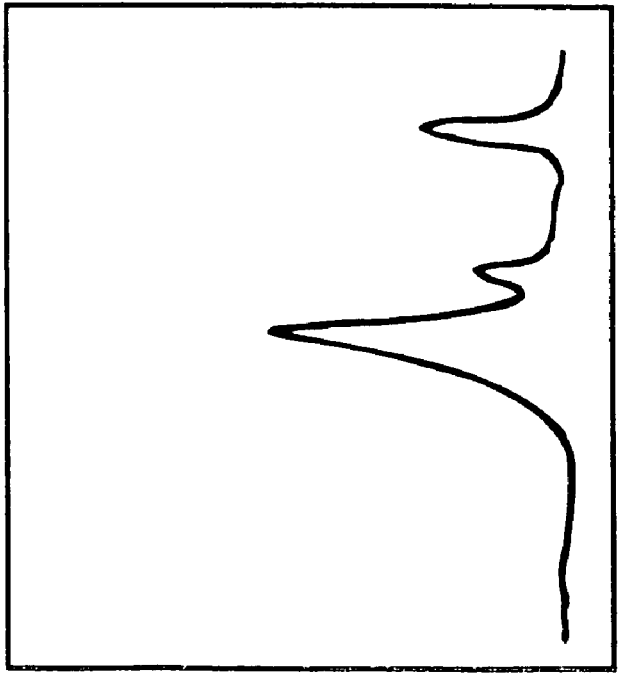
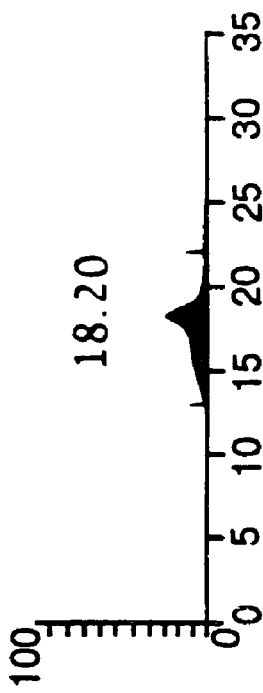
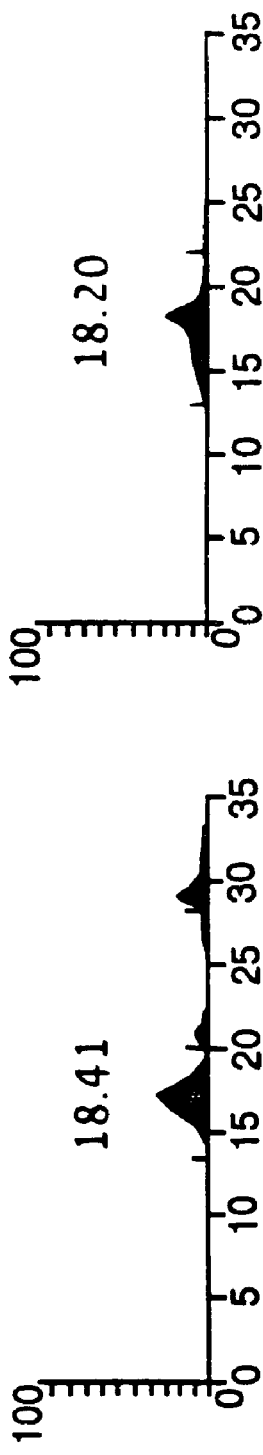
FIGURE 52B-1
FIGURE 52B-2
FIGURE 52A-1
FIGURE 52A-2

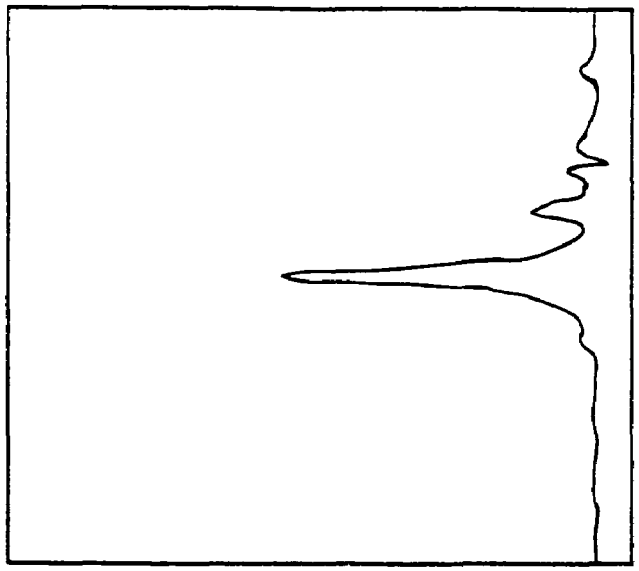
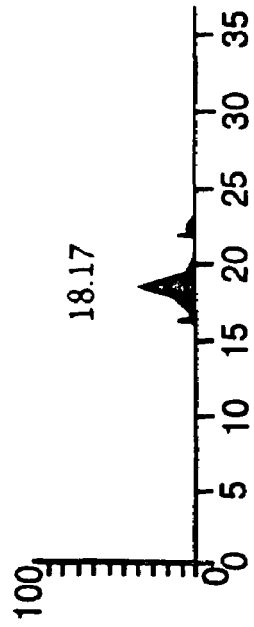
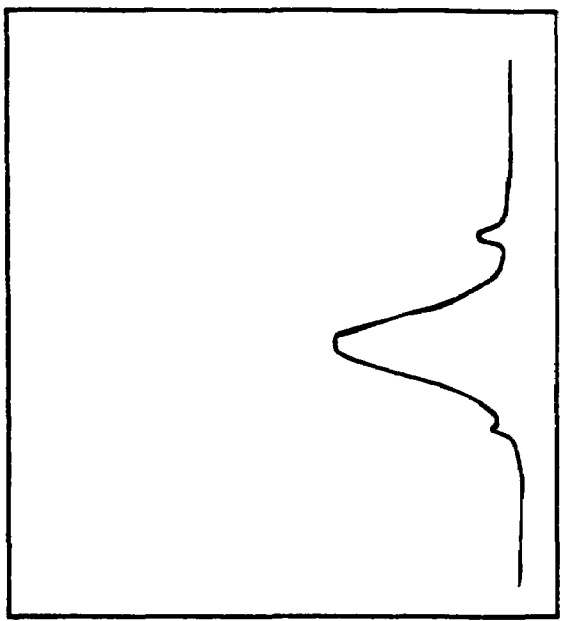
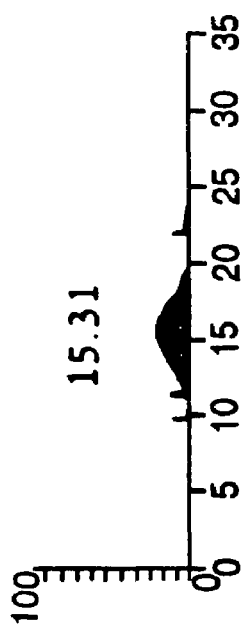
FIGURE 52D-2
FIGURE 52D-1
FIGURE 52C-1
FIGURE 52C-2

SEQUENCE LISTING

```
<160> NUMBER OF SEQ ID NOS: 40

<210> SEQ ID NO 1
<211> LENGTH: 11
<212> TYPE: DNA
<213> ORGANISM: Artificial Sequence
<220> FEATURE:
<223> OTHER INFORMATION: Synthetic Probe directed to Human Fibronectin

<400> SEQUENCE: 1
```
ctgtttaagc a                                                        11

<210> SEQ ID NO 2
<211> LENGTH: 15
<212> TYPE: DNA
<213> ORGANISM: Artificial Sequence
<220> FEATURE:
<223> OTHER INFORMATION: Synthetic Probe directed to Human Fibronectin

<400> SEQUENCE: 2
gacaaattcg tctag                                                    15

<210> SEQ ID NO 3
<211> LENGTH: 41
<212> TYPE: DNA
<213> ORGANISM: Artificial Sequence
<220> FEATURE:
<223> OTHER INFORMATION: Synthetic Probe directed to Human Fibronectin

<400> SEQUENCE: 3
tgagaagtgt tttgatcatg ctgctgggac ttcctatgtg g                       41

<210> SEQ ID NO 4
<211> LENGTH: 43
<212> TYPE: DNA
<213> ORGANISM: Artificial Sequence
<220> FEATURE:
<223> OTHER INFORMATION: Synthetic Probe directed to Human Fibronectin

<400> SEQUENCE: 4
tccgaccaga taggaagtcc cagcagcatg atcaaaacac ttc                     43

<210> SEQ ID NO 5
<211> LENGTH: 45
<212> TYPE: DNA
<213> ORGANISM: Artificial Sequence
<220> FEATURE:
<223> OTHER INFORMATION: Synthetic Probe directed to Human Fibronectin

<400> SEQUENCE: 5
tcggagaaac gtgggagaag ccctaccaag gctggatgat ggtag                   45

<210> SEQ ID NO 6
<211> LENGTH: 45
<212> TYPE: DNA
<213> ORGANISM: Artificial Sequence
<220> FEATURE:
<223> OTHER INFORMATION: Synthetic Probe directed to Human Fibronectin

<400> SEQUENCE: 6
acaatctacc atcatccagc cttggtaggg cttctcccac gtttc                   45

<210> SEQ ID NO 7
<211> LENGTH: 45
<212> TYPE: DNA
<213> ORGANISM: Artificial Sequence
<220> FEATURE:
<223> OTHER INFORMATION: Synthetic Probe directed to Human Fibronectin

<400> SEQUENCE: 7
attgtacttg cctgggagaa ggcagcggac gcatcacttg cactt                   45

<210> SEQ ID NO 8
<211> LENGTH: 44
<212> TYPE: DNA

<213> ORGANISM: Artificial Sequence
<220> FEATURE:
<223> OTHER INFORMATION: Synthetic Probe directed to Human Fibronectin

<400> SEQUENCE: 8
ctagaactgc aagtgatgcg tccgctgcct tctcccaggc aagt        44

<210> SEQ ID NO 9
<211> LENGTH: 38
<212> TYPE: DNA
<213> ORGANISM: Artificial Sequence
<220> FEATURE:
<223> OTHER INFORMATION: Synthetic Probe directed to Human Fibronectin

<400> SEQUENCE: 9
cctcctgttt ctccgtaagt gatcctgtaa tatctcac        38

<210> SEQ ID NO 10
<211> LENGTH: 33
<212> TYPE: DNA
<213> ORGANISM: Artificial Sequence
<220> FEATURE:
<223> OTHER INFORMATION: Synthetic Probe directed to Human Fibronectin

<400> SEQUENCE: 10
gaatcaagac ctgttttctg tcttcctcta aga        33

<210> SEQ ID NO 11
<211> LENGTH: 40
<212> TYPE: DNA
<213> ORGANISM: Artificial Sequence
<220> FEATURE:
<223> OTHER INFORMATION: Synthetic Probe directed to Human Fibronectin

<400> SEQUENCE: 11
ccaggtccct cggaacatca gaaactgttg attgttggcc        40

<210> SEQ ID NO 12
<211> LENGTH: 36
<212> TYPE: DNA
<213> ORGANISM: Artificial Sequence
<220> FEATURE:
<223> OTHER INFORMATION: Synthetic Probe directed to Human Fibronectin

<400> SEQUENCE: 12
aattctgtga cacagtggcc atagggaggc tggggg        36

<210> SEQ ID NO 13
<211> LENGTH: 42
<212> TYPE: DNA
<213> ORGANISM: Artificial Sequence
<220> FEATURE:
<223> OTHER INFORMATION: Synthetic Probe directed to Human Fibronectin

<400> SEQUENCE: 13
catgacccct tcattggttg tgcagatttc ctcgtgggca gc        42

<210> SEQ ID NO 14
<211> LENGTH: 14
<212> TYPE: DNA
<213> ORGANISM: Artificial Sequence
<220> FEATURE:
<223> OTHER INFORMATION: Synthetic Probe directed to Human Fibronectin

<400> SEQUENCE: 14 ctgttttaata agca        14

<210> SEQ ID NO 15
<211> LENGTH: 2327
<212> TYPE: PRT
<213> ORGANISM: Homo Sapiens

<400> SEQUENCE: 15

```
Ser Lys Arg Gln Ala Gln Gln Met Val Gln Pro Gln Ser Pro Val Ala
 1               5                  10                  15

Val Ser Gln Ser Lys Pro Gly Cys Tyr Asp Asn Gly Lys His Tyr Gln
                20                  25                  30

Ile Asn Gln Gln Trp Glu Arg Thr Tyr Leu Gly Asn Val Leu Val Cys
            35                  40                  45

Thr Cys Tyr Gly Gly Ser Arg Gly Phe Asn Cys Glu Ser Lys Pro Glu
        50                  55                  60

Ala Glu Glu Thr Cys Phe Asp Lys Tyr Thr Gly Asn Thr Tyr Arg Val
 65                  70                  75                  80

Gly Asp Thr Tyr Glu Arg Pro Lys Asp Ser Met Ile Trp Asp Cys Thr
                85                  90                  95

Cys Ile Gly Ala Gly Arg Gly Arg Ile Ser Cys Thr Ile Ala Asn Arg
            100                 105                 110

Cys His Glu Gly Gly Gln Ser Tyr Lys Ile Gly Asp Thr Trp Arg Arg
        115                 120                 125

Pro His Glu Thr Gly Gly Tyr Met Leu Glu Cys Val Cys Leu Gly Asn
    130                 135                 140

Gly Lys Gly Glu Trp Thr Cys Lys Pro Ile Ala Glu Lys Cys Phe Asp
145                 150                 155                 160

His Ala Ala Gly Thr Ser Tyr Val Val Gly Glu Thr Trp Glu Lys Pro
                165                 170                 175

Tyr Gln Gly Trp Met Met Val Asp Cys Thr Cys Leu Gly Glu Gly Ser
            180                 185                 190

Gly Arg Ile Thr Cys Thr Ser Arg Asn Arg Cys Asn Asp Gln Asp Thr
        195                 200                 205

Arg Thr Ser Tyr Arg Ile Gly Asp Thr Trp Ser Lys Lys Asp Asn Arg
    210                 215                 220

Gly Asn Leu Leu Gln Cys Ile Cys Thr Gly Asn Gly Arg Gly Glu Trp
225                 230                 235                 240

Lys Cys Glu Arg His Thr Ser Val Gln Thr Thr Ser Ser Gly Ser Gly
                245                 250                 255

Pro Phe Thr Asp Val Arg Ala Ala Val Tyr Gln Pro Gln Pro His Pro
            260                 265                 270

Gln Pro Pro Pro Tyr Gly His Cys Val Thr Asp Ser Gly Val Val Tyr
        275                 280                 285

Ser Val Gly Met Gln Trp Leu Lys Thr Gln Gly Asn Lys Gln Met Leu
    290                 295                 300

Cys Thr Cys Leu Gly Asn Gly Val Ser Cys Gln Glu Thr Ala Val Thr
305                 310                 315                 320

Gln Thr Tyr Gly Gly Asn Leu Asn Gly Glu Pro Cys Val Leu Pro Phe
                325                 330                 335

Thr Tyr Asn Gly Arg Thr Phe Tyr Ser Cys Thr Thr Glu Gly Arg Gln
            340                 345                 350

Asp Gly His Leu Trp Cys Ser Thr Ser Asn Tyr Glu Gln Asp Gln
        355                 360                 365

Lys Tyr Ser Phe Cys Thr Asp His Thr Val Leu Val Gln Thr Gln Gly
```

-continued

```
            370                 375                 380
Gly Asn Ser Asn Gly Ala Leu Cys His Phe Pro Phe Leu Tyr Asn Asn
385                 390                 395                 400

His Asn Tyr Thr Asp Cys Thr Ser Glu Gly Arg Arg Asp Asn Met Lys
                405                 410                 415

Trp Cys Gly Thr Thr Gln Asn Tyr Asp Ala Asp Gln Lys Phe Gly Phe
                420                 425                 430

Cys Pro Met Ala Ala His Glu Glu Ile Cys Thr Thr Asn Glu Gly Val
                435                 440                 445

Met Tyr Arg Ile Gly Asp Gln Trp Asp Lys Gln His Asp Met Gly His
    450                 455                 460

Met Met Arg Cys Thr Cys Val Gly Asn Gly Arg Gly Glu Trp Thr Cys
465                 470                 475                 480

Ile Ala Tyr Ser Gln Leu Arg Asp Gln Cys Ile Val Asp Asp Ile Thr
                485                 490                 495

Tyr Asn Val Asn Asp Thr Phe His Lys Arg His Glu Glu Gly His Met
                500                 505                 510

Leu Asn Cys Thr Cys Phe Gly Gln Gly Arg Gly Arg Trp Lys Cys Asp
            515                 520                 525

Pro Val Asp Gln Cys Gln Asp Ser Glu Thr Gly Thr Phe Tyr Gln Ile
            530                 535                 540

Gly Asp Ser Trp Glu Lys Tyr Val His Gly Val Arg Tyr Gln Cys Tyr
545                 550                 555                 560

Cys Tyr Gly Arg Gly Ile Gly Glu Trp His Cys Gln Pro Leu Gln Thr
                565                 570                 575

Tyr Pro Ser Ser Ser Gly Pro Val Glu Val Phe Ile Thr Glu Thr Pro
            580                 585                 590

Ser Gln Pro Asn Ser His Pro Ile Gln Trp Asn Ala Pro Gln Pro Ser
            595                 600                 605

His Ile Ser Lys Tyr Ile Leu Arg Trp Arg Pro Lys Asn Ser Val Gly
        610                 615                 620

Arg Trp Lys Glu Ala Thr Ile Pro Gly His Leu Asn Ser Tyr Thr Ile
625                 630                 635                 640

Lys Gly Leu Lys Pro Gly Val Val Tyr Glu Gly Gln Leu Ile Ser Ile
                645                 650                 655

Gln Gln Tyr Gly His Gln Glu Val Thr Arg Phe Asp Phe Thr Thr Thr
                660                 665                 670

Ser Thr Ser Thr Pro Val Thr Ser Asn Thr Val Thr Gly Glu Thr Thr
            675                 680                 685

Pro Phe Ser Pro Leu Val Ala Thr Ser Glu Ser Val Thr Glu Ile Thr
            690                 695                 700

Ala Ser Ser Phe Val Val Ser Trp Val Ser Ala Ser Asp Thr Val Ser
705                 710                 715                 720

Gly Phe Arg Val Glu Tyr Glu Leu Ser Glu Glu Gly Asp Glu Pro Gln
                725                 730                 735

Tyr Leu Asp Leu Pro Ser Thr Ala Thr Ser Val Asn Ile Pro Asp Leu
            740                 745                 750

Leu Pro Gly Arg Lys Tyr Ile Val Asn Val Tyr Gln Ile Ser Glu Asp
            755                 760                 765

Gly Glu Gln Ser Leu Ile Leu Ser Thr Ser Gln Thr Thr Ala Pro Asp
        770                 775                 780

Ala Pro Pro Asp Pro Thr Val Asp Gln Val Asp Asp Thr Ser Ile Val
785                 790                 795                 800
```

-continued

Val Arg Trp Ser Arg Pro Gln Ala Pro Ile Thr Gly Tyr Arg Ile Val
              805                 810                 815

Tyr Ser Pro Ser Val Glu Gly Ser Ser Thr Glu Leu Asn Leu Pro Glu
              820                 825                 830

Thr Ala Asn Ser Val Thr Leu Ser Asp Leu Gln Pro Gly Val Gln Tyr
              835                 840                 845

Asn Ile Thr Ile Tyr Ala Val Glu Glu Asn Gln Glu Ser Thr Pro Val
              850                 855                 860

Val Ile Gln Gln Glu Thr Thr Gly Thr Pro Arg Ser Asp Thr Val Pro
865                 870                 875                 880

Ser Pro Arg Asp Leu Gln Phe Val Glu Val Thr Asp Val Lys Val Thr
              885                 890                 895

Ile Met Trp Thr Pro Pro Glu Ser Ala Val Thr Gly Tyr Arg Val Asp
              900                 905                 910

Val Ile Pro Val Asn Leu Pro Gly Glu His Gly Gln Arg Leu Pro Ile
              915                 920                 925

Ser Arg Asn Thr Phe Ala Glu Val Thr Gly Leu Ser Pro Gly Val Thr
              930                 935                 940

Tyr Tyr Phe Lys Val Phe Ala Val Ser His Gly Arg Glu Ser Lys Pro
945                 950                 955                 960

Leu Thr Ala Gln Gln Thr Thr Lys Leu Asp Ala Pro Thr Asn Leu Gln
              965                 970                 975

Phe Val Asn Glu Thr Asp Ser Thr Val Leu Val Arg Trp Thr Pro Pro
              980                 985                 990

Arg Ala Gln Ile Thr Gly Tyr Arg Leu Thr Val Gly Leu Thr Arg Arg
              995                 1000                1005

Gly Gln Pro Arg Gln Tyr Asn Val Gly Pro Ser Val Ser Lys Tyr
        1010                1015                1020

Pro Leu Arg Asn Leu Gln Pro Ala Ser Glu Tyr Thr Val Ser Leu
        1025                1030                1035

Val Ala Ile Lys Gly Asn Gln Glu Ser Pro Lys Ala Thr Gly Val
        1040                1045                1050

Phe Thr Thr Leu Gln Pro Gly Ser Ser Ile Pro Pro Tyr Asn Thr
        1055                1060                1065

Glu Val Thr Glu Thr Thr Ile Val Ile Thr Trp Thr Pro Ala Pro
        1070                1075                1080

Arg Ile Gly Phe Lys Leu Gly Val Arg Pro Ser Gln Gly Gly Glu
        1085                1090                1095

Ala Pro Arg Glu Val Thr Ser Asp Ser Gly Ser Ile Val Val Ser
        1100                1105                1110

Gly Leu Thr Pro Gly Val Glu Tyr Val Tyr Thr Ile Gln Val Leu
        1115                1120                1125

Arg Asp Gly Gln Glu Arg Asp Ala Pro Ile Val Asn Lys Val Val
        1130                1135                1140

Thr Pro Leu Ser Pro Pro Thr Asn Leu His Leu Glu Ala Asn Pro
        1145                1150                1155

Asp Thr Gly Val Leu Thr Val Ser Trp Glu Arg Ser Thr Thr Pro
        1160                1165                1170

Asp Ile Thr Gly Tyr Arg Ile Thr Thr Thr Pro Thr Asn Gly Gln
        1175                1180                1185

Gln Gly Asn Ser Leu Glu Glu Val Val His Ala Asp Gln Ser Ser
        1190                1195                1200

-continued

| | | | | | | | | | |
|---|---|---|---|---|---|---|---|---|---|
| Cys | Thr | Phe | Asp | Asn | Leu | Ser | Pro | Gly | Leu | Glu | Tyr | Asn | Val | Ser |
| | 1205 | | | | 1210 | | | | 1215 | | | |

Cys Thr Phe Asp Asn Leu Ser Pro Gly Leu Glu Tyr Asn Val Ser
    1205                1210               1215

Val Tyr Thr Val Lys Asp Asp Lys Glu Ser Val Pro Ile Ser Asp
    1220                1225               1230

Thr Ile Ile Pro Ala Val Pro Pro Thr Asp Leu Arg Phe Thr
    1235                1240               1245

Asn Ile Gly Pro Asp Thr Met Arg Val Thr Trp Ala Pro Pro Pro
    1250                1255               1260

Ser Ile Asp Leu Thr Asn Phe Leu Val Arg Tyr Ser Pro Val Lys
    1265                1270               1275

Asn Glu Glu Asp Val Ala Glu Leu Ser Ile Ser Pro Ser Asp Asn
    1280                1285               1290

Ala Val Val Leu Thr Asn Leu Leu Pro Gly Thr Glu Tyr Val Val
    1295                1300               1305

Ser Val Ser Ser Val Tyr Glu Gln His Glu Ser Thr Pro Leu Arg
    1310                1315               1320

Gly Arg Gln Lys Thr Gly Leu Asp Ser Pro Thr Gly Ile Asp Phe
    1325                1330               1335

Ser Asp Ile Thr Ala Asn Ser Phe Thr Val His Trp Ile Ala Pro
    1340                1345               1350

Arg Ala Thr Ile Thr Gly Tyr Arg Ile Arg His His Pro Glu His
    1355                1360               1365

Phe Ser Gly Arg Pro Arg Glu Asp Arg Val Pro His Ser Arg Asn
    1370                1375               1380

Ser Ile Thr Leu Thr Asn Leu Thr Pro Gly Thr Glu Tyr Val Val
    1385                1390               1395

Ser Ile Val Ala Leu Asn Gly Arg Glu Glu Ser Pro Leu Leu Ile
    1400                1405               1410

Gly Gln Gln Ser Thr Val Ser Asp Val Pro Arg Asp Leu Glu Val
    1415                1420               1425

Val Ala Ala Thr Pro Thr Ser Leu Leu Ile Ser Trp Asp Ala Pro
    1430                1435               1440

Ala Val Thr Val Arg Tyr Tyr Arg Ile Thr Tyr Gly Glu Thr Gly
    1445                1450               1455

Gly Asn Ser Pro Val Gln Glu Phe Thr Val Pro Gly Ser Lys Ser
    1460                1465               1470

Thr Ala Thr Ile Ser Gly Leu Lys Pro Gly Val Asp Tyr Thr Ile
    1475                1480               1485

Thr Val Tyr Ala Val Thr Gly Arg Gly Asp Ser Pro Ala Ser Ser
    1490                1495               1500

Lys Pro Ile Ser Ile Asn Tyr Arg Thr Glu Ile Asp Lys Pro Ser
    1505                1510               1515

Gln Met Gln Val Thr Asp Val Gln Asp Asn Ser Ile Ser Val Lys
    1520                1525               1530

Trp Leu Pro Ser Ser Ser Pro Val Thr Gly Tyr Arg Val Thr Thr
    1535                1540               1545

Thr Pro Lys Asn Gly Pro Gly Pro Thr Lys Thr Lys Thr Ala Gly
    1550                1555               1560

Pro Asp Gln Thr Glu Met Thr Ile Glu Gly Leu Gln Pro Thr Val
    1565                1570               1575

Glu Tyr Val Val Ser Val Tyr Ala Gln Asn Pro Ser Gly Glu Ser
    1580                1585               1590

Gln Pro Leu Val Gln Thr Ala Val Thr Asn Ile Asp Arg Pro Lys

-continued

```
         1595                1600                1605
Gly Leu  Ala Phe Thr Asp Val Asp Val Asp Ser Ile  Lys Ile Ala
    1610                1615                1620

Trp Glu  Ser Pro Gln Gly Gln Val Ser Arg Tyr Arg  Val Thr Tyr
    1625                1630                1635

Ser Ser  Pro Glu Asp Gly Ile His Glu Leu Phe Pro  Ala Pro Asp
    1640                1645                1650

Gly Glu  Glu Asp Thr Ala Glu Leu Gln Gly Leu Arg  Pro Gly Ser
    1655                1660                1665

Glu Tyr  Thr Val Ser Val Val Ala Leu His Asp Asp  Met Glu Ser
    1670                1675                1680

Gln Pro  Leu Ile Gly Thr Gln Ser Thr Ala Ile Pro  Ala Pro Thr
    1685                1690                1695

Asp Leu  Lys Phe Thr Gln Val Thr Pro Thr Ser Leu  Ser Ala Gln
    1700                1705                1710

Trp Thr  Pro Pro Asn Val Gln Leu Thr Gly Tyr Arg  Val Arg Val
    1715                1720                1725

Thr Pro  Lys Glu Lys Thr Gly Pro Met Lys Glu Ile  Asn Leu Ala
    1730                1735                1740

Pro Asp  Ser Ser Ser Val Val Ser Gly Leu Met Val  Ala Thr
    1745                1750                1755

Lys Tyr  Glu Val Ser Val Tyr Ala Leu Lys Asp Thr  Leu Thr Ser
    1760                1765                1770

Arg Pro  Ala Gln Gly Val Val Thr Thr Leu Glu Asn  Val Ser Pro
    1775                1780                1785

Pro Arg  Arg Ala Arg Val Thr Asp Ala Thr Glu Thr  Thr Ile Thr
    1790                1795                1800

Ile Ser  Trp Arg Thr Lys Thr Glu Thr Ile Thr Gly  Phe Gln Val
    1805                1810                1815

Asp Ala  Val Pro Ala Asn Gly Gln Thr Pro Ile Gln  Arg Thr Ile
    1820                1825                1830

Lys Pro  Asp Val Arg Ser Tyr Thr Ile Thr Gly Leu  Gln Pro Gly
    1835                1840                1845

Thr Asp  Tyr Lys Ile Tyr Leu Tyr Thr Leu Asn Asp  Asn Ala Arg
    1850                1855                1860

Ser Ser  Pro Val Val Ile Asp Ala Ser Thr Ala Ile  Asp Ala Pro
    1865                1870                1875

Ser Asn  Leu Arg Phe Leu Ala Thr Thr Pro Asn Ser  Leu Leu Val
    1880                1885                1890

Ser Trp  Gln Pro Pro Arg Ala Arg Ile Thr Gly Tyr  Ile Ile Lys
    1895                1900                1905

Tyr Glu  Lys Pro Gly Ser Pro Arg Glu Val Val Pro  Arg Pro Arg
    1910                1915                1920

Arg Pro  Gly Val Thr Glu Ala Thr Ile Thr Gly Leu  Glu Pro Gly
    1925                1930                1935

Thr Glu  Tyr Thr Ile Tyr Val Ile Ala Leu Lys Asn  Asn Gln Lys
    1940                1945                1950

Ser Glu  Pro Leu Ile Gly Arg Lys Lys Thr Asp Glu  Leu Pro Gln
    1955                1960                1965

Leu Val  Thr Leu Pro His Pro Asn Leu His Gly Pro  Glu Ile Leu
    1970                1975                1980

Asp Val  Pro Ser Thr Val Gln Lys Thr Pro Phe Val  Thr His Pro
    1985                1990                1995
```

-continued

```
Gly Tyr Asp Thr Gly Asn Gly Ile Gln Leu Pro Gly Thr Ser Gly
    2000            2005                2010
Gln Gln Pro Ser Val Gly Gln Gln Met Ile Phe Glu Glu His Gly
    2015            2020                2025
Phe Arg Arg Thr Thr Pro Pro Thr Thr Ala Thr Pro Ile Arg His
    2030            2035                2040
Arg Pro Arg Pro Tyr Pro Pro Asn Val Gly Gln Glu Ala Leu Ser
    2045            2050                2055
Gln Thr Thr Ile Ser Trp Ala Pro Phe Gln Asp Thr Ser Glu Tyr
    2060            2065                2070
Ile Ile Ser Cys His Pro Val Gly Thr Asp Glu Glu Pro Leu Gln
    2075            2080                2085
Phe Arg Val Pro Gly Thr Ser Thr Ser Ala Thr Leu Thr Gly Leu
    2090            2095                2100
Thr Arg Gly Ala Thr Tyr Asn Ile Ile Val Glu Ala Leu Lys Asp
    2105            2110                2115
Gln Gln Arg His Lys Val Arg Glu Glu Val Val Thr Val Gly Asn
    2120            2125                2130
Ser Val Asn Glu Gly Leu Asn Gln Pro Thr Asp Asp Ser Cys Phe
    2135            2140                2145
Asp Pro Tyr Thr Val Ser His Tyr Ala Val Gly Asp Glu Trp Glu
    2150            2155                2160
Arg Met Ser Glu Ser Gly Phe Lys Leu Leu Cys Gln Cys Leu Gly
    2165            2170                2175
Phe Gly Ser Gly His Phe Arg Cys Asp Ser Ser Arg Trp Cys His
    2180            2185                2190
Asp Asn Gly Val Asn Tyr Lys Ile Gly Glu Lys Trp Asp Arg Gln
    2195            2200                2205
Gly Glu Asn Gly Gln Met Met Ser Cys Thr Cys Leu Gly Asn Gly
    2210            2215                2220
Lys Gly Glu Phe Lys Cys Asp Pro His Glu Ala Thr Cys Tyr Asp
    2225            2230                2235
Asp Gly Lys Thr Tyr His Val Gly Glu Gln Trp Gln Lys Glu Tyr
    2240            2245                2250
Leu Gly Ala Ile Cys Ser Cys Thr Cys Phe Gly Gly Gln Arg Gly
    2255            2260                2265
Trp Arg Cys Asp Asn Cys Arg Arg Pro Gly Gly Glu Pro Ser Pro
    2270            2275                2280
Glu Gly Thr Thr Gly Gln Ser Tyr Asn Gln Tyr Ser Gln Arg Tyr
    2285            2290                2295
His Gln Arg Thr Asn Thr Asn Val Asn Cys Pro Ile Glu Cys Phe
    2300            2305                2310
Met Pro Leu Asp Val Gln Ala Asp Arg Glu Asp Ser Arg Glu
    2315            2320                2325

<210> SEQ ID NO 16
<211> LENGTH: 7705
<212> TYPE: DNA
<213> ORGANISM: Homo Sapiens

<400> SEQUENCE: 16
gaagagcaag aggcaggctc agcaaatggt tcagcccag tccccggtgg ctgtcagtca         60
aagcaagccc ggttgttatg acaatggaaa acactatcag ataaatcaac agtgggagcg       120
```

-continued

```
gacctaccta ggtaatgtgt tggtttgtac ttgttatgga ggaagccgag gttttaactg      180
cgaaagtaaa cctgaagctg aagagacttg ctttgacaag tacactggga acacttaccg      240
agtgggtgac acttatgagc gtcctaaaga ctccatgatc tgggactgta cctgcatcgg      300
ggctgggcga gggagaataa gctgtaccat cgcaaaccgc tgccatgaag ggggtcagtc      360
ctacaagatt ggtgacacct ggaggagacc acatgagact ggtggttaca tgttagagtg      420
tgtgtgtctt ggtaatggaa aaggagaatg gacctgcaag cccatagctg agaagtgttt      480
tgatcatgct gctgggactc cctatgtggt cggagaaacg tgggagaagc cctaccaagg      540
ctggatgatg gtagattgta cttgcctggg agaaggcagc ggacgcatca cttgcacttc      600
tagaaataga tgcaacgatc aggacacaag gacatcctat agaatttgag acacctggag      660
caagaaggat aatcgaggaa acctgctcca gtgcatctgc acaggcaacg gccgaggaga      720
gtggaagtgt gagaggcaca cctctgtgca gaccacatcg agcggatctg gcccctcac      780 cgatgttcgt gcagctgttt accaaccgca gcctcacccc cagcctcctc cctatggcca      840
ctgtgtcaca gacagtggtg tggtctactc tgtggggatg cagtggttga agacacaagg      900
aaataagcaa atgctttgca cgtgcctggg caacggagtc agctgccaag agacagctgt      960
aacccagact tacggtggca acttaaatgg agagccatgt gtcttaccat tcacctacaa     1020
tggcaggacg ttctactcct gcaccacgga agggcgacag gacggacatc tttggtgcag     1080
cacaacttcg aattatgagc aggaccagaa atactctttc tgcacagacc acactgtttt     1140
ggttcagact caaggaggaa attccaatgg tgccttgtgc cacttcccct tcctatacaa     1200
caaccacaat tacactgatt gcacttctga gggcagaaga gacaacatga agtggtgtgg     1260
gaccacacag aactatgatg ccgaccagaa gtttgggttc tgccccatgg ctgcccacga     1320
ggaaatctgc acaaccaatg aagggggtcat gtaccgcatt ggagatcagt gggataagca     1380
gcatgacatg ggtcacatga tgaggtgcac gtgtgttggg aatggtcgtg gggaatggac     1440
atgcattgcc tactcgcaac ttcgagatca gtgcattgtt gatgacatca cttacaatgt     1500
gaacgacaca ttccacaagc gtcatgaaga ggggcacatg ctgaactgta catgcttcgg     1560
tcagggtcgg ggcaggtgga agtgtgatcc cgtcgaccaa tgccaggatt cagagactgg     1620
gacgttttat caaattggag attcatggga agtatgtg catggtgtca gataccagtg     1680
ctactgctat ggccgtggca ttggggagtg gcattgccaa cctttacaga cctatccaag     1740
ctcaagtggt cctgtcgaag tatttatcac tgagactccg agtcagccca actcccaccc     1800
catccagtgg aatgcaccac agccatctca catttccaag tacattctca ggtggagacc     1860
taaaaattct gtaggccgtt ggaaggaagc taccatacca ggccacttaa actcctacac     1920
catcaaaggc ctgaagcctg gtgtggtata cgagggccag ctcatcagca tccagcagta     1980
cggccaccaa gaagtgactc gctttgactt caccaccacc agcaccagca cacctgtgac     2040
cagcaacacc gtgacaggag agacgactcc ttttctcct cttgtggcca cttctgaatc     2100
tgtgaccgaa atcacagcca gtagctttgt ggtctcctgg gtctcagctt ccgacaccgt     2160
gtcgggattc cgggtggaat atgagctgag tgaggaggga gatgagccac agtacctgga     2220
tcttccaagc acagccactt ctgtgaacat ccctgacctg cttcctggcc gaaaatacat     2280
tgtaaatgtc tatcagatat ctgaggatgg ggagcagagt ttgatcctgt ctacttcaca     2340
aacaacagcg cctgatgccc ctcctgaccc gactgtggac caagttgatg acacctcaat     2400
tgttgttcgc tggagcagac cccaggctcc catcacaggg tacagaatag tctattcgcc     2460
atcagtagaa ggtagcagca cagaactcaa ccttcctgaa actgcaaact ccgtcacccct     2520
```

-continued

```
cagtgacttg caacctggtg ttcagtataa catcactatc tatgctgtgg aagaaaatca    2580
agaaagtaca cctgttgtca ttcaacaaga aaggactggc accccacgct cagatacagt    2640
gccctctccc agggacctgc agtttgtgga agtgacagac gtgaaggtca ccatcatgtg    2700
gacaccgcct gagagtgcag tgaccggcta ccgtgtggat gtgatccccg tcaacctgcc    2760
tggcgagcac gggcagaggc tgcccatcag caggaacacc tttgcagaag tcaccgggct    2820
gtcccctggg gtcacctatt acttcaaagt cttttgcagtg agccatggga gggagagcaa    2880
gcctctgact gctcaacaga caaccaaact ggatgctccc actaacctcc agtttgtcaa    2940
tgaaactgat tctactgtcc tggtgagatg gactccacct cgggcccaga taacaggata    3000
ccgactgacc gtgggcctta cccgaagagg ccagcccagg cagtacaatg tgggtccctc    3060
tgtcttcaag tacccctga ggaatctgca gcctgcatct gattacaccg tatccctcgt    3120
ggccataaag ggcaaccaag agagcccaa agccactgga gtctttacca cactgcagcc    3180
tgggagctct attccacctt acaacaccga ggtgactgag accaccatcg tgatcacatg    3240
gacgcctgct ccaagaattg gttttaagct gggtgtacga ccaagccagg gaggagaggc    3300
accacgagaa gtgacttcag actcaggaag catcgttgtg tccggcttga ctccaggagt    3360
agaatacgtc tacaccatcc aagtcctgag agatggacag gaaagagatg cgccaattgt    3420
aaacaaagtg gtgacaccat tgtctccacc aacaaacttg catctggagg caaaccctga    3480
cactggagtg ctcacagtct cctgggagag gagcaccacc ccagacatta ctggttatag    3540
aattaccaca accctacaa acggccagca gggaaattct ttggaagaag tggtccatgc    3600
tgatcagagc tcctgcactt ttgataacct gagtcccggc ctggagtaca atgtcagtgt    3660
ttacactgtc aaggatgaca aggaaagtgt ccctatctct gataccatca tcccagctgt    3720
tcctcctccc actgacctgc gattcaccaa cattggtcca gacaccatgc gtgtcacctg    3780
ggctccaccc ccatccattg atttaaccaa cttcctggtg cgttactcac ctgtgaaaaa    3840
tgaggaagat gttgcagagt tgtcaatttc tccttcagac aatgcagtgg tcttaacaaa    3900
tctcctgcct ggtacagaat atgtagtgag tgtctccagt gtctacgaac aacatgagag    3960
cacacctctt agaggaagac agaaaacagg tcttgattcc ccaactggca ttgactttttc    4020 tgatattact gccaactctt ttactgtgca ctggattgct cctcgagcca ccatcactgg    4080
ctacaggatc cgccatcatc ccgagcactt cagtgggaga cctcgagaag atcgggtgcc    4140
ccactctcgg aattccatca ccctcaccaa cctcactcca ggcacagagt atgtggtcag    4200
catcgttgct cttaatggca gagaggaaag tccccttattg attggccaac aatcaacagt    4260
ttctgatgtt ccgagggacc tggaagttgt tgctgcgacc cccaccagcc tactgatcag    4320
ctgggatgct cctgctgtca cagtgagata ttacaggatc acttacggag aaacaggagg    4380
aaatagccct gtccaggagt tcactgtgcc tgggagcaag tctacagcta ccatcagcgg    4440
ccttaaacct ggagttgatt ataccatcac tgtgtatgct gtcactggcc gtggagacag    4500
ccccgcaagc agcaagccaa tttccattaa ttaccgaaca gaaattgaca aaccatccca    4560
gatgcaagtg accgatgttc aggacaacag cattagtgtc aagtggctgc cttcaagttc    4620
ccctgttact ggttacagag taaccaccac tcccaaaaat ggaccaggac caacaaaaac    4680
taaaactgca ggtccagatc aaacagaaat gactattgaa ggcttgcagc ccacagtgga    4740
gtatgtggtt agtgtctatg ctcagaatcc aagcggagag agtcagcctc tggttcagac    4800
tgcagtaacc aacattgatc gccctaaagg actggcattc actgatgtgg atgtcgattc    4860
```

```
catcaaaatt gcttgggaaa gcccacaggg gcaagtttcc aggtacaggg tgacctactc    4920
gagccctgag gatggaatcc atgagctatt ccctgcacct gatggtgaag aagacactgc    4980
agagctgcaa ggcctcagac cgggttctga gtacacagtc agtgtggttg ccttgcacga    5040
tgatatggag agccagcccc tgattggaac ccagtccaca gctattcctg caccaactga    5100
cctgaagttc actcaggtca cacccacaag cctgagcgcc cagtggacac cacccaatgt    5160
tcagctcact ggatatcgag tgcgggtgac ccccaaggag aagaccggac caatgaaaga    5220
aatcaacctt gctcctgaca gctcatccgt ggttgtatca ggacttatgg tggccaccaa    5280
atatgaagtg agtgtctatg ctcttaagga cactttgaca agcagaccag ctcagggtgt    5340
tgtcaccact ctggagaatg tcagcccacc aagaagggct cgtgtgacag atgctactga    5400
gaccaccatc accattagct ggagaaccaa gactgagacg atcactggct tccaagttga    5460
tgccgttcca gccaatggcc agactccaat ccagagaacc atcaagccag atgtcagaag    5520
ctacaccatc acaggtttac aaccaggcac tgactacaag atctacctgt acaccttgaa    5580
tgacaatgct cggagctccc ctgtggtcat cgacgcctcc actgccattg atgcaccatc    5640
caacctgcgt ttcctggcca ccacacccaa ttccttgctg gtatcatggc agccgccacg    5700
tgccaggatt accggctaca tcatcaagta tgagaagcct gggtctcctc ccagagaagt    5760
ggtccctcgg ccccgccctg tgtcacaga ggctactatt actggcctgg aaccgggaac    5820
cgaatataca atttatgtca ttgccctgaa gaataatcag aagagcgagc ccctgattgg    5880
aaggaaaaag acagacgagc ttccccaact ggtaaccctt ccacacccca atcttcatgg    5940
accagagatc ttggatgttc cttccacagt tcaaaagacc cctttcgtca cccaccctgg    6000
gtatgacact ggaaatggta ttcagcttcc tggcacttct ggtcagcaac ccagtgttgg    6060
gcaacaaatg atctttgagg aacatggttt taggcggacc acaccgccca aacggccac     6120
ccccataagg cataggccaa gaccataccc gccgaatgta ggacaagaag ctctctctca    6180
gacaaccatc tcatgggccc cattccagga cacttctgag tacatcattt catgtcatcc    6240
tgttggcact gatgaagaac ccttacagtt cagggttcct ggaacttcta ccagtgccac    6300
tctgacaggc ctcaccagag gtgccaccta caacatcata gtggaggcac tgaaagacca    6360
gcagaggcat aaggttcggg aagaggttgt taccgtgggc aactctgtca acgaaggctt    6420
gaaccaacct acggatgact cgtgctttga ccccatacaca gtttcccatt atgccgttgg    6480
agatgagtgg gaacgaatgt ctgaatcagg cttttaaactg ttgtgccagt gcttaggctt    6540
tggaagtggt catttcagat gtgattcatc tagatggtgc catgacaatg gtgtgaacta    6600
caagattgga gagaagtggg accgtcaggg agaaaatggc cagatgatga gctgcacatg    6660
tcttgggaac ggaaaaggag aattcaagtg tgaccctcat gaggcaacgt gttacgatga    6720
tgggaagaca taccacgtag agaacagtg gcagaaggaa tatctcggtg ccatttgctc    6780
ctgcacatgc tttggaggcc agcggggctg gcgctgtgac aactgccgca gacctggggg    6840
tgaacccagt cccgaaggca ctactggcca gtcctacaac cagtattctc agagataccac   6900
tcagagaaca aacactaatg ttaattgccc aattgagtgc ttcatgcctt tagatgtaca   6960
ggctgacaga gaagattccc gagagtaaat catctttcca atccagagga acaagcatgt   7020
ctctctgcca agatccatct aaactggagt gatgttagca gacccagctt agagttcttc   7080
tttcttcctt aagccctttg ctctggagga agttctccag cttcagctca actcacagct   7140
tctccaagca tcccctggg agtttcctga gggttttctc ataaatgagg gctgcacatt    7200
gcctgttctg cttcgaagta ttcaataccg ctcagtattt taaatgaagt gattctaaga   7260
```

-continued

```
tttggtttgg gatcaatagg aaagcatatg cagccaacca agatgcaaat gttttgaaat      7320
gatatgacca aaattttaag taggaaagtc acccaaacac ttctgctttc acttaagtgt      7380
ctggcccgca atactgtagg aacaagcatg atcttgttac tgtgatattt taaatatcca      7440
cagtactcac tttttccaaa tgatcctagt aattgcctag aaatatcttt ctcttacctg      7500
ttatttatca attttccca gtattttat acggaaaaaa ttgtattgaa aacacttagt        7560
atgcagttga taagaggaat ttggtataat tatggtgggt gattattttt tatactgtat      7620
gtgccaaagc tttactactg tgaaagaca actgttttaa taaaagattt acattccaca       7680
aaaaaaaaaa aaaaaaaaa aaaaa                                             7705
```

<210> SEQ ID NO 17
<211> LENGTH: 71
<212> TYPE: DNA
<213> ORGANISM: Artificial Sequence
<220> FEATURE:
<223> OTHER INFORMATION: Synthetic Probe directed to Human Fibronectin

<400> SEQUENCE: 17

```
aattcatatg caggcacagc aaatggttca gccccagtcc ccggtggctg tcagtcaaag      60
caagcccggt t                                                           71
```

<210> SEQ ID NO 18
<211> LENGTH: 75
<212> TYPE: DNA
<213> ORGANISM: Artificial Sequence
<220> FEATURE:
<223> OTHER INFORMATION: Synthetic Probe directed to Human Fibronectin

<400> SEQUENCE: 18

```
ataacaacaa ccgggcttgc tttgactgac agccaccggg gactggggct gaaccatttg      60
ctgtgcctgc atatg                                                       75
```

<210> SEQ ID NO 19
<211> LENGTH: 71
<212> TYPE: DNA
<213> ORGANISM: Artificial Sequence
<220> FEATURE:
<223> OTHER INFORMATION: Synthetic Probe directed to Human Fibronectin

<400> SEQUENCE: 19

```
gttatgacaa tggaaaacac tatcatcaga taaatcaaca gtgggagcgg acctacctag      60
gtaatgtgtt g                                                           71
```

<210> SEQ ID NO 20
<211> LENGTH: 56
<212> TYPE: DNA
<213> ORGANISM: Artificial Sequence
<220> FEATURE:
<223> OTHER INFORMATION: Synthetic Probe directed to Human Fibronectin

<400> SEQUENCE: 20

```
ttacctaggt aggtccgctc ccactgttga tttatctgat agtgttttcc attgtc          56
```

<210> SEQ ID NO 21
<211> LENGTH: 57
<212> TYPE: DNA
<213> ORGANISM: Artificial Sequence
<220> FEATURE:
<223> OTHER INFORMATION: Synthetic Probe directed to Human Fibronectin

```
<400> SEQUENCE: 21
gtttgtactt gttatggagg aagccgaggt tttaactgcg aaagtaaacc tgaagct        57

<210> SEQ ID NO 22
<211> LENGTH: 71
<212> TYPE: DNA
<213> ORGANISM: Artificial Sequence
<220> FEATURE:
<223> OTHER INFORMATION: Synthetic Probe directed to Human Fibronectin

<400> SEQUENCE: 22
tctcttcagc ttcaggttta ctttcgcagt taaaacctcg gcttcctcca taacaagtac    60
aaaccaacac a                                                          71

<210> SEQ ID NO 23
<211> LENGTH: 69
<212> TYPE: DNA
<213> ORGANISM: Artificial Sequence
<220> FEATURE:
<223> OTHER INFORMATION: Synthetic Probe directed to Human Fibronectin

<400> SEQUENCE: 23
gaagagactt gctttgacaa gtacactggg aacacttacc gagtgggtga cacttatgag    60
cgtcctaaa                                                             69

<210> SEQ ID NO 24
<211> LENGTH: 57
<212> TYPE: DNA
<213> ORGANISM: Artificial Sequence
<220> FEATURE:
<223> OTHER INFORMATION: Synthetic Probe directed to Human Fibronectin

<400> SEQUENCE: 24
gacgctcata agtgtcaccc actcggtaag tgttcccagt gtacttgtca aagcaag        57

<210> SEQ ID NO 25
<211> LENGTH: 60
<212> TYPE: DNA
<213> ORGANISM: Artificial Sequence
<220> FEATURE:
<223> OTHER INFORMATION: Synthetic Probe directed to Human Fibronectin

<400> SEQUENCE: 25
gactccatga tctgggactg tacctgcatc ggggctgggc gagggagaat aagctgtacc    60

<210> SEQ ID NO 26
<211> LENGTH: 58
<212> TYPE: DNA
<213> ORGANISM: Artificial Sequence
<220> FEATURE:
<223> OTHER INFORMATION: Synthetic Probe directed to Human Fibronectin

<400> SEQUENCE: 26
cttattctcc ctcgcccagc cccgatgcag gtacagtccc agatcatgga gtctttag      58

<210> SEQ ID NO 27
<211> LENGTH: 71
<212> TYPE: DNA
<213> ORGANISM: Artificial Sequence
<220> FEATURE:
<223> OTHER INFORMATION: Synthetic Probe directed to Human Fibronectin

<400> SEQUENCE: 27
atcgccaacg ctgccatgaa gggggtcagt cctaccagat tggtgacacc tggaggagac    60
```
cacatgagac t                                                          71

<210> SEQ ID NO 28
<211> LENGTH: 85
<212> TYPE: DNA
<213> ORGANISM: Artificial Sequence
<220> FEATURE:
<223> OTHER INFORMATION: Synthetic Probe directed to Human Fibronectin

<400> SEQUENCE: 28
aaccaccagt ctcatgtggt ctcctccagg tgtcaccaat ctggtaggac tgaccccctt     60
catggcagcg tttgcgatgg tacag                                           85

<210> SEQ ID NO 29
<211> LENGTH: 72
<212> TYPE: DNA
<213> ORGANISM: Artificial Sequence
<220> FEATURE:
<223> OTHER INFORMATION: Synthetic Probe directed to Human Fibronectin

<400> SEQUENCE: 29
ggtggttaca tgttagagtg tgtgtgtctt ggtaatggaa aaggagaatg gacctgcaag     60
cccatagctg ag                                                         72

<210> SEQ ID NO 30
<211> LENGTH: 69
<212> TYPE: DNA
<213> ORGANISM: Artificial Sequence
<220> FEATURE:
<223> OTHER INFORMATION: Synthetic Probe directed to Human Fibronectin

<400> SEQUENCE: 30
gatcctcagc tatgggcttg caggtccatt ctccttttcc attaccaaga cacacacact    60
ctaacatgt                                                             69

<210> SEQ ID NO 31
<211> LENGTH: 51
<212> TYPE: DNA
<213> ORGANISM: Artificial Sequence
<220> FEATURE:
<223> OTHER INFORMATION: Synthetic Probe directed to Human Fibronectin

<400> SEQUENCE: 31
gggctgggcg agggagaata agctgtacca tcgcaaaccg ctaacagctg a              51

<210> SEQ ID NO 32
<211> LENGTH: 51
<212> TYPE: DNA
<213> ORGANISM: Artificial Sequence
<220> FEATURE:
<223> OTHER INFORMATION: Synthetic Probe directed to Human Fibronectin

<400> SEQUENCE: 32
agcttcagct gttagcggtt tgcgatggta cagcttattc tccctcgccc a              51

<210> SEQ ID NO 33
<211> LENGTH: 51
<212> TYPE: DNA
<213> ORGANISM: Artificial Sequence
<220> FEATURE:
<223> OTHER INFORMATION: Synthetic Probe directed to Human Fibronectin

<400> SEQUENCE: 33

```
gggctgggcg agggagaata agctgtacca tcgcaaaccg ccatatgtaa a          51
```

<210> SEQ ID NO 34
<211> LENGTH: 51
<212> TYPE: DNA
<213> ORGANISM: Artificial Sequence
<220> FEATURE:
<223> OTHER INFORMATION: Synthetic Probe directed to Human Fibronectin

<400> SEQUENCE: 34

```
agcttttaca tatggcggtt tgcgatggta cagcttattc tccctcgccc a          51
```

<210> SEQ ID NO 35
<211> LENGTH: 27
<212> TYPE: DNA
<213> ORGANISM: Artificial Sequence
<220> FEATURE:
<223> OTHER INFORMATION: Synthetic Probe directed to Human Fibronectin

<400> SEQUENCE: 35

```
atggccgtgg agacagctaa cagctga                                     27
```

<210> SEQ ID NO 36
<211> LENGTH: 31
<212> TYPE: DNA
<213> ORGANISM: Artificial Sequence
<220> FEATURE:
<223> OTHER INFORMATION: Synthetic Probe directed to Human Fibronectin

<400> SEQUENCE: 36

```
agcttcagct gttagctgtc tccacggcca t                                31
```

<210> SEQ ID NO 37
<211> LENGTH: 13
<212> TYPE: DNA
<213> ORGANISM: Artificial Sequence
<220> FEATURE:
<223> OTHER INFORMATION: Synthetic Probe directed to Human Fibronectin

<400> SEQUENCE: 37

```
ctgtatacca acc                                                    13
```

<210> SEQ ID NO 38
<211> LENGTH: 15
<212> TYPE: DNA
<213> ORGANISM: Artificial Sequence
<220> FEATURE:
<223> OTHER INFORMATION: Synthetic Probe directed to Human Fibronectin

<400> SEQUENCE: 38

```
taggttggta tacag                                                  15
```

<210> SEQ ID NO 39
<211> LENGTH: 4
<212> TYPE: PRT
<213> ORGANISM: Artificial Sequence
<220> FEATURE:
<223> OTHER INFORMATION: N-Terminus of Labeled Polypeptide

<400> SEQUENCE: 39

Gln Ala Gln Gln
1

<210> SEQ ID NO 40
<211> LENGTH: 5
<212> TYPE: PRT

```
                            -continued
<213> ORGANISM: Artificial Sequence
<220> FEATURE:
<223> OTHER INFORMATION: N-terminus of Labeled Polypeptide

<400> SEQUENCE: 40

Met Gln Ala Gln Gln
1               5
```

FIBRIN BINDING DOMAIN POLYPEPTIDES AND USES AND METHODS OF PRODUCING SAME

This application is a continuation of U.S. Ser. No. 08/909,140, filed Aug. 11, 1997, now U.S. Pat. No. 6,121,426, which is a divisional of U.S. Ser. No. 08/409,750, filed Mar. 24, 1995, now U.S. Pat. No. 5,965,383, which is a continuation of U.S. Ser. No. 08/058,241, filed May 4, 1993, now U.S. Pat. No. 5,455,158, issued Oct. 3, 1995; which is a divisional of U.S. Ser. No. 07/526,397, filed May 21, 1990, now U.S. Pat. No. 5,270,030, issued Dec. 14, 1993; which is a continuation-in-part of U.S. Ser. No. 07/345,952, filed Apr. 28, 1989, now abandoned; which was a continuation-in-part of U.S. Ser. No. 07/291,951, filed Dec. 29, 1988, now abandoned.

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference in this application in order to more fully describe the state of the art to which this invention pertains.

Atherosclerosis is the progressive narrowing of the lumen (inner passageway) of arterial blood vessels by layers of plaque (fatty and fibrous tissues). Atherosclerosis can occur in any artery. In coronary arteries it may result in heart attacks; in cerebral arteries it may result in strokes; and in peripheral arteries it may result in gangrene of the legs and feet.

Atherosclerosis is the single largest medical problem currently facing the United States and other developed countries. Approximately 40 million people in the United States are at risk of developing ather sclerosis. However, only 6 million people in the United States show overt signs of the disease. The rest remain undiagnosed until the disease manifests itself symptomatically, in the worst case as heart attack or stroke. Heart attack and stroke, respectively, represent the first and third leading causes of death in the United States. Over 500,000 people die of heart attacks every year and a significant sub-group of these patients expire without warning.

The endothelium is located between the blood and arterial tissue and serves as a barrier against the accumulation of blood components in the vascular wall. Formation of atherosclerotic lesions (plaques) in the sub-endothelium is associated with major coronary artery disease and stroke. The causes and detection of such lesions have been intensely investigated.

Endothelial injury is believed to be an initial step in the formation of the atherosclerotic lesions and may be caused by, i.e., hemodynamic strain, hypercholesterolemia, hypertension and immune complex disease. Endothelial injury leads to thickening of the intima, cell proliferation, cholesterol accumulation, and formation of connective tissue fibers. IgG and complement factor C3 accumulation in injured endothelial cells and nonendothelialized intima has been observed. Mononuclear cells derived from blood are also part of the cell population in atherosclerotic lesions. The mechanism of plaque formation is not fully known. However, a probable mechanism is that the earliest lesions, fatty streaks, consisting of mixtures of T cells and monocyte-derived macrophages, form in the subendothelium followed by a secretion of various cytokines, which leads to a migration of smooth cells into the intima and their accumulation.

Although atherosclerosis is generally a diffuse disease, human coronary atherosclerosis lends itself to bypass procedures because the major site of plaque formation is usually proximally distributed. As a result, direct coronary artery bypass has become the most frequently selected form of myocardial revascularization. The aorta-coronary artery vein graft of the internal mammary artery graft have become technically standardized and have high long-term patency rates. These long-term results, however, can be compromised by progressive atherosclerotic lesion distal to the graft anastomosis. Other cases are inoperable because of distal disease. Previously, distal lesions have been ignored or, in selected cases, treated by endarterectomy although neither approach has proved entirely satisfactory.

Most existing procedures for the diagnosis and treatment of atherosclerosis are invasive, costly, and of limited effectiveness in a significant percentage of patient cases.

The concept of plaque enhancement by application of a stain has been reported [Spears, J. et al., J. Clin. Invest. 71: 395–399 (1983)]. These stains mark the plaque surfaces with a fluorescent compound. Plaque destruction by photoactivation of hematoporphyrin derivatives using an intraluminal laser-transmitting optical fiber has been suggested [Abela, G. et al., Am. J. Cardio. 50: 1199–1205 (1982)]. Moreover, tetracycline stains have also been suggested. [Murphy-Chutorian, D. et al., Am. J. Cardiol. 54: 1293–1297 (1985)].

The above-identified stains were selected for their ability to bind to components of the atherosclerotic plaque. In principal, the stain absorbs laser light concentrating the light at the stained surface. Some staining of healthy tissue occurs causing stain associated damage to the surrounding tissue. Because laser light wavelength is limited to the absorption wavelength of the stain, chromophores offering optimum absorption of laser light must be used to provide best controlled ablation.

Imaging and detection of coronary thrombi, pulmonary emboli, deep venous thrombosis and atherosclerotic lesions are of great clinical importance especially in view of the new thrombolytic agents which have recently been developed. Several experimental approaches for non-invasive detection of thrombi by use of radiopharmaceutical agents have been reported but none has gained wide clinical recognition because of intrinsic drawbacks associated with each agent.

The basic characteristics of a radiopharmaceutical for early detection of intravascular atherosclerotic lesions and thrombi are the following: (i) high affinity for thrombus components; (ii) relatively fast pharmacokinetic blood clearance rate [in order to obtain a high ratio of thrombus (bound) to blood (unbound) radiolabeled tracer]; (iii) safety: non-toxic and non-immunogenic; and (iv) simplicity of preparation and use.

The various agents for imaging thrombi described in the literature and their drawbacks are as follows: (a) autologous platelets labeled with $^{111}$In: the procedure is cumbersome, time consuming and the blood clearance time is relatively long, viz. 2 days (2); (b) $^{131}$I-fibrinogen: the assay is based on the (low) affinity of injected radiolabeled fibrinogen for the thrombus but it is not suitable for rapid imaging tests because of its long residence time in blood and furthermore it does not become incorporated into older thrombi nor is it incorporated in the presence of heparin (3, 36); (c) fragment E1 of human fibrin: although it seems superior to fibrinogen it is difficult to prepare in sufficient quantities for widespread clinical use (4); (d) mouse anti-fibrin monoclonal antibodies:

although they are specific and have high affinities to thrombi they have a relatively long blood clearance time and are potentially immunogenic to human subjects (5, 33, 34); (e) mouse monoclonal antibodies specific for activated platelets (6, 7): disadvantage as (d); and (f) labeled fibronectin (1): although fibronectin (see below) has an affinity for a number of substances occurring in thrombi it has a relatively long blood clearance time and the buildup of radioactivity in the thrombus is slow. Thus there is a need in the art for a thrombus-specific radiopharmaceutical for rapid imaging of thrombi.

U.S. Pat. No. 4,343,734 (Lian et al.) describes specific gamma-carboxyglutamic acid (GLA) antibodies which can be labeled with fluorescein for immunofluorescence staining of tissue to determine the presence therein of GLA. Specific GLA antibodies bind to GLA which is present in advanced atherosclerotic plaque, having calcium deposits. Lian et al. report that GLA is not found in uncalcified plaques and that GLA is found in cardiac valves and aortas, and in circulating proteins such as prothrombin, clotting factors VII, IX and X, Protein C and Protein S. However, the GLA binding antibodies of Lian et al. do not selectively bind to atherosclerotic plaque.

Fibronectin is a glycoprotein composed of two identical subunits each of approximately 220,000 molecular weight. Two major forms of fibronectin are produced and secreted by human cells in culture and in vivo (8). The cell-associated fibronectin is relatively insoluble and participates in cell adhesion, wound healing, cell differentiation and phagocytosis. The plasma fibronectin, produced primarily in the liver, is a soluble serum protein with biological properties similar to those of cell fibronectin.

Fibronectin is considered a multifunctional modular protein since limited proteolytic cleavage produces polypeptides with distinct activities. The different functional domains of the fibronectin molecule have been obtained and defined by partial proteolytic digestion, and include heparin, DNA, fibrin, gelatin, and cell binding domains (8–13).

Baralle, F. E., European Patent Publication No. 207,751, published Jan. 7, 1989, discloses the complete cDNA sequence of fibronectin. Baralle also discloses the expression of fusion proteins containing a portion of the collagen binding domain of fibronectin fused to the *Escherichia coli* protein β-galactosidase. Similar fusion proteins are disclosed by Owens and Baralle (14). Obara et al. (1987) disclose the expression of a portion of the cell binding domain of human fibronectin fused to *Escherichia coli* β-galactosidase (15). Additionally, Obara et al. (1988) disclose the expression of portions of the cell binding domain fused to β-galactosidase which have been mutagenized, i.e., sit specific deletions of portions of the cell binding domain were obtained as fused proteins (16). The carboxy terminal fibrin-binding domain of human fibronectin has been expressed in mouse L cells as a fusion protein with the signal sequence of human protein C inhibitor (17).

None of the above references discloses the expression of the N-terminal fibrin binding domain of fibronectin; furthermore all the recombinant proteins they disclose are expression of fusion proteins.

This invention provides polypeptides having an amino acid sequence substantially present in the N-terminal fibrin binding domain of fibronectin. These polypeptides have varying molecular weights (31 kD, 20 kD and 12 kD), as defined by comparison markers on SDS gels under reducing conditions, and have the following characteristics which make them promising pharmaceutical agents: (i) have an amino acid sequence present in a human protein and thus are contemplated to not be immunogenic; (ii) high affinity to fibrin and able to become covalently cross-linked to growing as well as to preformed thrombi (clots); (iii) bind to extracellular matrix, which property may be exploited to detect atherosclerotic plaques; (iv) have a relatively short blood clearance time; (v) incorporate into clots in the presence of heparin; and (vi) are produced by recombinant techniques and can therefore potentially be manufactured on a large scale.

The subject invention provides an inexpensive, accurate method for imaging fibrin-containing substances, i.e., a thrombus and atherosclerotic plaque, both in vitro and in vivo. In addition, the subject invention provides plasmids for expressing polypeptides having an amino acid sequence substantially present in the fibrin binding domain of naturally-occurring human fibronectin and capable of binding to fibrin which are labeled and used for imaging the fibrin-containing substances, and methods of producing such polypeptides.

These polypeptides may also be used as anti-infective agents. The involvement of fibronectin in adhesion to, and invasion of, wounds by a wide range of gram positive bacteria is well established (18, 19). The polypeptides of the fibrin binding domain of fibronectin according to this invention may be used as anti-infective agents to prevent sepsis in wounds.

SUMMARY OF THE INVENTION

This invention provides an imaging agent which comprises a polypeptide labeled with an imageable marker, such polypeptide having an amino acid sequence substantially present in the fibrin binding domain of naturally-occurring human fibronectin and being capable of binding to fibrin.

Further provided is a method for imaging a fibrin-containing substance, i.e. a thrombus or atherosclerotic plaque, which comprises contacting the fibrin-containing substance to be imaged with the imaging agent disclosed above under conditions such that the agent binds to the fibrin-containing substance and imaging the bound agent and thereby imaging the fibrin-containing substance.

Also provided is a plasmid for expression of a polypeptide which having an amino acid sequence substantially present in the fibrin binding domain of naturally-occurring human fibronectin and being capable of binding to fibrin comprising DNA encoding the polypeptide and DNA encoding suitable regulatory elements positioned relative to the DNA encoding the polypeptide so as to effect expression of the polypeptide in a suitable host cell.

The invention also provides a purified polypeptide substantially free of other substances of human origin which has an amino acid sequence substantially present in the fibrin binding domain of naturally-occurring human fibronectin and being capable of binding to fibrin.

Further provided are methods of treatment using such polypeptides and methods of recovering and refolding and reoxidizing such polypeptides.

BRIEF DESCRIPTION OF THE FIGURES

In the figures, the numbers in brackets adjacent certain of the restriction enzyme sites shown correspond to the identically numbered positions along the nucleotide sequence of human fibronectin cDNA as shown in FIG. 1 (see also FIG. 3 of Baralle, F. E., European Patent Publication No. 207,751, published Jan. 7, 1987).

The following figures describe the construction of plasmids expressing polypeptides having an amino acid sequence substantially present in the amino-terminal fibrin binding domain (FBD) of fibronectin. The FBD commences at amino acid number 1 of mature fibronectin, which is glutamine and corresponds to the fourth amino acid (Q) shown in FIG. 1-1, i.e., the N-terminus of the FBD sequence is QAQQ (glutamine-alanine-glutamine-glutamine); the corresponding first nucleotide in the cDNA sequence of FIG. 1-1 is therefore number 14, indicated by an arrow. All the recombinant FBD polypeptides described in these figures and throughout the specification are numbered from this first glutamine as amino acid number 1 and all the corresponding cDNA sequences are numbered as shown in FIG. 1.

Some of the figures describe the construction of plasmids expressing an FBD polypeptide joined at its C-terminus to part of the cell binding domain (CBD) of fibronectin. The cDNA sequence corresponding to the CBD which applicants have cloned and expressed is missing the 270 bp extra domain (ED) segment which extends from nucleotides 4812 t 5081, inclusive, on the Baralle map (see FIG. 1). Thus, the cDNA sequence which is said to extend from nucleotide 3317 to 5566 on the Baralle map, contains only 1980 nucleotides, because it is missing the 270 nucleotides of the ED segment, namely from nucleotides 4812 to 5081 inclusive; this region is also known in the art as the ED-A region; concomitantly amino acid 1690 is changed from alanine to threonine. Similarly, the polypeptide expressed by that DNA fragment would encode from amino acid 1102 to amino acid 1851 on the Baralle map but would be missing the 90 amino acids encoded by the ED region, namely amino acids 1600–1689 inclusive, and thus it would contain only 660 amino acids. This is true for all CBD polypeptides described in this application which span the ED region. (The region known in the art as the ED-B region is missing both in Baralle's sequence and in applicants' DNA.)

The definition of the polypeptides expressed as 31 kD, 20 kD, 12 kD and 33 kD is an operational definition, based on their mobility on SDS polyacrylamide gels under reducing conditions compared to that of markers of known molecular weight.

Figures 1, 52F:
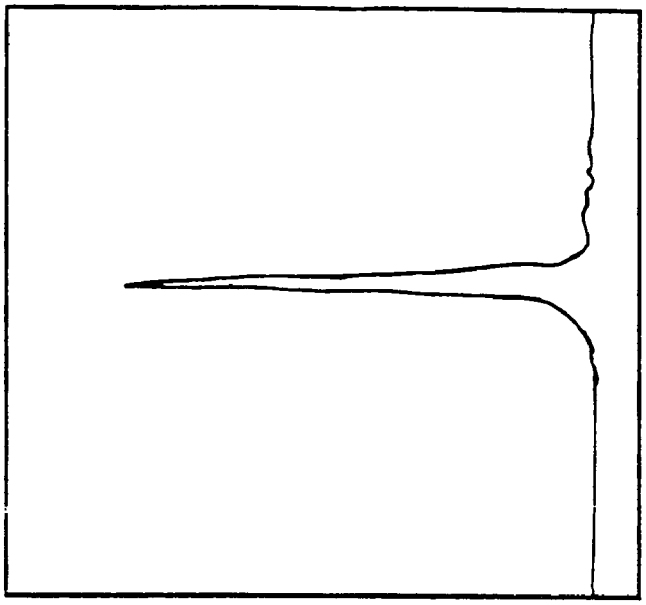

FIG. 1. All panels (A–H) of this figure show the nucleotide sequence (continued from panel to panel) of human fibronectin cDNA.

Figures 2, 52F:
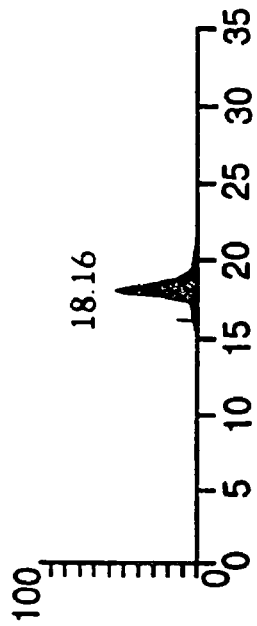
Figures 1, 52E:
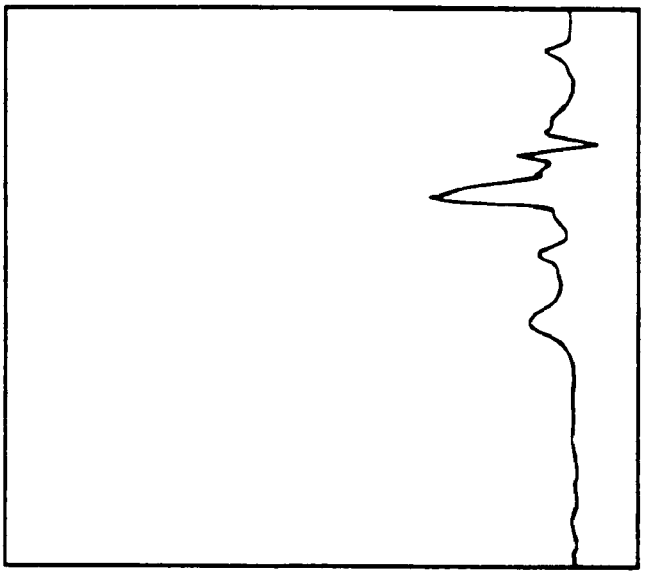
Figures 2, 52E:
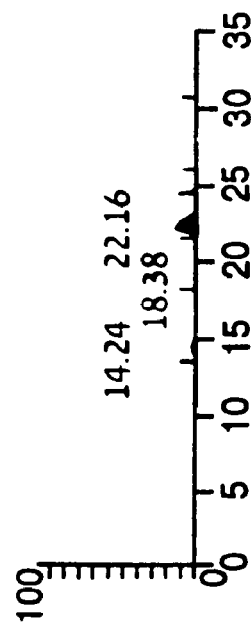
Figure 53A:
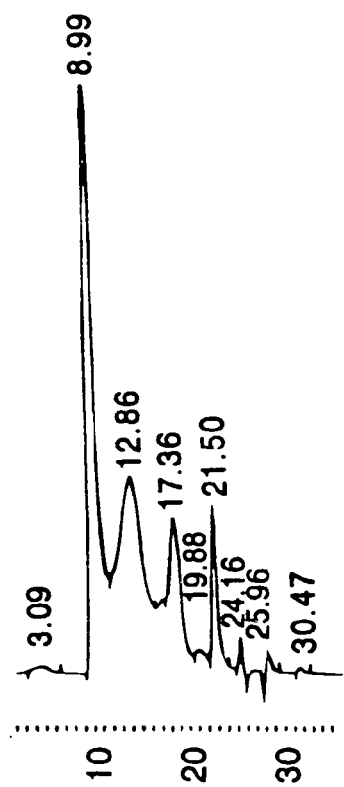
Figure 53B:
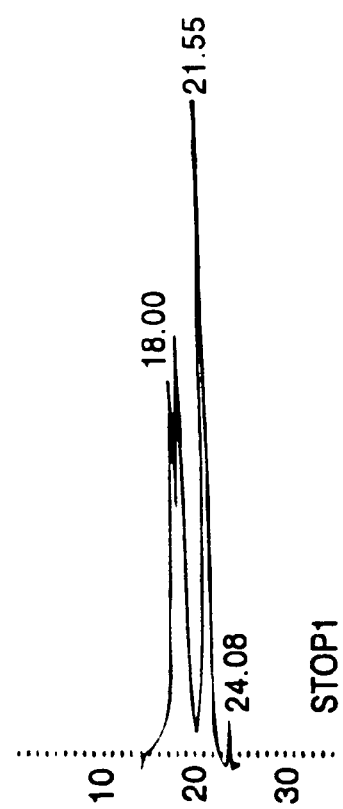
Figure 53C:
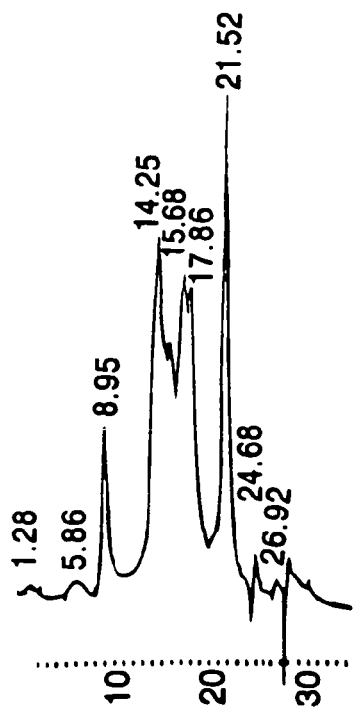
Figure 53D:
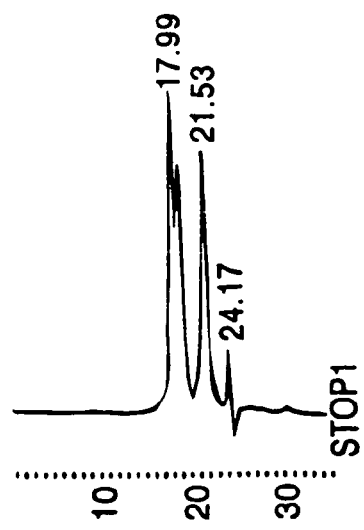
Figure 53E:
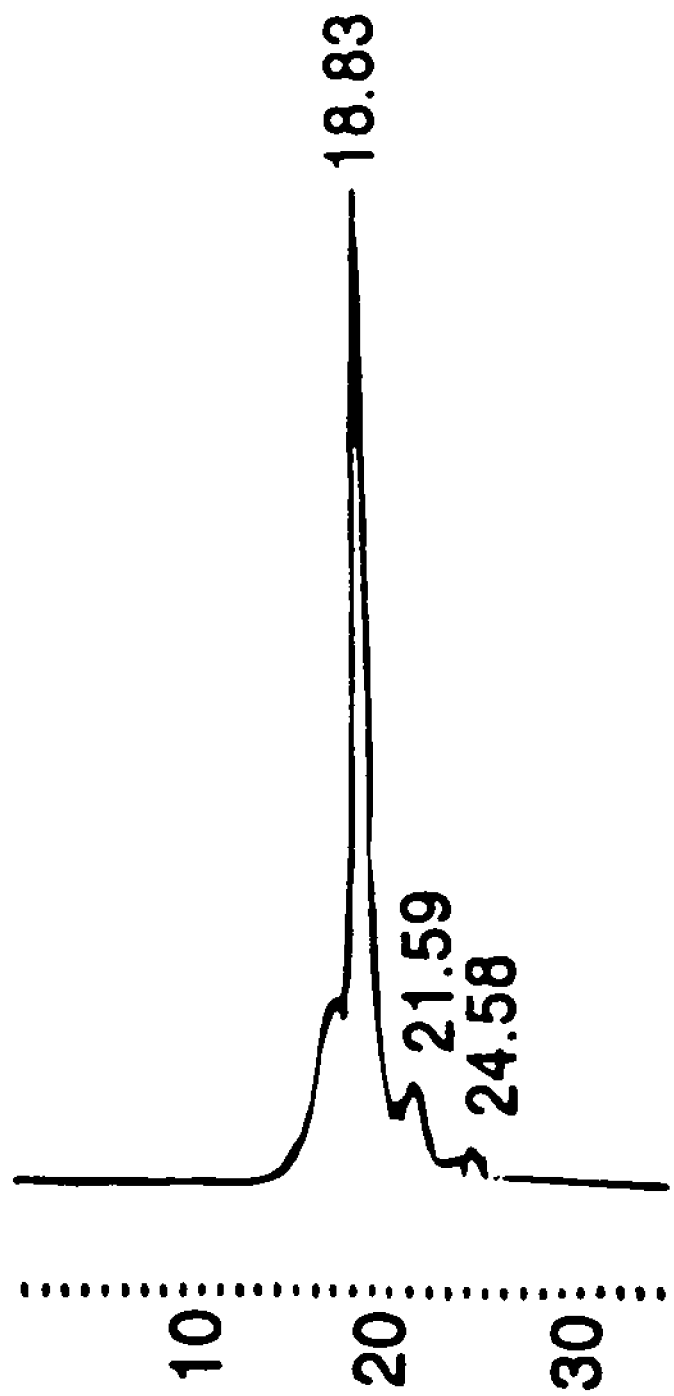

FIG. 2. Seven pairs of chemically synthesized oligomers were prepared (Panel A; pairs 1 to 4 and Panel B; pairs 5–7). The synthetic oligomers code for the first 153 N-terminal amino acids of human fibronectin (FN). This figure shows the sequence of these 7 pairs of synthetic oligomers.

Figure 3:
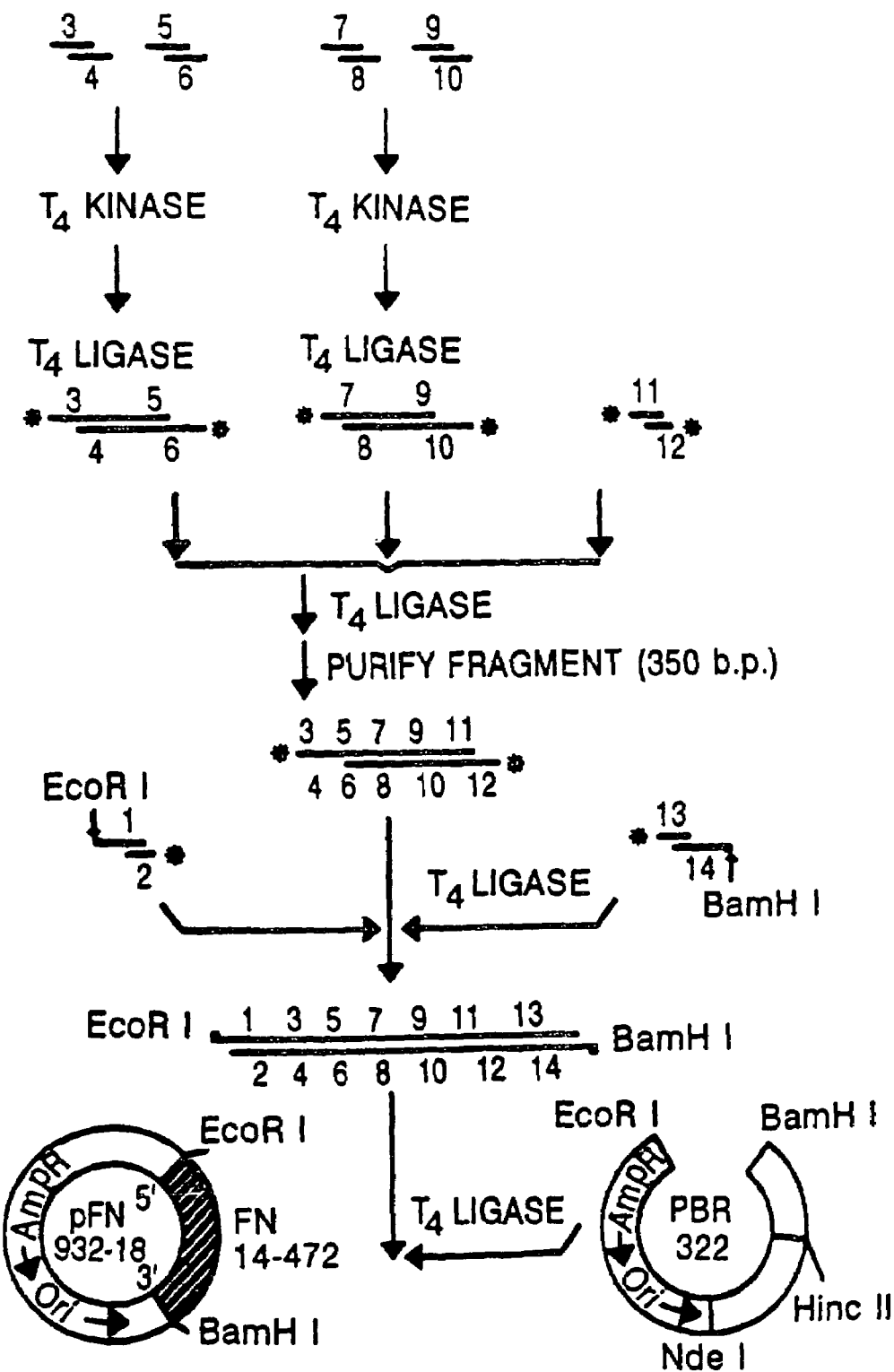

FIG. 3. The DNA fragment coding for amino acids 1 to 153 of the N-terminal domain of human FN was assembled from the 7 pairs of chemically synthesized oligomers shown in FIG. 3 as follows:

Oligomers 3/4, 5/6, 7/8 and 9/10, each pair in a separate tube, were annealed and then phosphorylated at the 5' end using T4 polynucleotide kinase enzyme.

In the second step, pairs 3/4 and 5/6 were ligated to each other using T4 DNA ligase. Similarly, reaction pairs 7/8 and 9/10 were ligated to each other. After each step of ligation an aliquot of the ligation mixture was analyzed on gel to determine the size of the newly formed fragments and the efficiency of ligation.

In the third step, the two above mentioned ligation mixtures were mixed together and pair 6, oligomers 11/12 which had been annealed and phosphorylated previously in a separate tube were added to the mixture. A 326 base pair DNA fragment obtained from the above ligation mixture was isolated from an agarose gel and purified.

The purified synthetic 326 fragment was added to two additional pairs of synthetic linkers: Pair 1, oligomers 1/2 and Pair 7 oligomers 13/14. In Pair 1 only oligomer 2 was phosphorylated at the 5' end and in Pair 7 only oligomer 13 was phosphorylated at the 5' end.

After ligation with T4 DNA ligase the mixture without any further isolation was added to pBR322 vector DNA digested with EcoRI and BamHI endonucleases.

The plasmid obtained, designated pFN 932-18 contained the entire synthetic EcoRI (5' end)-BamHI (3' end) restriction fragment coding for the N-terminal 153 amino acids of human FN, in a pBR322 vector.

Figure 4:
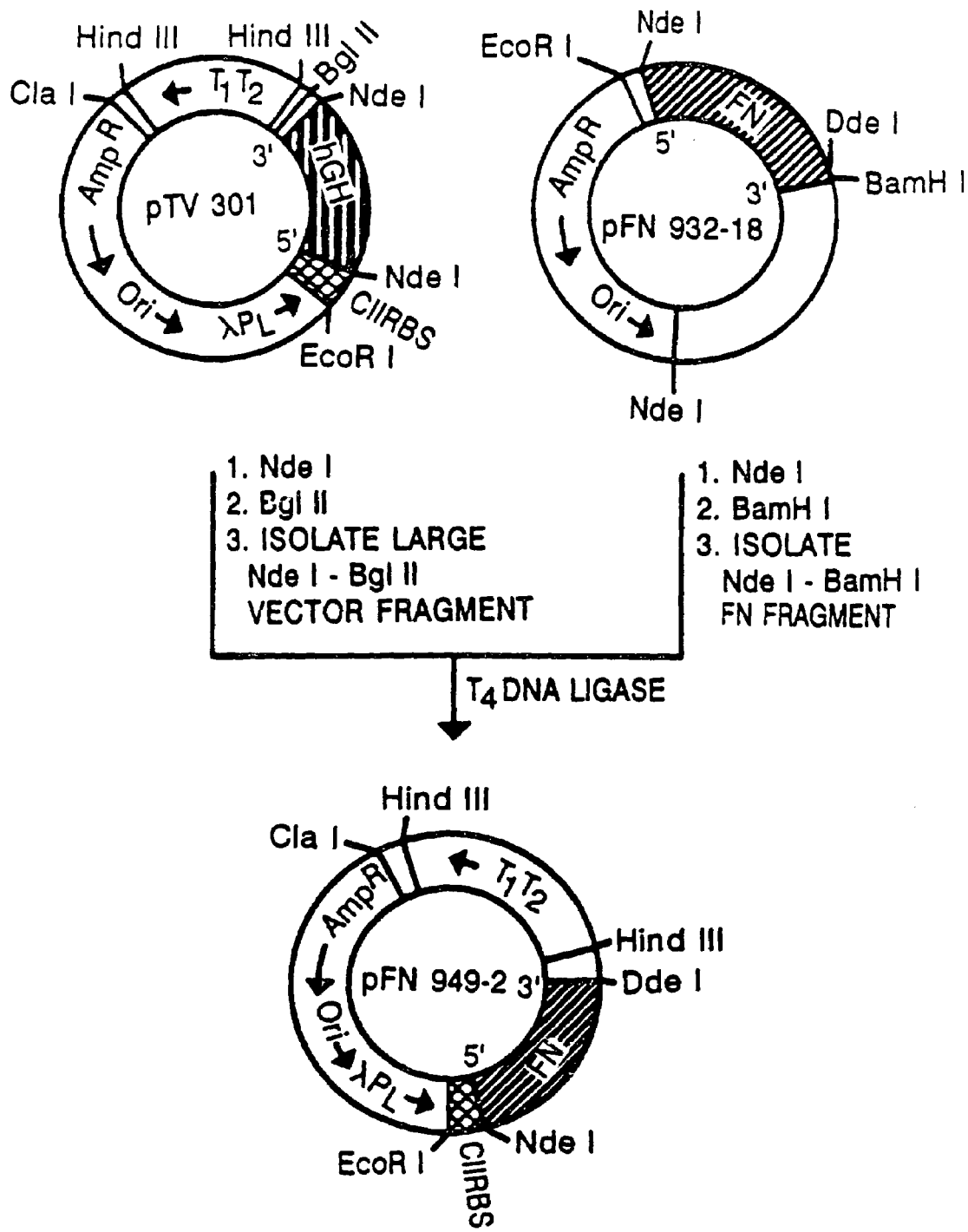

FIG. 4. Expression of the N-terminal 153 amino acid sequence of FN.

Plasmid pFN 932-18 was digested with NdeI and BamHI endonucleases. The NdeI-BamHI DNA fragment coding for FN (first 153 amino acids+additional N-terminal methionine) was isolated and ligated into the large fragment obtained by digestion of plasmid pTV301 with NdeI and BglII endonucleases. (Plasmid pTV301 (FIG. 33) expresses human growth hormone, hGH, under the control of λ $P_L$ promoter and the cII RBS).

The plasmid obtained was designated pFN949-2.

FIG. 5. Insertion of termination codon TAA at the 3' end of the N-terminal domain of FN (at amino acid 262)

A synthetic oligonucleotide containing a TAA termination codon and a BglII site having the following sequence:

CTGTTTAAGCA
GACAAATTCGTCTAG was ligated to the 3' end (PvuII site) of an EcoRI-PvuII FN fragment isolated from cDNA clone plasmid p931-5 (see FIG. 5) digested with EcoRI and PvuII. The ligation was carried out in the presence of DNA vector plasmid pBR322 digested with EcoRI and BamHI (large fragment). The plasmid obtained was designated pFN935-12.

FIG. 6. Subcloning of the carboxy-terminal region of FBD in λ $P_L$ expression vector Plasmid pFN 935-12 was digested with EcoRI and HincII. The EcoRI-HincII fragment coding for FN was isolated and ligated to DNA, the large fragment obtained by digestion of plasmid pTV194-80 with EcoRI and SmaI. (Plasmid pTV194-80 expresses human ApoE under the control of the λ $P_L$ promoter and β-lactamase promoter and RBS). The plasmid obtained was designated pFN 946-12. This plasmid is deleted of the PBLA sequences and therefore does not express the carboxy domain of FBD.

Figure 31:
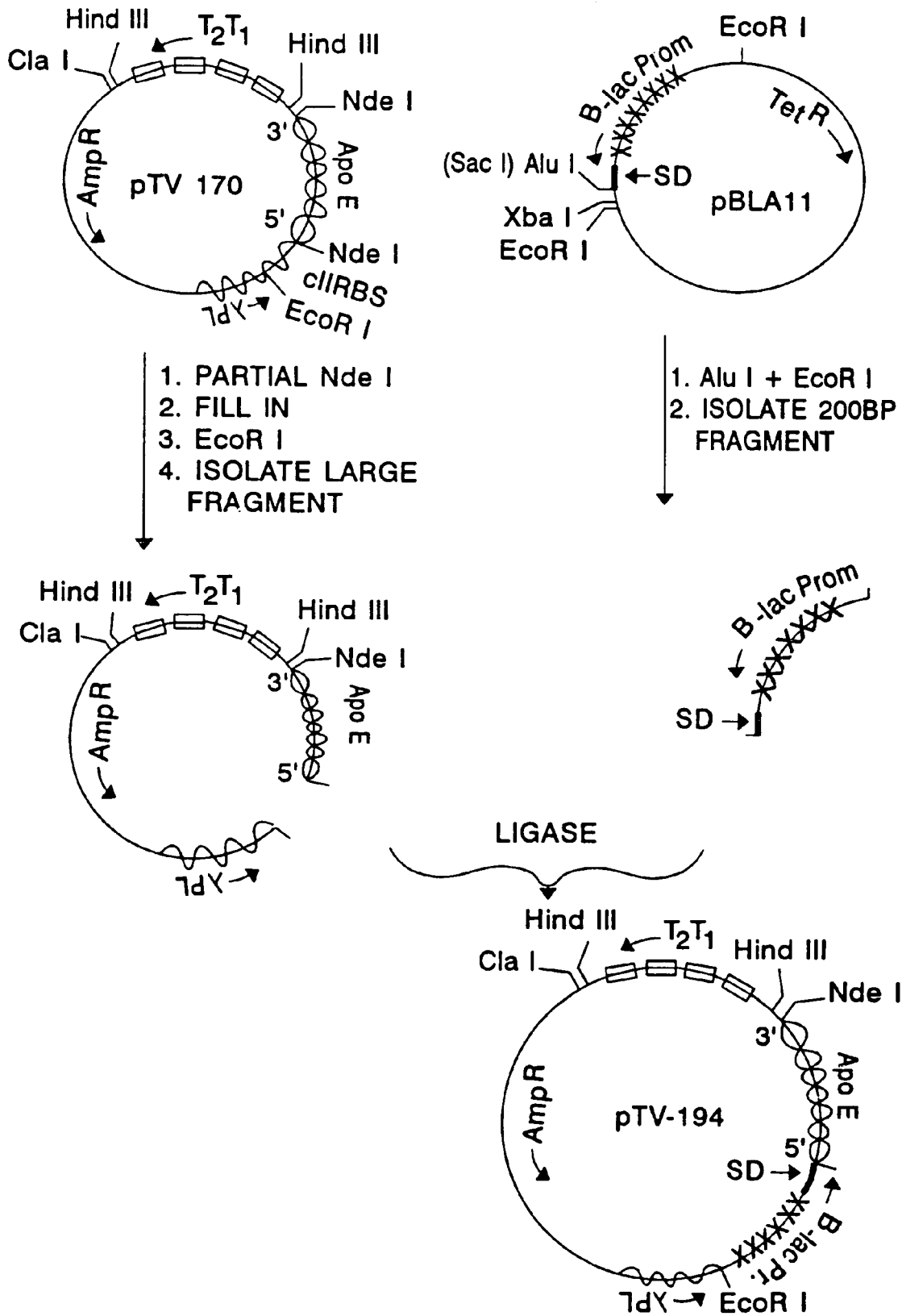

The construction of pTV–194-80 from plasmid p579 (FIG. 34) is shown in FIGS. 30 and 31.

Figure 7:
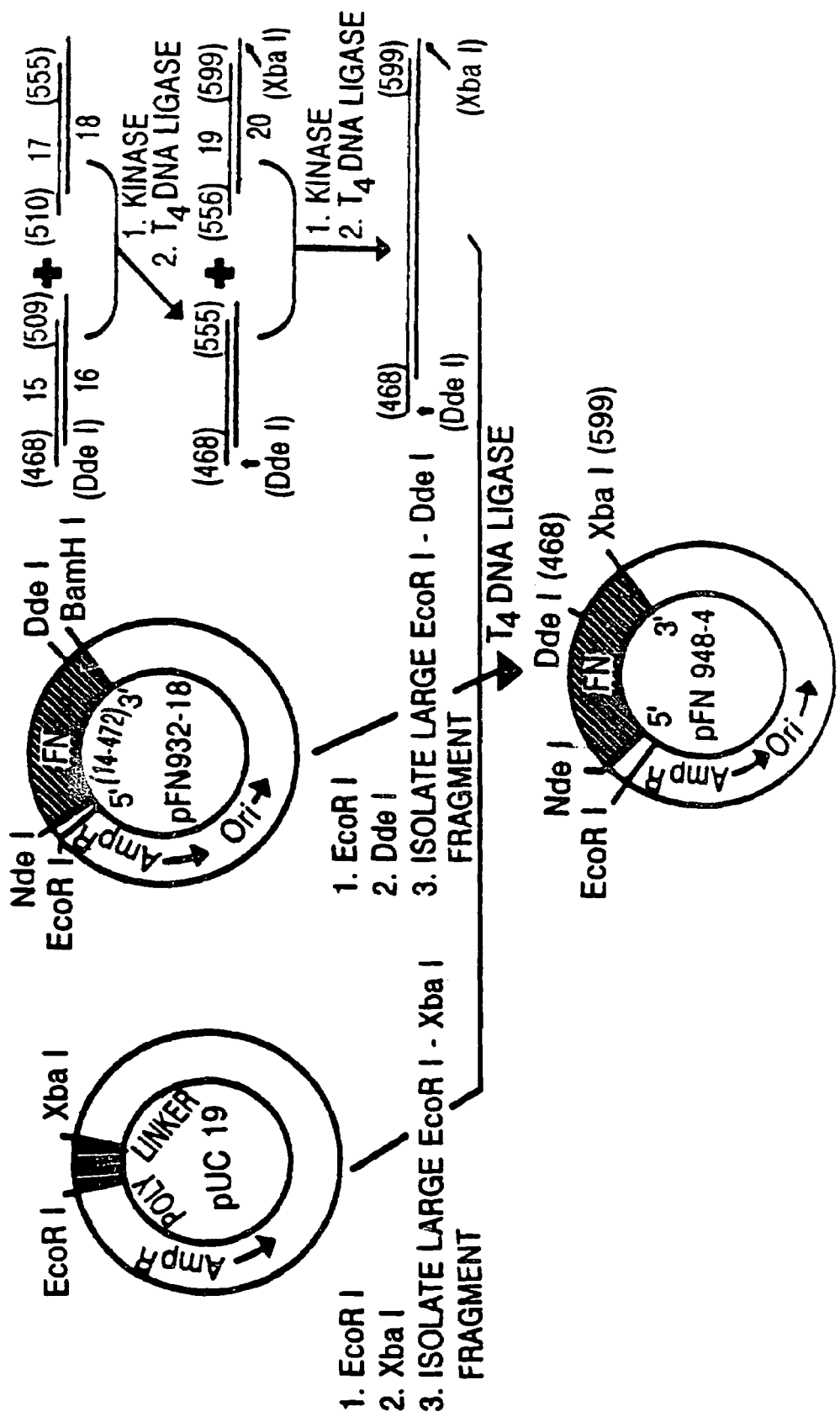

FIG. 7. Construction of the DNA fragment coding for the FBD from nucleotide No. 14 to nucleotide No. 599

Three pairs of chemically synthesized oligomers with the following DNA sequences:

Pair 1

15 5'-TGAGAAGTGTTTTGATCATGCTGCTGGGAC TTCCTATGTGG-3'

16 3'-CTTCACAAAACTAGTACGACGACCCTGAA GGATACACCAGCCT-5'

Pair 2

17 5-TCGGAGAAAcGTGGGAGAAGcCCTAccAAG GCTGGATGATGGTAG-3'

18 3- CTTTGCACCCTCTTCGGGATGGTTCCGACC TACTACCATCTAACA-5'

Pair 3

19 5'-ATTGTACTTGCCTGGGAGAAGGCAGCGGA CGCATCACTTGCACTT-3'

20 3'- TGAACGGACCCTCTTCCGTCGCCTGCGTA GTGAACGTGAAGATC-5' were used to carry out this construction.

Oligomers 15/16 and 17/18 were annealed and phosphorylated at the 5' end each in a separate tube and then mixed together for ligation using T4 DNA ligase. After 3 hours of ligation, oligomers 19/20 (previously annealed and kinased at their 5' ends) were added for an additional 3 hours ligation at room temperature.

The synthetic DNA fragment obtained was used for further ligation with an EcoRI-DdeI FN coding sequence obtained from plasmid pFN 932-18 digested with EcoRI and DdeI. The ligation was carried out in the presence of plasmid pUC19 digested with EcoRI and XbaI (large fragment).

The plasmid obtained was designated pFN948-4.

Figure 8:
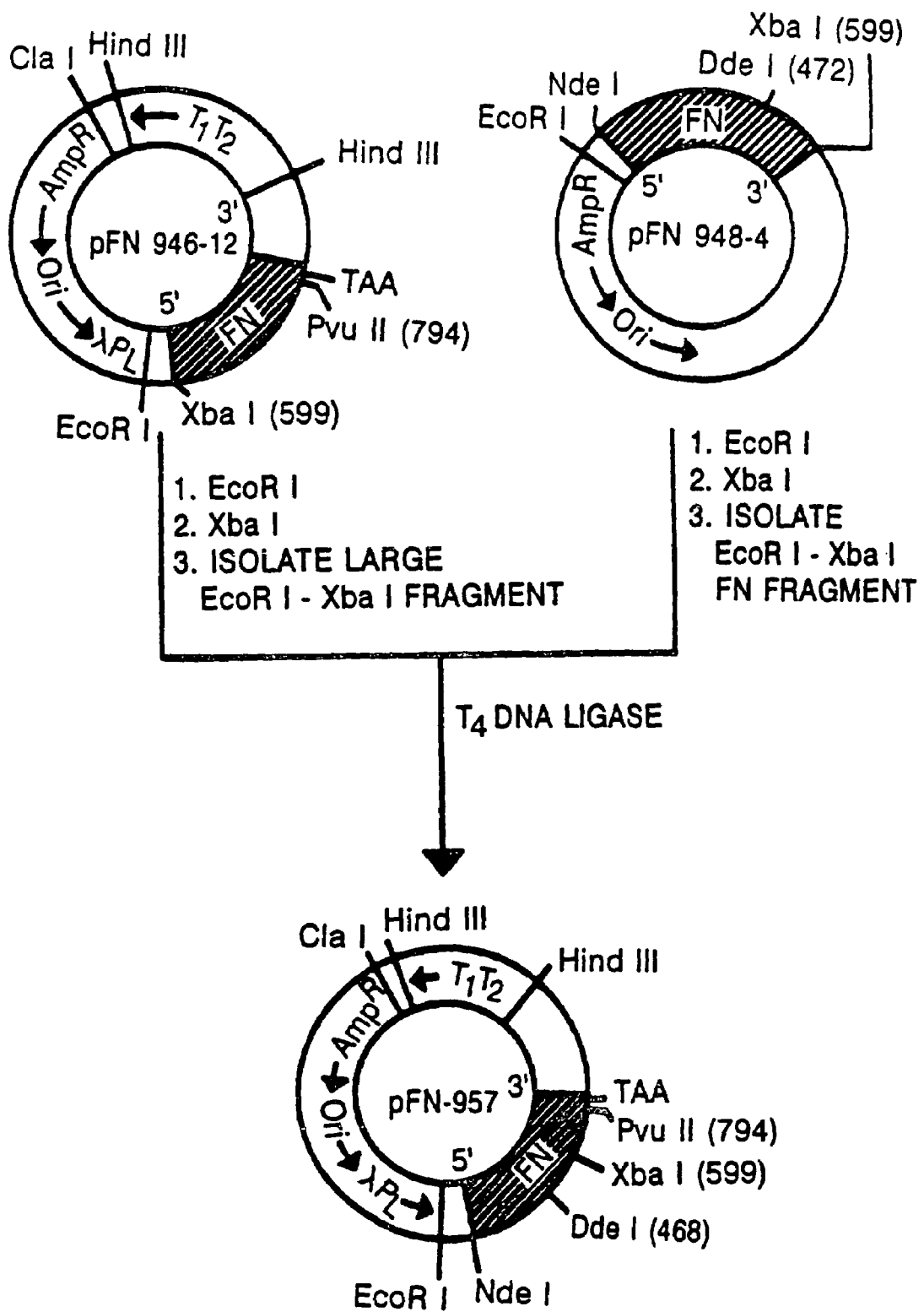

FIG. 8 Construction of the entire FBD region

Plasmid pFN948-4 was digested with EcoRI and XbaI. The EcoRI-XbaI fragment coding for the N-terminal region of FBD was isolated and ligated to the carboxy terminal region of FBD by digestion of plasmid pFN946-12 with EcoRI and XbaI (using the large fragment). The plasmid obtained was designated pFN 957.

Figure 9:
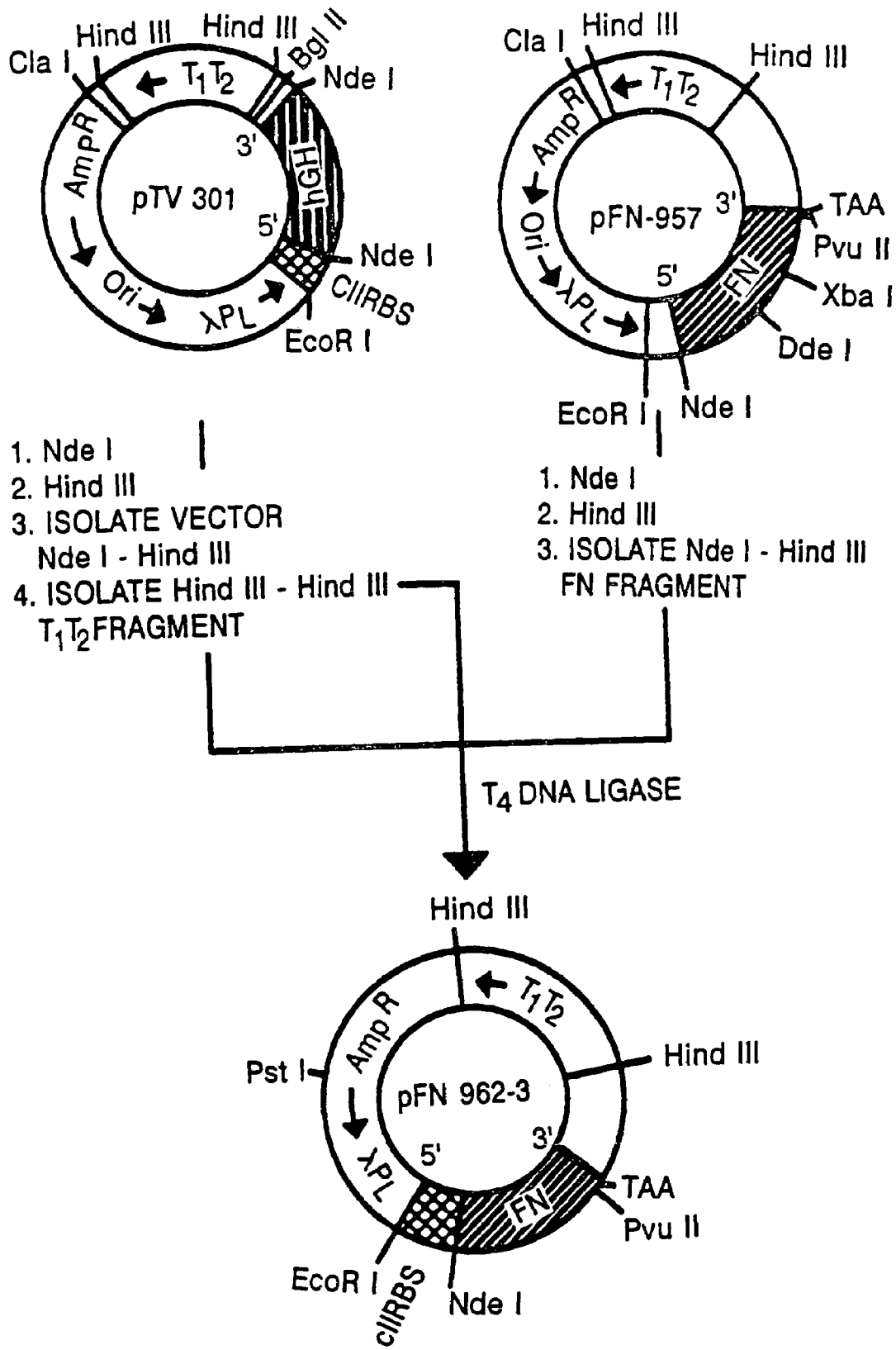

FIG. 9. Expression of the entire FBD polypeptide under the control of the $\lambda$ $P_L$ promoter and $\lambda$ cII RBS Plasmid pFN 957 was digested with NdeI and HindIII. The NdeI-HindIII fragment coding for the FBD was isolated and ligated into the isolated vector fragment of plasmid pTV301 digested with NdeI and HindIII in the presence of isolated purified HindIII-HindIII $T_1T_2$ coding DNA fragment. The plasmid obtained was designated pFN962-3.

Figure 10:
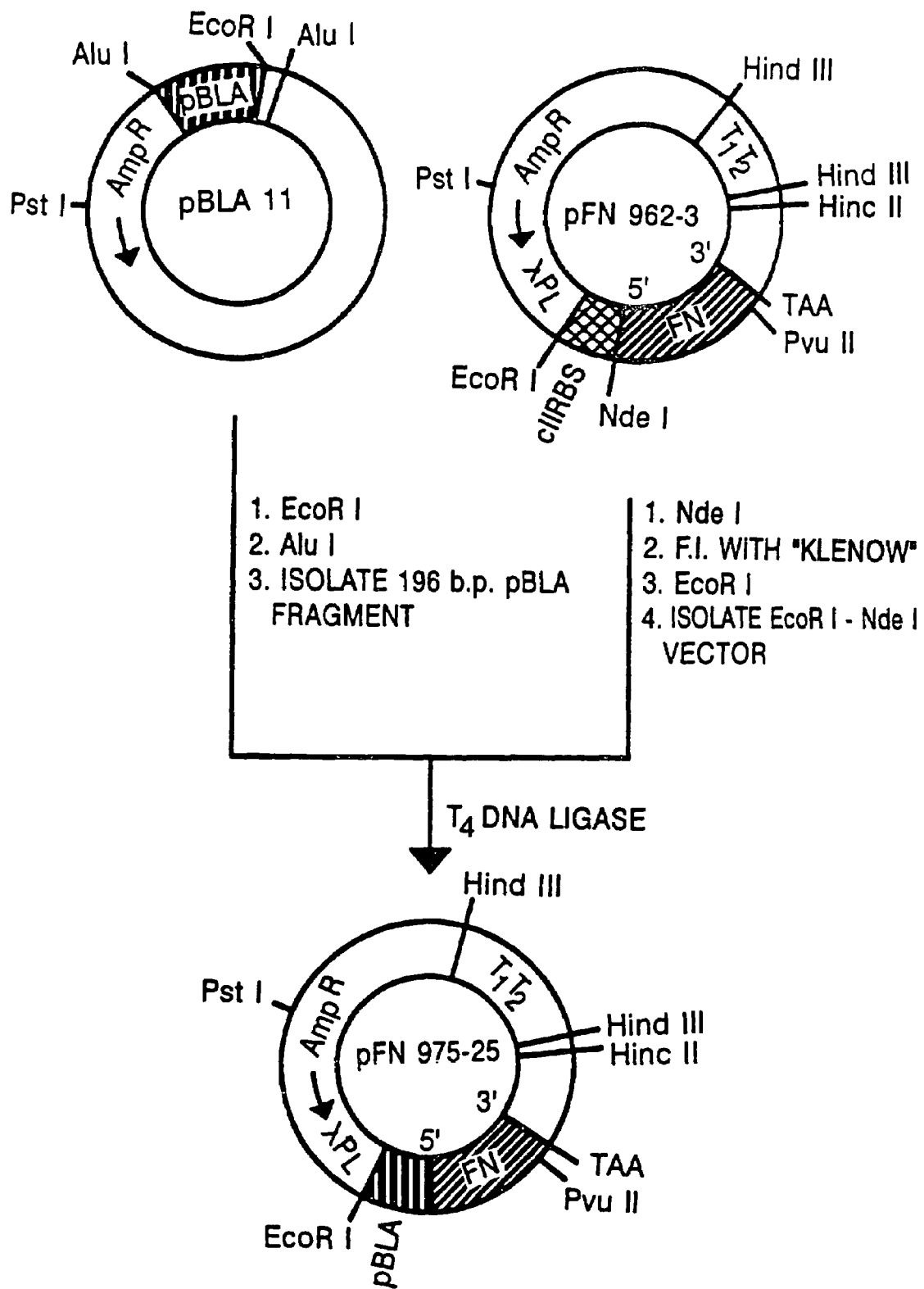

FIG. 10 Expression of the entire FBD polypeptide under $\lambda$ $P_L$ promoter and PBLA ribosomal binding site Plasmid pBLA11 (ATCC Accession No. 39788) was digested with EcoRI and AluI. The EcoRI-AluI fragment coding for the $\beta$-lactamase promoter and $\beta$-lactamase RBS was isolated and ligated into plasmid pFN962-3 (FIG. 9) digested with NdeI, then treated with Klenow enzyme in the presence of all four dNTPs to fill in the NdeI site and digested with EcoRI (using the large fragment). The plasmid obtained was designated pFN 975-25.

Figure 11:
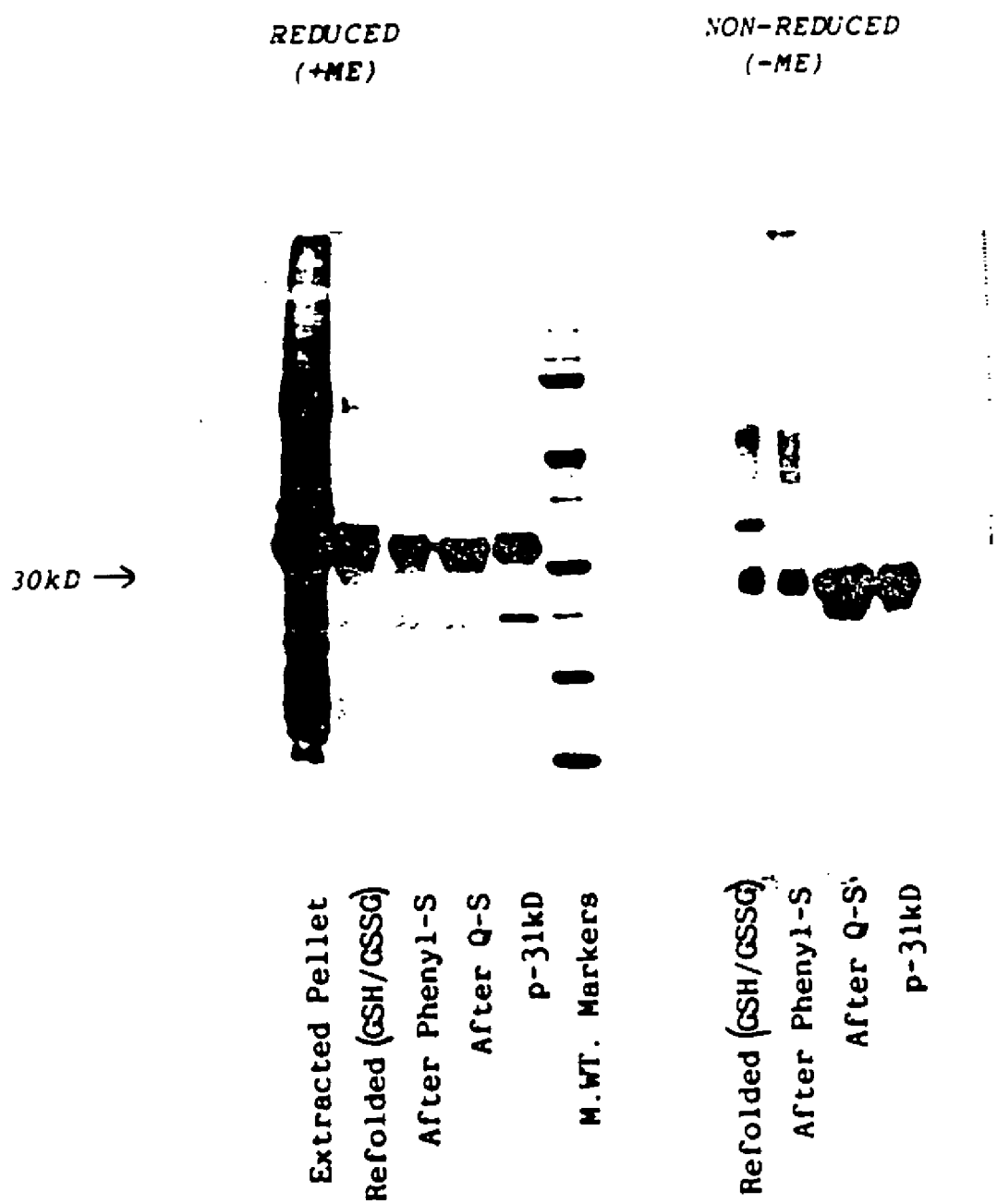

FIG. 11. Refolding/reoxidation and purification of r31 kD as followed by SDS-PAGE under reducing and non-reducing conditions The gel (12% acrylamide) under reducing conditions (with $\beta$-mercaptoethanol (ME)) monitors the process of purification, whereas the non-reducing conditions (without ME) are indicative of the refolding/r oxidation, 1 ading to fast removing and less diffuse bands. Note (in the absence of ME) that the band of 'After Phenyl-S' is much sharper than that of 'Refolded', indicating that reoxidation continues even during the purification.

Refolded (GSH/GSSG):r31 kD which has been refolded/ re- oxidized—after having been extracted from the crude pellet in the presence of GSH/GSSG 3 mM/0.3 mM at pH 8.0; Phenyl-S; Phenyl-Sepharose; Q-S; Q-Sepharose; p31 kD; plasma-derived 31 kD (obtained by tryptic digestion); molecular weight markers: Low Molecular Weight protein calibration kit (Pharmacia Fine Chemicals), containing markers whose molecular weights are 94 kD, 67 kD, 43 kD, 30 kD, 20.1 kD and 14.4 kD.

Figure 12:
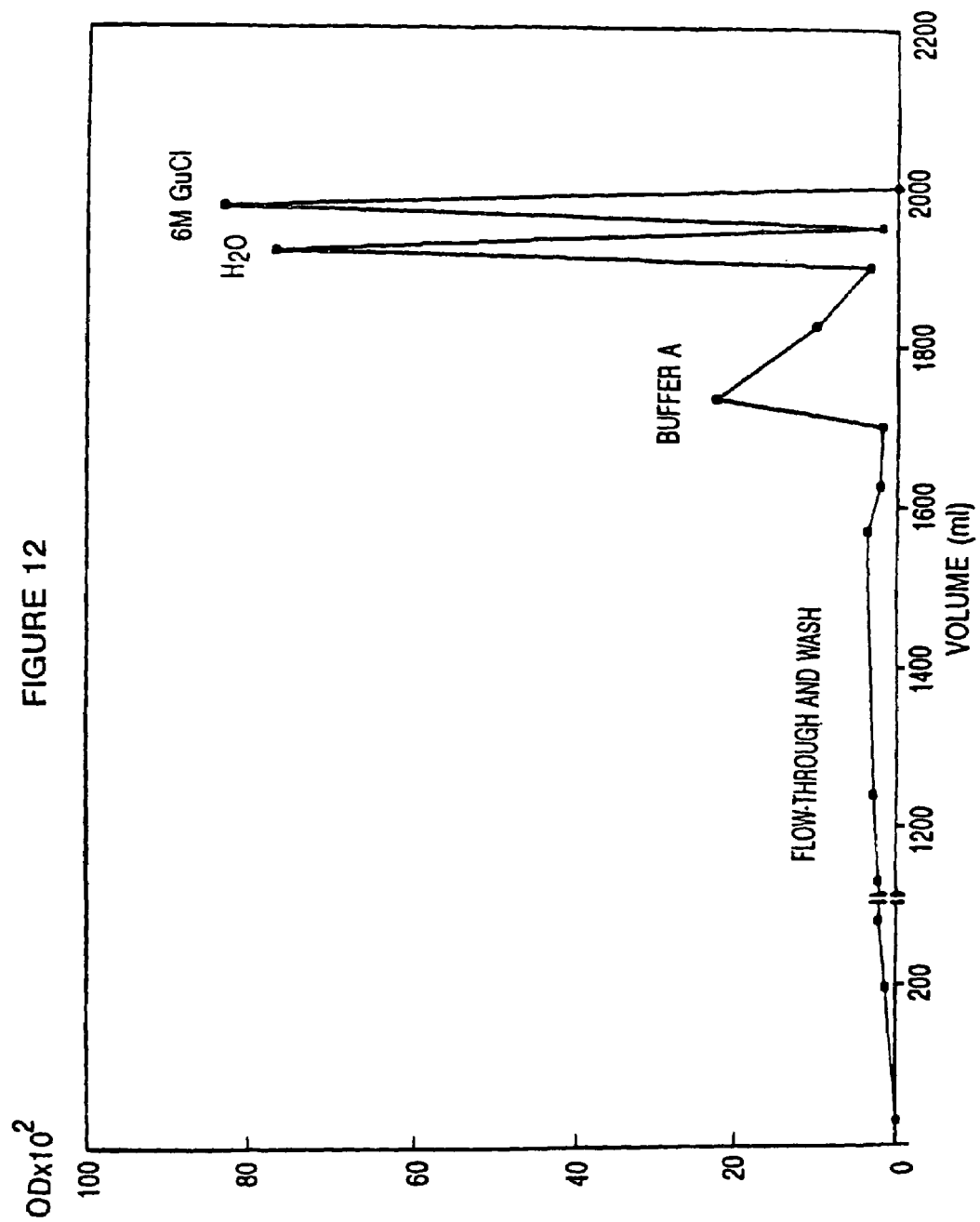

FIG. 12. Purification of GSH/GSSG-refolded r31 kD by Phenyl-Sepharose chromatography A suspension of refolded/reoxidized and "scrambled" 31 kD, as well as insoluble contaminants, which has been extracted from 10 grams of pellet, was subjected to centrifugation at 13,000 rpm (see Section 3.1 in Example 5). The supernatant (1,280 ml) was brought to 0.2 M in ammonium sulfate (AS) and loaded onto a 45 ml column of phenyl-Sepharose previously equilibrated with Buffer A at pH 8.5, containing also 0.2 M AS. The column was washed with 150 ml of the same solution, followed by 150 ml of Buffer A, 50 ml of water and 50 ml of 6 M GuCl. The purified r31 kD appeared in the Buffer A fraction and at this stage it was more than 85% pure. Absorbance was measured at 280 nm.

Figure 13:
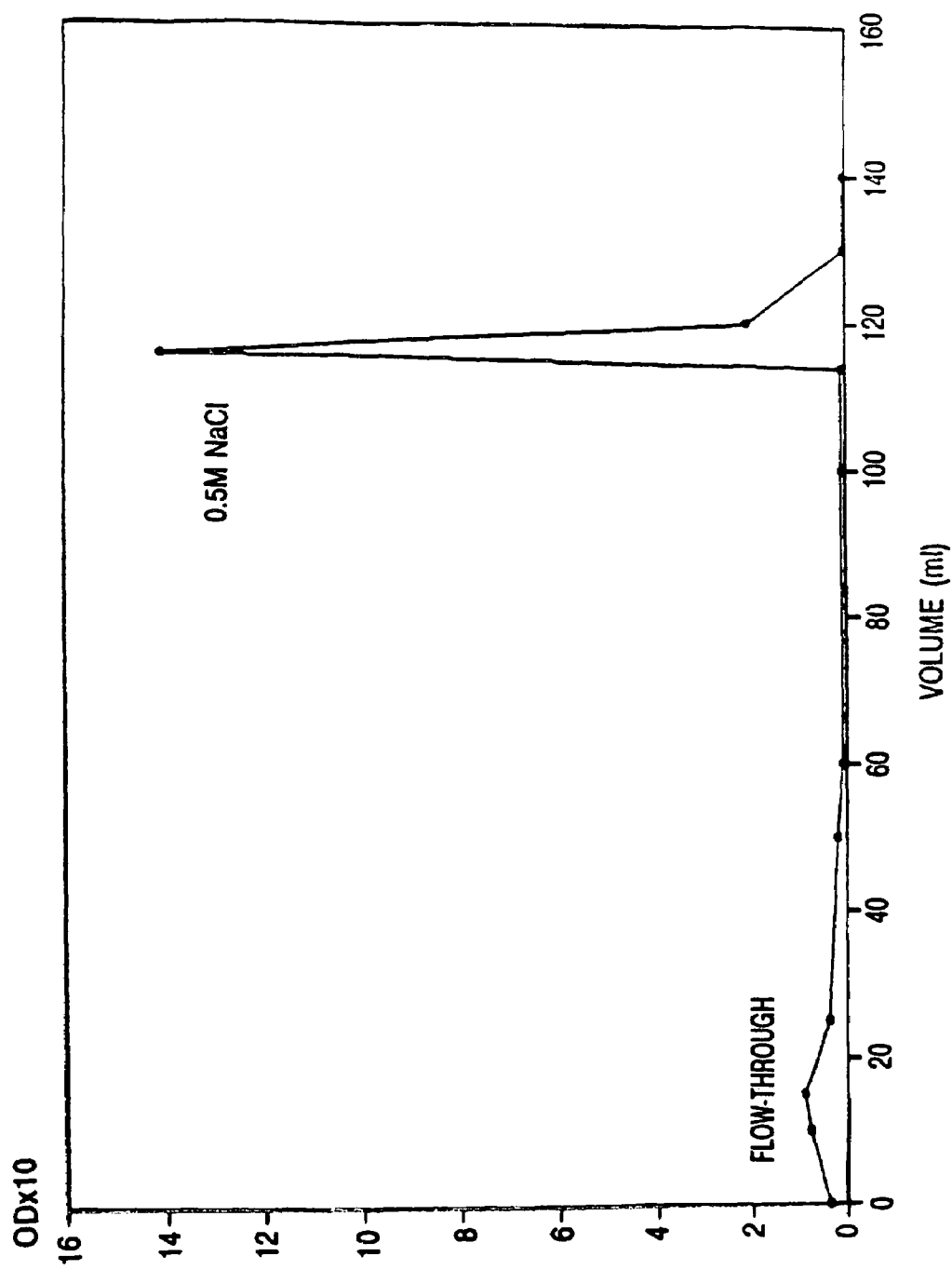

FIG. 13. Concentration and purification of r31 kD by Heparin-Sepharose chromatography Approximately ½ of the Buffer A peak from the phenyl-Sepharose step (see FIG. 12) was concentrated and purified on a 10 ml Heparin-Sepharose column, from which it was eluted by a solution of 0.5 M NaCl in Buffer A. At this stage the r31 kd is more than 90% pure. Absorbance was measured at 280 nm.

Figure 14:
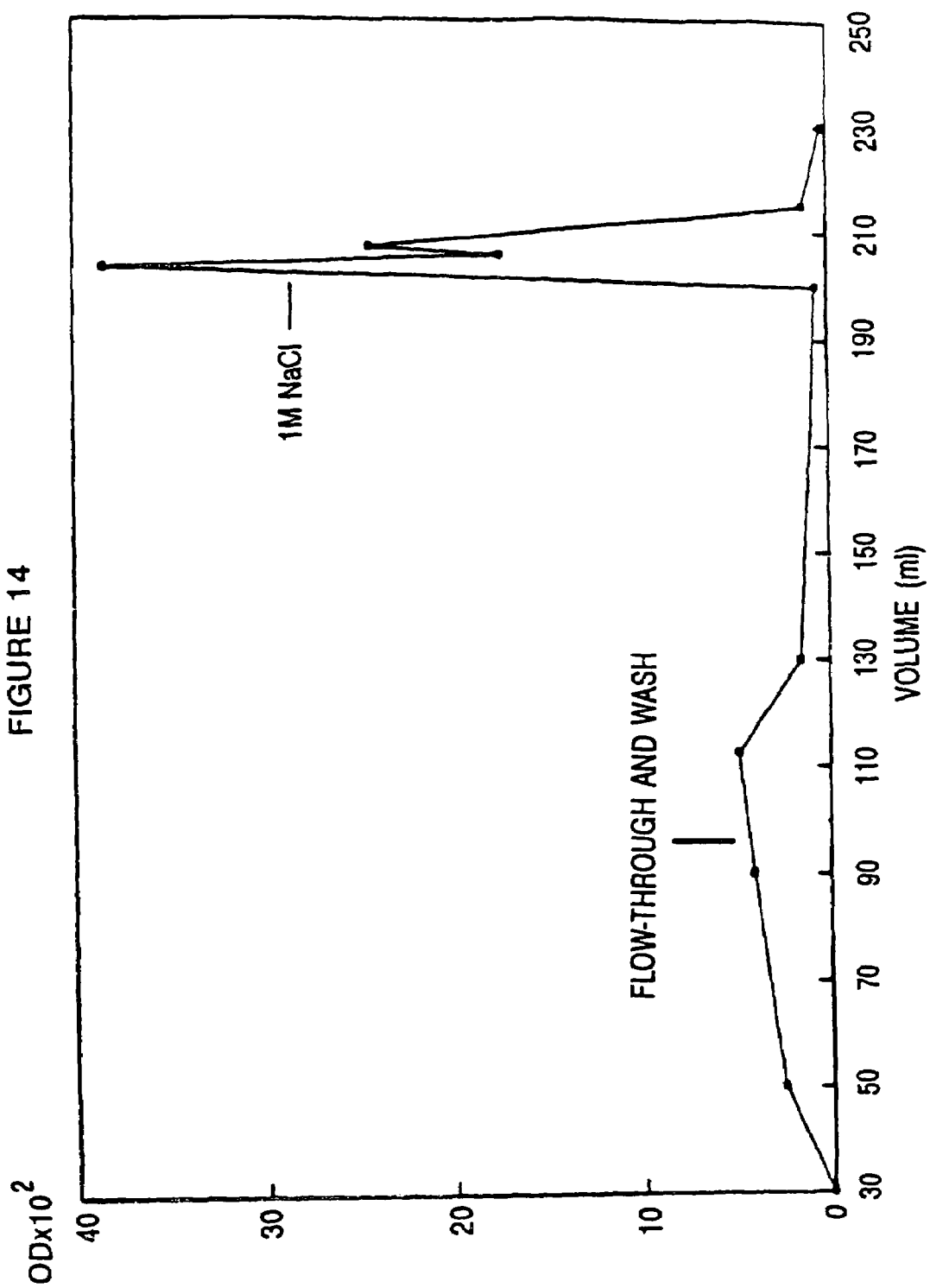

FIG. 14. Purification of r31 kD by O-Sepharose chromatography

Concentrated r31 kD (FIG. 13), which had been dialyzed against Buffer A, pH 8.5, was loaded on a 40 ml column of Q-Sepharose, which had previously been equilibrated with the same buffer. The purified r31 kD, which eluted in the flow-through and wash fractions, was concentrated by lyophilization. The column was washed free from the contaminant proteins by a step of 1 M NaCl. The purified r31 kD is at this stage more than 95% pure. Absorbance was measured at 280 nm.

Figure 15:
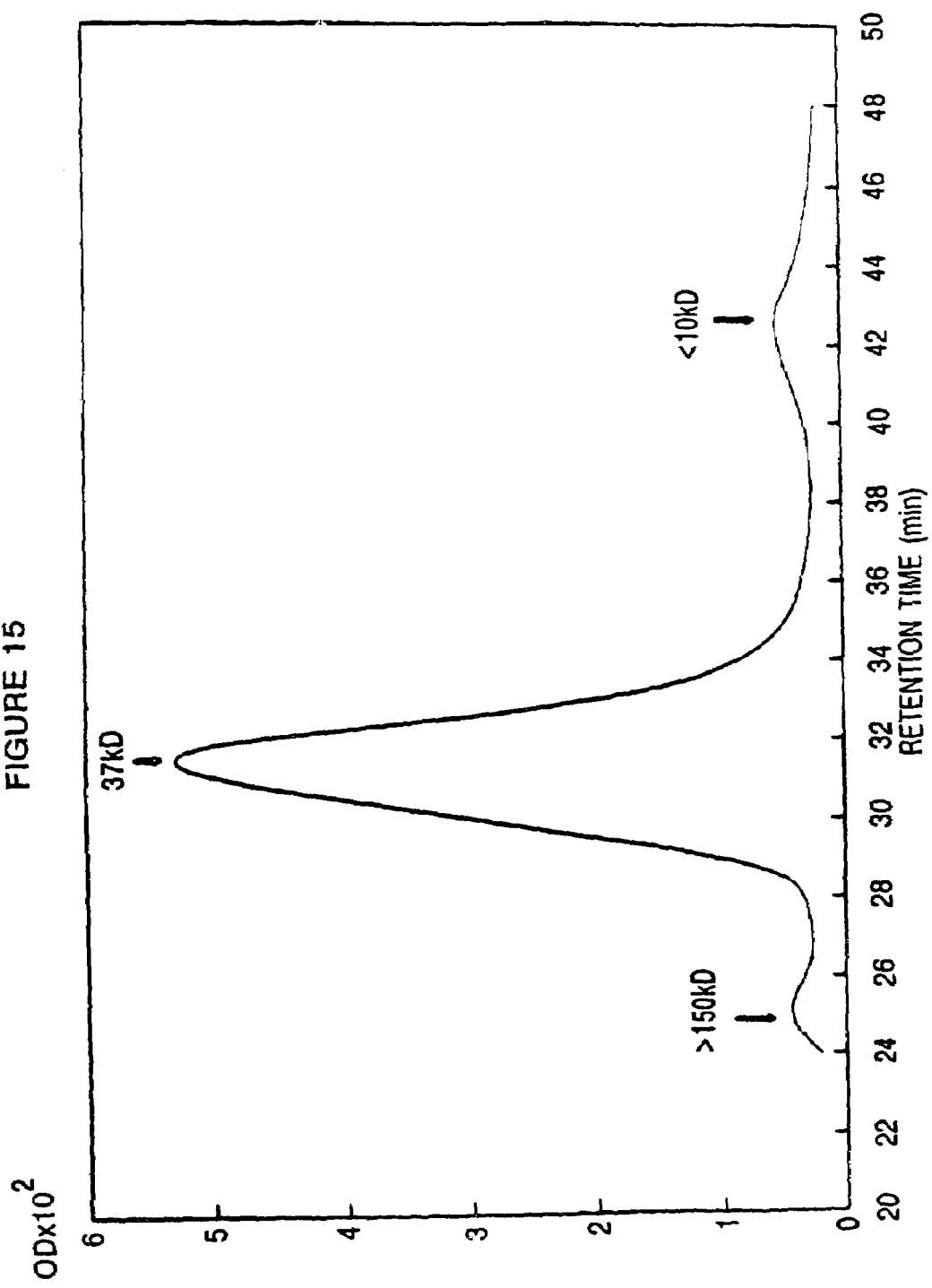

FIG. 15. Analytical FPLC-gel permeation of r31 kD on a Superose 12 column

A mixture of plasma derived and recombinant 31 kD (100 μl at 0.8 mg/ml) in running buffer (20 mM Tris.HCl—150 mM NaCl. pH 7.8) was applied onto the Superose 12 column (HR 10/30), pre-equilibrated in running buffer, and eluted from it in the same buffer. Flow rate—0.4 ml/minute; chart speed—0.25 cm/minute; absorption units full scale—0.1; detection wavelength—280 nm; run time—60 minutes. The retention times of both the plasma derived and recombinant 31 kD, when run separately, was identical to that obtained for the mixture, and correspond to an apparent molecular weight of 37 kD.

Figure 16:
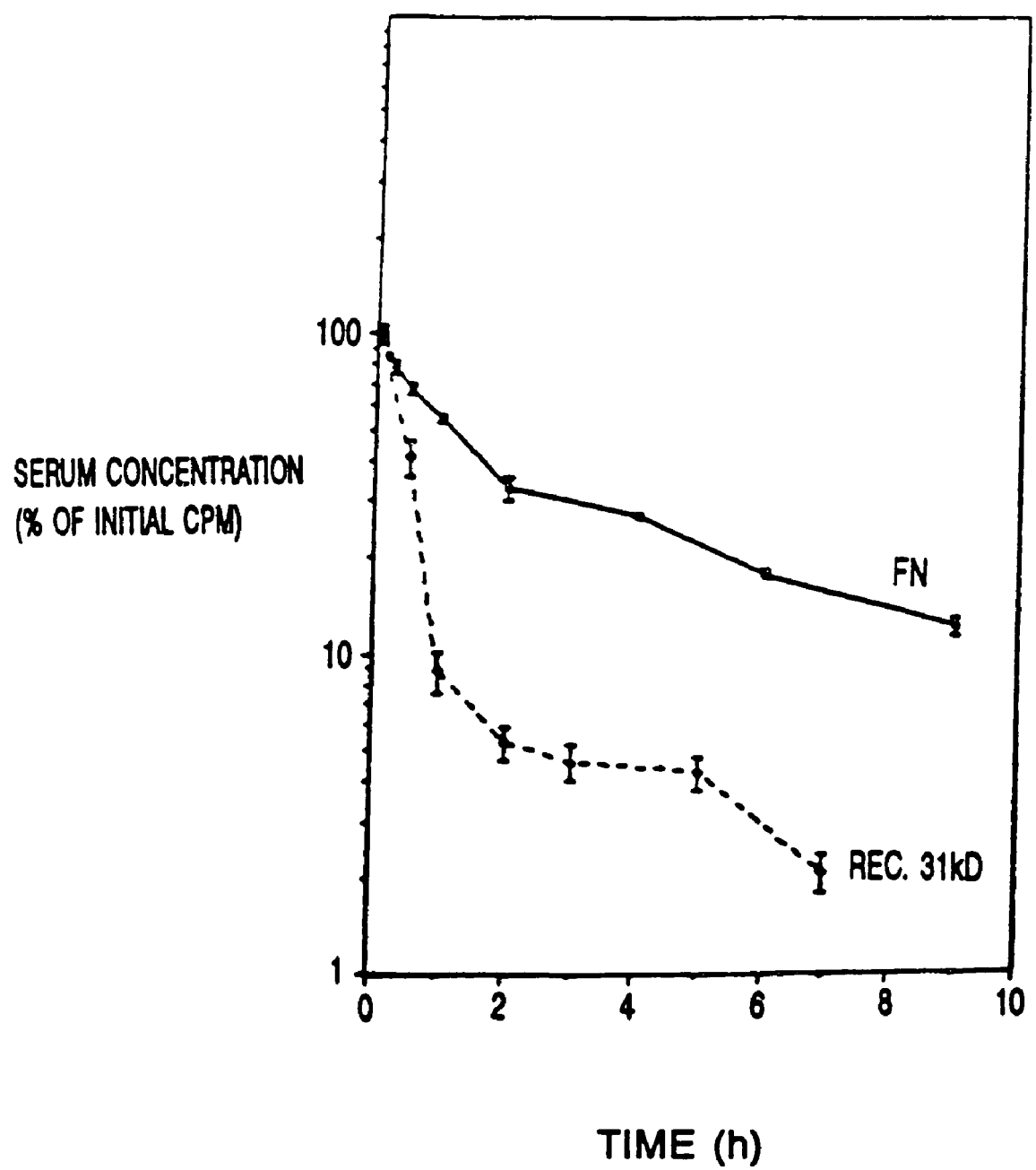

FIG. 16. Comparison of the pharmacokinetics of fibronectin (FN) and r31 kD FBD in rats $^{125}$I-FN (0.1 mg/kg; 5×10$^6$ cpm) or $^{125}$I-r31 FBD (0.1 mg/kg; 5×10$^6$ cpm) were injected intravenously and at the time indicated blood samples were withdrawn. Insoluble radioactivity in the blood samples was determined by trichloroacetic acid precipitation; at zero time, the 100% value represents 40,000 cpm/ml for FN and 46,000 cpm/ml for FBD.

Figure 17:
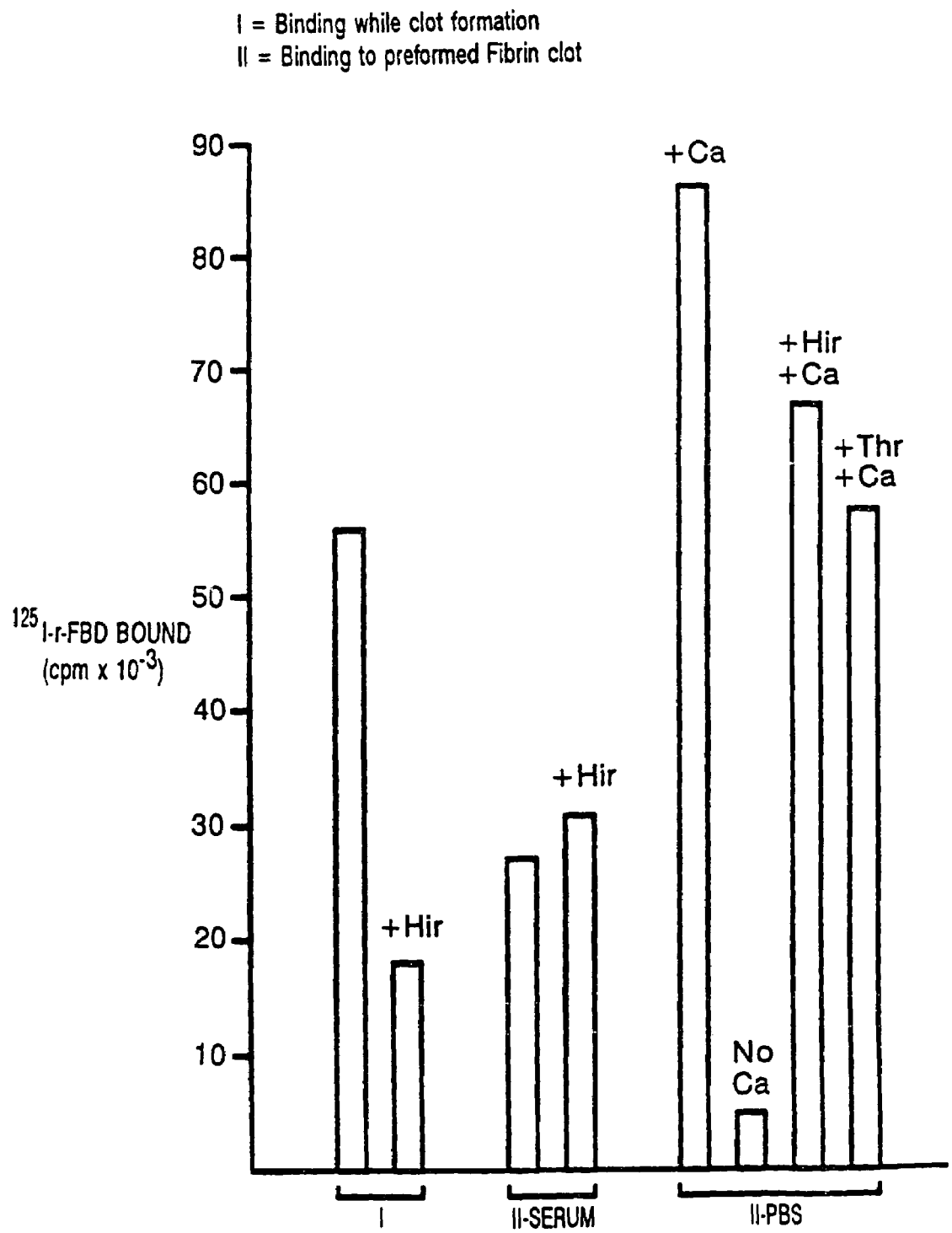

FIG. 17. Binding of $^{125}$I-r31 kD to fibrin: effect of thrombin and ca$^{++}$ ions Reaction I was carried out as described in Example 7 using 20 μl citrated whole blood, 0.15 μM $^{125}$I-r-FBD (r31 kD) (5.6×10$^5$ cpm/μg).

Reaction II was initiated with the formation of unlabeled Fibrin clot using 20 μl citrated whole blood as described in Example 7. After the first incubation, 0.15 μM $^{125}$I-r-FBD was added to the existing reaction tube ("Serum") or to the Fibrin pellet following centrifugation and resuspension in PBS ("PBS"). When CaCl$_2$ and Hirudin were added the concentrations were 5 mM and 3 U/ml, respectively. Reaction II was continued thereafter as described in Example 7.

Figure 18:
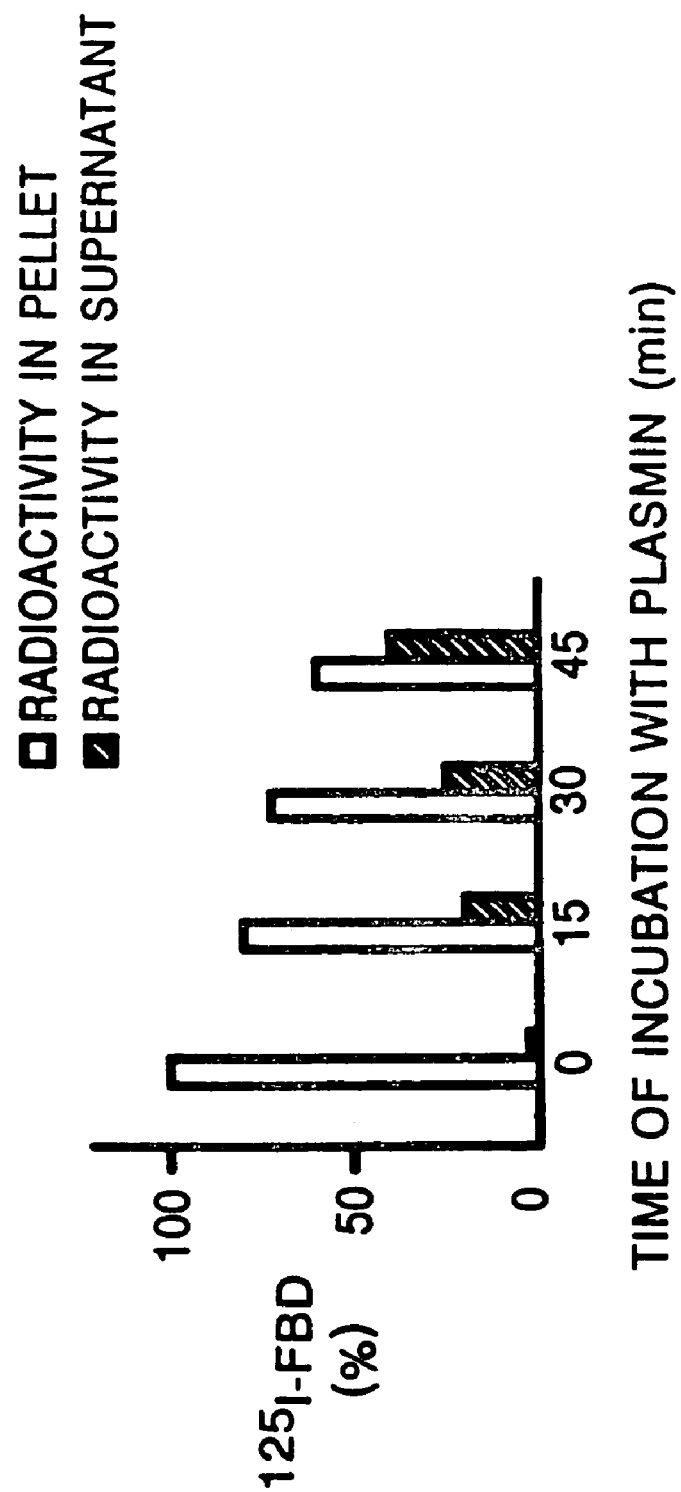

FIG. 18. Release of $^{125}$I-FBD (p31 kD) from Fibrin

Reaction I was carried out using several tubes containing 100 µl citrated whole blood and 0.3 µM $^{125}$I-P-FBD (5.0×10$^4$ cpm/µg). At the end of the incubation, the pellet was collected by centrifugation and then resuspended in PBS solution containing 1 µ/ml plasmin (from porcine blood, Sigma) and was further incubated at 37° C. for the indicated time intervals. The reaction was terminated by cooling and immediate centrifugation. The radioactivity in the supernatant and the pellet was measured by a gamma counter.

The pellet and the supernatant were resuspended in gel electrophoresis sample buffer (final concentration of 3% glycerol, 2% BME, 1% SDS, 0.2% Bromophenol Blue), boiled for 15 minutes, and electrophoresed in 10% PAGE-SDS. The gel was then autoradiographed on x-ray film. No radioactivity was detected from the pellet. Radioactivity from the supernatant was detected in a position corresponding to control $^{125}$I-FBD incubated with plasmin (results not shown).

FIG. 19.

The binding of 0.15 µM $^{125}$I-r-FBD ($^{125}$I-r31 kD; 5.6×10$^5$ cpm/µg) to 20 µl citrated whole blood was performed using reaction I conditions (see Example 7). The reaction was performed either without competitors (C) or in the presence of various concentrations of unlabeled "folded proteins", "reduced" FBD and related molecules.

rI="Fully reduced" r31 kD FBD rII="Reduced carboxyamidated" r31 kD FBD (i.e. reduced/blocked 31 kD FBD)

p=31 kD FBD from Trypsin cleavage of plasma derived Fibronectin.

Figure 20:
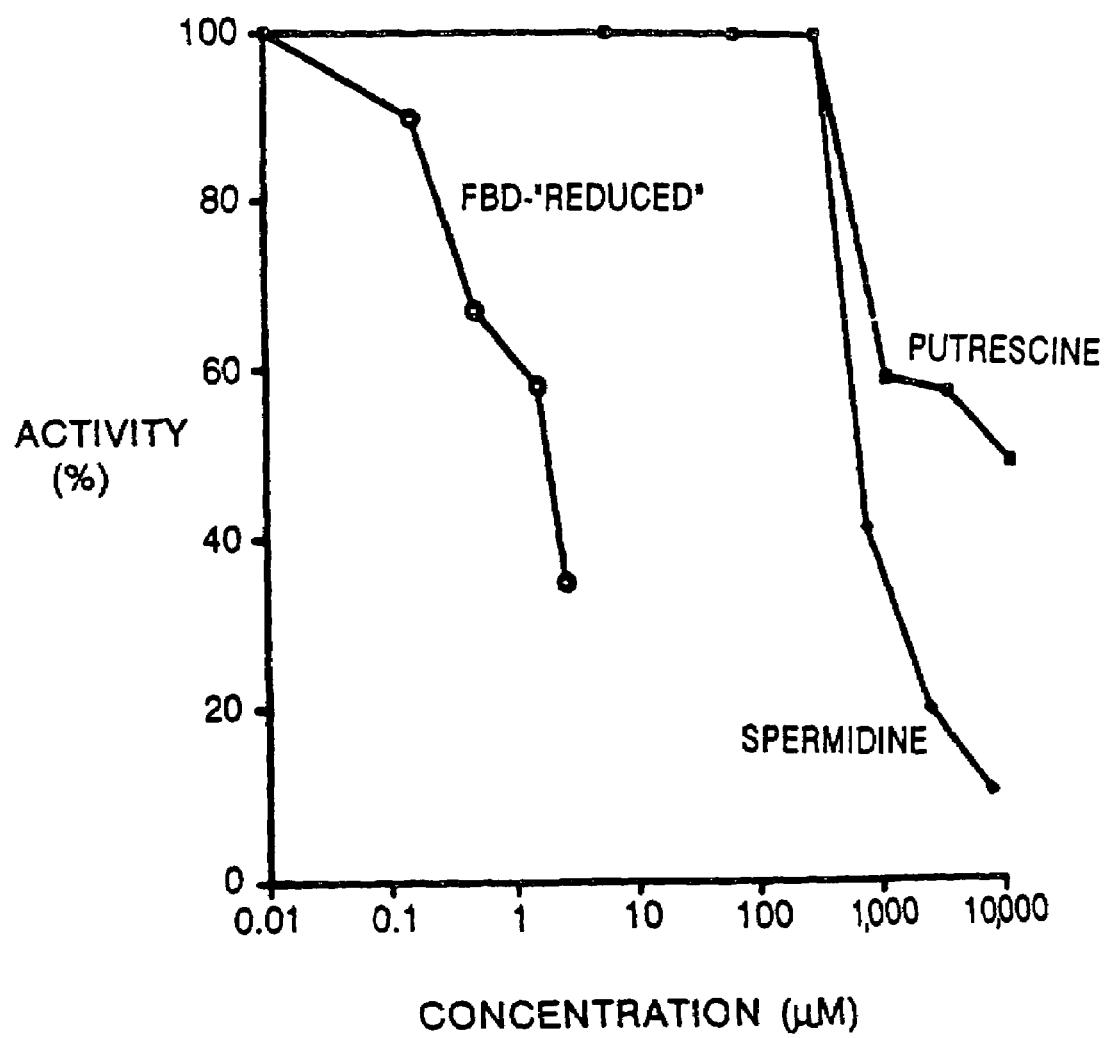

FIG. 20. Binding of $^{125}$I-r31 kp to fibrin (Reaction II), Effect of transglutaminase inhibitors and related molecules Unlabeled fibrin clot was formed using 20 µl citrated whole blood and using the conditions described for reaction II in Example 7.

At the end of the first incubation period, and prior to the addition of r-125I-FBD (0.15 µM; 2.9×10$^4$ cpm/µg), the indicated concentrations of spermidin, putrescine and FBD-"R" ("Reduced-carboxyamidated" plasma derived FBD) were added to the specified reactions.

Figure 21:
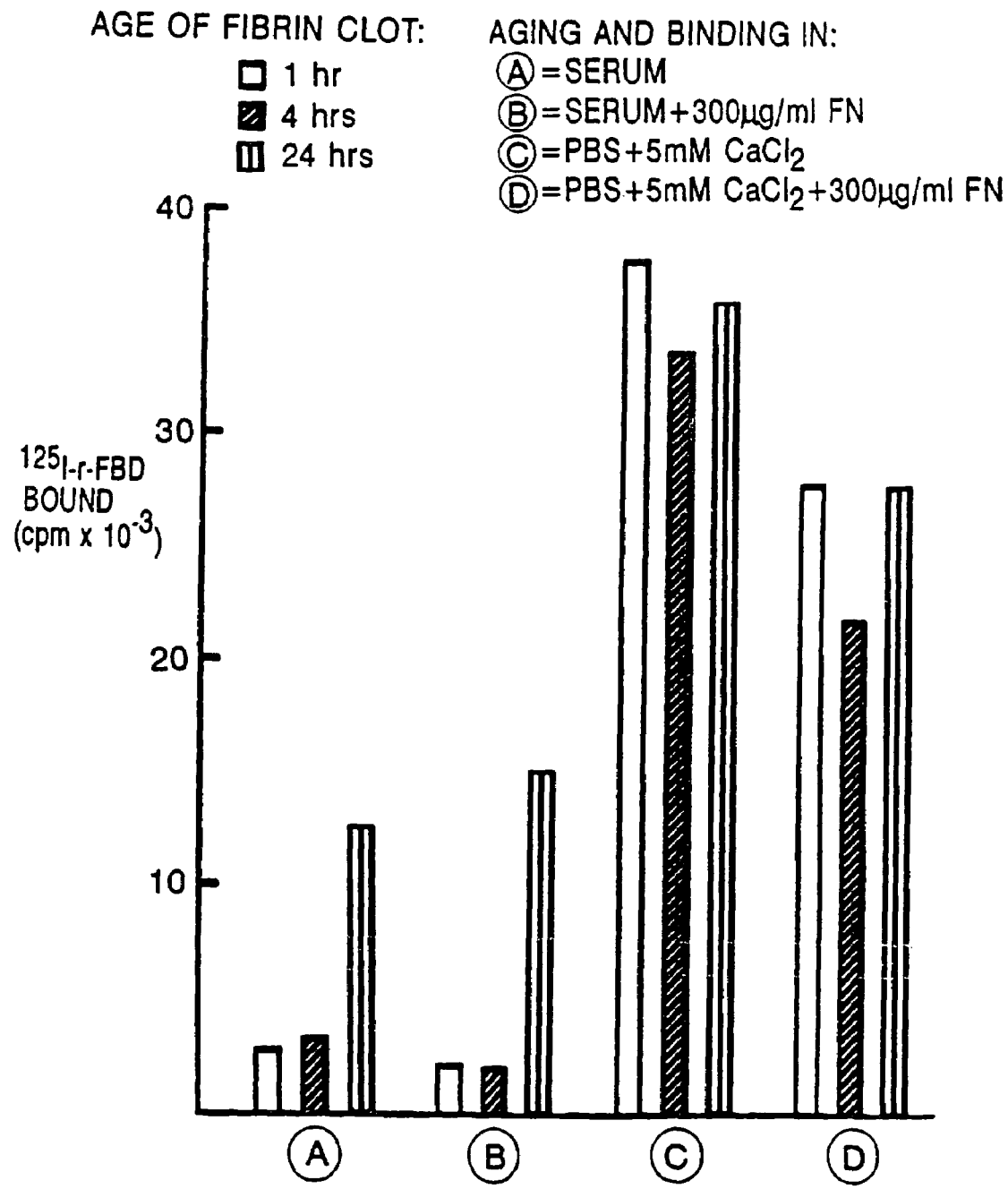

FIG. 21. Binding of $^{125}$I-r31 kD to preformed fibrin clot (Reaction II): effect of fibrin clot age The unlabeled fibrin clot was formed using 20 µl citrated whole blood and using the conditions described for reaction II in Example 7.

At the end of the first incubation period, half of the samples were centrifuged and the fibrin pellet was resuspended in PBS solution containing 5 mM CaCl$_2$ (Reaction "C") or PBS containing 5 mM CaCl$_2$ and 300 µg/ml FN (Reaction "D"). No additions or changes were performed to the samples designated "A". 300 µg/ml FN was added to the sample designated "B". Subsequently, the reaction mixtures were allowed to incubate at 37° C. for 1 hour, 4 hours, or 24 hours (as indicated in the figure). Then $^{125}$I-r31 kD (0.15 µM final concentration, 5.4×10$^5$ cpm/µg) was added and the incubation was continued f r an additional 30 minutes. The reaction was terminated as described in Example 7.

Figure 22:
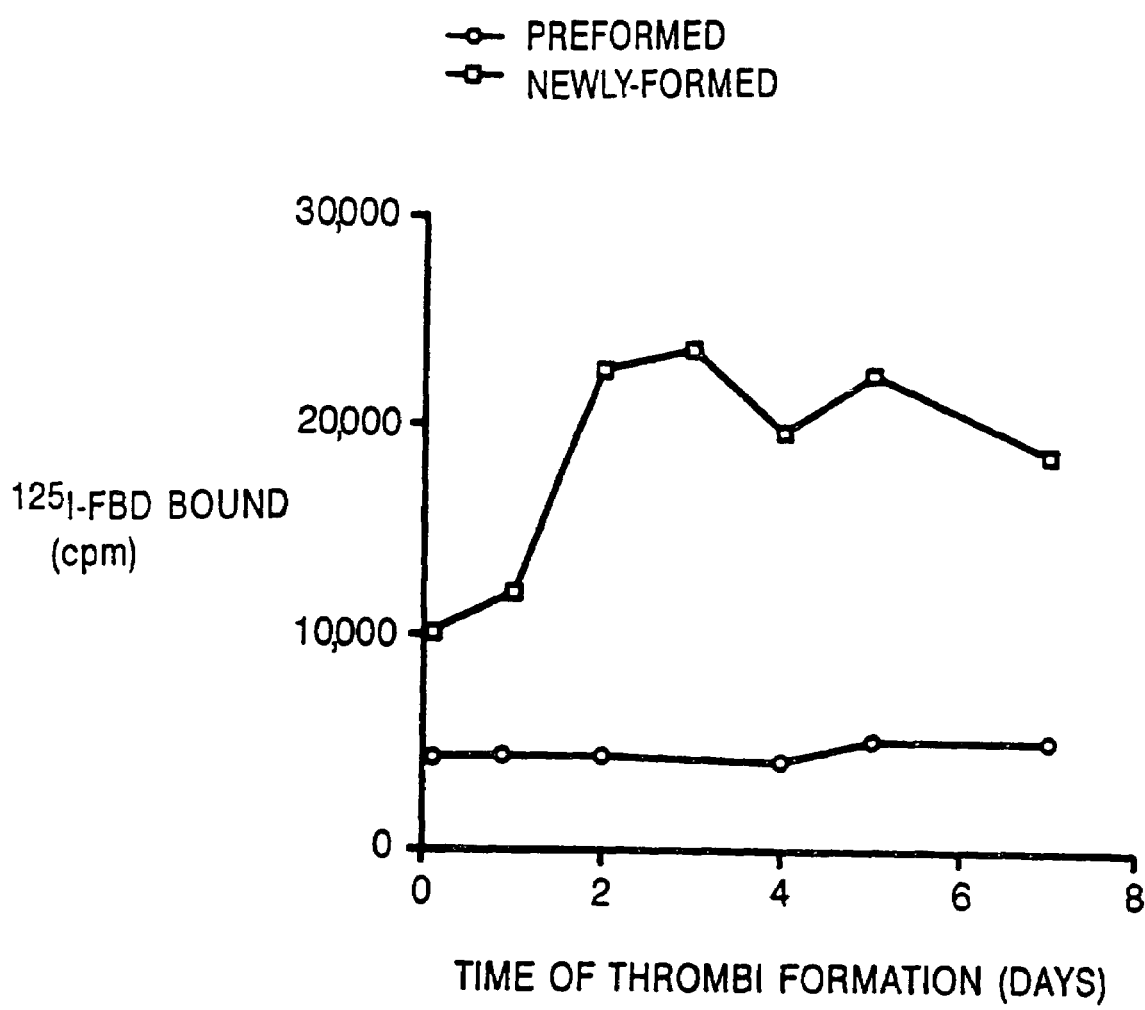

FIG. 22. Binding of $^{125}$I-r31 kD to "Naive" Thrombi (reactions I and II): effect of thrombii age on the binding Aliquots of 20 µl non-citrated fresh whole human blood were incubated in non-siliconized tubes at 37° C. with either 0.15 µM $^{125}$I-r31 kD or alone (reaction I and II, respectively). At the indicated time intervals, reactions were either terminated (reaction I) or 0.15 µM $^{125}$I-r31 kD (2.9×10$^4$ cpm/µg) was added, and incubation terminated after an additional 2 hours (reaction II).

Figure 23:
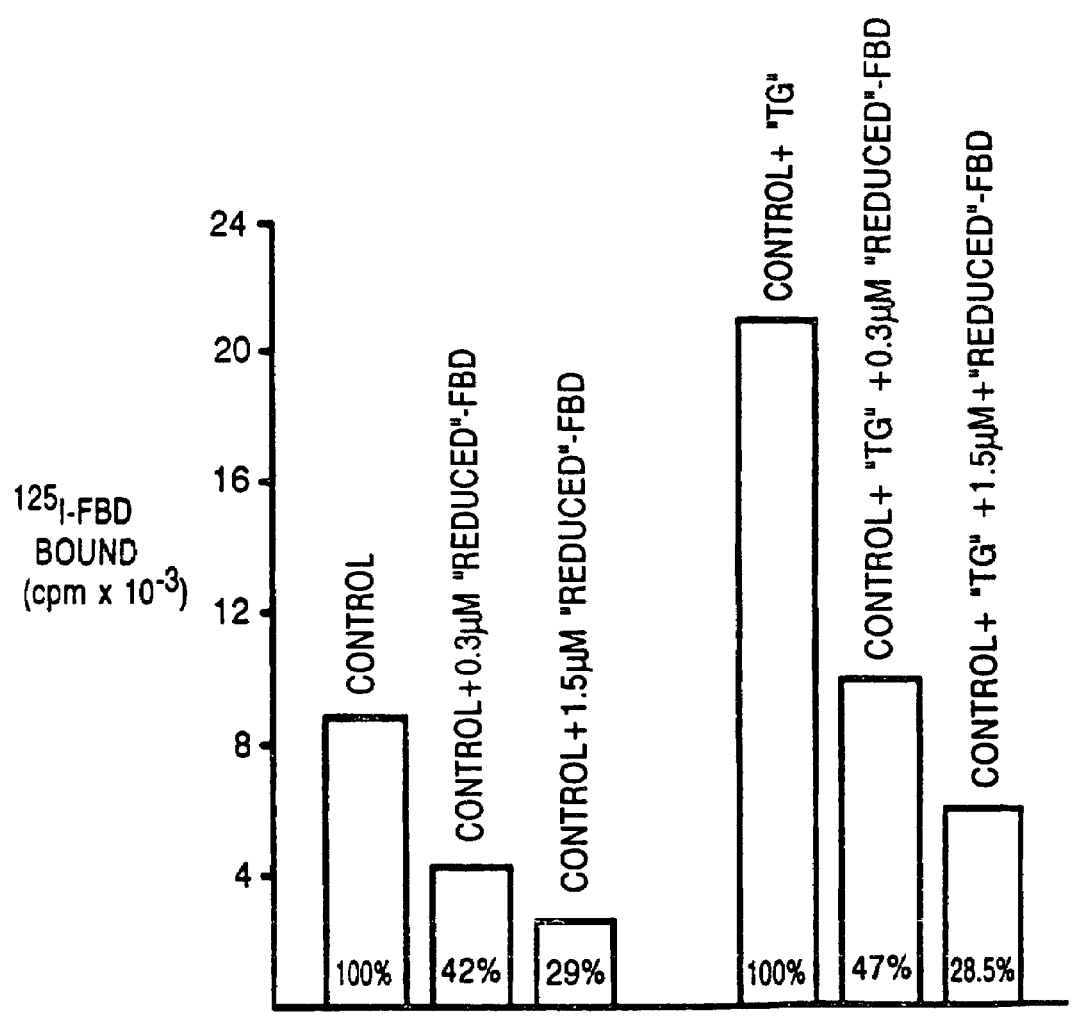

FIG. 23. Binding of $^{125}$I-r31 kD to Fibrin (Reaction II: Effect of Exogenous Transglutaminase and "Reduced" FBD 20 µl aliquots of noncitrated whole human blood were incubated with 0.15 µM $^{125}$I-r31 kD (2.9×10$^4$ cpm/µg) alone ("control") or together with pig liver Transglutaminase ("control+T.G.", 0.2 units/ml; Sigma).

Some of the tubes contained "Reduced" (carboxamidated) p31 kD as indicated in the figure.

The addition of exogenous Transglutaminase to the binding reaction increased the binding values by more than a factor of two. When "reduced-carboxamidated" r31 kD was added to the reaction we observed a similar extent of inhibitory effect as with the exogenous factor XIIIa (inhibition of 53% and 71% by 0.3 µM and 3.0 µM, respectively), indicating an identical inhibitory effect of the reduced FBD on both types of Transglutaminase.

Figure 24:
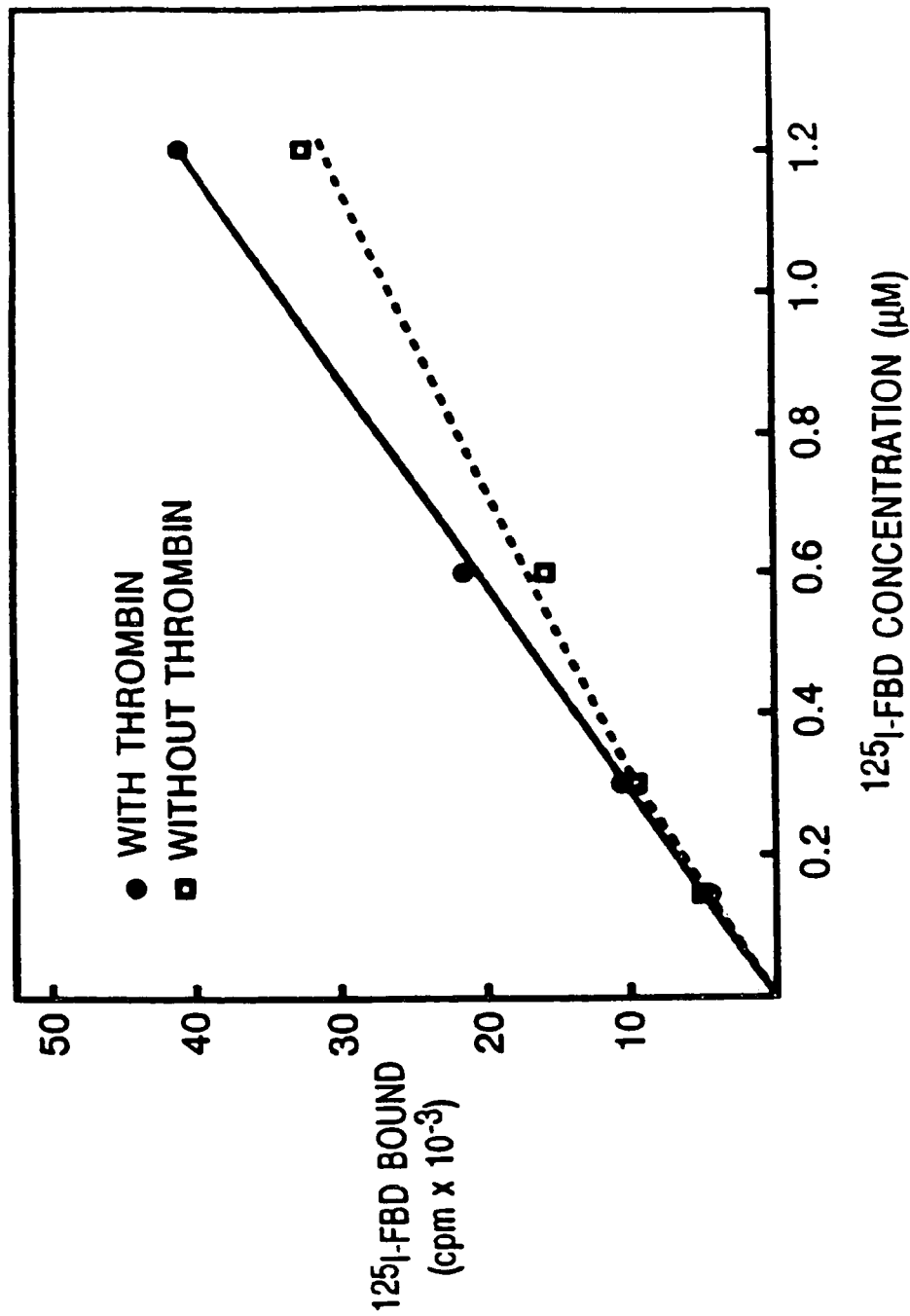

FIG. 24. Binding of FBD to ECM

The biological activity of the FBD was studied in a model of vascular injury using the Extra Cellular Matrix, "ECM", of cultured endothelial cells (20).

33 mm ECM plates following 3× washing in PBS were incubated at 37° C. in a CO$_2$ incubator with 0.5 ml DMEM-10% FCS containing 2.5 mM CaCl$_2$, 1 µ/ml Thrombin, and the indicated concentrations of $^{125}$I-P-FBD (about 4.4×10$^5$ cpm/µg). Parallel plates were incubated in the absence of thrombin as indicated in the figure. Following 45 minutes of incubation, the plates were washed 3 times with 1 ml PBS, extracted with 0.5 ml of 0.1% SDS-PBS solution, and radioactivity was measured by a gamma counter. The values described in the figure represent an average of two plates.

Figure 25:
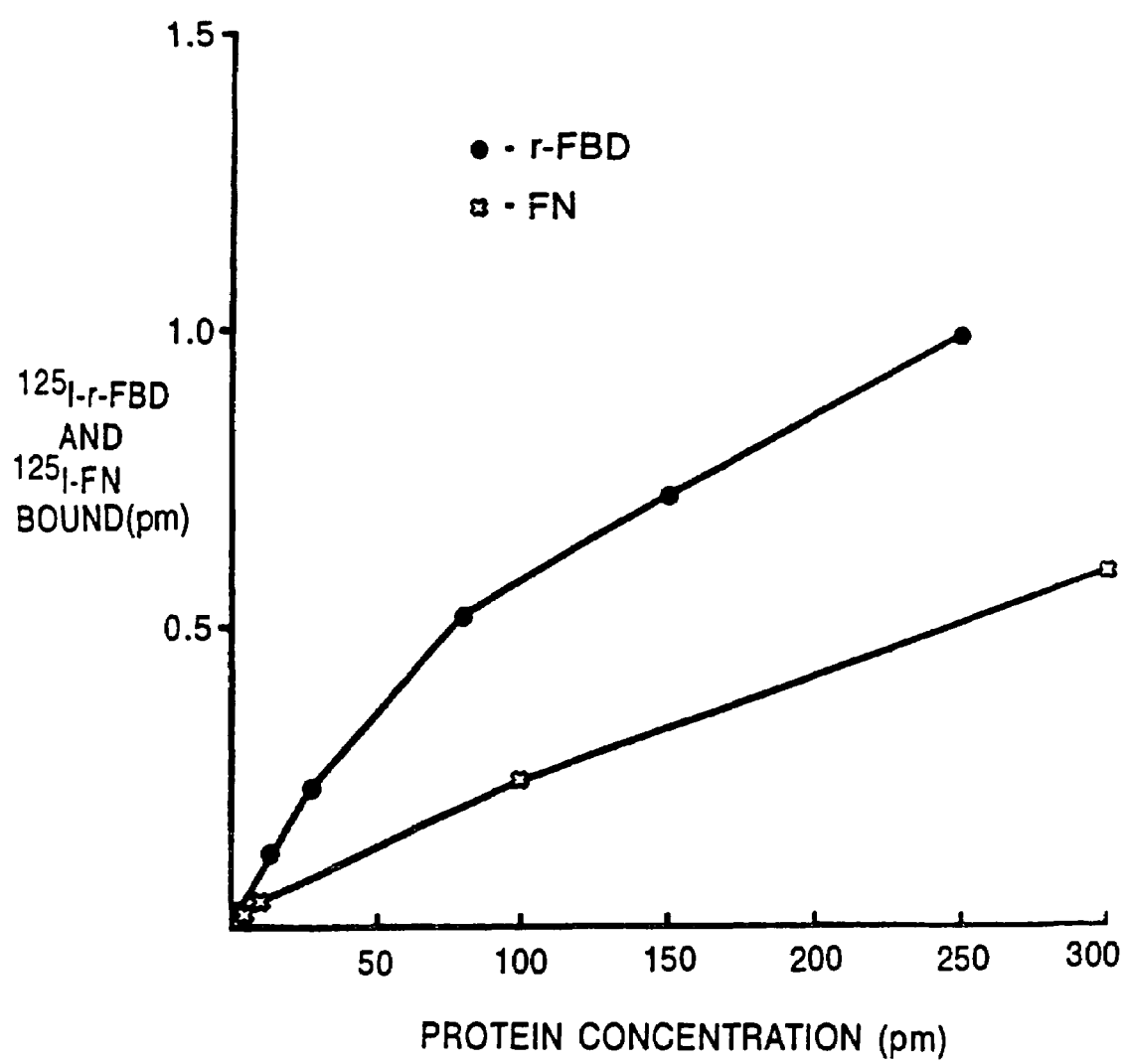

FIG. 25. Binding of FN and FBD to S. aureus

The binding reaction was carried out in a solution using 5×10$^8$ PFU/ml of S. aureus SA113 (ATCC Accession No. 35556) and $^{125}$I-FN (4×10$^4$ cpm/µg) or $^{125}$I-FBD (1.3×10$^5$ cpm/µg; r31 kD FBD, "reoxidized-refolded") at concentrations indicated in the figure and as described in methods. The concentration of the labeled molecules described is calculated using molecular weights of 220,000 and 31,000 daltons for FN and r31 kD, respectively.

Figure 26:
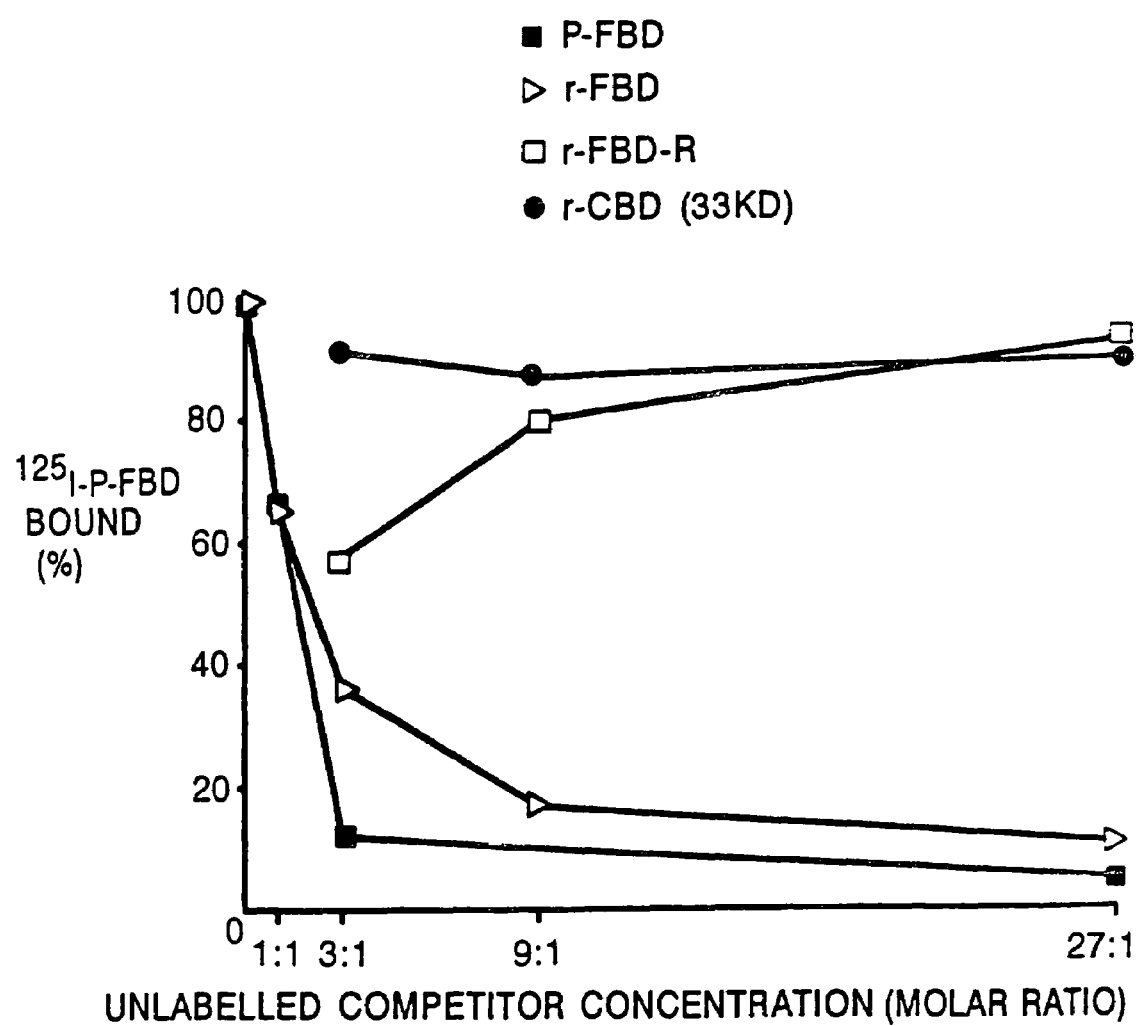

FIG. 26. Binding of FBD to S. aureus: competition with folded and reduced forms

Binding in solution of 1.25 µg $^{125}$I-p31 kD (2.3×10$^5$ cpm/µg) to 5×10$^8$ PFU/ml of S. aureus SA113 was carried out in the presence of the indicated concentrations of the following unlabeled proteins: P-FBD (p31 kD), r-FBD (r31 kD FBD "reoxidized-refolded"), r-FBD-R (r31 kD FBD "Reduced Carboxyamidated), and r-CBD (r-33 kD cell binding domain of FN). The binding reaction was carried out as indicated in the methods section.

Figure 27:
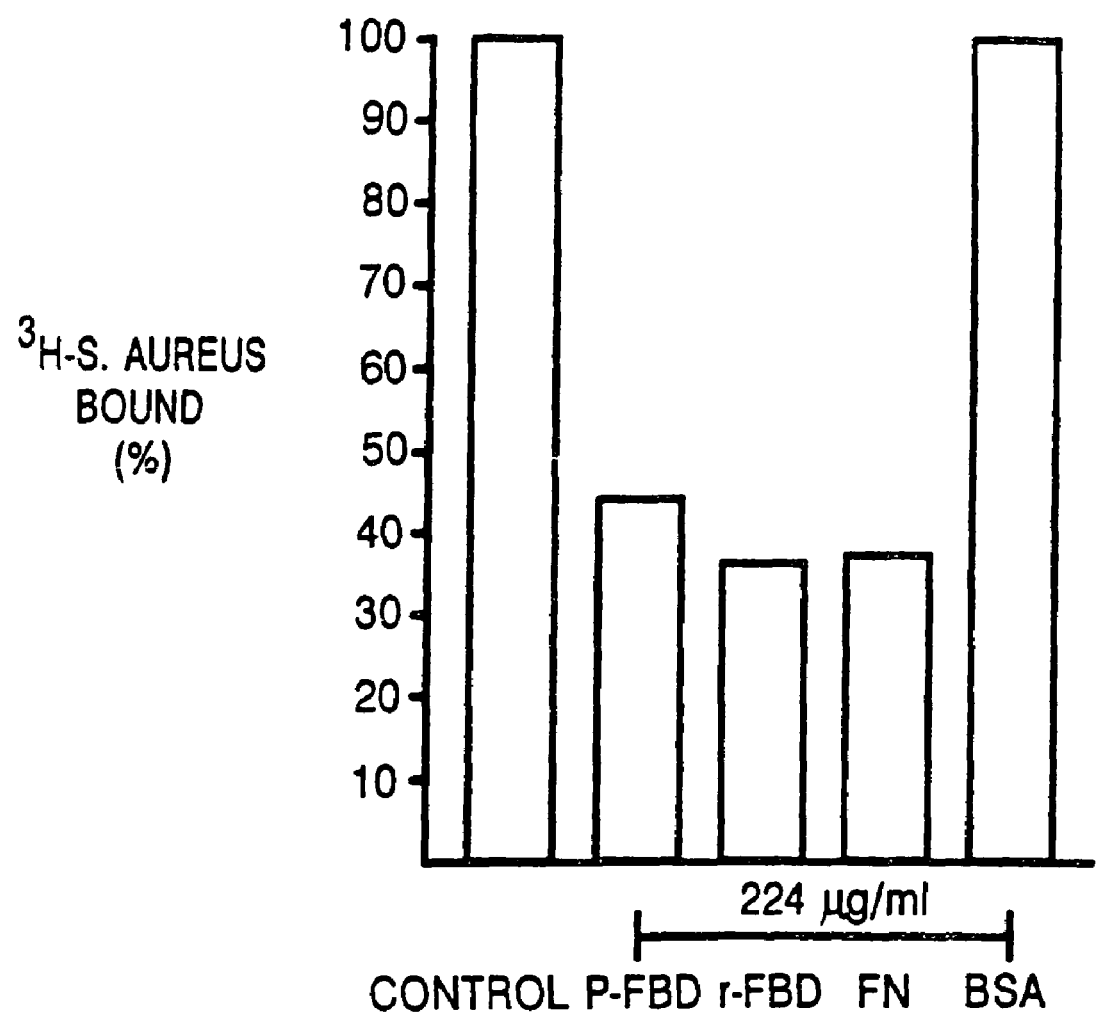

FIG. 27. Binding of S. aureus to immobilized FN

Binding of 7.5×10$^8$ PFU/ml of 3H-leucine-S. aureus (5.8 cpm/10$^5$ PFU) to FN immobilized onto plastic vials was carried out as described in methods and in the presence of human plasma FN, r-FBD (r31 kD FBD "reoxidized-refolded"), P-FBD (p31 kD), or BSA (Bovine Serum Albumin, Sigma). Binding of "control" reaction in the absence of competitors (9.3% of input bacteria) was normalized to 100%.

Figure 28:
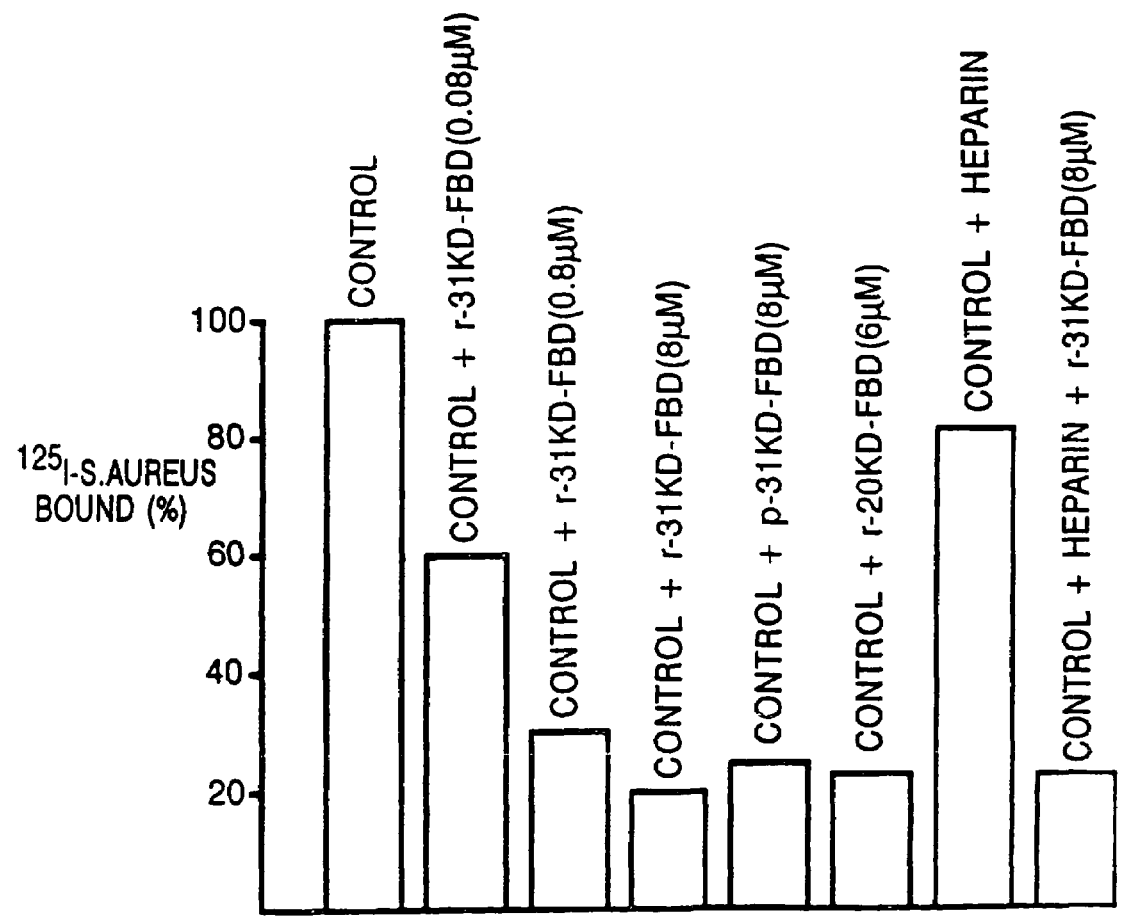

FIG. 28. Binding of S. aureus to Catheters

Binding of 3.0×10$^6$ PFU/ml of $^{125}$I-S. aureus (1 CPM/3 PFU) to "Uno" bronchial plastic catheters (3 cm for each reaction, in duplicate) coated with FN was carried out as described in methods. When competition reaction was performed, the bacteria and the added protein were preincubated at room temperature for 30 minutes and then added to the catheters for further incubation as described in the methods section.

The polypeptides used in the competition reactions were: P-31 (p31 kD), r-20 (recombinant derived 20 kD FBD) and r-31 (reoxidated and refolded r31 kD). Some of the reactions (see figure) were measured in the presence of 5 μm Heparin (from porcine intestinal mucosa, molecular weight of 10,000; Sigma).

The binding of "control" reaction in the absence of competitors (8.8% of input bacteria) was normalized to 100%.

Figure 29A:
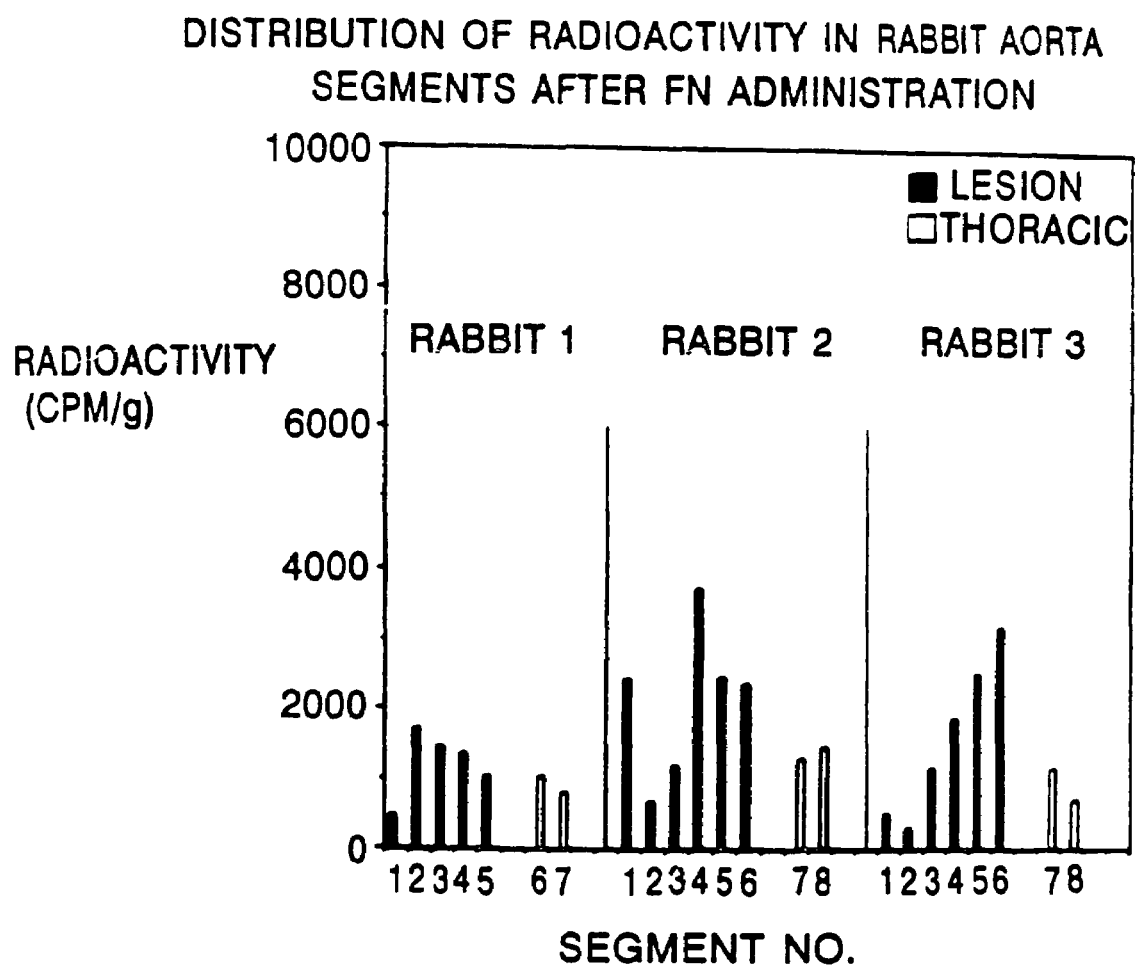
Figure 29B:
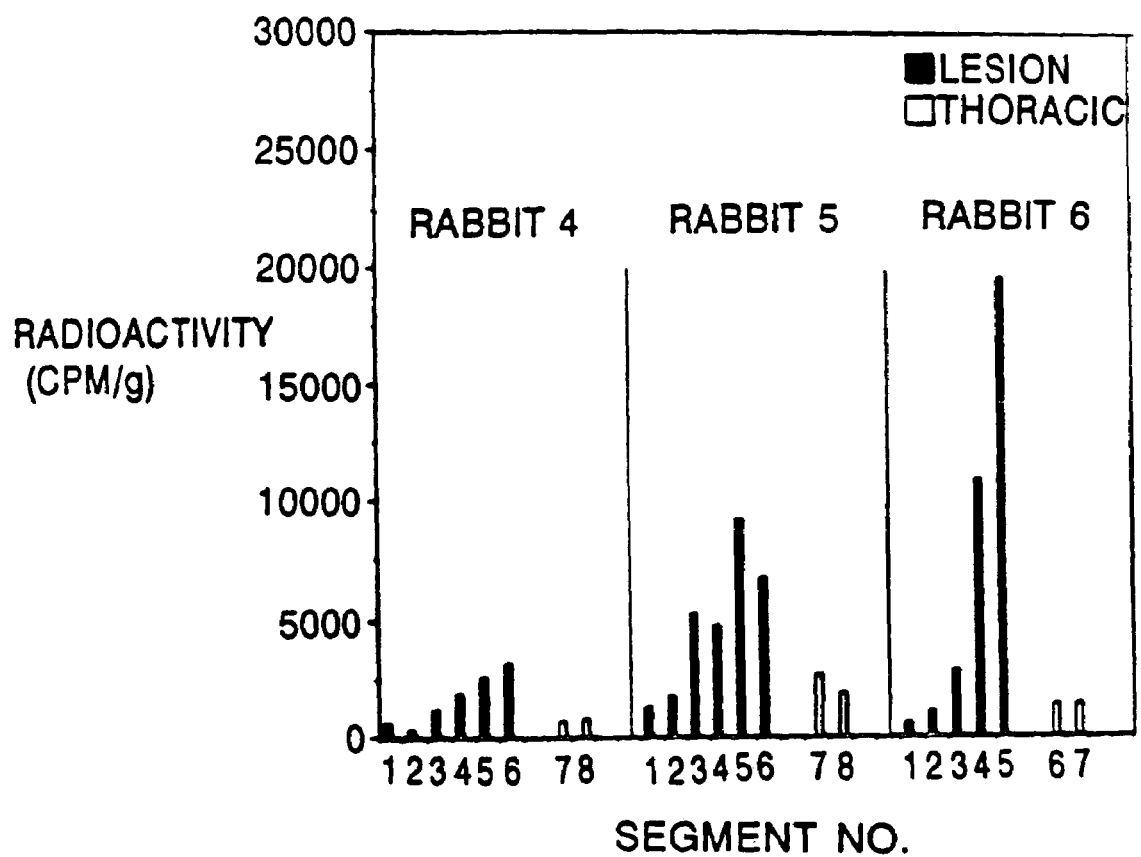

FIG. 29. Adhesion of p31 kD in Rabbit Aorta Lesion Model

The figure shows the distribution of radioactivity in serially sectioned aorta segments from balloon catheterized rabbits. The measurements were take 72 hours after injection of $^{125}$I-labeled Fibronectin (FN) (Panel A) or plasma derived 31 kD FBD (31 kD) (Panel B).

FIG. 30. Construction of pTV-170

The NdeI-NdeI ApoE fragment was isolated from plasmid pApoE-EX2 (ATCC Accession No. 39787) and inserted into the unique NdeI site of the expression vector p579 (FIG. 34) which had been digested with NdeI. The resulting plasmid pTV-170 expresses an analog of natural human ApoE protein having a methionine residue added at the N-terminus.

FIG. 31. Construction of pTV-194-80

The β-lactamase promoter and ribosomal binding site fragment was isolated from plasmid pBLA11 (ATCC Accession No. 39788) after digestion with EcoRI and AluI. This fragment was ligated to the large fragment of pTV-170 (FIG. 30) plasmid which had b en digested with NdeI, filled in with DNA polymerase I (Klenow) and then digested with EcoRI.

FIG. 32. Recombinant polypeptides of fibronectin domains compared to full-length fibronectin This figure shows the alignment of cDNA clones encoding various recombinant polypeptides relative to one another and to the full-length sequence of fibronectin cDNA and to a schematic representation of the various domains present within the human fibronectin molecule.

Figure 33:
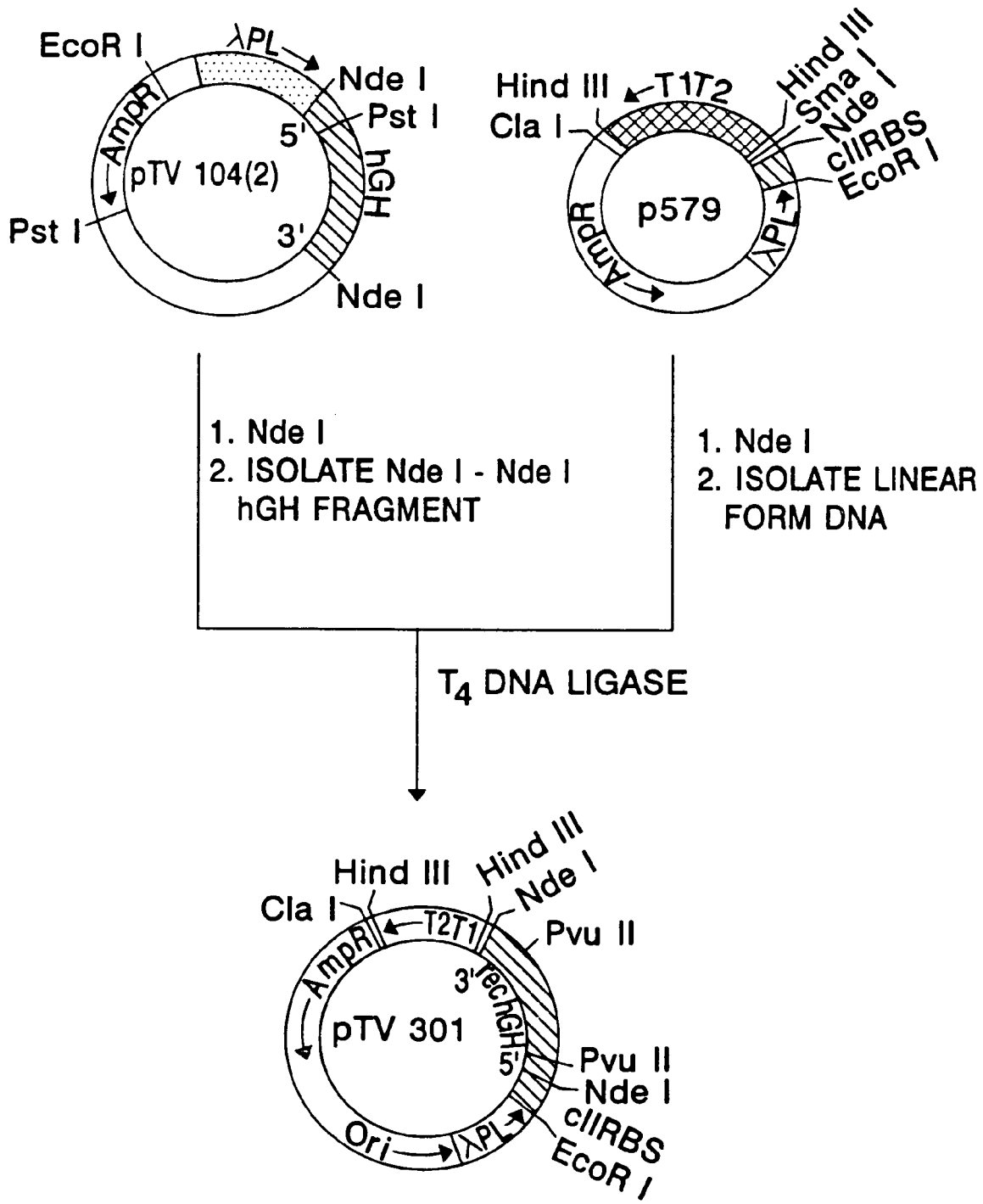

FIG. 33. Construction of plasmid pTV301 from plasmids pTV104(2) and p579

Plasmid pTV301 directs the expression of a human growth hormone analog under the control of the λ $P_L$ promoter and the cII ribosomal binding site. The plasmid also contains a $T_1T_2$ transcription terminator downstream of the cDNA encoding human growth hormone.

FIG. 34. Construction Of plasmid p579

The rRNA operon $T_1T_2$ transcription termination fragment was isolated from plasmid pPS1 (deposited with the ATCC under Accession No. 39807) which had been digested with HindIII. The $T_1T_2$ fragment was inserted into the unique HindIII site of pRO211 (FIG. 35) which had been digested with HindIII. The resulting expression vector, p579, contains the λ $P_L$ promoter and the $C_{11}$ ribosomal binding site, followed by the $T_1T_2$ transcription termination sequences.

Figure 35:
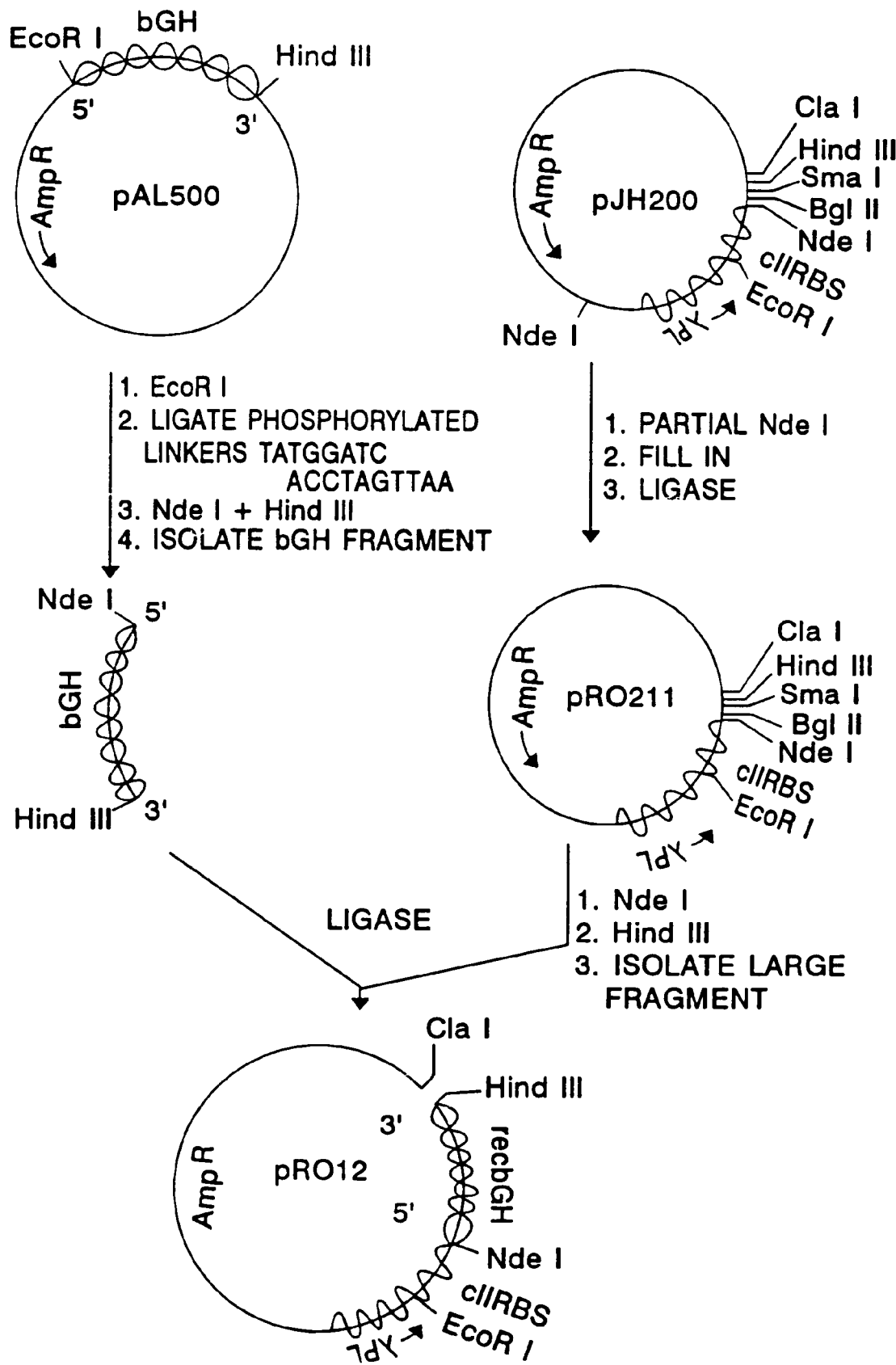

FIG. 35. Construction of plasmids pRO211 and pRO12

The plasmid pJH200 (deposited with the ATCC under Accession No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bovine growth hormone (bGH) fragment isolated from pAL500 (deposited with the ATCC under Accession No. 39782) to give pRO12. (The NdeI-HindIII fragment was produced from pAL500 by digesting it with EcoRI and ligating to the ends of the digestion product synthetic linkers with the sequence:

TATGGATC

ACCTAGTTAA

The ligation mixture was digested with NdeI and HindIII and the resulting NdeI-HindIII bGH fragment isolated).

Figure 36:
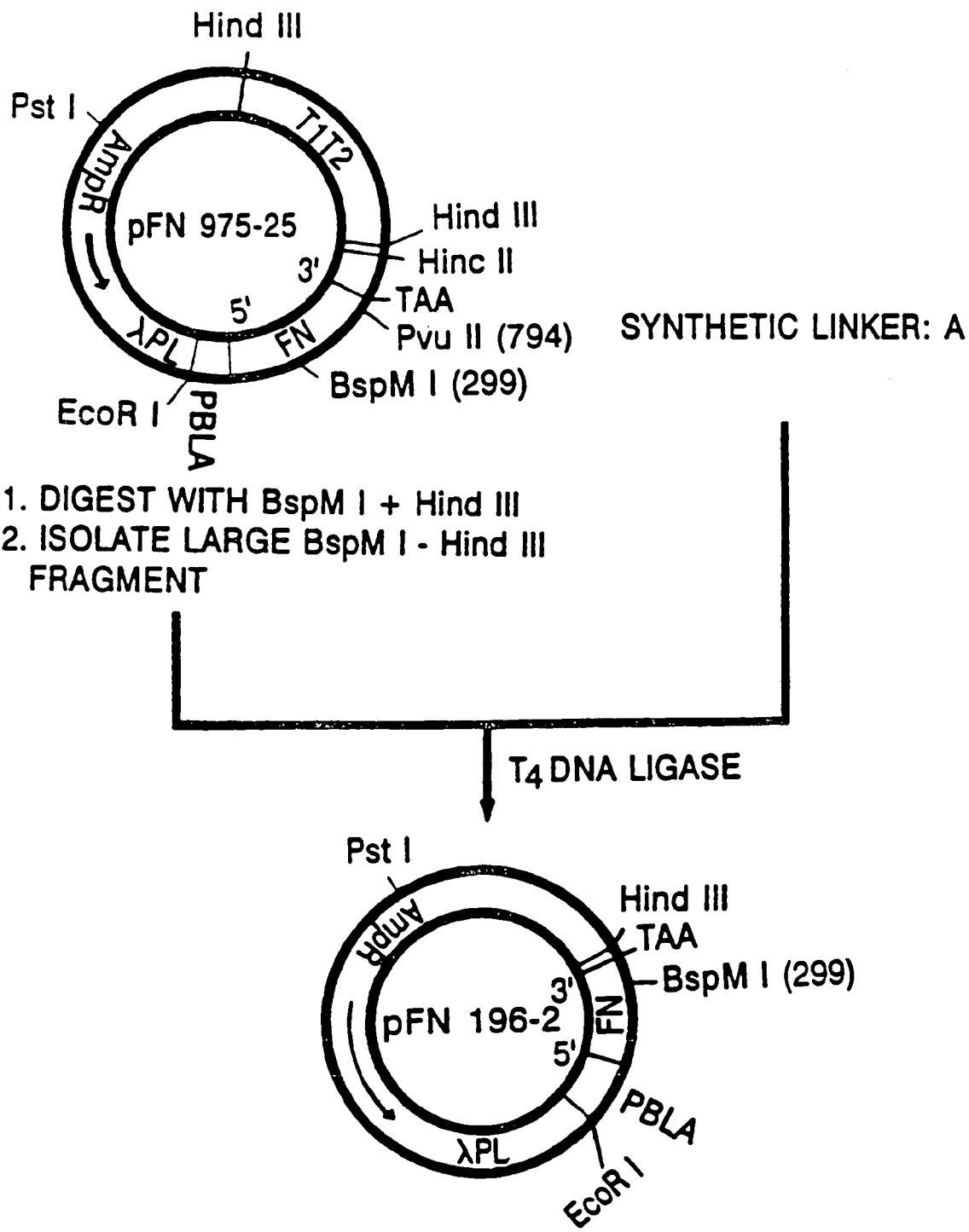

FIG. 36. Construction of plasmid pFN 196-2 which expresses the r12 kD FBD polypeptide The large BspMI-HindIII fragment obtained by digestion of plasmid pFN 975-25 (FIG. 10) with BspMI and HindIII was ligated by T4 DNA ligase to the synthetic pair of linkers A (see FIG. 41). Plasmid pFN 196-2 was produced, transformed into *Escherichia coli* strain A1645 and retransformed into *Escherichia coli* strain A4255. Plasmid pFN 196-2 contains the 5'-terminal sequence of fibronectin cDNA from nucleotide 14 to nucleotide 340, i.e., it encodes the first 109 amino acids of the FBD of fibronectin terminating with an arginin residue; it is not yet known if an additional N-terminal methionine is present in the final polypeptide. Plasmid pFN 196-2 gives good expression of an r12 kD FBD polypeptide under the control of the λ promoter and β-lactamase ribosomal binding site, and has been deposited in the ATCC under Accession No. 68328.

Figure 37:
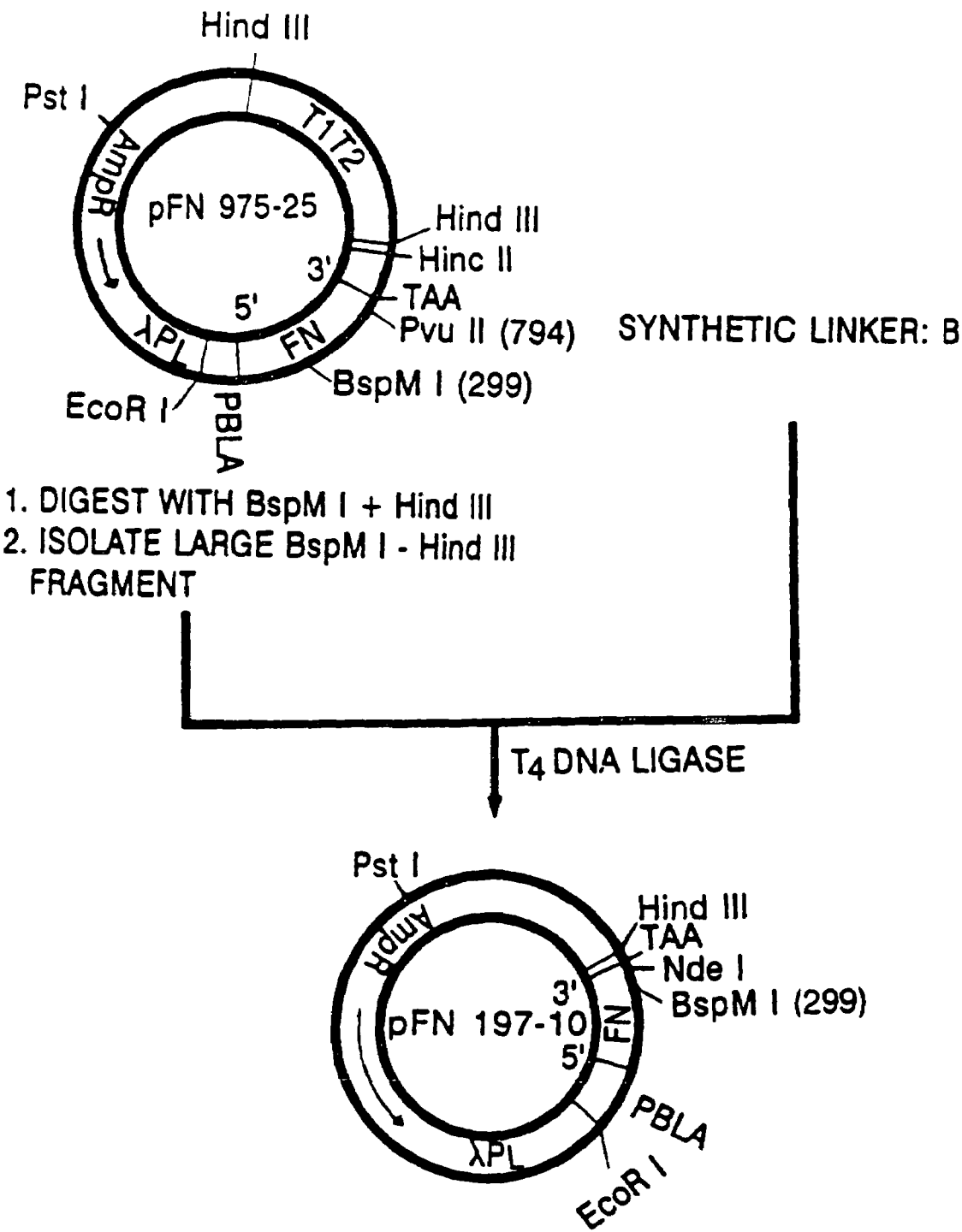

FIG. 37. Construction of plasmid pFN 197-10, which expresses a modified 12 kD FBD polypeptide (12kD')

Plasmid pFN 975-25 was treated as described in FIG. 36 except that a different pair of linkers, B (see FIG. 41) was used. The ligation produced plasmid pFN 197-10 which encodes the N-terminal sequence of the FBD of FN; however, a modification after nucleotide 340 to produce an NdeI site (CATATG) before the stop codon results in the encoding of a polypeptide containing 111 amino acids where the first 109 amino acids correspond to those of the r12 kD polypeptide followed by two additional amino acid residues, viz. histidine and methionine; it is not yet known if an additional N-terminal methionine residue is present in the final polypeptide. Plasmid pFN 197-10 was transformed into *Escherichia coli* strain A1645 and hence into *Escherichia coli* strain A4255, and gave good expression of a modified r12 kD (12 kD') FBD polypeptide under the control of the λ promoter and the β-lactamase ribosomal binding site.

Figure 38:
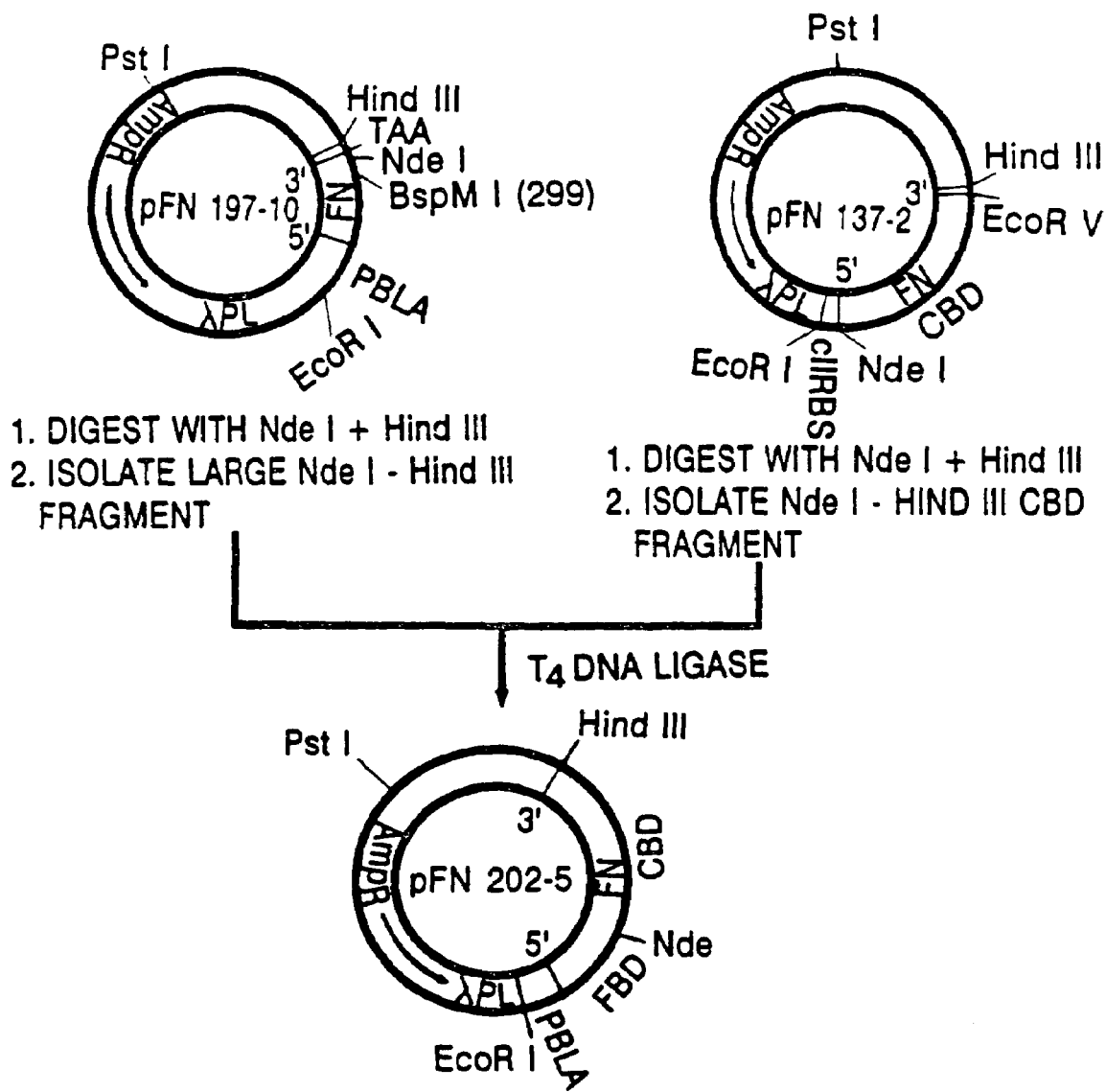

FIG. 38. Construction of plasmid pFN 202-5 which expresses r12 kD' FBD fused to the r33 kD cell binding domain (CBD) of fibronectin The large fragment produced after NdeI and HindIII digestion of plasmid pFN 197-10 (FIG. 37) was ligated by T4 DNA ligase to the NdeI-HindIII CBD (cell binding domain) fragment of plasmid pFN 137-2. Plasmid pFN 137-2, deposited in the ATCC under Accession No. 67910 has been described in the parent patent application, U.S. Ser. No. 345,952; the r33 kD CBD sequence contains amino acids numbered 1329–1722 of fibronectin (see FIG. 1) excluding the 90 amino acids numbered 1600–1689 encoded by the ED-A region (see preface to Brief Description of the Figures).

The resulting plasmid, pFN 202-5, was transformed into *Escherichia coli* strain A1645 and thence to *Escherichia coli* strain A4255. Plasmid pFN 202-5 contains the cDNA sequence of the 111 amino acids encoded by plasmid pFN 197-10 followed by the cDNA sequence for r33 kD CBD commencing with the codon for serine (the first amino acid of the r33 kD CBD). This plasmid gave good expression of an approximately 45 kD polypeptide comprising the r12 kD fibrin binding domain and the 33 kD cell binding domain of fibronectin; this fused polypeptide was expressed under the control of the A promoter and the β-lactamase ribosomal binding site.

Figure 39:
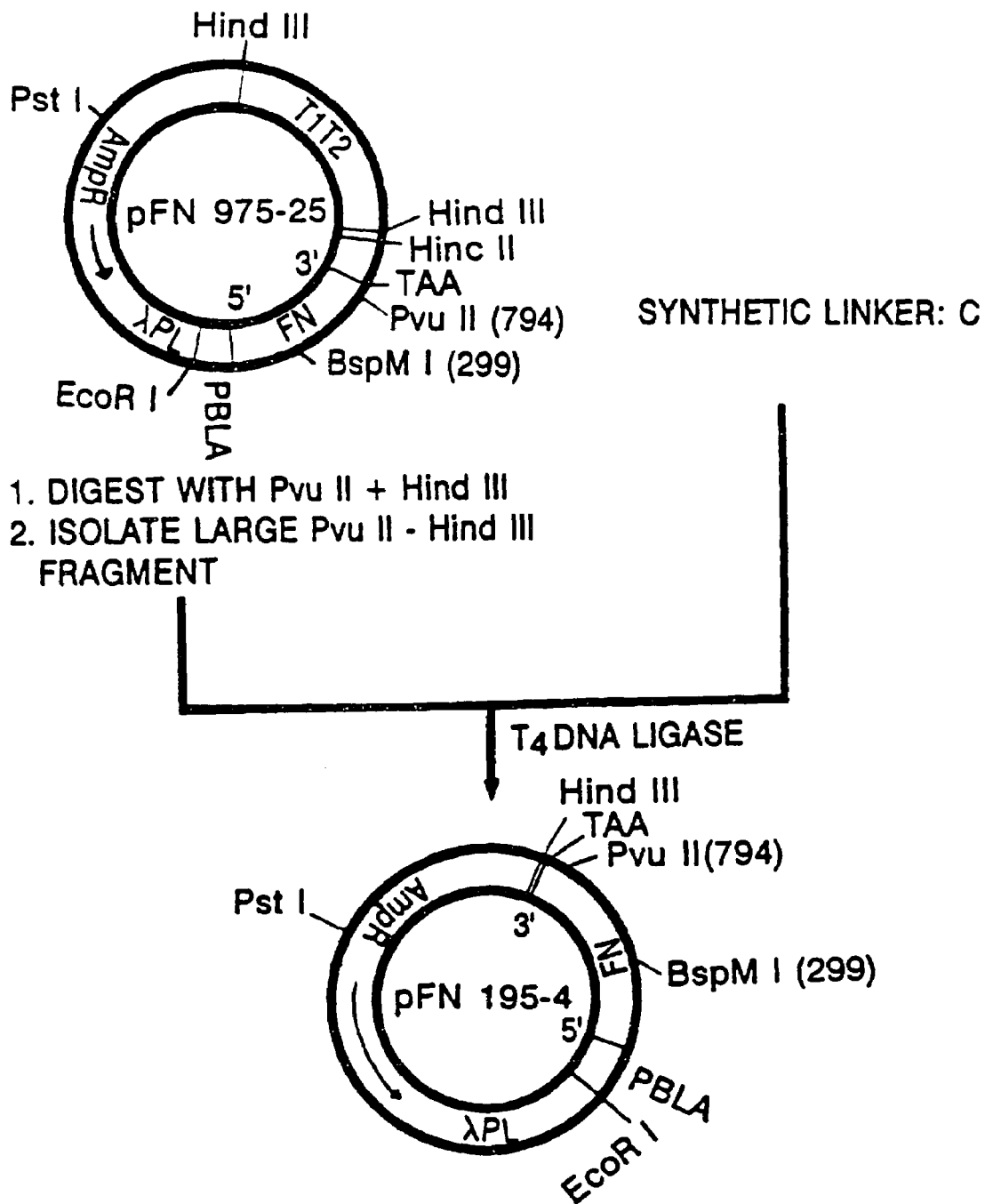

FIG. 39. Construction of plasmid pFN 195-4 which expresses the r31 kD FBD fused to the sequence DGRGDS The large fragment obtained by digestion of plasmid pFN 975-25 (FIG. 10) with PvuII and HindIII was isolated and ligated with T4 DNA ligase to a pair of synthetic linkers, C (see FIG. 41). The resulting plasmid, designated pFN 195-4 was transformed into *Escherichia coli* strain A1645 and thence to *Escherichia coli* strain A4255. Plasmid pFN 195-4 contains the full-length FBD cDNA sequence from nucleotide 14 to nucleotide 793 (encoding 260 amino acids) followed by a sequence encoding asp-gly-arg-gly-asp-ser, i.e., the polypeptide encoded has a total of 260 amino acids followed by the sequence DGRGDS; it is not known if an additional N-terminal methionine residue is present in the final polypeptide. Plasmid pFN 195-4 is a good expresser of the r31 kD fibrin binding domain fused to the sequence asp-gly-arg-gly-asp-ser (DGRGDS), under the control of the λ promoter and the β-lactamase ribosomal binding site.

Figure 40:
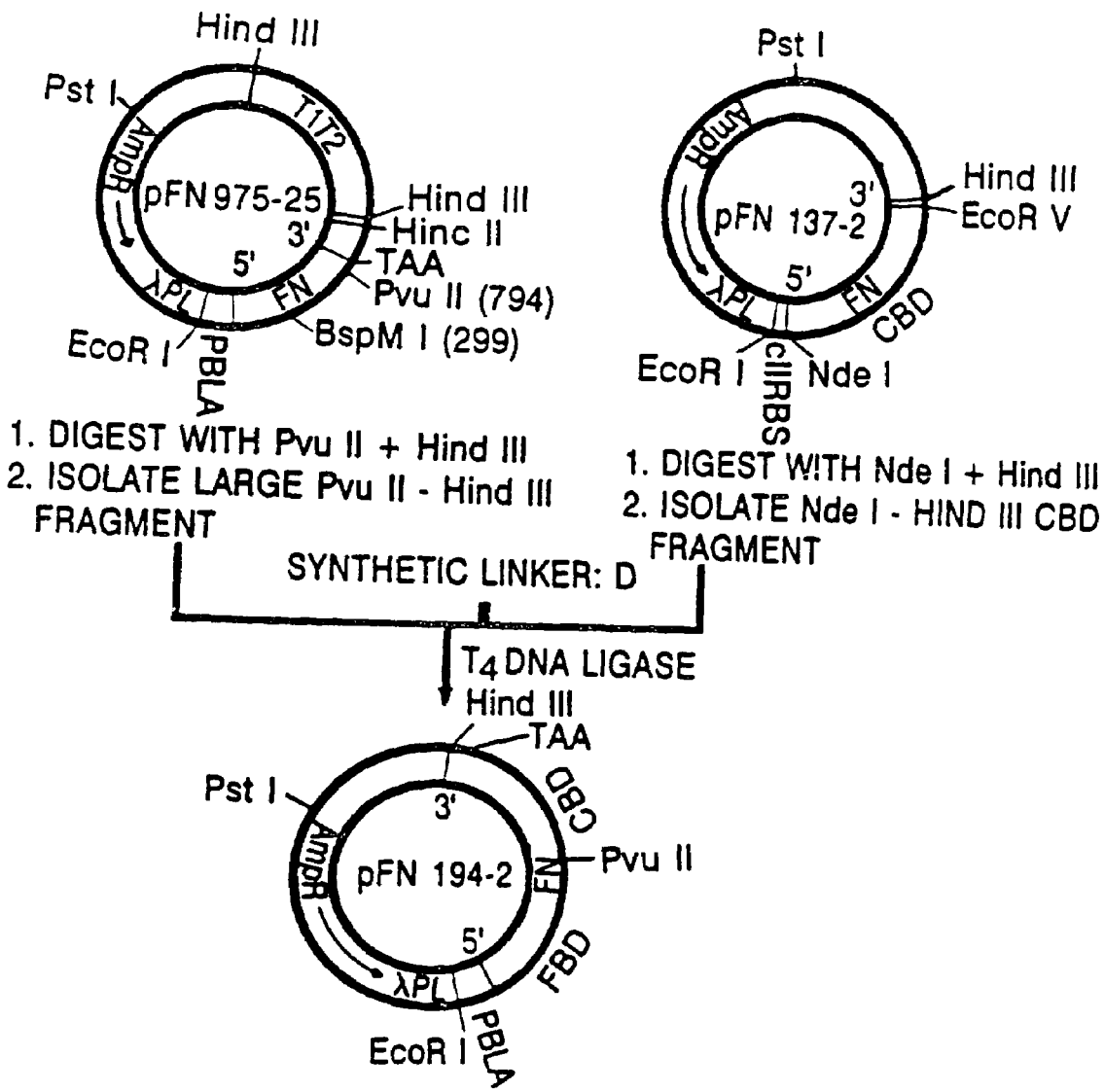

FIG. 40. Construction of plasmid pFN 194-2 which expresses a fused 31 kD FBD-33 kD CBD polypeptide The large PvuII-HindIII fragment produced by digestion of plasmid pFN 975-25 (FIG. 10) with PvuII and HindIII was isolated and ligated with T4 DNA ligase to a pair of linkers, D (FIG. 41) and then ligated to the cell binding domain (CBD) fragment obtained by digestion of plasmid pFN 137-2 (ATCC Accession No. 67910) with NdeI and HindIII; see FIG. 38 for definition of the CBD domain. The resulting plasmid, designated pFN 194-2, was transformed to *Escherichia coli* strain A1645 and thence to *Escherichia coli* strain A4255. Plasmid pFN 194-2 is a low expresser of a fused r31 kD FBD-r33 kD CBD polypeptide of approximate molecular weight 64 kD, under the control of the $\lambda P_L$ promoter and the β-lactamase ribosomal binding site. The polypeptide encoded by plasmid pFN 194-2 contains DNA encoding the first 265 amino acids of fibronectin fused to a methionine codon, followed by the cDNA sequence for the CBD of fibronectin, commencing at the codon for amino acid serine at position 1 of the CBD.

FIG. 41. Oligonucleotide linkers used in construction of plasmids

Four pairs of chemically synthesized oligomers (A, B, C and D) were prepared and were used to construct plasmids as described in FIGS. 36, 37, 39 and 40, respectively).

FIG. 42. Uptake of labeled r31 kD FBD by stainless steel coil-induced venous thrombi The bars and vertical brackets represent the mean±SEM (N=10) of the specific radioactivity associated with isolated thrombi, vein segments carrying the thrombus ("thrombi in-situ"), or peripheral blood samples 24 h after administration of $^{125}$I-31 kD FBD. For details, see Example 12, Section A.

Figure 43:
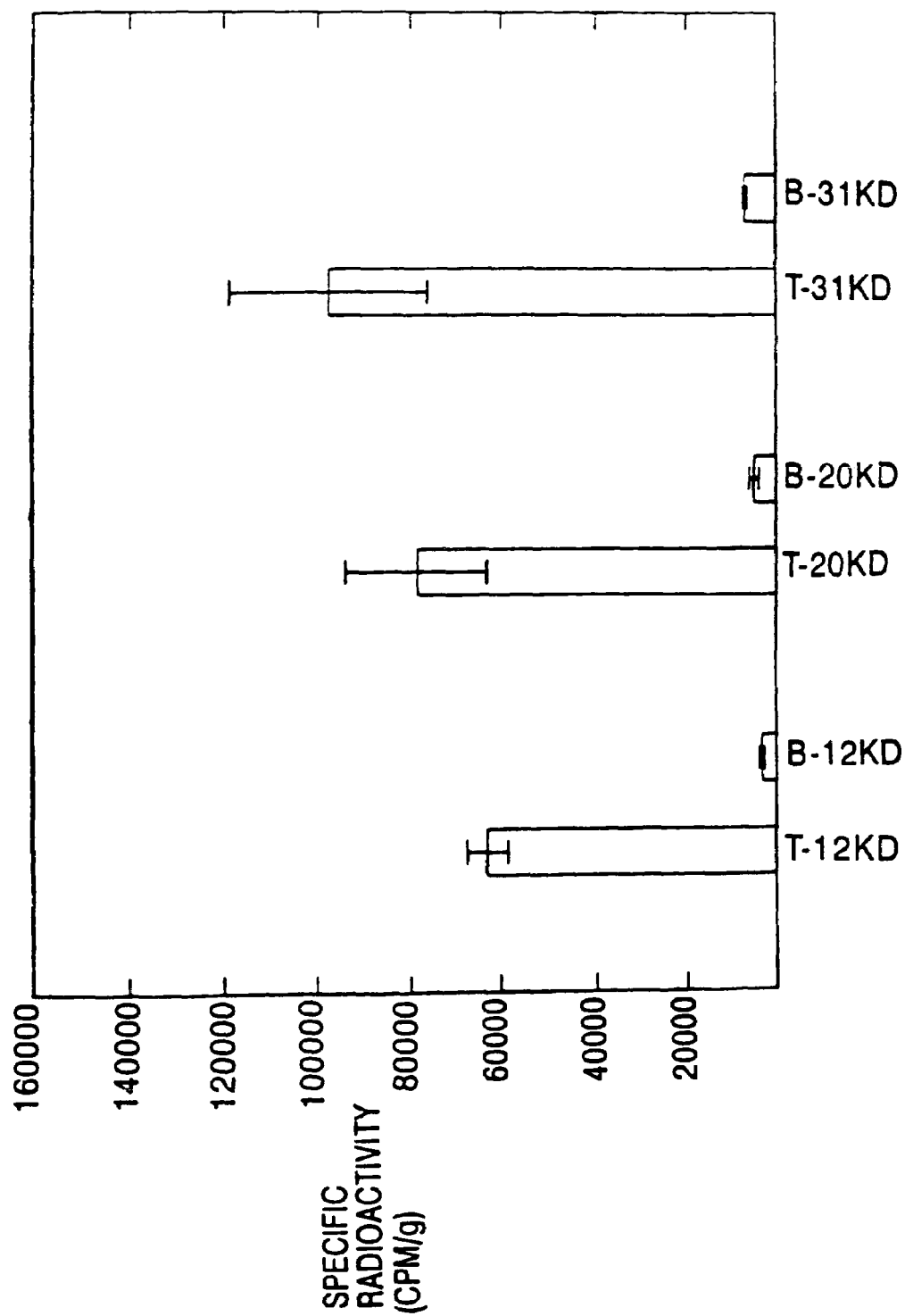

FIG. 43. Comparison of labeled r12 kD, r20 kD and r31 kD FBD polypeptides in the rat venous thrombus model The bars and vertical brackets represent the mean±SEM (N=5) of the specific radioactivity associated with isolated thrombi (T) or blood (B) 24 hours after administration of the $^{125}$I-labeled recombinant polypeptides, as indicated. For details, see Example 12, Section B.

Figure 44:
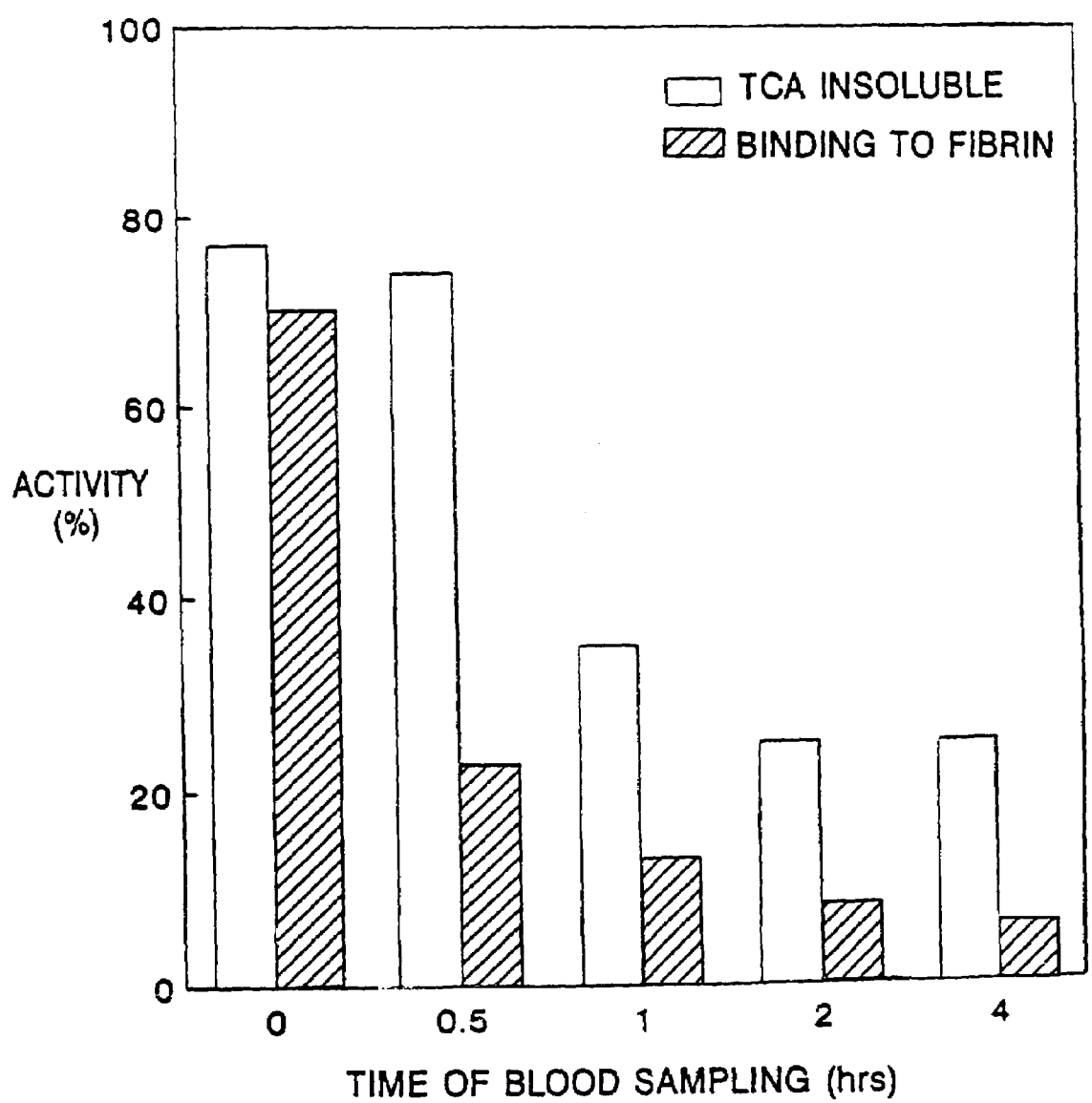

FIG. 44. Metabolic stability of $^{125}$I-labeled r31 kD FBD in rats

Rats were injected intravenously with $^{125}$I-r31 kD FBD ($5 \times 10^6$ cpm/rat) in a similar experiment to that described in FIG. 16. At the time intervals indicated blood samples were removed, placed in Na citrate containing tubes (final N-citrate concentration=0.38%) and blood aliquots resulting were directed as follows: either (a) treated with 20% TCA and the TCA insoluble counts (after TCA precipitation) were measured; or (b) incubated with preformed clot (using 20 μl whole blood from control rat); binding of the $^{125}$I-31 kD FBD to the preformed clot was measured under the conditions of the two-step reaction II (Example 11). The radioactivity was measured by a gamma counter and the activity of each sample was calculated as a percentage of total cpm present in the reaction mixture. (Normally TCA precipitation includes placing sample aliquots on filters which are counted for total cpm, washing the filter 3 times with 20% TCA followed by twice with 20% ethanol to extract TCA, and recounting filters for TCA insoluble counts whereby the percentage of TCA-insoluble counts can be calculated.)

Figure 45:
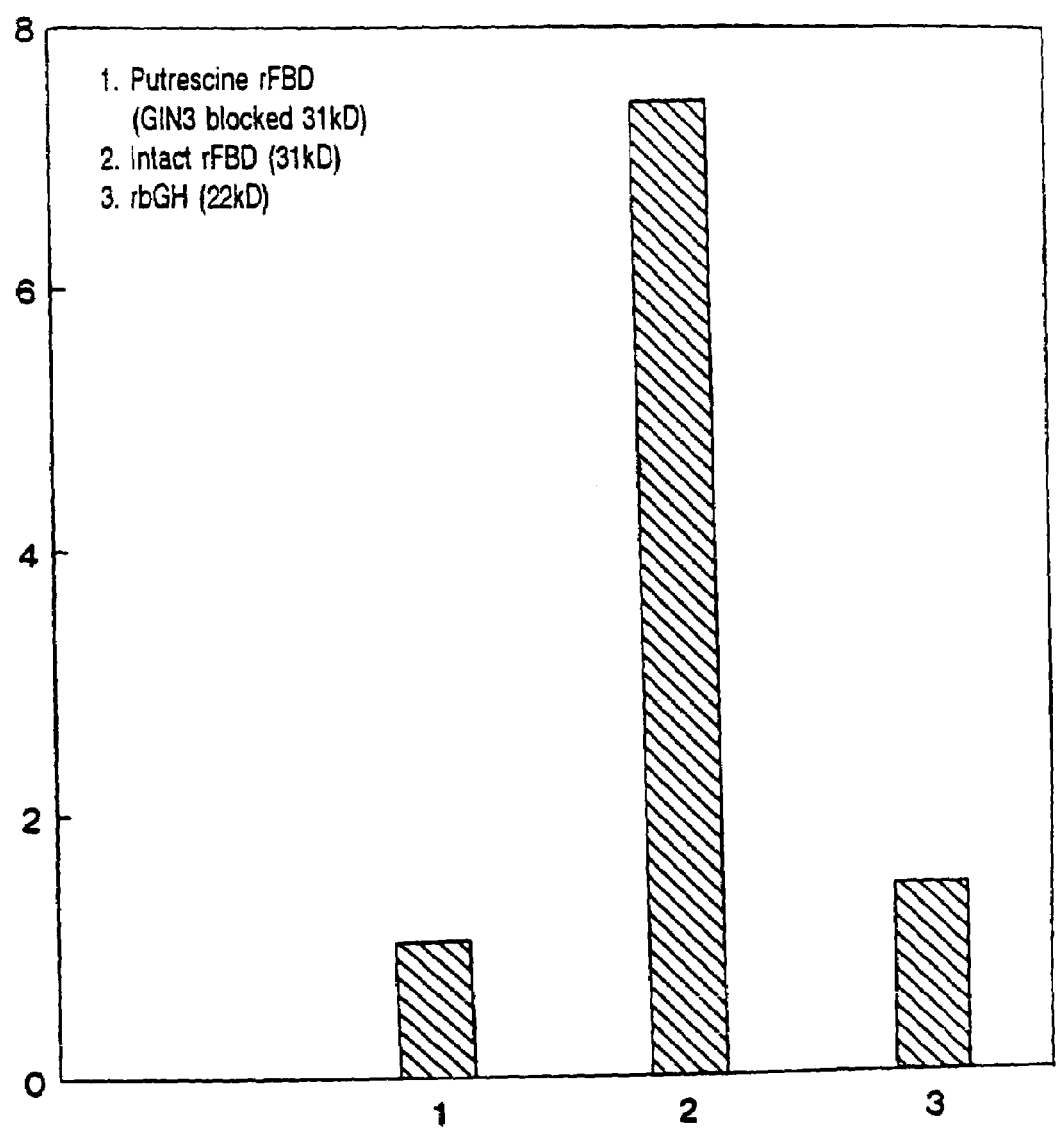

FIG. 45. Specificity of binding to fibrin: effect of transglutaminase on the binding of r31 kD to a fibrin clot The binding of $^{14}$C-putrescine-r31 kD, $^{125}$I-r31 kD FBD and $^{125}$I-recombinant growth hormone in the presence or absence of transglutaminase was tested as described in Example 11, B. The radioactivity of the washed fibrin pellet was measured using a β-counter for the $^{14}$C labeling and a gamma counter for the 125I labeling and the ratio of counts in the presence and absence of transglutaminase was calculated for each protein.

Figure 46B:
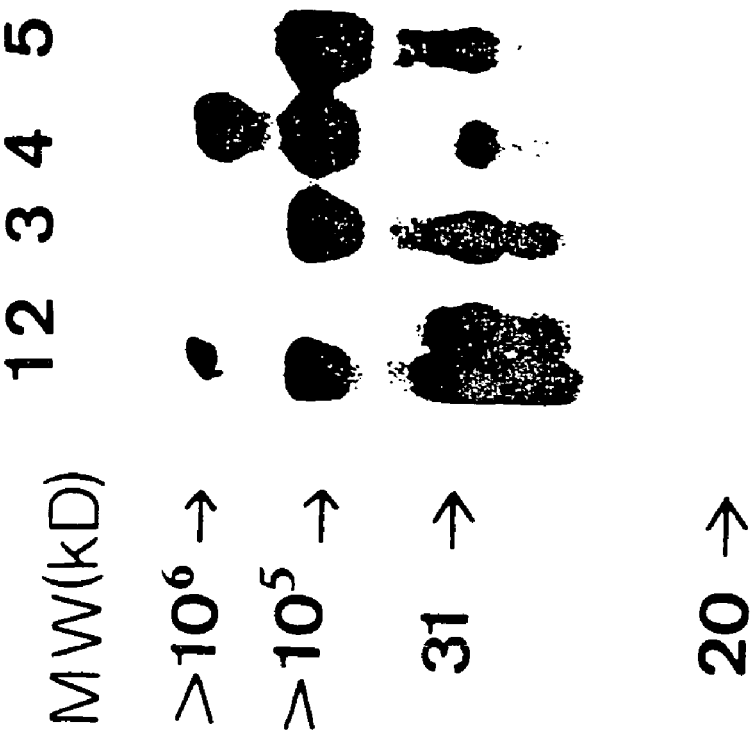
Figure 46A:
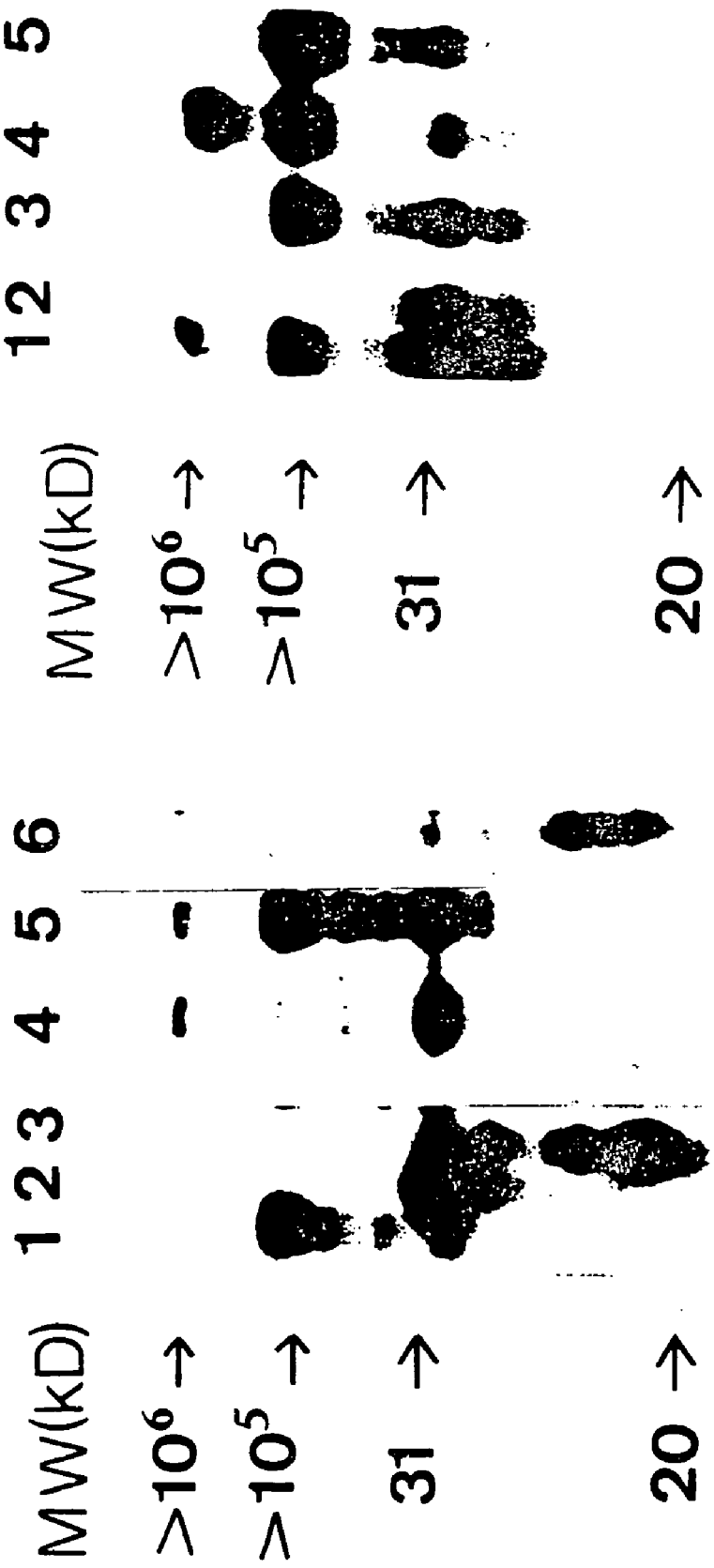

FIG. 46. Characterization of r31 kD FBD—fibrin complex by SDS polyacrylamide gel electrophoresis $^{125}$I-r31 kD FBD was incubated with preformed fibrin clot derived from either 20 μl whole human blood (A) or 250 μl of 0.8 μM solution of human fibrinogen (B). In one of the experiments (B) dental coils were added to the tubes together with the fibrinogen.

Binding of 125I-r31 kD fibrin clot was measured using the two step Reaction II as described in Example 11 using 0.15 μM $^{125}$I-r31 FBD in the presence of 5 μM CaCl$_2$. The reaction was terminated by washing three times with PBS and the pellet, after the various treatments described below, was centrifuged. 15 μl aliquots of the supernatant were electrophoresed in SDS-polyacrylamide gels (15% gel). An autoradiogram was developed which is shown in the figure. The tracks of the gel are as follows:

A. 1. plasmatic FN (220 kD)
   2. r31 kD FBD
   3. r31 kD FBD incubated for 1 hour with 2 units/ml plasmin (Sigma)
   4–6. Binding experiments with rFBD incubated with preformed fibrin clot derived from citrated whole blood.
   4. $^{125}$I-r31 kD—fibrin pellet was boiled in sample buffer for 10 minutes (Sample buffer=0.7 M β-mercaptoethanol/3% SDS/60 mM tris HCl, pH 6.8).
   5. Binding conditions as described above with the addition of 0.02 units/ml guinea-pig liver transglutaminase (Sigma); pellet treated as in 4.
   6. Binding conditions as described in (5); the pellet was incubated with 2 units/ml plasmin for 1 hour.

B. 1–3. Experiments with r31 kD FBD incubated with preformed fibrin clot derived from pure human fibrinogen in the presence of transglutaminase.
   1. Boiling of $^{125}$I-r31—FBD—fibrin pellets in sample buffer.
   2. Boiling of $^{125}$I-r31 kD—FBD—fibrin pellets in phosphate-saline buffer.
   3. Boiling of $^{125}$I-r31 kD—FBD—fibrin pellets in sample buffer plus 4 M urea.
   4–5. Experiments as B. 1–3 above, but clots were formed in the presence of dental coils. Coils containing the clots were removed to different tubes and then the binding of $^{125}$I-r31 kD to the clot was measured. The binding reaction was terminated by removal of the coils and analysis of the $^{125}$I-r31 kD—fibrin complex attached to the coils.
4. Boiling of $^{125}$I-r31 kD—FBD—fibrin pellet in sample buffer.
5. Boiling of $^{125}$I-r31 kD—FBD—fibrin pellet in sample buffer plus 4 M urea.

FIG. 47. Binding of $^{125}$I-r31 kD FBD to preformed fibrin clots: effect of fibronectin (FN) and heparin Experiments A and B were performed essentially as described for the two step Reaction II in Example 11.

A. Fibrin clots were formed during a 45 minute incubation period using 20 µl citrated whole blood, 5 mM CaCl$_2$, 1 unit/ml thrombin in a final volume of 250 µl. The fibrin pellets, after centrifugation, were placed in 200 µl PBS-5 mM CaCl$_2$ solution with or without purified plasma-derived FN (1 µM) and $^{125}$I-r31 kD FED (0.15 µM, specific activity 4×10$^5$ cpm/µg). The binding of $^{125}$I-r31 kD was determined after an additional incubation period of 30 minutes by measurement of radioactivity by a gamma counter.

B. Fibrin clots were formed as indicated in A. At the end of the first incubation period, 125I-r31 kD FBD (0.15 µM, specific activity 3×10$^4$ cpm/µg) was added together with various concentrations of heparin of average molecular weight 10,000 daltons (Laboratoire Choay, Paris, France; stock solution 5000 i.u./ml); the incubation was continued for an additional 30 minutes. The binding of $^{125}$I-r31 kD was then determined by measurement of radioactivity by a gamma counter.

Figure 48:
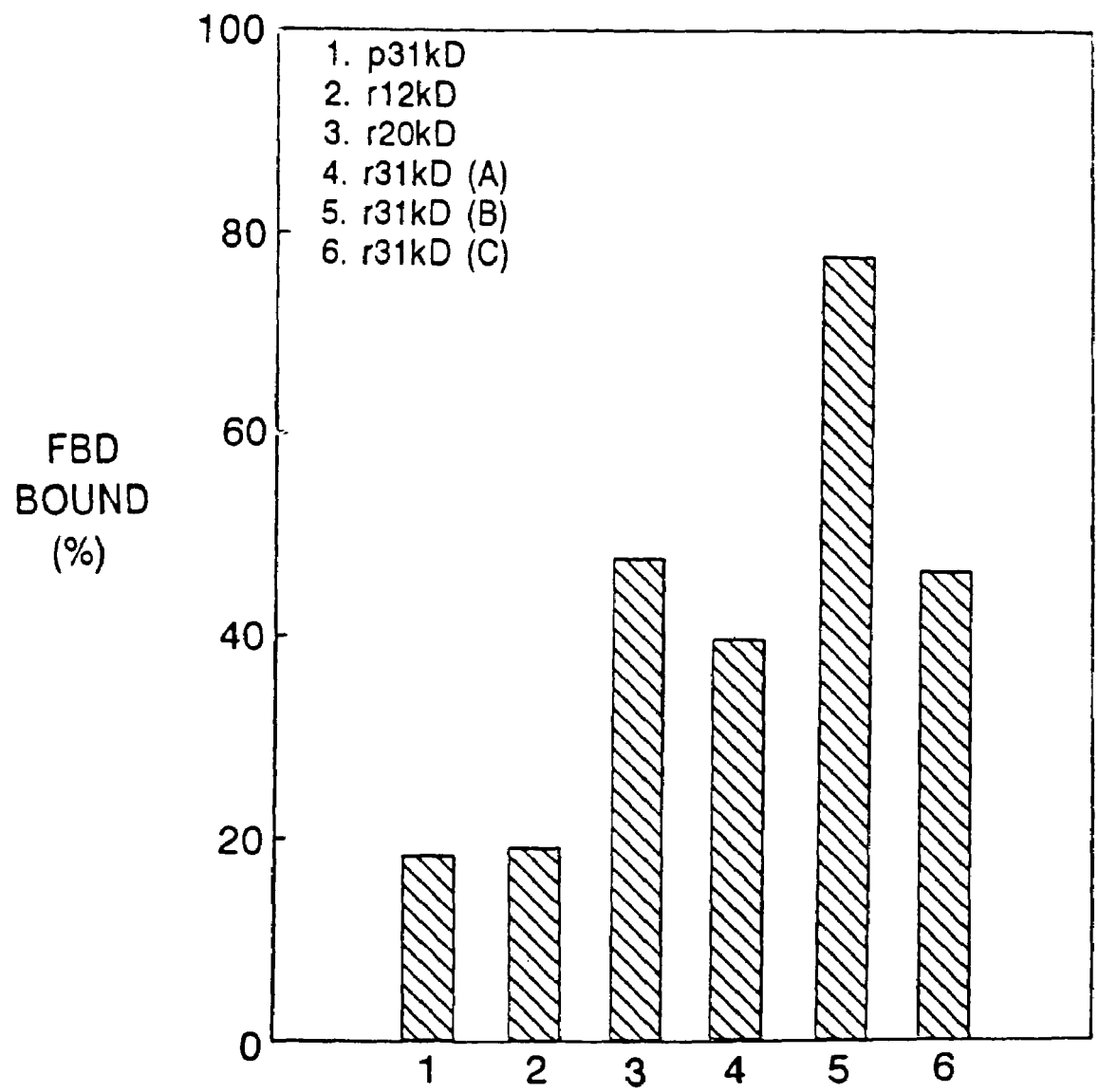

FIG. 48. Binding of fibrin binding domain polypeptides to the fibrin clot

This experiment was carried out essentially as described for the two-step Reaction II (Example 11). 0.15 µM $^{125}$-I of one of the fibrin binding domain polypeptides as indicated below was incubated at 37° C. with preformed fibrin clot derived from 20 µl citrated whole blood. The binding was measured in the presence of 5 mM CaCl$_2$ and 0.02 units/ml transglutaminase. The reaction was terminated, after a 45 minute incubation, by centrifugation; the pellet was washed three times with PBS and the radioactivity was measured in a gamma counter.
1. plasmatic 31 kD FBD (p31 kD)
2. r12 kD
3. r20 kD
4. r31 kD (Batch A)
5. r31 kD (Batch B)
6. r31 kD (Batch C)

Figure 49:
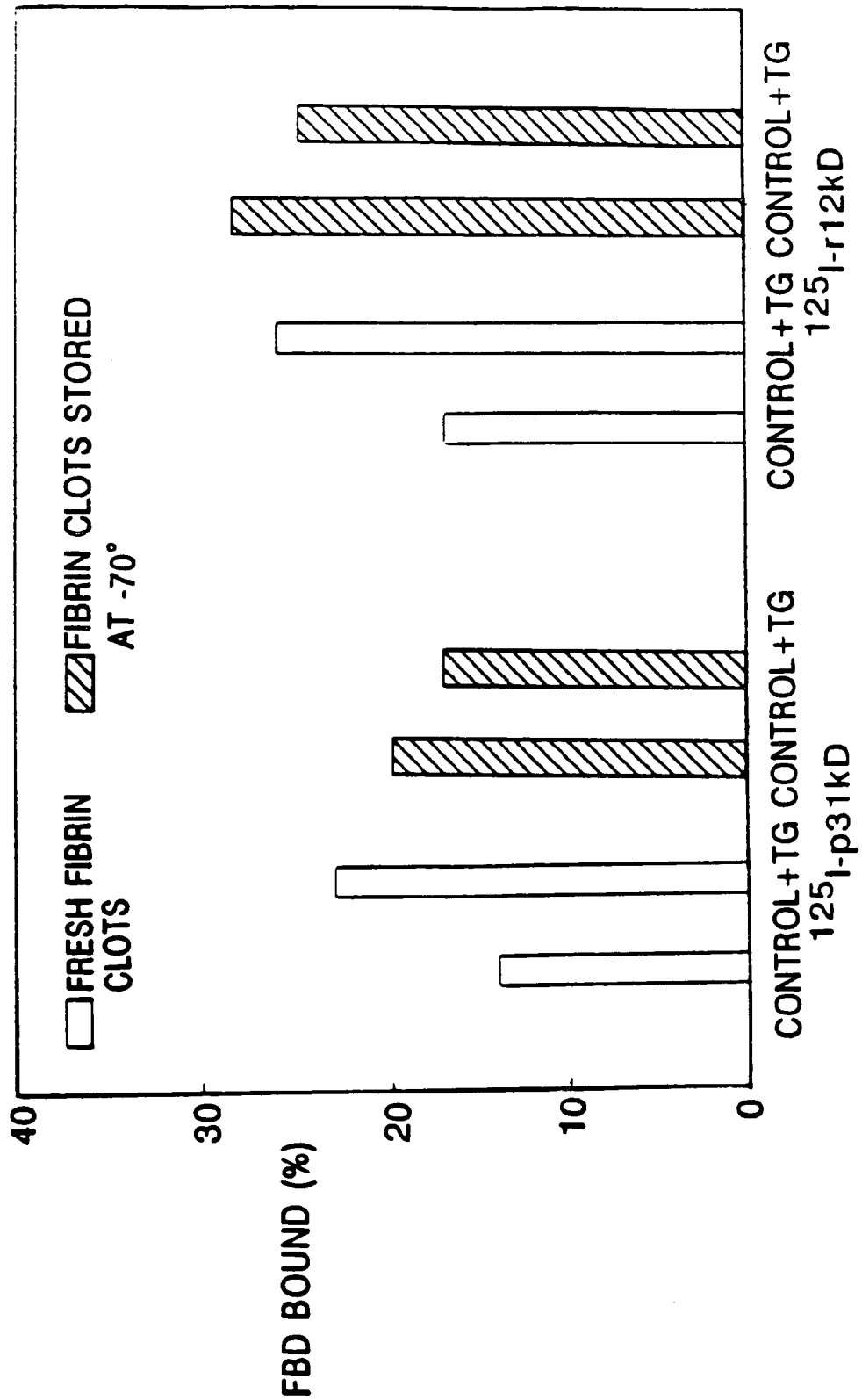

FIG. 49. Comparison of binding of $^{125}$I-r12 kD to fresh and frozen fibrin clots This experiment was carried out essentially as described for the two-step Reaction II (Example 11). Preformed fibrin clots derived from 20 µl citrated whole human blood were either frozen at −70° C. for 7 days (frozen clots) or used immediately after their formation (fresh clots).

The fibrin clots were incubated with 0.15 µM $^{125}$I-r12 kD in the presence or absence of 0.02 units/ml guinea-pig liver transglutaminase (Sigma). The binding to fibrin clots was measured as described in Example 11.

FIG. 50. Conditions for binding of $^{125}$I-r31 kD FBD to preformed clots

This experiment was carried out essentially as described for the two-step Reaction II (Example 11).

The fibrin clot was produced in citrated blood (A) and "naive" blood (B). The clots were incubated for the binding step at 37° C. in a final volume of 250 µl PBS with 0.15 µM $^{125}$I-rFBD and other constituents as indicated in the figure and below. The concentrations given are the final concentration in the reaction mixture.
1. Control (no added constituents)
2. 5 µM CaCl$_2$
3. 5 mM CaCl$_2$/2 units/ml hirudin (Sigma)
4. 5 µM CaCl$_2$/2 units/ml hirudin/0.02 units/ml transglutaminase
5. 5 mM CaCl$_2$/0.02 units/ml transglutaminase
6. 0.02 units/ml transglutaminase (All the exogenous transglutaminase used in the experiments described in this application was guinea-pig liver transglutaminase from Sigma).

Figure 51:
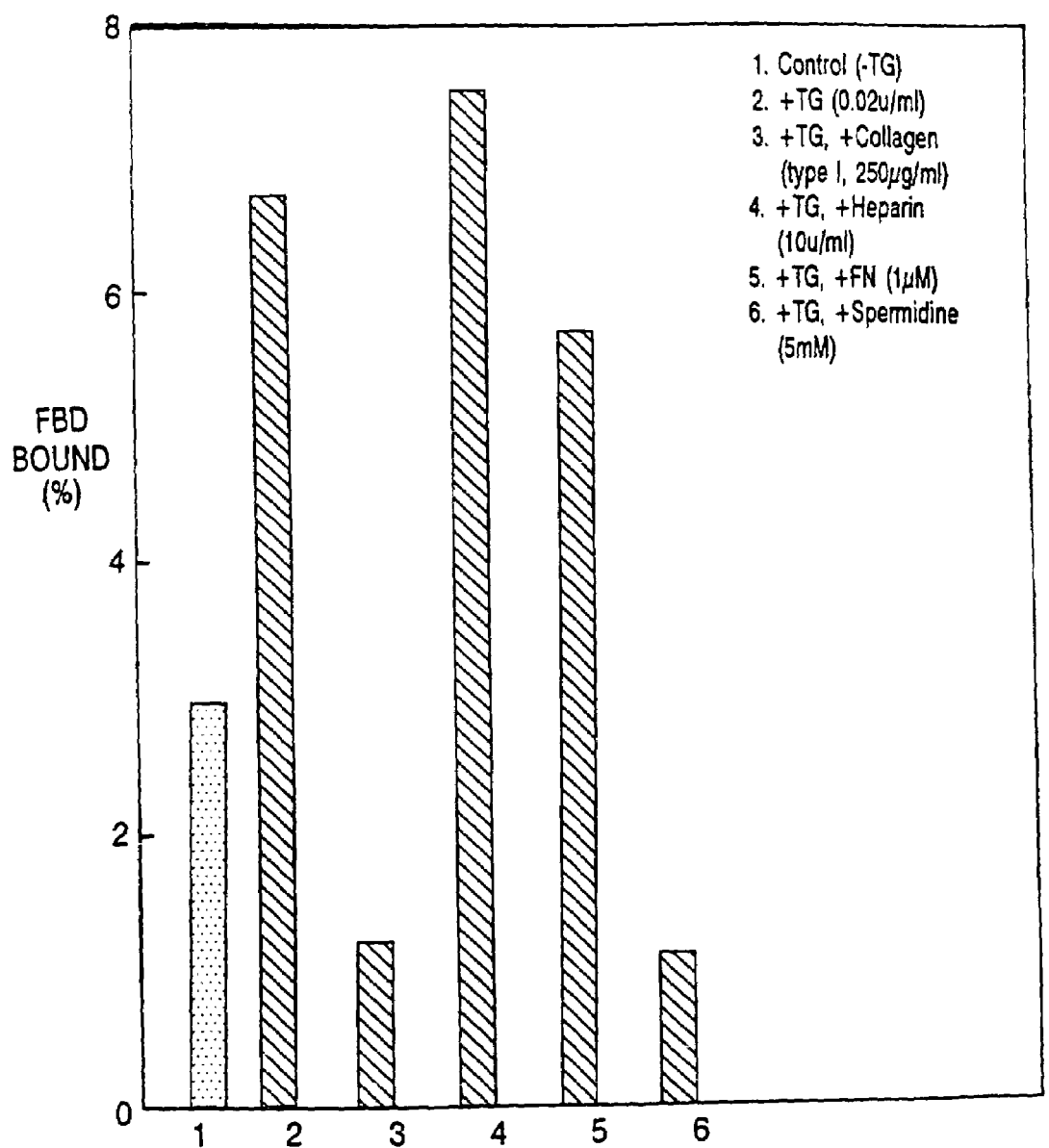

FIG. 51. Binding of $^{125}$I-r31 kD FBD to ECM in the presence of various constituents 0.3 µM of $^{125}$I-r31 kD FBD was incubated with extracellular matrix of endothelial cells (ECM) as described by Eldr et al. (20) in a 37° C. CO$_2$-incubator in the presence of saline, 3 mM CaCl$_2$ and 0.02 units/ml of guinea-pig liver transglutaminase (TG) and other constituents as indicated in the figure. The control was done in the absence of transglutaminase.

The reactions were terminated after 45 minutes by washing five times with PBS. Plates were extracted with a solution of 0.5% SDS and aliquots of the extracted material were measured in a gamma counter.

FIG. 52. Refolding and purification of the r20 kD polypeptide as monitored by elution profiles from a Superose 12 column (attached to a FPLC)

Aliquots of 200 µl of the r20 kD polypeptide at various stages of the refolding and purification process were injected on top of a Superose 12 column (attached to a FPLC). The column was equilibrated and eluted with a solution of 150 mM NaCl/20 mM Tris HCl, pH 7.8, at a flow rate of 0.8 ml/min. The lower trace is from the FPLC Controller LCC-500. A. Pellet of r20 kD polypeptide solubilized in 6 M Guanidine-HCl and reduced with 50 mM β-mercaptoethanol; B. Refolded and air-reoxidized r20 kD polypeptide; C. Q-Sepharose bound polypeptides, i.e., material which was separated from the purified r20 kD; D. Flow-through from the Q-Sepharose column; E. Flow-through from the Heparin-Sepharose column, i.e., material which was separated from the purified r20 kD; F. Purified 20 kD polypeptide (retention time=18.16 min), eluted from the Heparin-Sepharose column with 0.5 M NaCl. Note that there is no peak at this retention time of 18.16 min in Profile A, where the material is in reduced form, nor in Profiles C & E, which contain incorrectly folded forms of the 20 kD polypeptide.

FIG. 53. Refolding and purification of the r12 kD polypeptide as monitored by elution profiles from a Superose 12 column (attached to a Waters HPLC system)

Aliquots of 25–100 µl of the r12 kD polypeptide at various stages of the refolding and purification process were injected on top of a Superose 12 column (attached to a Waters HPLC system). The column was equilibrated and eluted with a solution of 150 mM NaCl/20 mM Tris HCl, pH 7.8, at a flow rate of 0.8 ml/min. A. Pellet of r12 kD polypeptide solubilized in 6 M Guanidine-HCl and reduced with 50 mM β-mercaptoethanol; B. Refolded and air-reoxidized r12 kD polypeptide; C. Q-Sepharose bound polypeptides, i.e., material which was separated from the purified r12 kD; D. Flow-through from both the Q- and Heparin-Sepharose columns (in this case, the columns were connected in series and the flow-through from the Q-Sepharose was therefore automatically loaded on the Heparin-Sepharose column), i.e., material which was separated from the purified r12 kD; E. Purified r12 kD polypeptide (retention time—18.83 min), eluted from the Heparin-Sepharose column with 0.5 M NaCl. Note that there is no peak at this retention time of 18.83 min in Profile A, where the material is in reduced form, nor in Profiles C & D, which contain incorrectly folded forms of the r12 kD polypeptide.

DETAILED DESCRIPTION OF THE INVENTION

The plasmids pFN 975-25, pFN 949-2, pFN 137-2, and pFN 196-2 were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 67832, 67831, 67910, and 68328 respectively. Similarly, many of the other ATCC deposits referred to in the subject application were also deposited pursuant to, and in satisfaction of, the requirements of the Budapest Treaty.

The fibrin binding domain of plasma fibronectin consists of five repetitive finger-like loops of 41–52 amino acids in length. Each loop has two adjacent intra-loop disulfide bonds, i.e. 4 cysteine residues per loop. This repeat structure is termed Type I homology (8).

The recombinant fibrin binding domain (FBD) polypeptides described in this application comprise either the full length fibrin binding domain (the r31 kD polypeptide) or smaller proteins (r20 kD and r12 kD polypeptides) of the fibrin binding domain. These smaller polypeptides are smaller than 31 kD and comprise part of the sequence of the fibrin binding domain. Many other polypeptides of the fibrin binding domain may be expressed by additional plasmids constructed, using methods known in the art, from plasmids described in this application and these polypeptides may be refolded, reoxidized, and purified using methods described in this application.

The full length recombinant fibrin binding domain (the r31 kD polypeptide) described in this application comprises the first 262 amino acids of fibronectin which the sequence arg-ala-ala-val at the carboxy-terminus. It is not yet known if an additional methionine residue is present at the amino terminus of the final polypeptide. The plasmatic fibrin binding domain derived by tryptic digestion of plasma fibronectin comprises the first 259 amino acids of fibronectin, i.e. with arginine at the carboxy-terminus.

The r31 kD polypeptide has five of the Type I homology loops discussed above (i.e. 10 disulfide bonds), the r20 kD polypeptide has three loops (i.e. 6 disulfide bonds), and the r12 kD polypeptide has two loops (i.e. 4 disulfide bonds). The presence of these disulfide bonds explains the necessity and also the difficulty of the refolding/reoxidation procedure developed to obtain and purify correctly folded FBD polypeptides which have the correct disulfide bonds. The correctly folded FBD polypeptides are biologically active, i.e. they can bind to fibrin and/or to *Staphylococcus aureus*.

The recombinant FBD polypeptides are produced in inclusion bodies which are contained in the pellet produced after disruption of the cell cake.

This invention discloses the production of recombinant fibronectin fibrin binding domain (FBD) polypeptides for use in thrombus imaging, prevention of thrombus formation, and prevention of bacterial infection. These polypeptides may also be bound to a thrombolytic agent for targeting the agent to a thrombus.

The recombinant cells which produce the FBD polypeptides can be any cells in which a DNA sequence encoding an FBD polypeptide has been introduced by recombinant DNA techniques. The cell must be capable of expressing the DNA sequence and producing the polypeptide product. The cell may be a mammalian cell, a fungal cell such as a yeast cell, or a bacterial cell.

The bacterial cell can be any strain including auxotrophic, prototrophic and lytic strains, $F^+$ and $F^-$ strains, strains harboring the cI857 repressor sequence of the $\lambda$ prophage and strains deleted for the deo repressors or the deo gene.

Examples of wild type *Escherichia coli* strains are prototroph ATCC No. 12435, and auxotroph MC1061 (ATCC Accession No. 67361).

Examples of *Escherichia coli* strains which harbor the $\lambda$ cI857 repressor sequence are the auxotrophs A1645 harboring plasmid pTVR 279-8 (ATCC No. 53216), A1637 harboring plasmid pTV 104(2) (ATCC No. 39384), and A2097 harboring plasmid pSODα2 (ATCC No. 39786), and the prototrophs A4255 harboring plasmid pFN 975-25 (ATCC No. 67832) and biotin-independent A4346 harboring plasmid pHG44 (ATCC No. 53218).

An example of a lytic *Escherichia coli* strain is A4048 which harbors plasmid pHG44 (ATCC No. 53217).

Examples of $F^-$ strains are *Escherichia coli* sϕ930 ($F^-$) harboring plasmid pMF 5534 deposited under ATCC No. 67703 and *Escherichia coli* W31100 ($F^-$) harboring plasmid pEFF 920 deposited under ATCC No. 67706.

Examples of *Escherichia coli* strains deleted for the deo gene or deo repressors are Sϕ732 harboring plasmid pMF 2005 (ATCC No. 67362), Sϕ540 harboring plasmid pJBF 5401 (ATCC No. 67359), and Sϕ930 harboring plasmid pEFF 920 (ATCC No. 67706) (see European Patent Application Publication No. 0303972, published Feb. 22, 1989).

The plasmids of this invention may be introduced into suitable bacterial host cells, preferably *Escherichia coli*. An example of a suitable *Escherichia coli* cell is strain A4255 ($F^+$) [ATCC Accession No. 67832], but other *Escherichia coli* strains and other bacteria can also be used as host cells for the plasmids. Such bacteria include *Pseudomonas aeruginosa* and *Bacillus subtilis*.

All of the *Escherichia coli* host strains described above can be "cured" of the plasmids they harbor by methods well known in the art, e.g. the ethidium bromide methods described by R. P. Novick in Bacteriol. Review 33: 210 (1969).

The bacterial cell may contain the FBD sequence encoding the FBD polypeptide in the body of a vector DNA molecule such as a plasmid. The vector or plasmid is constructed by recombinant DNA techniques so that the sequence encoding the FBD polypeptide is incorporated at a suitable position in the molecule.

Plasmids used for production of the FBD polypeptides can harbor a variety of promoters such as the $\lambda$ promoter or the deo promoters.

Among the plasmids which may be used for production of FBD polypeptides are the following:

a) Plasmid pFN. 975-25 which expresses the r31 kD FBD and which has been deposited in *Escherichia coli* strain A4255 in the ATCC under Accession No. 67832;

b) Plasmid pFN 949-2 which expresses the r20 kD FBD and which has been deposited in *Escherichia coli* strain A4255 in the ATCC under Accession No. 67831;

c) Plasmid pFN 196-2 which expresses the r12 kD FBD and which has been deposited in *Escherichia coli* strain A4255 in the ATCC under Accession No. 68328;

d) Plasmid pFN 197-10 which expresses a modified 12 kD FBD polypeptide, and which has been described in FIG. 37 of this application;

e) Plasmid pFN 195-4 which expresses the r31 kD polypeptide fused to the sequence DGRGDS, and which has been described in FIG. 39 of this application;

f) Any plasmid, derived from the above plasmids, containing FBD sequences encoded by the above plasmids; and g) Any plasmid which contains FBD sequences encoded by the above plasmids.

The subject invention provides an imaging agent which comprises a polypeptide labeled with an imageable marker, such polypeptide having an amino acid sequence substantially present in the fibrin binding domain of naturally-occurring human fibronectin and being capable of binding to fibin. Also provided is a composition comprising an effective imaging amount of such an imaging agent and a physiologically acceptable carrier.

The polypeptides which are labeled with an imageable marker may be, i.e., fragments of the fibrin binding domain of human fibronectin; they may be produced using recombinant DNA techniques; or they may be synthesized in a DNA synthesizer. Applicants have provided three examples of such polypeptides, with the preferred embodiment being the 12 kD polypeptide. As would be understood by one skilled in the art, the terms "having an amino acid sequence substantially present in the fibrin binding domain of naturally-occurring human fibronectin" encompasses, i.e., naturally-occurring allelic variations and recombinant variations, such as site-directed mutagenesis. These are all encompassed by applicants' "polypeptide", the only limitation being the ability to bind to fibrin.

The imageable marker used is a matter of choice to one skilled in the art. It is preferred that the marker be a radioactive isotope, an element which is opaque to X-rays, or a paramagnetic ion.

Radioactive isotopes are commonly used in medicine and are well known to those skilled in the art. It is presently preferred that the marker be indium-111, technetium-99m, iodine-123, iodine-125, iodine-131, krypton-81m, xenon-133, or gallium-67, or mixtures thereof. Most preferably, the marker is technetium or indium.

The detectable marker may also be a paramagnetic ion. Paramagnetic ions are also commonly used in medicine. Examples of such markers include chelated metal ions of chromium (III), manganese (II), iron (III), iron (II), cobalt (II), nickel (II), copper (II), praseodymium (III), neodymium (III), samarium (III), gadolinium (III), terbium (III), dysprosium (III), holmium (III), erbium (III), ytterbium (III), or mixtures thereof.

Preferably, the imaging agent comprises a polypeptide which is a 31 kD polypeptide corresponding to an amino acid sequence present in the fibrin binding domain and having the amino acid sequence of amino acids 1–262 as shown in FIG. 1, i.e. the full length, of the fibrin binding domain of human fibronectin; a 20 kD polypeptide corresponding to an amino acid sequence present in the fibrin binding domain of human fibronectin and having the amino acid sequence of amino acids 1–153 as shown in FIG. 1; the 20 kD polypeptide comprising less than about 20 additional amino acids; or a 12 kD polypeptide corresponding to an amino acid sequence present in the fibrin binding domain of human fibronectin and having the amino acid sequence of amino acids 1–109 as shown in FIG. 1.

The subject invention also provides a method for imaging a fibrin-containing substance, i.e. a thrombus or atherosclerotic plaque, which comprises contacting the fibrin-containing substance to be imaged with the agent as disclosed above under conditions such that the agent binds to the fibrin-containing substance and imaging bound agent and thereby imaging the fibrin-containing substance.

Further provided is a method for imaging a fibrin-containing substance in a subject which comprises:

(a) administering to the subject a composition of the agent as disclosed above under conditions permitting the imaging agent therein to enter the blood stream and bind to fibrin present in the blood vessels;

(b) imaging bound agent within the blood vessels; and thereby (c) imaging the fibrin-containing substance.

Preferably, the polypeptide of the reagent used in the above methods for imaging a fibrin-containing substance is a 31 kD polypeptide corresponding to an amino acid sequence present in the fibrin binding domain and having the amino acid sequence of amino acids 1–262 as shown in FIG. 1, i.e. the full length, of the fibrin binding domain of human fibronectin; a 20 kD polypeptide corresponding to an amino acid sequence present in the fibrin binding domain of human fibronectin and having the amino acid sequence of amino acids 1–153 as shown in FIG. 1; the 20 kD polypeptide comprising less than about 20 additional amino acids; or a 12 kD polypeptide corresponding to an amino acid sequence present in the fibrin binding domain of human fibronectin and having the amino acid sequence of amino acids 1–109 as shown in FIG. 1.

Preferred markers used in the above methods for imaging a fibrin-containing substance are radioactive isotopes, elements which are opaque to X-rays, or paramagnetic ions. Most preferred markers are radioactive isotopes, such as indium-111, technetium-99m, iodin -123, iodine-125, iodine-131, krypton-81m, xenon-133, and gallium-67.

Imaging may be done through any of the methods known to one skilled in the art. These methods include but are not limited to X-ray, CAT scan, PET scan, NMRI, and fluoroscopy. Preferably, the imaging of the fibrin-containing substance by the above methods is carried out using a gamma camera.

Further provided is a plasmid for expression of a polypeptide having an amino acid sequence substantially present in the fibrin binding domain of naturally-occurring human fibronectin and being capable of binding to fibrin comprising DNA encoding the polypeptide and DNA encoding suitable regulatory elements positioned relative to the DNA encoding the polypeptide so as to effect expression of the polypeptide in a suitable host cell.

Applicants have provided four examples of fibrin binding domain polypeptides. These include the p31 kD, r31 kD, r20 kD, and r12 kD polypeptides. These polypeptides exhibit the binding and adhesive properties of portions of naturally-occurring human fibronectin. The scope of the claims of the subject application are not intended to be limited to these four FBD polypeptides, which are examples of preferred embodiments only.

Three forms of the r31 kD fibrin binding domain polypeptide are defined in Example 5 as:

(a) the polypeptide as it is obtained from a washed pellet, after dissolution in 6 M GuCl, i.e. in "scrambled" form;

(b) the fully reduced polypeptide, present after treatment with a reducing agent such as GSH in the presence of 6 M GuCl; and (c) the reoxidized-refolded polypeptide, obtained by treatment with the GSH/GSSG as described in Example 5.

The "scrambled" r31 kD polypeptide is apparently improperly folded due to the formation of one or more incorrect disulfide bonds.

Unless otherwise stated, the r31 kD polypeptide described is correctly folded, i.e. form (c). Similarly, the 20 kD and 12 kD polypeptides may also occur in these three forms but the 20 kD and 12 kD polypeptides used in the experiments are correctly folded.

In preferred embodiments, the polypeptide is about a 31 kD polypeptide corresponding to an amino acid sequence present in the fibrin binding domain of human fibronectin; about a 20 kD polypeptide corresponding to an amino acid sequence present in the fibrin binding domain of human fibronectin; or about a 12 kD polypeptide corresponding to an amino acid sequence present in the fibrin binding domain of human fibronectin.

In more preferred embodiments, the polypeptide is a 31 kD polypeptide corresponding to an amino acid sequence present in the fibrin binding domain and having the amino acid sequence of amino acids 1–262 as shown in FIG. 1, i.e. the full length, of the fibrin binding domain of human fibronectin; a 20 kD polypeptide corresponding to an amino acid sequence present in the fibrin binding domain of human fibronectin and having the amino acid sequence of amino acids 1–153 as shown in FIG. 1; the 20 kD polypeptide comprising less than about 20 additional amino acids; or a 12 kD polypeptide corresponding to an amino acid sequence present in the fibrin binding domain of human fibronectin and having the amino acid sequence of amino acids 1–109 as shown in FIG. 1.

Naturally-occurring human fibronectin is as it occurs in the human body (in plasma).

As used throughout this application, a substantial portion is at least one fifth (⅕). A polypeptide which has the biological activity of the fibrin binding domain of naturally-occurring human fibronectin exhibits binding or adhesive properties similar to the fibrin binding domain of naturally-occurring human fibronectin when the level of such activity is assayed or determined.

In this invention, the amino acid sequence of the various functional domains are determined by cleavage of the cDNA which encodes the domains with restriction enzymes, and do not necessarily correspond to the amino acid sequence of the domains as obtained and defined by proteolytic digestion of fibronectin.

The plasmid of this invention further comprises suitable regulatory elements positioned relative to the DNA encoding the polypeptide so as to effect expression of the polypeptide in a suitable host cell, such as promoters and operators, e.g. $\lambda\ P_L O_L$, ribosomal binding sites, e.g. $C_{11}$, and repressors. Other suitable regulatory elements include, for example, the lac, trp, tac, lpp and deo promoters (European Patent Application Publication No. 0303972, published Feb. 22, 1989).

The suitable regulatory elements are positioned relative to the DNA encoding the polypeptide so as to effect expression of the polypeptide in a suitable bacterial host cell. In preferred embodiments of the invention, the regulatory elements are positioned close to and upstream of the DNA encoding the polypeptide.

The invention provides a plasmid designated pFN 975-25 and deposited in *Escherichia coli* strain A4255 (F+) under ATCC Accession No. 67832. Plasmid pFN 975-25 encodes a 31 kD polypeptide of the fibrin binding domain of human fibronectin comprising amino acids 1–262.

Further provided is a plasmid designated pFN 949-2 and deposited in *Escherichia coli* strain A1645 under ATCC Accession No. 67831. Plasmid pFN 949-2 encodes a 20 kD polypeptide of the fibrin binding domain of human fibronectin comprising amino acids 1–153 and less than 20 additional amino acids.

Also provided is a plasmid designated pFN 196-2 and deposited in *Escherichia coli* strain A4255 under ATCC Accession No. 68328, Plasmid pFN 196-2 encodes a 12 kD polypeptide of the fibrin binding domain of human fibronectin comprising amino acids 1–109.

In presently preferred embodiments, the invention provides an *Escherichia coli* cell containing the plasmid designated pFN 975-25 and wherein the cell is deposited under ATCC Accession No. 67832; an *Escherichia coli* cell containing the plasmid designated pFN 949-2 and wherein the cell is deposited under ATCC Accession No. 67831; and an *Escherichia coli* cell containing the plasmid designated pFN 196-2 and wherein the cell is deposited under ATCC Accession No. 68328.

The invention provides a method of producing a polypeptide having an amino acid sequence substantially present in the fibrin binding domain of naturally-occurring human fibronectin and being capable of binding to fibrin which comprises treating a cell containing a plasmid comprising DNA encoding the polypeptide so that the DNA directs expression of the polypeptide and recovering from the cell the polypeptide so expressed.

Preferably, the polypeptide so produced is a 31 kD, 20 kD, or 12 kD polypeptide of the fibrin binding domain.

Further provided is a purified polypeptide substantially free of other substances of human origin which has an amino acid sequence substantially present in the fibrin binding domain of naturally-occurring human fibronectin and being capable of binding to fibrin.

Preferably, the polypeptide is a 31 kD polypeptide corresponding to an amino acid sequence present in the fibrin binding domain and having the amino acid sequence of amino acids 1–262 as shown in FIG. 1, i.e. the full length, of the fibrin binding domain of human fibronectin; a 20 kD polypeptide corresponding to an amino acid sequence present in the fibrin binding domain of human fibronectin and having the amino acid sequence of amino acids 1–153 as shown in FIG. 1; the 20 kD polypeptide comprising less than about 20 additional amino acids; or a 12 kD polypeptide corresponding to an amino acid sequence present in the fibrin binding domain of human fibronectin and having the amino acid sequence of amino acids 1–109 as shown in FIG. 1.

The invention further provides such a purified polypeptide substantially free of other substances of human origin fused to a second polypeptide, the second polypeptide comprising a substantial portion of the amino acid sequence of the cell binding domain of naturally-occurring human fibronectin.

Preferably, the fused polypeptide is a 45 kD fused polypeptide, wherein the purified polypeptide is a 12 kD polypeptide and the second polypeptide which comprises a substantial portion of the cell binding domain of naturally-occurring human fibronectin is a 33 kD polypeptide. The fused polypeptide may also comprise a 31 kD purified polypeptide and a second polypeptide which contains the amino acid sequence GRGDS. Another preferred fused polypeptide is a 64 kD fused polypeptide, wherein the purified polypeptide is a 31 kD polypeptide and the second polypeptide which comprises a substantial portion of the cell binding domain of naturally-occurring human fibronectin is a 33 kD polypeptide.

The invention also provides a plasmid for expression of the 45 kD fused polypeptide, disclosed above, designated pFN 202-5; a plasmid for expression of the 31 kD/GRGDS fused polypeptide, disclosed above, designated pFN 195-4; and a plasmid for expression of the 64 kD fused polypeptide, disclosed above, designated pFN 194-2.

As used throughout the subject application, "fused" or "bound" encompasses polypeptides bound covalently, non-covalently, or conjugated. The polypeptides may be conjugated through other chemical moieties including amino acid or polypeptide cross-linkers, which are standardly used in the art and are well-known to those skilled in the art to which the subject invention pertains.

This invention further provides a method of treating a subject susceptible to, or afflicted with, a bacterial infection which comprises administering to the subject an amount of any of the disclosed polypeptides effective to prevent or treat the bacterial infection. The susceptibility to bacterial infection may be due to the presence of a catheter or an implant in the subject.

Numerous methods are known in the art for detection of thrombi, such as radioactive labeling (nuclear medicine use of isotopes), radio-opaque labeling (such as CAT scan), and Magnetic Resonance Imaging (MRI). Any of these labeling methods can be used in the method of the subject invention for detecting the thrombus. In each of these detection methods the polypeptide is used as a diagnostic agent for detecting the thrombus.

The invention provides a coated medical device comprising a medical device and the polypeptides of the fibrin binding domain of naturally-occurring human fibronectin applied as a coating to the surface of the medical device. Examples of medical devices which may be coated include catheters, medical implants (such a hip replacement and prostheses), tubings and syringes.

The invention provides a method of minimizing risk of bacterial infection associated with use of medical devices, preferably a catheter, which comprises:
(a) applying the polypeptide of the fibrin binding domain of fibronectin as a coating to a surface of the device; and
(b) employing the resulting coated device rather than an uncoated device.

The invention also provides a method of minimizing risk of bacterial infection associated with the use of medical devices which comprises employing a device coated with the polypeptides disclosed in the subject application rather than an uncoated device.

Also provided is a method of refolding and reoxidizing a polypeptide having an amino acid sequence substantially present in the fibrin binding domain of naturally-occurring human fibronectin and being capable of binding to fibrin which comprises contacting the polypeptide with a thiol-containing compound and a disulfide so as to refold and reoxidize the polypeptide.

Preferably, the thiol-containing compound is selected from the group consisting of glutathione, thioredoxin, β-mercaptoethanol, and cysteine.

Preferably, the thiol-containing compound is β-mercaptoethanol and the disulfide is produced in situ by introduction of air.

Preferably, the polypeptide is selected from the group consisting of a 31 kD polypeptide, a 20 kD polypeptide and a 12 kD polypeptide.

The method of refolding and reoxidizing may additionally comprise contacting the polypeptide with a denaturant. Preferred denaturants are guanidine hydrochloride and urea.

Preferably, the polypeptide is at a low concentration, such as below 600 µg/ml.

The subject invention also provides a method for recovering a purified biologically active polypeptide having an amino acid sequence substantially present in the fibrin binding domain of naturally-occurring human fibronectin and being capable of binding to fibrin from a cell in which the polypeptide has been produced by means of expression of a plasmid containing DNA encoding the polypeptide which comprises:
(a) disrupting the cell so as to produce a lysate containing the polypeptide;
(b) centrifuging the lysate so as to concentrate the polypeptide;
(c) separating the concentrated polypeptide;
(d) solubilizing the separated, concentrated polypeptide;
(e) refolding and reoxidizing the solubilized polypeptide;
(f) separating the refolded and reoxidized polypeptide; and
(g) recovering the purified, refolded and reoxidized polypeptide.

Preferably, the refolding and reoxidizing comprises contacting the polypeptide with a thiol-containing compound and a disulfide so as to refold and reoxidize the polypeptide. Preferably, the thiol-containing compound is selected from the group consisting of glutathione, thioredoxin, β-mercaptoethanol, and cysteine.

In one preferred embodiment, the thiol-containing compound is β-mercaptoethanol and the disulfide is produced in situ by introduction of air.

Preferably, the polypeptide is selected from the group consisting of a 31 kD polypeptide, a 20 kD polypeptide and a 12 kD polypeptide.

The method may additionally comprises contacting the polypeptide with a denaturant, such as guanidine hydrochloride or urea.

Preferably, the polypeptide is at a low concentration, such as below 600 µg/ml.

Preferably, the separating of the concentrated polypeptide in step (c) comprises chromatography, preferably Heparin-Sepharose chromatography.

The subject invention also provides a method of inhibiting thrombus formation in a subject susceptible to thrombus formation which comprises administering to the subject an amount of a polypeptide (selected from the polypeptides and fused polypeptides disclosed above) effective to inhibit thrombus formation. The polypeptide may be reduced or alternatively the S—H groups may be blocked (e.g. by carboxyamidation to prevent reoxidation).

The subject invention also provides a polypeptide as disclosed above bound to a thrombolytic agent for targeting of thrombolytic agents. The thrombolytic agents may be selected from tissue plasminogen activator (TPA), urokinase, streptokinase, prourokinase, Anisoylated Plasminogen-Streptokinase Activator Complex (Eminase™), TPA analogs, or a protease.

Further provided is a method for achieving thrombolysis of a thrombus which comprises administering to a subject an amount of the polypeptide bound to a thrombolytic agent effective to achieve thrombolysis.

EXAMPLES

All the references to map positions correspond to the identically numbered positions along the nucleotide sequence of human fibronectin cDNA shown in FIG. 1 (see also FIG. 3 of Baralle, F. E., European Patent Publication No. 207,751, published Jan. 7, 1987).

This patent application is directed to polypeptides of the N-terminus fibrin binding domain (FBD). Some of the proteins described are fusion proteins comprising an FBD fragment joined at its C-terminus to a fragment of the cell binding domain (CBD).

The cDNA sequence corresponding to the CBD which applicants have cloned and expressed is missing the 270 bp extra domain (ED) segment which extends from nucleotides 4812 to 5081, inclusive, on the Baralle map (see FIG. 1). Thus, the cDNA sequence which is said to extend from nucleotide 3317 to 5566 on the Baralle map, contains only 1980 nucleotides, because it is missing the 270 nucleotides of the ED segment, namely from nucleotides 4812 to 5081 inclusive; this region is also known in the art as the ED-A region; concomitantly amino acid 1690 is changed from alanine to threonine. Similarly, the polypeptide expressed by that DNA fragment would encode from amino acid 1102 to amino acid 1851 on the Baralle map but would be missing the 90 amino acids encoded by the ED region, namely amino acids 1600–1689 inclusive, and thus it would contain only 660 amino acids. This is true for all CBD fragments described in this application which span the ED region. (The region known in the art as the ED-B region is missing both in Baralle's sequence and in applicants' cDNA.)

The EcoRI cleavage site shown at position 3317 was constructed by applicants during the cloning procedure by use of EcoRI linkers. This GAATTC sequence at positions 3313 to 3318 differs in 1 nucleotide from the corresponding Baralle sequence GATTC. This introduces a single nucleotide change C to A at nucleotide 3315. This changes the corresponding amino acid from Thr to Asn.

Example 1

Preparation of a Fibronectin cDNA Library

A cDNA library was prepared in λgt11 from poly A+ mRNA isolated from human liver according to the published procedures (13,14). The cDNA fragments were cloned using EcoRI linkers and the cDNA library was screened for fibronectin (FN) positive plasmids using the following synthetic DNA probes.

Probes for Cell Binding Domain (CBD):

| Probes for cell binding domain (CBD): | |
|---|---|
| Probe | Nucleotides |
| (3') CACTCTATAATGTCCTAGTGAATGCCT CTTTGTCCTCC | (4355–4392) |
| (3') AGAATCTCCTTCTGTCTTTTGTCCAGA ACTAAG | (3967–3999) |
| (3') CCGGTTGTTAGTTGTCAAAGACTACAA GGCTCCCTGGACC | (4200–4239) |

Probes for N-Terminal Fibrin Binding Domain (FBC):

| Probes for N-terminal fibrin binding domain (FBD): | |
|---|---|
| (3') GGGGGTCGGAGGGATACCGGTG ACACAGTGTCTTAA | (817–850) |
| (3') CGACGGGTGCTCCTTTAGACGT GTTGGTTACTTCCCCAGTAC | (1310–1340) |

A series of FN cDNA clones covering the entire region of fibrin, collagen, heparin and cell binding domains was identified and isolated (FIG. 32). The cDNA fragments were subcloned into the Eco R1 site of pBR322.

The mRNA of FN is alternatively spliced and therefore different length cDNA's have been reported in the literature. Applicants' cDNA corresponding to the cell binding domain has a 270 base pair deletion from base 4811 to base 5080 on the FN physical map (the complete non spliced cDNA).

Example 2

Expression and Purification of Fibrin Binding Domain (FBD) Polypeptides

A. Expression of a partial FBD 20 kD polypeptide

The FN cDNA clones obtained as described in Example 1 and depicted in FIG. 32, did not include DNA encoding amino acids 1–190 of the FN molecule. These amino acids are part of the FBD. The DNA corresponding to nucleotides 14 to 472 and coding for amino acids 1–153 (FIG. 1A) was constructed by ligation of 7 pairs of chemically synthesized nucleotides (FIGS. 2A, 2B and 3). The synthetic DNA fragment was designed to contain an ATG initiation codon at the 5' end as well as convenient restriction sites for introduction into various expression vectors. To enable further manipulation of the DNA sequence coding for the FBD, nucleotide number 19, thymidine (T) was changed to adenine (A), thereby eliminating a DdeI restriction site without altering the amino acid sequence. (The site of the nucleotide change is denoted by an asterisk in linker #1 shown in FIG. 2A.) The various steps for the cloning of the above synthetic DNA fragment into pBR322 plasmid vector digested with EcoRI and BamHI are described in FIG. 3. The plasmid obtained was designated pFN 932-18. The DNA fragment coding for the first 153 N-terminal amino acids of fibronectin from plasmid pFN 932-18, was inserted into pTV 301, a λ $P_L$ expression vector, between the NdeI and BglII sites replacing the DNA sequence coding for human growth hormone (hGH) in plasmid pTV 301 (FIG. 4).

The resulting plasmid, pFN 949-2, was deposited with the American Type Culture Collection under Accession No. 67831. Plasmid pFN 949-2 was used to transform *Escherichia coli* prototroph A4255. These transformed *Escherichia coli* cells were found to express the partial FBD polypeptide in amounts comprising about 5% of the total cellular proteins. The polypeptide has a mobility of about 20 kD on reduced SDS polyacrylamide gels as determined from the mobility of the size markers. The polypeptide comprises the first 153 amino acids of fibronectin followed by 4 amino acids coded for by a synthetic linker and then several amino acids resulting from readthrough into the pBR322 vector, i.e., a total of 153 amino acids plus less than 20 additional amino acids, if the additional N-terminal methionine is present. Throughout this specification the polypeptide is referred to as the r20 kD polypeptide or the r20 kD FBD.

B. Expression of a "complete" FBD polypeptide

In order to obtain expression of the entire FBD polypeptide containing amino acids 1 to 262 the following plasmids were constructed:

1. Insertion of Termination Codon TAA at the 3' end

A synthetic oligonucleotide containing a TAA termination codon and a BglII site having the following sequence:

5'CTGTTTAA<u>TAA</u>GCA
3'GACAAATTCGTCTAG was ligated to the 3' end of an EcoRI-PvuII fragment isolated from FN cDNA clone p931-5 and to a pBR322 vector digested with EcoRI and BamHI as described in FIG. 5. The plasmid obtained was designated pFN935-12.

2. Subcloning of Carboxy Terminal Region of FBD in a λ $P_L$ Expression Vector

An EcoRI-HincII DNA fragment coding for the carboxy terminal region of the FBD was isolated from plasmid pFN935-12 and ligated to plasmid pTV 194-80 digested with EcoRI and SmaI as described in FIG. 6. The plasmid obtained was designated pFN 946-12.

3. Syntheses and Cloning of DNA Corresponding to Nucleotides 468–599 of FN

Three pairs of chemically synthesized nucleotides were ligated to an EcoRI-DdeI FN fragment isolated from plasmid pFN932-18 (FIG. 3) in the presence of pUC19 vector DNA (purchased from GIBCO BRL Co.) digested with EcoRI and XbaI as described in detail in FIG. 7. The plasmid obtained was designated pFN 948-4.

4. Construction of a Plasmid Encoding the Complete FBD Region

In order to construct a plasmid which codes for the entire FBD, amino acid 1 to amino acid 262, an EcoRI-XbaI DNA fragment coding for FN was isolated from plasmid pFN948-4 and inserted into plasmid pFN 946-12 digested with EcoRI and XbaI as described in FIG. 8. The plasmid obtained was designated pFN-957. This plasmid contains the complete coding sequence for FBD but does not express the FBD polypeptide as it lacks a ribosomal binding site (RBS).

5. Expression of the FBD Under λ $P_L$ Promoter and cII RBS

An NdeI-HindIII fragment containing the FBD coding region and the $T_1T_2$ transcription terminators was isolated from plasmid pFN-957 and inserted into plasmid pTV 301 (FIG. 33) digested with NdeI and HindIII as described in FIG. 9. The resulting plasmid, designated as pFN 962-3, directs the expression of a FBD polypeptide under the control of λ $P_L$ promoter and cII ribosomal binding site. *Escherichia coli* strains A1645 and A4255 transformed with this plasmid expressed only small amounts of the FBD polypeptide. The expression of the FBD polypeptide was detectable only by Western blot analysis using polyclonal antibodies directed against human plasma derived FN.

6. Expression of an FBD Polypeptide Under the λ $P_L$ Promoter and the β-Lactamase Promoter and Ribosomal Binding Site As the level of expression of the FBD polypeptide obtained with plasmid pFN 962-3 was low, we added a DNA fragment coding for the β-lactamase promoter and β-lactamase RBS (PBLA). The DNA fragment coding for PBLA was isolated from plasmid pBLA11 (ATCC Accession No. 39788) and inserted into plasmid pFN 962-3 digested with NdeI, filled in with Klenow enzyme and digested with EcoRI as described in FIG. 10. The plasmid obtained, designated pFN 975-25, was deposited with the American Type Culture Collection under ATCC Accession No. 67832. This plasmid was used to transform *Escherichia coli* prototroph A4255 (F+).

These *Escherichia coli* cells were found to express the "complete" FBD polypeptide at levels comprising about 5–8% of the total cellular proteins. The polypeptide migrated on SDS-PAGE gels with an apparent molecular weight of 31 kD, hence it is referred to as the 31 kD polypeptide or the r31 kD FBD.

C. Fermentation and Growth Conditions

The clone expressing the r31 kD FBD polypeptide was fermented in rich medium (yeast extract and casein hydrolysate) containing ampicillin. Growth was carried out at 30° C. Expression was obtained upon induction at 42° C. for 2 hours, and subsequently bacterial cell cake containing the r31 kD FBD polypeptide was obtained. Similarly, the clone expressing the r20 kD FBD was fermented and bacterial cell cake containing the r20 kD FBD polypeptide was obtained.

D. Refolding and purification of recombinant fibrin binding domain (r31 kD) Polypeptide The process is made up of three stages:
1. Crude processing of the bacterial cake.
2. Refolding/reoxidation.
3. Purification.

1. Crude Processing

The cake is disrupted first in 5 volumes of 50 mM Tris-HCl/50 mM Na-EDTA, pH 8 (Buffer 1); the pellet is then treated with 1.2 volumes of Buffer 1 containing 100 mg/liter lysozyme (2 hours agitation at 37° C.). Triton X 100 is added to the resulting suspension (to 1%), and after 30 min. at room temperature the suspension is centrifuged and the pellet is resuspended and washed twice with water. All these steps are performed by disruption of the pellet and centrifugation and the 31 kD stays in the pellet, as evidenced from SDS-PAGE gels.

The washed pellet is suspended in 14 volumes of 10 mM Tris-HCl/5 mM EDTA/2 mM PMSF/2 mM 6-aminocaproate, pH 7.5 (Buffer A) and then treated successively with Buffer A containing: 1% decyl sulfate, 1% decyl sulfate/5% glycerol and 5% glycerol. The final treatment is with Buffer A without additives.

2. Refolding/Reoxidation

Principle: To dissolve the pellet in 6M guanidine-HC1-GuC1—in the presence of a thiol reducing agent, such as glutathione—GSH—and to refold/reoxidize at a lower GuCl concentration by the addition of oxidized glutathione-GSSG.

The washed pellet from step 1 above is dissolved in 150–700 volumes of 6M GuCl/3 mM GSH in Buffer A. The concentration of GuCl is lowered gradually, i.e., first 2 M, then 1 M and 0.5 M, while keeping the concentration of all other components constant, except for the volume, which at this stage is brought to 500–1000 fold higher than that of the pellet. At one of the intermediate concentrations of GuC1, i.e., between 0.5 and 2 M, refolding is initiated by the addition of 0.3 mM of GSSG and incubation at room temperature for 24–48 hours. The refolded 31 kD is then dialyzed against Buffer A without additives.

3. Purification

Concentration: The large volume of refolded 31 kD is first centrifuged to remove the insoluble pellet that contains no 31 kD and is then dialyzed against Tris-HCl, pH 7.8, before being concentrated and initially purified on a Heparin-Sepharose column.

Example 3

Bacterial Binding Activity

Experiments have been performed on the binding of r31 kD FBD to bacterial suspensions of *Staphylococcus aureus*. Identical binding curves were obtained for radio-iodinated intact plasma fibronectin, the proteolytic 31 kD amino terminal fragment (p31 kD) derived from human plasma fibronectin, and r31 kD FBD.

The inhibition of bacterial binding by [$^{125}$I] p31 kD indicated that the recombinant 31 kD FBD competes with the authentic proteolytic fragment.

The bacterial binding activity of the r31 kD FBD is described in more detail in Example 7, Section II: Bacterial Binding Activity.

Example 4

Inhibition of Bacteria Adhesion

To estimate the capacity of r31 kD FBD to interfere with the adherence of bacteria to the extracellular matrix in wounds, a competition assay was developed. In this assay, adherence of *Staphylococcus aureus* to a plastic surface coated with fibronectin and the interference of FBD with adherence were measured. Both authentic FBD and r31 kD FBD were active in inhibiting bacterial adhesion to the fibronectin coated surface.

Example 5

Refolding and Purification of Recombinant 31 kD Fibrin-Binding Polypeptide of Fibronectin The following is an improved procedure for the purification of the recombinant 31 kD fibrin-binding domain polypeptide (r31 kD) produced as described in Example 2.

The process is made up of three stages:
1. Crude processing of the bacterial cake.
2. Refolding/reoxidation.
3. Purification.
1. Crude processing
1.1 Washing of the pellet: The bacterial cell cake is disrupted first in 5 volumes of 50 mM Tris-HC1/50 mM Na-EDTA, pH 8 (Buffer 1). The pellet is then successively treated with Buffer 1 containing 100 mg/liter lysozyme (2 hours at 37° C.), Buffer 1 containing 1% Triton X-100 (30 minutes at room temperature) and twice with water. All these steps are performed by disruption of the pellet and centrifugation; the r31 kD stays in the pellet, as evidenced from SDS-PAGE gels.
1.2 Extraction of the pellet: The washed pellet is suspended in 14 volumes of 10 mM Tris-HC1/5 mM EDTA/2 mM PKSF/2 mM epsilon-aminocaproate (Buffer A) pH 7.5, and then treated successively with Buffer A containing: (a) 1% decyl sulfate; (b) 1% decyl sulfate/5% glycerol; and (c) 5% glycerol. The final treatment is with Buffer A without additives.
2. Solubilization and Refolding/Reoxidation A refolding/reoxidation procedure for the recombinant 31 kD polypeptide (r31 kD) has been developed and refined.
2.1 Principle: To dissolve the pellet in 6 M guanidine-HCl (GuCl) in the presence of a thiol reducing agent, such as glutathione (GSH) and to refold/reoxidize at a lower GuCl concentration by the addition of oxidized glutathione (GSSG).
2.2 Procedure: The extracted pellet is dissolved in 100–700 volumes of 6 M GuCl/3 mM GSH in Buffer A, pH 8.0. The concentration of GuCl in the dialysis buffer is lowered gradually, e.g., first 3 M, then 1.5 M and finally 0.5 M, while keeping the concentration of all other components constant. At one of the intermediate concentrations of GuCl, i.e., between 2 M and 1 M, refolding is initiated by the addition of 0.3 mM of GSSG and incubation at pH 8 at room temperature for 48–72 hours. The refolded r31 kD is then dialyzed against Buffer A at pH 8.5, without additives.

Example: Approximately 10 grams of extracted pellet (see 1.2) were homogenized and dissolved in 1 liter of Buffer A/6 M GuCl/3 mM GSH/pH 8 and the suspension was stirred for 14 hours until it was a clear solution. This solution was dialyzed for 24 hours against four liters f Buffer A which additionally contained 3 mM GSH and 3 M GuCl, pH 8. Subsequently, the resulting solution was dialyzed for 24 hours against 8 liters of Buffer A containing 3 mM GSH, pH 8. The resulting solution was dialyzed twice against 10 liters of Buffer A containing 0.3 mM GSH and 0.3 mM GSSG, pH 8. The process of dialysis, during which reoxidation also occurred, lasted approximately 80 hours. Finally, the glutathione was removed from the refolded protein by dialysis against 10 liters of Buffer A, pH 8.3–8.5. This step was performed twice. Subsequently, the solution was loaded on a phenyl-Sepharose column.
2.3 Alternative procedure: Similar results have been obtained when cysteine (3 mM) was used instead of glutathione and cystine (0.3 mM) instead of oxidized glutathione.
2.4 Use of thioredoxin: Attempts were also made to increase the rate of reoxidation of the r31 kD, by using thioredoxin. BAsed on SDS-PAGE profiles run in the absence of mercaptoethanol (ME), thioredoxin reduction and reoxidation of "scrambled" material seems to yield a more homogeneous preparation of r31 kD, but the concentration of thioredoxin which had to be used was about 100 µM. "Scrambled material" is r31 kD polypeptide which is apparently improperly folded due to the formation of one or more incorrect disulfide bonds.
3. Purification
3.1 Phenyl-Sepharose chromatography: The large volume of r folded r31 kD is first centrifuged to remove the insoluble pellet which contains either "scrambled" r31 kD or contaminants. The supernatant is brought to 0.2 M ammonium sulfate in Buffer A and loaded onto a phenyl-Sepharose column equilibrated with Buffer A containing the same ammonium sulfate concentration. The r31 kD polypeptide is then purified by lowering the salt concentration, i.e., by elution in Buffer A.

Example: After reoxidation of the crude protein mixture, extracted from a 10 gram pellet, the suspension of refolded and "scrambled" r31 kD, as well as insoluble contaminants, is subjected to centrifugation at 13,000 rpm (17,000×g) in a high-speed Beckman centrifuge equipped with a J-14 rotor. The supernatant (1,280 ml) was brought to 0.2 M in ammonium sulfate (AS) and loaded onto a 45 ml column of phenyl-Sepharose previously equilibrated with Buffer A containing 0.2 M AS. The column was washed with 150 ml of the same solution, followed by 150 ml of Buffer A, 50 ml of water and 50 ml of 6 M GuCl (FIGS. 11 and 12).
3.2 Heparin-Sepharose and ion-exchange chromatographies: The final step of purification of the r31 kD polypeptide is chromatography on Q-Sepharose from which it elutes in the flow-through fraction or on Heparin-Sepharose from which it is eluted by using a salt gradient. It also binds to S-Sepharose, but the eluted material is still contaminated with most of the impurities.

Example: Approximately ½ of the Buffer A peak was concentrated and purified on a 10 ml Heparin-Sepharose column, from which it was eluted by a solution of 0.5 M NaCl in Buffer A (FIG. 13). The concentrated 31 kD was dialyzed against Buffer A, pH 8.5, before being loaded on a 40 ml column of Q-Sepharose, which had previously been equilibrated with the same buffer. The purified r31 kD polypeptides, which eluted in the flow-through and wash fractions were concentrated by lyophilization, before being characterized. The column was washed free of the contaminant proteins by a step of 1 M NaCl (FIG. 14). The purified material is greater than 95% pure (FIG. 11).
3.3 Re-extraction of the pellet: After the refolding procedure the pellet was re-extracted and treated as above, since it still contained more than 50% of the r31 kD polypeptide probably in "scrambled" form. The total yield (including the re-extraction step) of the process, after 3 columns, was about 10% (Table A).

3.4 Characterization: The r31 kD polypeptide has been characterized and compared to its plasma derived counterpart in terms of its purity (purity profile on reduced gels of SDS-PAGE), migration position in non-reduced gels of SDS-PAGE (FIG. 11), apparent molecular weight (approximately 37 kD) on Superose 12 (FIG. 15), immunoblot and behavior on Heparin- Sepharose (the NaCl concentration for elution of both materials from Heparin-Sepharose was found to be approximately 0.32 M). In all of these assays the r31 kD polypeptide is similar to plasma derived fibrin binding domain.

4. Comparison Between Various Forms of the r31 kD in Terms of their Reoxidation-Refolding Three different forms of the r31 kD polypeptide have been defined:

Form a: The polypeptide as it is obtained from the washed pellet, after dissolution in 6 M GuCl, i.e., in "scrambled" form.

Form b: The fully reduced polypeptide, present after treatment with a reducing agent such as GSH in the presence of 6 M GuCl.

Form c: The reoxidized-refolded polypeptide, obtained by treatment with the GSH/GSSG as described above.

These three forms can be distinguished from one another by:

(i) Their migration on SDS-PAGE gels in the absence of reducing reagents (i.e., without ME), and in the presence of the thiol-trapping agent iodoacetamide (FIG. 11); and (ii) Their reaction with anti-plasmatic 31 kD on immunoblots of gels run in the absence of ME. Only the correctly reoxidized-refolded form reacted with the antibody.

Characterization of the fully reduced r31 kD polypeptide: This polypeptide form is both more soluble and more homogeneous than the "scrambled" one. After solubilization in 6 M GuCl in the presence of GSH (or DTT or cysteine), and then lowering the concentration of denaturant to almost zero, the "reduced" polypeptide can be purified on phenyl-Sepharose in the presence of GSH. Finally, the polypeptide is "reoxidized" with GSSG at $\frac{1}{10}$ of the concentration of GSH, i.e., 0.3 mM. This did not yield refolded 31 kD, but a form of "scrambled" polypeptide different from that described in the previous paragraph, probably because the reduced polypeptide slowly autooxidizes to a scrambled form, even before it is exposed to GSSG.

5. Preparation of reduced-carboxamidated 31 kD polypeptide

Purified plasma derived or recombinant 31 kD polypeptide (approximately 0.6 mg/ml) were reduced in 4.3 M Guanidinium Hydrochloride (GuCl), 40 mM β-mercaptoethanol (ME), in 10 mM Tris-HCl, pH 8.5 for 24 hours at room temperature.

Carboxamidation was achieved by adding iodoacetamide to the polypeptide in four-fold excess over the concentration of ME and the solution incubated for 1 hour at room temperature. Subsequently the GuCl concentration was reduced by gradual dialysis (to 3M, 2M, 1M and 0.5M GuCl), before being dialyzed against Buffer A. The precipitate formed was centrifuged and the concentration of the resulting 31 kD polypeptide in the supernatants were 0.34 and 0.19 mg/ml for the plasma derived and recombinant 31 kD, respectively. The reduced carboxyamidated polypeptide is also termed a reduced/blocked polypeptide because the S—H groups are blocked to prevent reoxidation.

TABLE A

Purification of r31kD

| STEP | VOLUME (ml) | PROTEIN CONC. (mg/ml) | TOTAL PROTEIN (mg) | PURITY (%) | AMOUNT 31kD (mg) | YIELD (%) | PURIF. DEGREE |
|---|---|---|---|---|---|---|---|
| Extracted pellet | | | 2000 | 35 | 700 | 100 | 1 |
| Refolding | 1280 | 0.332 | 425 | 70 | 295 | 42 | 2.0 |
| Phenyl-S. | 220 | 0.56 | 123 | 85 | 105 | 15 | 2.4 |
| *(½) | | | 61 | | 52 | | |
| Heparin-S. | 16 | 2.19 | 35 | 90 | 32 | 9 | 2.6 |
| Q-Sepharose | 100 | | 23ª | >95 | 22 | 6 | >2.7 |
| Re-extracted pellet | | | 234 | | | 23 | |
| Phenyl-S. | | | 96 | | | 14 | |

% Purity determined from SDS-PAGE gels (+NE)
ªMeasured after lyophilisation.

The work described above on reoxidation in the presence of GSH/GSSG (or in the presence of cysteine/cystine) has shown that the r31 kD polypeptide refolds with time to form (c) which is indistinguishable from that of the plasma derived fibrin binding domain.

Characterization of the "scrambled" r31 kD polypeptide: The polypeptide seems to be less soluble in this form, as evidenced from the large amounts remaining in the pellet after extraction.

Also the scrambled polypeptide differs from the refolded polypeptide in its binding characteristics to both phenyl-Sepharose and Q-Sepharose.

Example 6

Pharmacodynamics of the r31 kD, r20 kD and r12 kD Fibrin Binding Domain Polypeptides The intensity and resolution of a clot (thrombus) image is governed by the interplay of the rate of incorporation of the radiopharmaceutical and its blood clearance rate. In order to elucidate the metabolic behavior of the r31 kD fibrin-binding domain, and to compare it to fibronectin (FN), the r31 kD fibrin binding domain and plasma fibronectin were both iodinated with $^{125}$I by the IC1 method (24) and injected intravenously into rats. The results are shown in FIG. 16 which represents the pharmacokinetic behavior of $^{125}$I-r31 kD FBD and 125I-FN. Blood samples were withdrawn at the times shown on the graph.

FIG. 16 demonstrates that the clearance rates of the two radioactive molecules are different and after 5 hours, only 3% of the r31 kD FBD but 20% of FN respectively remain in circulation.

Some of the rats were kept in individual metabolic cages, and accumulated urine and feces were collected at 7 hours and 24 hours. About 30% of the injected $^{125}$I-r31 kD radioactivity was excreted in the urine during the first 7 hours, and more than 90% was excreted after 24 hours. All of the urinary radioactivity was trichloroacetic acid-soluble, which is indicative of proteolytic degradation. The analysis of a variety of organs (kidney, stomach, liver, lung, uterus, ovary, adrenal, colon, ileum, skin, brain, eye, muscle, bladder, heart, spleen, trachea, aorta and vena-cava) did not reveal any specific accumulation, and the kinetics of disappearance of the radioactivity followed a pattern similar to that of the blood. In most of the organs, the specific radioactivity (cpm/gram tissue) was lower than that of the serum.

The results indicate that exogenous recombinant 31 kD amino-terminal polypeptide of FN is moderately degraded and excreted in the body. The pharmacokinetic behavior is not consistent with a first-order kinetics, which may indicate that the polypeptide is moderately distributed in the tissues and body compartments other than blood. This is also evident from the finding that the degree of degradation does not increase during the 4–24 hour period, thus reflecting a gradual release of the polypeptide from body compartments. The exclusive and relatively early appearance of the metabolites in the urine indicates that the polypeptide is readily excreted through the kidneys. The lack of accumulation of the material in the liver may be an indication that this organ is not a major locus of degradation and is not involved in detoxification.

The relatively short half-life of r31 kD FBD is important for its possible use in diagnostic imaging of thrombi. The recombinant 31 kD FBD (r31 kD) may be labeled radioactively or by other means and then introduced into the blood for the purpose of imaging thrombi.

The shorter half-life of the molecule is also important when utilizing it to prevent clot formation. By contrast, heparin, the current therapeutic agent of choice, suffers from a very long half-life.

A similar experiment was performed using iodinated 31 kD fibrin binding domain of plasmatic fibronectin and similar pharmacokinetics and distribution of radioactivity were observed.

The 31 kD polypeptide was obtained by cleavage of plasmatic FN as follows: the plasmatic FN was purified on a Gelatin-Sepharose column from which it was eluted and stored in 1 M guanidinium hydrochloride. Thereafter, 206 mg of FN, after dialysis against 10 μM of Tris-HCl, were digested with 0.01% of TPCK-trypsin at 37° C. for 5 minutes. The tryptic digest was loaded on a DE52 column (6 ml) and ⅕ of the flow-through fraction (50 ml) was applied to a CM-Sepharose column (3 ml) and eluted with a NaCl gradient (0–0.5 M). About 80% of the polypeptide was recovered in the salt gradient (peak at about 220 mN) and after dialysis to remove the salt about ½ of the polypeptide was loaded on a Heparin-Sepharose column (1.5 ml) and eluted with 0.5 M NaCl. Approximately 75% of the polypeptide was recovered in this fraction, i.e., about 1 mg (about 40% of the theoretical yield). This fraction was >90% pure 31 kD polypeptide, and was iodinated by the method described above.

Note that plasmatic 31 kD FBD contains the first 259 amino acids of FN, whereas the recombinant 31 kD FBD contains the first 262 amino acids of FN.

Pharmacokinetics of the r20 kD and r12 kD Fibrin Binding Domain Polypepetides

Similar experiments were performed using labeled r20 kD and r12 kD fibrin binding domain polypeptides produced as described in Examples 2, 9 and 10. The pharmacokinetics of these polypeptides was found to be very similar to that of the r31 kD polypeptide.

Example 7

Biological Activity of the Recombinant Fibrin Binding Domain (r31 kD)

The biological activity of the purified recombinant 31 kD FBD polypeptide was compared to biological activity of either human plasma derived FN or a 31 kD FBD polypeptide derived from partial tryptic digest (Example 6) of human plasma derived FN. The biological activities assayed were binding to fibrin clot in vivo and in vitro, binding to bacteria (*Staphylococcus aureus*) and binding to extracellular matrix.

I. Fibrin Binding Activity

Two sets of experiments were carried out. In the first set, the binding of $^{125}$I-r31 kD to fibrin was monitored during clot formation (Reaction I), while in the second set of experiments, the binding of $^{125}$I-r31 kD to fibrin was monitored at various time periods after clot formation (Reaction II). Thrombin or $Ca^{++}$ were added to the mixtures in order to enable clot formation in citrated blood.

Materials and Methods

Fibronectin Fibrin Binding Domain: FBD

A. Binding of FBD to Fibrin:

Plasma derived 31 kD FBD was derived by partial tryptic digest of human fibronectin (see Example 6).

Production of r31%D FBD in *Escherichia coli* and its subsequent purification from the pellet of cell lysate was performed according to Example 5. Fibronectin was obtained from human plasma. $^{125}$I-labeling of FBD and FN was carried out by the IC1 method (24). The labeled polypeptides having specific activity of 20–200 cpm/ng, were stored at −20° C. in small aliquots in a solution of 0.1% BSA-PBS and used within 2 weeks.

1. Binding of $^{125}$I-FBD to Fibrin Clot During its Formation (Reaction I):

The complete reaction mixture in siliconized microfuge tubes contained in a final volume of 250 μl the following components:

20–200 μl human whole blood (fresh, non-citrated, or 1–7 days old, citrated, as indicated in the figure legends)
0.1% BSA
5 mM $CaCl_2$
1 U/ml Thrombin
$^{125}$I-r31 kD FBD When binding was measured using non-citrated blood, $CaCl_2$ and thrombin was not added ("Naive Thrombii").

All ingredients were prepared in PBS. The reaction was incubated at 37° C. for 30 minutes. The reaction was terminated by the addition of EDTA (25 mM), and centrifugation in a microfuge centrifuge at maximum speed for 3 minutes. The supernatant was discarded and the pellet was washed twice in 1 ml PBS, 0.1% BSA, 5 mM EDTA, 1 mM PMSF. The radioactivity in the pellet was monitored by a gamma counter.

When competition with non-radioactive polypeptide was carried out, the competing polypeptide was added together with the $^{125}$I-labeled polypeptide at the concentrations indicated in the figure legends.

2. Binding of $^{125}$I-r31 kD FBD to Preformed Fibrin Clots (Reaction II):

The reaction mixture contains the same components as indicated for Reaction I, except for the $^{125}$I-r31 kD. The first incubation was carried out at 37° C. for 30 minutes, and only then the $^{125}$I-r31 kD was added and the reaction was further incubated for a second period of 30 minutes. Reaction II was terminated and measured as described above for Reaction I.

Results

A. Binding of $^{125}$I-r31 kD to Fibrin: Effect of Thrombin and $Ca^{++}$

The effect of thrombin and $Ca^{++}$ on $^{125}$I-r31 kD binding to fibrin during clot formation (Reaction I) or to preformed clots (Reaction II) was studied in citrated human whole blood (FIG. 17).

Hirudin, a specific inhibitor of thrombin (25) reduced the binding of $^{125}$I-r31 kD to the fibrin clot in Reaction I, indicating that thrombin is needed for the binding. When thrombin is inhibited there is a reduction in clot formation and less fibrin is available for binding. The addition of citrate to blood significantly reduces the concentration of free $Ca^{++}$ in the serum and therefore the addition of $Ca^{++}$ for fibrin clot formation is obligatory. However, binding of r31 kD to a preformed clot is reduced when carried out in serum which has been already depleted of free $Ca^{++}$ ions by the preformed clot. Addition of $Ca^{++}$ to the $Ca^{++}$ depleted serum increases the r31 kD binding. This effect of $Ca^{++}$ on binding was dramatically demonstrated when binding was measured in PBS. The addition of $Ca^{++}$ increased the binding, even to a higher extent than observed in reaction I. Thus, both clot formation and r31 kD binding are $Ca^{++}$ ion dependent.

Thus, binding of $^{125}$I-r31 kD to fibrin in Reaction II increases when the assay is carried out in PBS (Phosphate Buffer Saline solution) instead of serum.

B. Release of $^{125}$-r31 kD from Fibrin Clot by Plasmin

In order to determine whether the $^{125}$I-r31 kD is covalently bound to the fibrin in the clot, plasmin, which is known (26, 27) to cleave the N-terminal domain of plasma derived FN between amino acids $Arg^{259}$ and $Thr^{260}$ was added to the clot after $^{125}$I-r31 kD was bound. The incubation with plasmin was carried out for various time intervals (FIG. 18).

The results demonstrate that plasmin caused a reduction in the radioactivity bound to the clot (pellet). Reduction of radioactivity in the pellet was time dependent and could be attributed to the fact that plasmin cleaved the r31 kD FBD. The amount of radioactivity monitored in the supernatant increased with time. Upon loading of the plasmin soluble reaction fraction (the supernatant) on SDS polyacrylamide gels it is possible to detect the shortened form of the cleaved $^{125}$I-r31 kD. The release of $^{125}$I-r31 kD from the fibrin clot occurs only by plasmin cleavage and not by heating with a solution containing SDS, EDTA and β-mercaptoethanol to 100° C., thus demonstrating that $^{125}$I-r31 kD is covalently bound to the fibrin clot.

Figure 19:
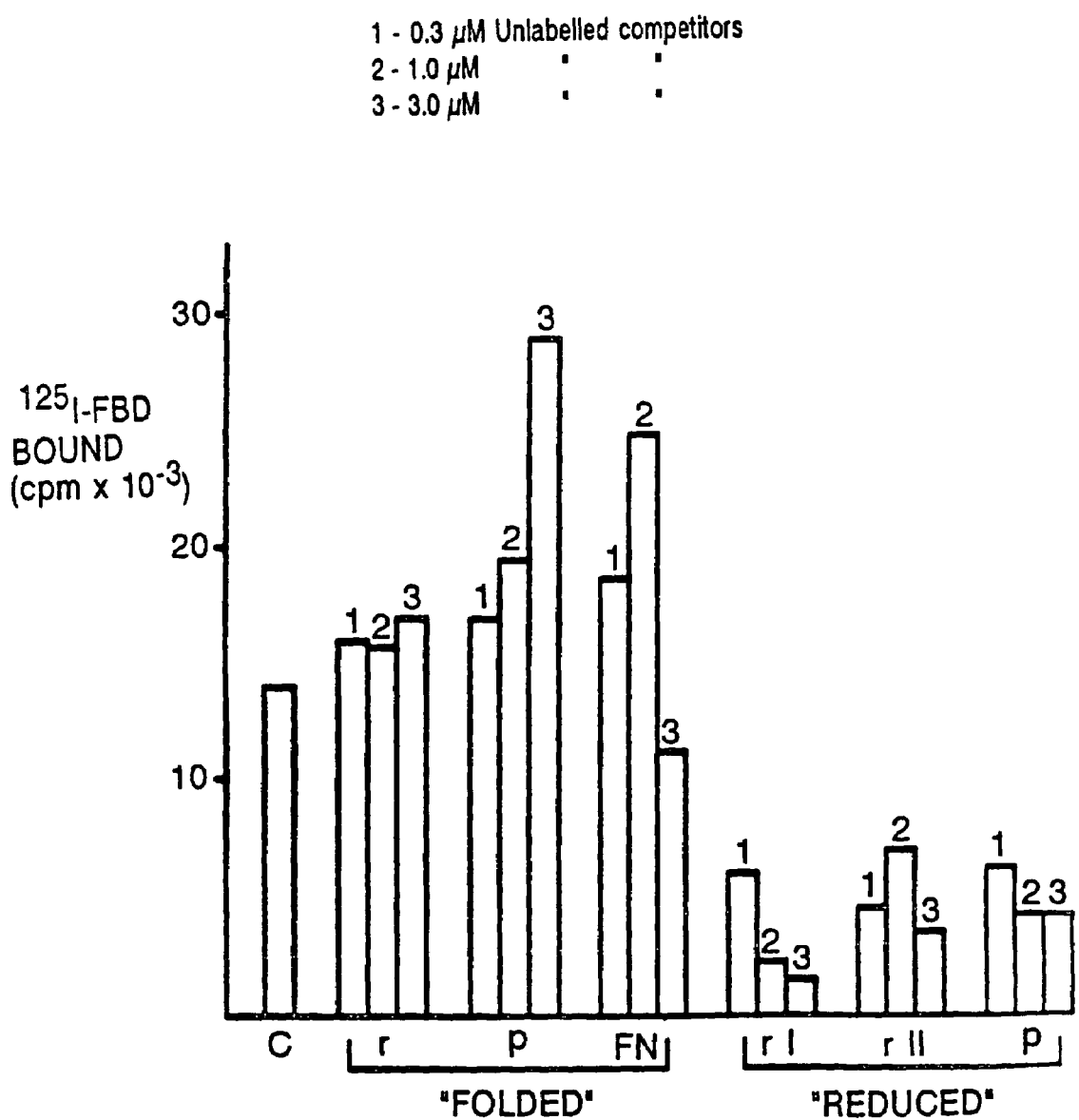

3. Binding of $^{125}$I-r31 kD to Fibrin During Clot Formation: Effect of Unlabeled r31 kD and Other Molecules The ability of various cold recombinant and plasma derived FBD preparations as well as human plasma derived fibronectins at different concentrations to interfere with the binding of $^{125}$I-rFBD to fibrin during clot formation (Reaction I) was studied (FIG. 19). The results obtained demonstrate that the binding of 0.15 μM $^{125}$I-rFBD to fibrin was similar or even increased in the presence of unlabeled r31 kD, unlabeled plasma derived 31 kD or unlabeled FN at concentrations up to 20 folds excess (3 μM).

However, when the amount of newly formed fibrin clot was reduced, using either suboptimal concentrations of $CaCl_2$ and thrombin (1 mM and 0.3 units/ml, respectively), or by reducing the volume of the blood in the reaction to 1/10 of the amount originally specified, the competition between the unlabeled FBD and the binding of $^{125}$I-FBD for binding to the clot became significant.

In order to further study the specificity of the FBD binding reaction, we compared the binding of r31 kD to the binding of its reduced forms (Example 5).

For these studies we used on batch of reduced-carboxamidated plasma derived 31 kD, on batch of reduced-carboxamidated r31 kD and one batch of fully-reduced r31 kD all prepared as described in Example 5. Surprisingly, these various reduced forms of 31 kD FBD caused a dramatic reduction in the binding of the $^{125}$-FBD (reduction of 40–80% by 0.3–3.0 μM; FIG. 19). We have also noticed a dramatic decrease in the size of the newly formed clot (Reaction I) in the presence of the fully reduced FBD. Clot formation was totally inhibited in the presence of high concentrations of the fully reduced FBD (above 5 μM).

Since a similar inhibitory effect was exhibited by the various reduced forms of the 31 kD proteins on the binding of refolded $^{125}$I-FBD to a preformed fibrin clot (Reaction II), the possibility of interference with the crosslinking reaction of the FBD to the fibrin clot catalyzed by the serum transglutaminase factor XIIIa, was suggested.

4. Binding of $^{125}$I-FBD to the Fibrin Thrombi (Reaction II): Effect of Transglutaminase Inhibitors Transglutaminases are a class of calcium ion-dependent enzymes that catalyze an amidation reaction in which a carboxamide group of peptide bound glutaminyl residues and primary amines, including the epsilon amino group of peptide bound lysyl residues, are crosslinked. Plasma FN is a substrate for transglutaminase from plasma, factor XIIIa, (thrombin activated blood coagulation factor XIII) or liver; FN can be crosslinked to itself, fibrin and collagen.

The glutaminyl residues which are susceptible to factor XIII crosslinking are localized in the FBD region of FN (28).

The binding of $^{125}$I-FBD to preformed fibrin clot (Reaction II) in the presence of various concentrations of the primary amines spermidine and putrescine, the classical transglutaminase inhibitors, was studied (FIG. 20). The reaction was 50% inhibited by about 5 mM spermidine or putrescine. In parallel to the expected inhibition by the primary amines, a dramatic inhibition of the binding was also observed by the reduced-carboxamidated FBD, with a half maximal reduction at around 2.5 μM.

5. Binding of $^{125}$I-r31 kD to Preformed Fibrin Clot: Effect of Aging on Binding For imaging purposes, it was important to determine the effect of clot aging on FBD binding capacity.

The binding of $^{125}$I-r31 kD to preformed fibrin clot was determined. $^{125}$I-r31 kD was added to the preformed clots (1, 4 or 24 hours) and binding to fibrin was monitored (FIG. 21).

The binding of $^{125}$I-r31 kD to the fibrin clot was higher after 24 hours than the binding after 1 or 4 hours, presumably due to the fact that the clot formed became larger with time.

As indicated in experiment I of this example, the presence of free Ca$^{++}$ ions in citrated blood is important in order to obtain optimal binding and crosslinking of $^{125}$I-r31 kD to the fibrin clot. Thus, in serum where Ca$^{++}$ was already depleted by the preformed clot the binding of $^{125}$I-r31 kD to the fibrin clot was low while in the PBS containing 5 μM CaCl$_2$, the binding was high at all incubation times.

When 300 μg/ml of plasma derived FN was added as competitor in the presence of Ca$^{++}$, there was a 20% reduction in $^{125}$I-r31 kD binding to the fibrin clot probably due to some competition on the available fibrin binding sites.

6. Binding of $^{125}$I-r31 kD to "Naive" Thrombi (Reactions I and II): Effect of Thrombi Age on the Binding The ability to differentiate between "old" (preformed) and "newly formed" thrombi, is an important requirement of a probe for thrombus imaging. FIG. 22 shows experiments designed to compare $^{125}$I-r31 kD binding to "old" and "newly formed" clots. In the first experiment $^{125}$I-r31 kD was added at the same time as the initiation of clot formation ("newly formed") and was allowed to interact with the clot during seven days of incubation. It is evident that FBD is incorporated efficiently and the amount incorporated increased during the first two days, probably representing an increase in the clot size during that period. In the second experiment $^{125}$I-r31 kD was added to aged clots (1–7 days old) for a limited period of 2 hours ("preformed"). The extent of FBD incorporation remained constant, regardless of the clot age. Note, however, that binding in this protocol is lower than in that of the first experiment. These experiments suggest that the probe $^{125}$-r31 kD may be used in two different protocols to differentiate between "old" clots—thrombi and those which are still in the process of growing.

7. Plasma "Thrombin Time" ("TT")

The effect of the r31 kD polypeptide on clotting of whole blood was measured using the clinical laboratory parameter defined as Thrombin-Time. In this reaction aliquots of 100 μl citrated healthy human plasma were mixed with 100 μl PBS and either the transglutaminase inhibitor spermidine, or with reduced-carboxyamidated p31 kD or reoxidized-refolded r31 kD. 200 μl thrombin solution was added to each aliquot while continuously mixing. The time from the addition of the thrombin to the formation of clot was measured, and is expressed as "TT" in seconds (Table B).

8. Binding of $^{125}$I-r31 kD to Fibrin (Reaction I): Effect of Exogenous Transglutaminase and "Reduced-Carboxamidated" FBD In Section 4 of this example we demonstrated that transglutaminase inhibitors reduce the binding of $^{125}$I-r31 kD to clots. In this section we studied the effects of exogenous transglutaminase from pig liver on the binding reaction.

The results presented in FIG. 23 demonstrate that the addition of the exogenous transglutaminase dramatically increases the binding of $^{125}$I-r31 kD to clots, indicating that this enzyme may be a rate limiting step in this reaction.

Moreover, both endogenous and exogenous transglutaminase dependent binding activities were equally decreased by the reduced-carboxamidated FBD (approximately 56% and 72% inhibition by 0.3 μM and 1.5 μM "reduced" FBD, respectively).

These results strongly indicate that the "reduced" forms of FBD inhibit the binding of the refolded form of FBD to the fibrin clot by interfering with the transglutamination and cross-linking reaction. This probably causes destabilization of the fibrin clot.

9. Binding of $^{125}$I-FBD to Extra Cellular Matrix (ECM)

Adhesive molecules such as von Willebrand factor, fibronectin, fibrinogen, thrombospondin, collagen and laminin bind to ECM formed by removal of endothelial cells. r31 kD FBD can serve for imaging the initial steps in plaque formation at the site of injury. The binding of $^{125}$I-r31 kD at various concentrations to ECM was studied in the presence or absence of thrombin. The results demonstrated that the binding of $^{125}$I-r31 kD at low concentrations to ECM was not affected by thrombin (0.3 μM). At higher concentrations of the thrombin binding of r31 kD was slightly higher indicating that the number of binding sites naturally present are limited and thrombin digestion might expose additional binding sites (FIG. 24).

The fact that 125I-r31 kD binds to ECM indicates that it will be useful for imaging the initial plaque formation in the denudated blood vessel.

TABLE B

THROMBIN TIME ("TT")
Effect of FBD ("reduced" and "folded") and Related Molecules

| | Thrombin Conc. (μ/ml) | Additions | "TT" Values (Seconds) | (%) | (\) |
|---|---|---|---|---|---|
| I | 2.5 | — | 25.5 | 100 | — |
| | | 1 mM Spermidin | 44 | 172 | 72 |
| | | 1 μM "R"FBD | 34 | 133 | 33 |
| | | 2.5 μM "R"FBD | 39 | 152 | 52 |
| | | 2.5 μM "F"FBD | 26.5 | 103 | 03 |
| II | 1.25 | — | 55.4 | 100 | — |
| | | 1 mM Spermidine | 114 | 205 | 105 |
| | | 2.5 μM "R"FBD | 81 | 146 | 46 |
| | | 2.5 μM "F"FBD | 58 | 104 | 04 |

"R" FBD = Reduced-carboxamidated p31kD.
"F" FBD = Refolded r31kD.

II. Bacterial Binding Activity

The involvement of fibronectin in adhesion to, and invasion of, wounds by a wide range of gram-positive bacteria is well established (18). The fibrin binding domain of authentic plasma derived FN has been shown to interact with high affinity to specific receptors on the surface of bacteria. The sites at which *Staphylococcus aureus* typically initiates infection are rich in FN, e.g. blood clots and subendothelium. Furthermore, exogenous FN enhances bacterial adhesion to these sites. FN binds to *S. aureus* through saturable, specific surface protein receptors. Scatchard analysis has revealed high affinity receptors with binding constant of $5 \times 10^{-9}$ M, and a range of 100–20,000 receptors per bacterium (19). The expression of FN receptors correlates with invasiveness and pathogenicity of the clinical isolates. Removal of the receptors from *S. aureus* by mechanical means, or by growth of the bacteria in the presence of antibiotics decreases their ability to adhere to FN. As FN is a divalent molecule consisting of multiple functional domains with cell binding and collagen binding activities in addition to bacterial binding, it can anchor the bacteria to the wound via the various components of the extracellular matrix as well as via the FN receptor in tissue cells.

Materials and Methods

Binding of Bacteria to Labeled FN or FBD in Solution

A. Direct Binding Reaction

Various concentrations of $^{125}$I-r31 kD FBD or $^{125}$I-FN, were added to 5×10$^8$ S. aureus bacteria in a PBS solution additionally containing 0.1% Tween and 1% BSA. The final volume was 1 ml. Total radioactivity in the reaction was assayed using a 20 µl aliquot taken immediately after the addition of the bacteria.

The mixture was incubated for 2 hours at 20° C.

The amount of binding was assayed by removing 100 µl of the incubation mixture and layering on top of 0.5 ml PBS layered on 3 ml 10% percol, 0.15 M NaCl in a 5 ml siliconized tube. This was then centrifuged at 1,350×g (4,000 rpm in SW bucket rotor) for 15 minutes at 20° C. The supernatant was aspirated and the pellet assayed for radioactivity.

B. Competition with Unlabeled FN, FBD and Related Molecules

The procedure followed was identical to the above procedure except that 3 µg/ml $^{125}$I-p31 kD was used and the specified amounts of the competing molecule (FM or FBD) was also added to the initial binding mixture.

II. Binding of Radioactively Labeled Bacteria to Immobilized FN

Plastic vials were coated with 0.3 ml of 50 µg/ml FN, or 1% BSA.

The tubes were incubated with shaking at 4° C. overnight. The tubes were then washed with 5 ml PBS three times. Then 0.3 ml of 1% BSA in PBS was added and the tubes were further incubated with shaking for 2–3 hours at 20° C. (for blocking free sites).

In indirect-binding experiments, the bacteria were preincubated with inhibitor, at 4° C. for 2 hours.

The bacteria (4×10$^6$ pfu/ml, 3 pfu/cpm) were added to the vials at concentrations indicated in the figure legends. The final volume of the assay mix was 0.3 ml PBS. The mix was slowly agitated at 4° C. for 90–120 minutes.

The tubes were then decanted and washed with 5 ml PBS three times.

5 ml of scintillation-liquid was added when assaying for binding of 3H-labeled bacteria.

III. Binding of Labeled Bacteria to Catheters

Catheters ["UNO" sterile bronchial plastic catheters (18 CH size; Unoplast A/S, Denmark)], were cut to 1 cm and 2 cm pieces, weighed and then cut once lengthwise.

The catheter pieces were incubated with 50 µg/ml FN at 4° C. overnight with shaking. The controls were incubated with PBS under the same conditions.

The FN solution was then decanted and the catheters were washed three times in PBS. BSA-blocking was performed by adding 1% BSA in PBS for 1–2 hours at 20° C. The catheters were again washed three times with PBS.

Bacterial binding was performed as described in the previous section except that the catheter pieces were added to the assay mixture. The final volume used was 3 ml. The reaction was performed in 10 ml tubes. The reaction was incubated for 2 hours at 20° C. For the binding assay $^{125}$I-S. aureus (4×10$^6$ pfu/ml, 3 pfu/cpm) were used. (When H3-leucine-labeled S. aureus was used the specific activity was 1 cpm/3.3×10$^3$ pfu. Labeling was performed according to P. B. Russel et al. (29). When $^{125}$I-labeled S. aureus was used the specific activity was 1 cpm/3 pfu. Labeling was performed according to A. E. Bolton and W. M. Hunter (30).) The competing molecules at the designated concentrations were preincubated with the bacteria for 30 minutes at 20° C. The catheters were then washed three times with PBS and then directly counted in a gamma counter.

Results

A. Binding of Bacteria to $^{125}$I-FN or FBD in Solution

I. Direct Binding

Experiments were performed in order to determine the binding of $^{125}$I-FN or $^{125}$-rFBD to S. aureus bacteria in suspension. Various amounts of radioactive FN or r31 kD were added to 5×10$^8$ bacteria incubated for 2 hours and then centrifuged over a 10% Percoll-saline solution. Radioactivity was monitored in the pellet (FIG. 25).

The results showed increased binding of $^{125}$I-rFBD (r31 kD) to the bacteria in suspension as compared to the binding of the $^{125}$I-FN.

This increased binding of $^{125}$I-rFBD to S. aureus as compared to $^{125}$I-FN binding to S. aureus can be attributed to a higher affinity of a monovalent domain in comparison to bivalent multidomain of intact plasma derived FN.

II. Binding of $^{125}$I-Plasma Derived 31 kD FBD (p31 kD) to S. aureus: Competition with "native" Unlabeled FN, FBD and Related Molecules A fixed amount of $^{125}$I-p31 kD (3 µg/ml) was incubated with 5×10$^8$ bacteria in the presence of increasing amounts of various FBD molecules as competitors (FIG. 26).

The results demonstrate that "native" FN, p31 kD or rFBD inhibited the binding of $^{125}$I-p31 kD to S. aureus in a similar fashion, indicating that rFBD is as active as the natural plasma derived molecules. However, the reduced forms of recombinant or plasma derived FBD only minimally inhibit the binding of $^{125}$I-FBD to the bacteria, indicating that proper folding is necessary for binding. A related recombinant polypeptide (33 kD cell binding domain of FN) which does not have a bacterial binding site did not inhibit $^{125}$I-pFBD binding to S. aureus.

B. Binding of Labeled S. aureus to Immobilized FN

To estimate the capacity of rFBD (r31 kD) to interfere with the adherence of bacteria to the extracellular matrix in wounds, a competition assay was developed. In this assay, adherence of S. aureus to plastic surface coated with FN, and the interference of FBD with the binding was measured (see FIG. 27).

The results demonstrate that the adhesion of S. aureus to FN coated plastic vials was inhibited following preincubation of S. aureus with FN, pFBD or rFBD. The extent of inhibition by these molecules was similar. A non-related protein, BSA, which does not have S. aureus binding sites, did not cause any inhibition in adhesion of radioactive labeled S. aureus to FN coated plastic vials.

C. Binding of S. aureus to Bronchial Catheters: Effect of FBD and Heparin

Catheter sepsis due to various species of S. aureus contributes to the high incidences of serious clinical complications.

We have examined the ability of S. aureus to bind FN coated catheters. FIG. 28 demonstrates that the binding of S. aureus to the FN coated catheters is quite high, approximately 10$^4$ PFU/cm$^2$.

Preincubation of bacteria with increasing concentrations of r31 kD reduced the binding of the bacteria to the catheters. The $IC_{50}$ for this inhibition is between 0.08–0.8 µM (FIG. 28). Similar inhibition was also obtained with r20 kD FBD and p31 kD FBD.

Systemic administration of heparin and/or the use of heparin bonded polyurethane catheters is reported to decrease the incidence of thrombosis.

Therefore we also measured the inhibitory effect of FBD on *S. aureus* attachment to the catheters in the presence of 5 µM heparin. The results (FIG. 28) demonstrate that heparin did not affect the binding of the bacteria to catheters, however, r-FBD inhibition of bacterial binding remains constant even in the presence of heparin. This indicates the utility of r31 kD for inhibition of *S. aureus* colonization and sepsis in a clinical setting, even in the presence of heparin.

CONCLUSION

These results demonstrate that the r31 kD FBD or the plasma derived 31 kD FBD may be used therapeutically in preventing bacterial colonization of wounds. The various FBD polypeptides will be formulated in suitable pharmaceutical formulations well-known to the average man of the art, and then used to "irrigate" or "flood" or treat the wound area for a suitable period of time, thereby preventing bacterial colonization of the wound.

Example 8

Adhesion of Plasma Derived 31 kD FBD to Thrombi in a Rabbit Aorta Lesion Model

In order to demonstrate the ability of the fibrin binding domain to adhere to thrombi in vivo, a model of thrombus formation in rabbits was used. In this model, the endothelial layer of a segment of the aortal wall is removed with a balloon catheter, thus exposing the lamina intima. This results in the subsequent formation of a film of thrombi in the lesion area. It has been demonstrated by Uehara et al. (1) that labeled FN given systemically to rabbits exhibited extensive binding to such thrombi, as indicated by a higher specific radioactivity in the lesion part of the aorta as compared to adjacent untreated segments.

In order to compare the plasma derived 31 kD FBD polypeptide with intact plasma-derived FN, the two molecules were iodinated with $^{125}I$ using the ICL method. Two hours after de-endothelialization, the radio-labeled molecules were injected intravenously into rabbits (20 µCi; 100 µg/kg; 3 rabbits per group). At 72 hours after injection, the aortas were removed, the scraped (abdominal) and intact (thoracic) areas were separated and each part was cut into several segments (5–6 segments for the lesion part and 2 segments for the control part). The tissue pieces were weighed and radioactivity counted.

FIG. 29 summarizes the specific activity values found in the sequential aorta slices rabbits injected with $^{125}I$-FN (rabbits No. 1–3 FIG. 29, panel A) or $^{125}I$-p31 kD FBD (rabbits 4–6 FIG. 29, panel B). As can be seen in FIG. 29, enhanced localization of the labeled molecules was found in the de-endothelialized segments (thrombus zone). Also nor radioactivity was localized in the clots when labeled p31 kD FBD was used than when labeled FN was used.

These results demonstrate that molecules comprising the FBD moiety should be useful for the imaging of arterial thrombus clots.

When used for imaging it may be desirable to attach to the FBD (plasma derived or recombinant) other markers useful in imaging such as enzymes or radio-opaque inert molecules.

Example 9

Expression and Fermentation of Additional Fibrin Binding Domain (FBD) Polypeptides In Example 2 the expression of a partial r20 kD FBD and the full-length r31 kD FBD was described and in Example 24 an improved procedure for refolding and purification of the 31 kD FBD was disclosed. The construction of plasmids for expression of additional FBD polypeptides is now described.

A. Expression of r12 kD FBD Polypeptide

Plasmid pFN 975-25 (FIG. 10) expresses the full-length r31 kD FBD of fibronectin and from it plasmid pFN 196-2 which expresses a partial FBD was constructed as shown in FIG. 36. This plasmid was transformed into *Escherichia coli* strain A1645 and thence into *Escherichia coli* strain A4255 and deposited in A4255 in the ATCC under Accession No. 68328. These transformed cells were found to be good expressors of the partial FBD polypeptide in amounts comprising about 5% of the total cellular protein. The polypeptide has a mobility of about 12 kD on reduced SDS polyacrylamide gels as determined from the mobility of the size markers. The polypeptide comprises the first 109 amino acids of fibronectin; it is not yet known if an additional methionine residue is present at the N-terminus of the final polypeptide. Throughout this specification this polypeptide is referred to as the r12 kD polypeptide or the r12 kD FBD.

B. Expression of a Modified 12 kD (12 kD') Partial FBD Polypeptide

Plasmid pFN 975-25 (FIG. 10), which expresses the full-length r31 kD FBD, was used to construct plasmid pFN 197-10 which expresses a modified r12 kD polypeptide (r12 kD') as shown in FIG. 37. The fibronectin FBD sequence was modified to produce an NdeI site immediately after nucleotide 340. This plasmid was transformed into *Escherichia coli* strain A1645 and thence into *Escherichia coli* strain A4255. These transformed cells were found to be good expressors of the modified r12 kD partial FBD in amounts comprising about 5% of the total cellular protein. The polypeptide has a similar mobility to the unmodified 12 kD FBD as determined on reduced SDS polyacrylamide gels. The polypeptide comprises the first 109 amino acids of fibronectin followed by additional amino acids histidine and methionine; it is not yet known if an additional methionine residue is present at the N-terminus of the final polypeptide. This polypeptide is designated the r12 kD' polypeptide or the r12 kD' FBD.

C. Expression of a Modified r12 kD FBD Fused to the 33 kD Cell Binding Domain

Plasmid pFN 197-10 which contains an NdeI site at the 3' terminus of the modified 12 kD FBD was used to construct a plasmid, designated pFN 202-5, which encodes the modified 12 kD FBD fused to the 33 kD cell binding domain (CBD). This construction was performed as shown in FIG. 38 where the 33 kD CBD fragment was taken from plasmid pFN 137-2 (deposited in the ATCC under ATCC Accession No. 67910). Plasmid pFN 202-5 was transformed to *Escherichia coli* strain A1645 and thence to *Escherichia coli* strain A4255 and is a good xpressor (8% of total protein). The 45 kD ppolypeptide consists of the 12 kD FBD fused to the 33 kD CBD (first 109 amino acids of FBD followed by amino acid residues histidine and methionine followed by the CBD commencing with serine; it is not yet known if an additional methionine residue is present at the N-terminus of the final polypeptide).

D. Expression of a 31 kD FED Polypeptide Fused to the Amino Acid Sequence DGRGDS In order to obtain expression of a 31 kD FBD polypeptide fused at the carboxy terminus to the sequence asp-gly-arg-gly-asp-ser (DGRGDS) the following construction was made. Plasmid pFN 975-25 which expresses the 31 kD FBD was digested with PvuII and HindIII and ligated to a synthetic linker as shown in FIG. 39. The resulting plasmid, designated pFN 195-4, was used to transform *Escherichia coli* strain A1645 and thence *Escherichia coli* strain A4255. These cells were found to be good expressors of the 31 kD-GRGDS polypeptide, at levels of about 8% of total cellular protein. The sequence of this polypeptide is described in the description of FIG. 39.

E. Expression of a Fused 31 kD FBD-33 kD CBD

In order to obtain expression of a "full length" r31 kD FBD polypeptide fused to the r33 kD CBD the following construction was made.

Plasmid pFN 975-25 which expresses the 31 kD FBD was digested with PvuII and HindIII, and the large fragment resulting was ligated to a synthetic linker and to the r33 kD cell binding domain obtained from plasmid pFN 137-2 after NdeI and HindIII digestion (as shown in FIG. 40). The resulting plasmid, designated pFN 194-2, encodes the r31 kD FBD linked to the 33 kD CBD. Plasmid pFN 194-2 was transformed to *Escherichia coli* strain A1645 and then to *Escherichia coli* strain A4255, and the resulting cells were low expressors of a 64 kD polypeptide which comprises the 31 kD FBD fused to the 33 kD CBD. The sequence of this polypeptide is described in the description of FIG. 40.

Fermentation and Growth Conditions

The clone expressing the r12 kD FBD polypeptide was fermented in rich medium (yeast extract and casein hydrolysate) containing ampicillin. Growth was carried out at 30° C. Expression was -obtained upon induction at 42° C. for 2 hours and subsequently bacterial cell cake containing the r12 kD FBD polypeptide was obtained. Similarly, cell cake containing other proteins described above was obtained.

Example 10

Refolding and Purification of Recombinant 20 kD and 12 kD Fibrin-Binding Polypeptides of Fibronectin.

The process for refolding and purification of the r20 kD and r12 kD polypeptides is made up of three stages:

1. Crude processing of the bacterial cake.

2. Refolding/reoxidation.

3. Purification.
   1. Crude Processing
1.1 Washing and extraction of the pellet: The bacterial cell cake, obtained as described in Example 2 for the r20 kD polypeptide and as described in Example 9 for the r12 kD polypeptide, is disrupted and washed essentially as for the r31 kD polypeptide (Example 5); however, changes were introduced in the extraction procedure used for both the r20 kD and the r12 kD polypeptides. The following is an example of the washing and extraction procedure performed on the bacterial cell cake of the r20 kD polypeptide; the r12 kD polypeptide is extracted in a similar way.
1.2 Procedure: Bacterial cake containing the r20 kD polypeptide was produced as described in Example 2 by fermentation of *Escherichia coli* strain A4255 harboring plasmid pFN 949-2. A portion of this bacterial cak (14.8 g) was suspended in 10 volumes of 50 mM Tris HCl, 50 mM EDTA (Buffer B), pH 7.5. The suspension was homogenized for 15–30 seconds at a medium speed, sonicated 3 times for 4 minutes with pulsing, and centrifuged at 15,000 rpm for 30 minutes. The pellet was resuspended in 2.4 volumes (36 ml) of Buffer B. Lysozyme (0.1 mg/ml) was added and the suspension was incubated in a water bath at 37° C. for 2 hours with stirring. Triton X-100 was added to a final concentration of 1%, stirred at room temperature for 30 minutes and centrifuged. The pellet was resuspended three times in 148 ml of water (i.e., 10 times the volume of the original pellet), homogenized, stirred for 30 minutes at room temperature and centrifuged. The final pellet weighed approximately 1.5 g, i.e., only 10% of the original weight; however, both the r20 kD and the r12 kD polypeptides stay in the pellet, as evidenced by SDS-polyacrylamide gel- electrophoresis. The washed and extracted pellet was kept frozen at −20° C. until further processed.

2. Solubilization and Refolding of the extracted Pellet 2.1 The reagents and procedure used for the refolding/-reoxidation are different in this case from those used for the r31 kD polypeptide. The extracted pellet of the r20 kD or the r12 kD polypeptide is dissolved in 6 M guanidine-HCl (GuCl) in the presence of 50 mM β-mercaptoethanol and, following a tenfold dilution, is allowed to reoxidize by air.

2.2 Procedure: The frozen r20 kD pellet (1.5 g) was solubilized and homogenized in 10 volumes of 10 mM Tris HCl, 5 mM EDTA (Buffer C), pH 8.0, containing additionally 6 M Guanidine-HCl. The sample was reduced by the addition of 57 μl of undiluted β-mercaptoethanol (final concentration: 50 mM) and stirred in the absence of air, i.e., in a sealed container, for 30 minutes. It was then dripped at the rate of about 5 ml/min into 10 volumes (148 ml) of Buffer C, pH 8.0 and allowed to oxidize while being constantly and gently stirred, in an open beaker for 48–72 hours at room temperature. Although at this stage some polypeptide precipitation had already occurred, the suspension, including the precipitate, was dialyzed over 24 hours against 15 volumes of Buffer C, pH 8.5 with three changes of buffer. The dialysate was then subjected to centrifugation for 45 minutes at 15,000 rpm (22,500×g) in a high-speed Beckman centrifuge equipped with a JA-17 rotor. This removes many contaminant proteins and aggregates of the r20 kD or r12 kD, which have been produced during reoxidation.

3. Purification and Characterization

Since the location of the heparin binding site within the fibrin binding domain was not known, it therefore could not be known in advance if the new shorter r20 kD and r12 kD polypeptides would bind to Heparin-Sepharose. However, we found that the shorter molecules did in fact bind to Heparin-Sepharose.

We found that there was no need for a phenyl-Sepharose column, as in the case of the r31 kD, in order to purify the reoxidized r20 kD or r12 kD polypeptides. In fact, the material could be directly purified on Heparin-Sepharose, but considerable improvement, with respect to removal of contaminants, incorrectly folded molecules and dimers, was achieved when the sample was chromatographed on a Q-Sepharose column before chromatography on a Heparin-Sepharose column. In some cases, the polypeptide was concentrated on a Pellicon system (Millipore Corp.), using membranes with appropriate cut-off points, i.e., 10 kD for the r20 kD polypeptide and 3 kD for the r12 kD polypeptide, prior to being loaded on the Q-Sepharose column. The Heparin-Sepharose column is also used for concentration of both polypeptides. The following is an example of the purification procedure used in the case of the r20 kD polypeptide.

3.1. Q-Sepharose Chromatography: One-third of the reoxidized r20 kD (47 ml) was applied to a 10 ml column of Q-Sepharose Fast Flow column, which had been pre-equilibrated in Buffer C, pH 8.5 at 1.2 ml/min flow-rate. The flow-through fraction was collected and saved (70 ml). The polypeptides which adhered to the column were eluted with Buffer C, pH 8.5 containing 0.5 M NaCl and the column was regenerated with 0.5 M NaOH.

3.2 Heparin-Sepharose Chromatography: The flow-through from the Q-Sepharose column was applied to a 10 ml column of Heparin-Sepharose pre-equilibrated in pH 8.5 buffer at a flow rate of 0.5 ml/min. The flow-through fraction contained mostly contaminants and incorrectly folded r20 kD polypeptide. The purified (>95% pure) r20 kD polypeptide was eluted in Buffer C, pH 8.5 containing 0.5 M NaCl and the column was regenerated in the same buffer containing additionally 6M Guanidine-HCl. Representative purification tables for the r20 kD (Table C) and r12 kD (Table D) polypeptides are provided.

3.3 Characterization: Supernatants from the processing of the bacterial cake for both the r20 kD and the r12 kD polypeptide, as well as aliquots from subsequent column fractions, were assayed for polypeptide and analyzed by SDS-polyacrylamide gel electrophoresis; their elution profiles were obtained on a Superose 12 column attached to either a FPLC or a HPLC. These profiles at various stages of the refolding, as well as of the purification, are shown for the r20 kD (FIG. 52) and the r12 kD (FIG. 53). The purified r20 kD or r12 kD polypeptides elute as single sharp bands. These profiles corroborate the results seen on SDS-PAGE gels under non-reducing conditions; the bands of both the 20 kD and the r12 kD polypeptides samples are non-diffuse, indicating a single molecular form. In the case of the r20 kD, the band of the non-reduced polypeptide runs (as in the case of the r31 kD polypeptide) faster than that of the reduced form; this is a similar effect to that seen in the case of the r31 kD polypeptide. However, no such difference is observed in the case of the r12 kD polypeptide.

These FBD polypeptides are available for radiolabeling in order to use them as radiopharmaceuticals for imaging of thrombi and atherosclerotic lesions. The FBD polypeptides may also be used for therapeutical inhibition or prevention of bacterial colonization and sepsis.

The advantages of using the smaller FBD polypeptides (r20 kD and r12 kD) for the above-mentioned purposes as opposed to using the larger r31 kD polypeptide is that we have developed after considerable effort a simpler method for the preparation of the smaller molecules, i.e., the methods described above for the refolding and purification of the r20 kD and r12 kD polypeptides are faster and easier than the method for refolding and purification of the r31 kD polypeptide. In addition, these methods result in a higher yield and a higher concentration of polypeptide than does the method for the r31 kD polypeptide.

TABLE C

PURIFICATION OF THE r20 kD FBD

| Step | Volume (ml) | Protein Conc (mg/ml) | Total Protein (mg) | Purity[a] (1%) | Amount of FBD (mg) | Yield (1%) | Degree of purification |
|---|---|---|---|---|---|---|---|
| Solubilized & Reduced Pellet | 14.8 | 12.4 | 183.5 | 35 | 64.2 | 100 | 1 |
| Oxidised Supernatant | 148 | 0.72 | 106.5 | 45 | 48.0 | 74.7 | 1.3 |
| Oxidised Supernatant (⅓) | 47 | | 33.8 | | 15.2 | | |
| Q-Sepharose Flow-through | 70 | 0.20 | 14.0 | 80 | 11.2 | 54.9 | 2.3 |
| Heparin-Sepharose 0.5 M NaCl | 9 | 0.71 | 6.1 | 98 | 6.0 | 29.4 | 2.8 |

[a]Estimated from either SDS-PAGE gels under reducing conditions or from Sepharose 12 elution profiles.
This is a representative purification table for the refolding and purification of the r20 kD polypeptide, processed as described in Example 10, Sections 2 and 3.

TABLE D

PURIFICATION OF THE r12 kD FBD

| Step | Volume (ml) | Protein Conc (mg/ml) | Total Protein (mg) | Purity[a] (1%) | Amount of FBD (mg) | Yield (1%) | Degree of purification |
|---|---|---|---|---|---|---|---|
| Solubilized & Reduced Pellet | 100 | 6.66 | 666 | 10 | 66.6 | 100 | 1 |
| Oxidised[b] Supernatant | 500 | 0.20 | 100 | 58 | 58.0 | 87.1 | 5.8 |
| Q-Sepharose Flow-through | 500 | 0.13 | 65 | 80 | 52 | 78.1 | 8.0 |
| Heparin-Sepharose 0.5 M NaCl | 14 | 0.75 | 10.5 | 98 | 10.3 | 15.4 | 9.8 |

[a]Estimated from either SDS-PAGE gels under reducing conditions or from Sepharose 12 elution profiles.
[b]Concentrated on a Pellicon system.
This is a representative purification table for the refolding and purification of the r12 kD polypeptide, processed as described in Example 10, Sections 2 and 3.

Example 11

Biological Activity of the r31 kD, r20 kD and r12 kD Fibrin Binding Domain Polypeptides The biological activity of the r31 kD FBD was described (in Example 7) relating to its binding to fibrin clot in vivo and in vitro, binding to bacteria and binding to extracellular matrix. In this example, additional results relating to the r31 kD polypeptide are presented and the biological activity of the 20 kD and 12 kD FBD polypeptides is demonstrated.

In this Example the binding of the recombinant fibrin binding domains to fibrin clots was measured as follows:

Binding of $^{125}$I-rFBD (r31 kD, r20 kD or r12 kD) to a Preformed Fibrin Clot (Two-Step Reaction II)

Step 1 Formation of fibrin clot: This may be done in one of two ways:

Either (a) Incubation at 37° C. of 20 µl citrated human whole blood with 5 mM CaCl$_2$, 1 unit/ml thrombin and PBS in a final volume of 250 µl. The reaction is terminated after 45 minutes by centrifugation and washing of the pellet (twice) with 1 ml PBS;

or (b) Incubation at 37° C. of 20 µl non-citrated whole human blood ("naive" blood). The reaction is terminated after 150 minutes by centrifugation and washing as in (a).

Step 2 Binding of the $^{125}$I-FBD Polypeptide to the Preformed Fibrin Clot

Clots are incubated at 37° C. in a final volume of 250 µl PBS with $^{125}$I-rFBD polypeptide. Other constituents may be added as indicated for each experiment. The binding reaction is terminated after 45 minutes by centrifugation and washing three times with PBS. The tubes containing the $^{125}$I-rFBD—fibrin pellet were measured for radioactivity in a gamma counter.

Results

A. Metabolic Stability of $^{125}$I-Labeled r31 kD FBD in Rats: Ex-Vivo Binding to Fibrin Versus TCA Insolubility As described in the description of FIG. 44, rats were injected intravenously with r31 kD FBD labeled with $^{125}$I and blood samples taken at intervals were added to Na citrate. Aliquots of the blood were treated as follows: either (a) treated with 20% TCA and the TCA insoluble counts were measured; or (b) incubated with preformed clot (using 20 µl whole blood from control rat); binding of the $^{125}$I-31 kD FBD to preformed clot was measured under the conditions of the two-step Reaction II described above.

The radioactivity was measured by a gamma counter and the activity of each sample was calculated as a percentage of total cpm present in the reaction mixture.

The results demonstrated in FIG. 44 indicate a good correlation between the physical decay of the r31 kD (as measured by the decrease in TCA insolubility) and the functional decay (as measured by the decrease in ex-vivo binding of the r31 kD to a preformed fibrin clot.) However, at the initial stage of the comparative studies there are marked differences; at 30 min. the functional decay is several fold higher than the physical decay. These results, which suggest a much faster decrease of functional stability than physical degradation, can be explained since the main site for the covalent reaction of the FBD with the fibrin clot is the glutamine residue located at the extreme amino terminus of the FBD molecule at amino acid no. 3; this glutamine residue, being located in a 20 amino acid stretch outside the type 1 finger structure, is not protected from degradation by the tertiary structure, which is typical of the rest of the FBD domain.

B. Specificity of Binding of r31 kD to fibrin: Effect of Transglutaminase

The covalent binding of the fibrin binding domain of plasmatic fibronectin to fibrin in a clot is mainly due to the reaction of amino acid no. 3 of fibronectin (glutamine) with fibrin; this binding reaction is enzymatically controlled by the enzyme transglutaminase which specifically recognizes the amino acid sequence containing this glutamine residue.

The following experiment was performed to investigate if transglutaminase is involved in the binding of the recombinant r31 kD FBD to clots. All the exogenous transglutaminase used in the experiments described in this application is guin a-pig liver transglutaminase (Sigma).

The binding of 0.3 µM solution of the following molecules to preformed fibrin clot derived from 20 µl of whole human blood was measured in the presence and absence of transglutaminase using the two-step Reaction II described above: $^{14}$C-putrescine-r31 kD FBD, $^{125}$I-r31 kD FBD and $^{125}$I-recombinant bovine growth hormone (control). The $^{14}$C-putrescine-r31 kD protein complex where the glutamine residue at position 3 is blocked by covalent reaction with $^{14}$C-putrescine, was prepared as follows:

A solution containing 3 µM r31 kD FBD, 10 mM CaCl$_2$, 0.015 units/ml transglutaminase and 60 µM $^{14}$C putrescine (specific activity 100 mc/mmole) was incubated at 37° C. for 5 hours. The amount of $^{14}$C-putrescine incorporated into the 31 kD FBD was measured by TCA precipitation of an aliquot of this reaction solution and demonstrated the incorporation of an equivalent amount to 2.8–3 µM solution of $^{14}$C-putrescine into the r31 kD protein; this indicates that more than 90% of the glutamine at position number 3 of the FBD covalently reacted with the $^{14}$C-putrescine. The $^{14}$C-putrescine r31 kD material was stored at 0° C. and used within a few days without further treatment. The r31 kD FBD (prepared as described in Example 5) and the control recombinant bovine growth hormone analog (bGH) prepared as described in EPO Publication No. 131843 were labeled with $^{125}$I using the IC1 method described in Example 6.

Results

The counts bound in the two-step Reaction II in the presence and absence of transglutaminase were obtained and the ratio of counts bound in the presence and absence of transglutaminase was calculated for each polypeptide tested (see FIG. 45). This ratio differs dramatically when intact 31 kD FBD is compared to putrescine-FBD ("blocked" FBD) or to the control bGH. In the two latter cases the ratio of counts is close to 1 which shows that transglutaminase does not affect the binding and total cpm present in the clot is 10–15% of total cpm in the reaction). In the case of the intact 31 kD FBD the ratio is dramatically higher than 1 (in different experiments the ratio varied between 1.8–7 depending on the quality and freshness of the blood and the transglutaminase) and total cpm present in the clot is 40–70% of total cpm in the reaction) i.e., transglutaminase greatly increased the binding of r31 kD polypeptide to the clot.

These results indicate the strong effectiveness of unblocked glutamine at position number 3 for the binding of the r31 FBD polypeptide to the fibrin clot in the presence of transglutaminase.

Other experiments have shown that the addition of transglutaminase to the two-step Reaction II increases the binding of the r20 kD and r12 kD polypeptides to the clot, comparable to the effect observed with the r31 kD.

C. Characterization of r31 kD FBD-Fibrin Complex by SDS Polyacrylamide Gel Electrophoresis In order to determine the size of complex formed by the binding of r31 kD to a fibrin clot the following series of experiments (as described in the description of FIG. 46) was undertaken. Clots were derived from either 20 µl whole human blood (A) or 250 µl of a solution of 0.8 µM human fibrinogen (B). In some of the fibrinogen experiments dental coils (as described in Example 12) were added to the tubes together with the fibrinogen.

The binding of $^{125}$I-r31 FED to the fibrin clot was measured using the two-step Reaction II described above, in the presence of 0.15 μM $^{125}$-r31 kD FBD and 5 mM CaCl$_2$.

The reaction was terminated by three times washing with PBS. The pellet, after the various treatments described below, was centrifuged and 15 μl aliquots of the supernatant (i.e., the soluble material) were electrophoresed on polyacrylamide gels which separates the material of molecular weight >10$^6$ from molecular weight >10$^5$ and from lower molecular weight materials. An autoradiogram was produced (FIG. 46) which shows the following: in the presence of transglutaminase high molecular weight forms of r31 kD-fibrin complex appears which are resistant to boiling in the presence of the strong ionic detergent SDS and β-mercaptoethanol, which reduces S—S bonds.

Additionally, FIG. 46 demonstrates that when 4M urea is included in the boiling reaction the very high molecular weight forms (>10$^6$) are quantitatively converted to the intermediate molecular weight forms (>100,000) as expected for hydrophobic bonded aggregates of high molecular weight fibrin clots. The amount of free r31 kD polypeptide in the clots is normally small; this is the material released on boiling with phosphate-saline buffer only. The resistance of the intermediate molecular weight forms to additional treatment with urea supports the involvement of a covalent linkage between the $^{125}$I-r31 kD and the fibrin.

D. Effect of Fibronectin and Heparin on the Binding of $^{125}$I-r31 kD to Preformed Fibrin Clots (i) Effect of Fibronectin (FN)

Figure 47A:
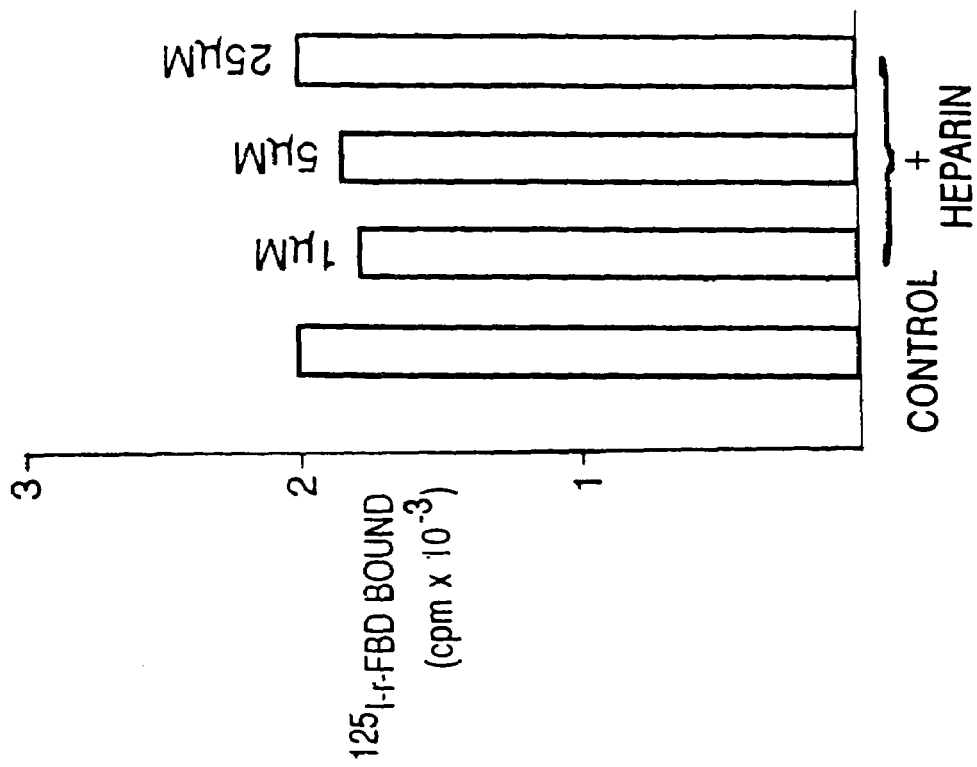
Figure 47B:
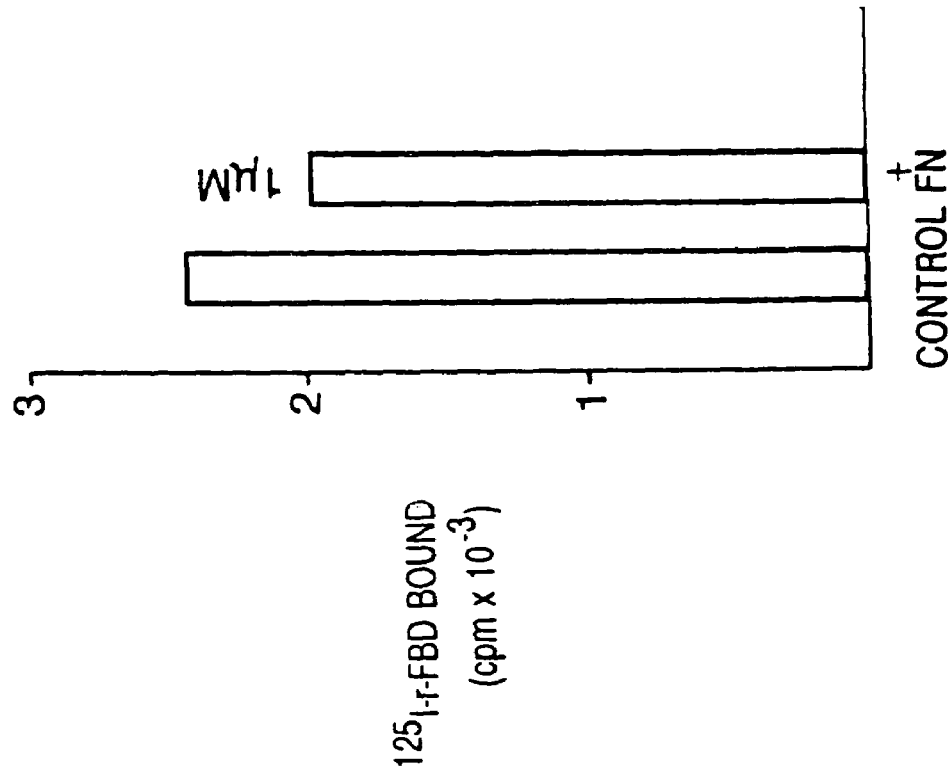

Human plasma contains substantial levels of FN (300 μg/ml) which potentially could compete with the binding of $^{125}$I-r31 kD polypeptide to preformed clots. Such competition may affect the efficiency of clot radiolabeling and subsequently the imaging process. To examine the effect of FN, $^{125}$I-r31 kD (0.15 μM) was added together with purified FN (1 μM) to a preformed clot in PBS (FIG. 47A). Although FN was added in a molar excess of 7 relative to $^{125}$I-r31 kD, the binding of the latter polypeptide was only slightly affected (20% inhibition). The observation that excess FN does not compete with $^{125}$I-r31 kD binding could be interpreted in two ways: the number of sites for crosslinking onto the clot is in excess to accommodate both FN and $^{125}$I-FBD, or the affinity of FBD to the clot is much higher than that of FN. Based on several observations, we believe that both excess binding sites and higher affinity of the 125I-r31 kD enable its binding to the clot in the presence of plasma concentrations of FN.

(ii) Effect of Heparin

Some radioscintigraphic agents such as $^{111}$In-labeled platelets and labeled fibrinogen are ineffective in the presence of therapeutic heparin. It was important, therefore, to analyze the effect of heparin on the incorporation of $^{125}$I-r31 kD to the clots. The results shown in FIG. 47B indicate that heparin has no significant effect on the binding of r31 kD FBD to preformed clots. Other experiments showed that the same amount of heparin affects dramatically the binding of r31 kD to a fibrin clot during its formation, i.e., Reaction I (see Example 7).

E. Comparison of the Binding of Various Recombinant FBD Polypeptides and Plasmatic FBD to Preformed Clots To compare the binding to preformed clots of the various recombinant FBD polypeptides (r31 kD, r20 kD and r12 kD) and plasmatic 31 kD FBD, a series of experiments using the two-step Reaction II was carried out as described in FIG. 48. The results show that the plasmatic 31 kD binds to a similar level as the r31 kD whereas the r20 kD and r12 kD polypeptides both bind at about half the level of the larger (31 kD) molecule. The level of binding of the r20 kD and r12 kD polypeptides is still sufficiently high to demonstrate the potential of radiolabeled r20 kD and r12 kD polypeptides as radiopharmaceuticals for thrombus imaging. Similar experiments using the r31 kD-DGRGDS polypeptide (Example 9, D and FIG. 39) showed that it binds at about the same level as the r31 kD.

F. Binding of $^{125}$I-r12 kD to Fresh or Frozen Clots

In order to study the effect of freezing the clots prior to use in binding experiments with FBD polypeptides, the following experiment was carried out. Fibrin clots were either used fresh or after storage at −70° C. in a two-step Reaction II binding experiment with $^{125}$I-r12 FBD, prepared as described in Example 10.

The experiment was carried out as described in the Description of FIG. 41 in the presence or absence of transglutaminase. FIG. 49 shows that there is little significant effect of freezing on the abilities of clots to bind r12 kD FBD. Normally, frozen clots without added transglutaminase yield binding results similar to fresh clots in the presence of transglutaminase; there is no effect on the binding reaction when exogenous transglutaminase is added to frozen clots, probably because of the release of endogenous transglutaminase from the frozen red blood cells.

As noted in Section B above, there is a wide range of response to addition of exogenous transglutaminase in Reaction II.

G. Conditions for Binding of $^{125}$I-r31 kD FBD to Preformed Clots

To investigate the conditions for binding of $^{125}$I-r31 kD to preformed clots, the following series of experiments were carried out. The binding of $^{125}$I-r31 kD polypeptide to preformed clots formed from citrated or "naive" blood was examined, using the two step Reaction II method, and in the presence or absence of various constituents (calcium, hirudin, transglutaminase). The results are shown in FIG. 50. The pattern of results using the "citrated" blood or "naive" blood clots is similar although the binding of the r31 kD polypeptide is higher to citrated blood.

Hirudin (Sigma) is a specific inhibitor of any thrombin-mediated reaction and the hirudin was therefore added in order to investigate the effect of thrombin on the binding reaction (step 2). No effect of hirudin was shown and therefore thrombin has no effect on the binding of the r31 kD polypeptide to the clot. However, the same amount of hirudin totally inhibits the binding when added at step 1 where fibrin is formed from fibrinogen, as was expected.

These results also show that exogenous transglutaminase increases the binding of r31 kD FBD to clots and furthermore that this transglutaminase reaction is dependent on the presence of calcium ions. Since the exogenous transglutaminase used is tissue transglutaminase (in its active form) we expect that the serum transglutaminase, factor XIII, which has to undergo activation by thrombin to form factor XIIIa, will be highly sensitive to hirudin inhibition.

H. Conditions for binding $^{125}$I-r31 kD FBD to the extracellular matrix (ECM)

The binding of $^{125}$I-r31 kD to the extracellular cell matrix of endothelial cells (ECM) was demonstrated in Example 7 (Section 9) and in FIG. 24. The binding was now further characterized by examination of the binding of 0.3 μM $^{125}$I-r31 kD FBD to ECM in the presence and absence of exogenous transglutaminase; additionally the binding in the presence of transglutaminase was examined in the presence of each of heparin, fibronectin or spermidine.

The results of these experiments are shown in FIG. 51 which demonstrates that the binding of the r31 kD FBD to ECM is increased by the addition of transglutaminase. Heparin has no significant effect on the binding whereas spermidine, a known inhibitor of transglutaminase, inhibits the binding. Collagen also inhibits the binding, suggesting the possible involvement of collagen as an acceptor molecule on the matrix of the endothelial cells. Fibronectin has little effect on the binding reaction.

These results give more support to the potential use of radiolabeled recombinant FBD polypeptides as radiopharmaceuticals for imaging the initial plaque formation in denudated blood vessels.

Example 12

Uptake of Recombinant $^{125}$I-31 kD FBD and Fragments Thereof by Stainless Steel Coil-Induced Venous Thrombi in Rats The stainless steel coil-induced venous thrombus model in rats was used to study the uptake of labeled r31 kD, r20 kD and r12 kD FBD polypeptides. The model employed was as described by Maffrand et al. [Thrombosis and Haemostasis 59: 225-230 (1988)].

Experimental Details

A. Investigation of the Uptake of $^{125}$I-31 kD by the Stainless Steel Coil-Induced Venous Thrombus Wistar-derived female rats (200–250 g) were anaestetized by Ketamine HCl plus Xylazin HCl. A midline abdominal incision was made and the inferior vena cava was exposed. A stainless steel wire coil (a dental paste carrier, fine No. 31, 21 mm long) was inserted into the lumen of the vein at the site just below the junction, and the incision was sutured. Each inserted device was individually weighed before insertion and each weight recorded. Three hours after the operation, the animals were given an i.v. injection of 1 ml of 0.9% NaI solution in order to saturate the thyroid iodide pool. One hour later, the rats received an i.v. injection of $^{125}$I-r31 kD FBD (5×10$^6$ cpm; 100 µg/kg). The r31 kD polypeptide was labeled as described in Example 6. At 24 hours after the administration of the labeled polypeptide, blood was drawn by cardiac puncture, and the rats were sacrificed. The segment of the vein carrying the coil was removed while taking car to drain away all residual blood. In one group, the segments carrying the coil were weighed as such and taken for measurement of radioactivity (the "Thrombus in Situ" group). In another group the vein sections were incised longitudinally, and the coils carrying the thrombi were carefully removed, weighed and the radioactivity was measured. The blood radioactivity levels were measured using peripheral blood.

Calculation of the Results:

In the two groups, the initial weight of each coil was subtracted from its final weight, and the specific radioactivity in each case was calculated by division of the cpm value by the net weight. The specific activity of the peripheral blood samples was also calculated.

Results:

At 24 hours, the blood levels of radioactivity were around 5000–10,000 cpm/g, while in the isolated blood clot the specific radioactivity was around 300,000 cpm/g, i.e., 30 to 60 fold higher (see FIG. 42). When the entire segment of the vein carrying the clot was included in the analysis, and a so-called "specific radioactivity" value calculated, the resultant values were 4–5 fold higher than those of the blood, thus indicating that a good signal-to-noise ratio may be obtained for gamma-camera imaging of blood clots in vivo using labeled r31 kD FBD.

The effect of heparin pretreatment was studied in this model. This kind of experiment is essential because patients that are candidates for thrombus imaging are usually treated with this anticoagulation agent. In order to study this question, a group of rats were treated with heparin (500 units/rat intravenously) 10 minutes before administration of the labeled polypeptide. This treatment of heparin did not affect the uptake of label, as measured 24 hours later.

These results demonstrate that thrombus imaging using the FBD of FN may be done in the presence of heparin.

B. Comparison of Recombinant 12 kD, 20 kD and 31 kD-FBD Polypeptides in the Stainless Steel Coil-Induced Venous Thrombus Model The three recombinant polypeptides were labeled with $^{125}$I as described in Example 6 and utilized in the rat model as described in A above. The results, shown in FIG. 43, indicate that each of the three molecules was specifically localized in the clots as compared to the blood, by comparing the specific radioactivities; the specific radioactivity of the clots appeared to be higher with the longer molecules than the shorter polypeptides (143,000, 78,500 and 63,000 cpm/g clot for the r31 kD, r20 kD and r12 kD polypeptides, respectively), but the differences were not statistically significant. The specific radioactivity values for blood (after 24 hours) were similarly related to the molecular size (7040, 5016 and 3300 cpm/g for the r31 kD, r20 kD and r12 kD polypeptides, respectively) and might reflect differences in the blood clearance rates of these molecular species. Hence, the calculations of the ratio of clot to blood specific radioactivity resulted in values that were similar for the three different polypeptides, and ranged around 20. These results suggest that all three FBD species (or other fragments of the FBD) could serve for thrombus imaging.

Example 3

Labeling of the Fibrin Binding Domain Polypeptides for Imaging Atherosclerotic Lesions and Thrombi The fibrin binding domain polypeptides described in this application (the r31 kD, the r20 kD and the r12 kD polypeptides), or other FBD fragments, may be radioactively labeled to carry a radiotracer to a thrombus in order to permit its external detection by gamma camera imaging. This application discloses in Example 6 the labeling of these three polypeptides by means of iodine-125 ($^{125}$I), which has a long half life of 60 days.

Another radioiodine is iodine-131 ($^{131}$I) which may be used to label the FBD polypeptides using known methods such as described by Uehara et al (1). However, $^{131}$I has a relatively long half life of 8 days.

Optimally, a radiopharmaceutical for clinical imaging of atherosclerotic lesions and thrombi should yield positive results within the first few hours after injection (33). For such a test a shorter lived radiolabel could be used. Recent studies have suggested that indium-111 ($^{111}$In) or technetium-99m ($^{99m}$Tc) may be more suitable as radio-tracers, since they have half-life of 67 hours and 6 hours, respectively (32); another short-lived low energy label is iodine-123 ($^{123}$I) with a half-life of 13.3 hours.

We have therefore labeled the r31 kD, r20 kD and r12 kD polypeptides and the plasmatic 31 kD fragment by means of $^{111}$In using the method described for human serum albumin by Hnatowich, D. J., Layne, W. W. and Childs, R. L. in J. Appl. Radiat. Inst. 33: 327 (1982). Preliminary experiments have shown that the labeled FBD polypeptides bind to preformed thrombi in vitro, measured by the two-step Reaction II (Example 11) and to thrombi in vivo measured by the model described in Example 12, and giving a high thrombus: blood ratio in the range of 80–200 after 24 hours.

The labeling of the FBD polypeptides by $^{99m}$Tc may be carried out using known methods (21, 33, 34, 35). $^{99m}$Tc is a very suitable diagnostic single photon radionuclide because of its short half-life, a detection level of 140 KeV with the gamma counter, no particulate radiation and inexpensive, convenient availability. These attributes allow the routine administration of doses of 30 m Ci that result in high photon-flux levels facilitating lesion detection by single photon emission computerized tomography (32, 35).

Other radiolabels which may be used to label the FBD polypeptides include krypton-81m ($^{81m}$Kr) and xenon-133 (133Xe), which has a half-life of 5.3 days, as reviewed by Knight (4). Another potential radiolabel is gallium-67 (67Ga) as described by Yamamoto (36); $^{67}$Ga has a half-life of 78 hours.

NMRI, ultrasound and X-ray imaging with metal chelates are described in U.S. Pat. No. 4,647,447. In addition, antibody coupling with metal chelates is mentioned at column 7, line 42. Monoclonal antibodies labeled with polymeric paramagnetic chelates and their use in NMRI methods have also been described [Shreve, P. et al., Magnetic Resonance in Medicine 3: 336–340 (1986) and Brady, T. et al. in Proceedings of the Society of Magnetic Resonanc in Medicine, Second Annual Meeting, Soc. of Magnetic Resonance in Medicin , Inc., San Francisco, p 10, 1983 refernced by Koutcher, J. et al., J. Nucl. Med. 25: 506–513 (1984)].

REFERENCES

1. Uehara, A., et al., J. Nuclear Med. 29: 1264–1267 (1988).
2. Zoghbi, S. S., et al., Invest. Radio. 20: 198–202 (1985).
3. Kakkar, V. V., et al., Lancet 1: 540–542 (1970).
4. Knight, L. C., Nuclear Med. Commun. 2: 849–857 (1988).
5. Knight, L. C., Nuclear Med. Commun. 9: 823–829 (1988).
6. Som. P., et al., J. Nuc. Med. 27: 1315–1320 (1986).
7. Palabrica, T. M., et al., Proc. Nat. Acad. Sci. USA 86: 1036–40 (1989).
8. Akiyama, S. K. and Yamada, K. M., Adv. Enzymol. 57: 1–57 (1987).
9. Pierschbacher, M. D., et al., J. Biol. Chem. 257: 9593–9597 (1982).
10. Pande, H. and Shively, J. E., Arch. Biochem. Biophys. 213: 258–265 (1982).
11. Hayashi, M. and Yamada, K. M., J. Biol. Chem. 258: 3332–3340 (1983).
12. Sekiguchi, K. and Hakomori, S.-I., Proc. Natl. Acad. Sci. USA 77: 2661–2665 (1980).
13. Ruoslahti, E., et al., J. Biol. Chem. 256: 7277–7281 (1981).
14. Owens, R. J. and Baralle, F. E., EMBO J. 5: 2825–2830 (1988).
15. Obara, M., et al., FEBS Letters 2: 261–264 (–1987).
16. Obara, M., et al., Cell 53: 699 (1988).
17. Ichihara-Tanaka, K., et al., J. Biol. Chem. 265: 401–407 (1990).
18. Mandel, et al., Principal and Practice of Infectious Disease 2: 1531–1552 (1979).
19. Proctor, R. A., et al., J. Biol. Chem. 255: 1181–1188 (1980).
20. Eldor, A., et al., Thrombosis and Haemostatis 56(3): 333–339 (1986).
21. Fritzberg, A. R., Nucl. Med. 26: 7–12 (1987).
22. Young, R. A. and Davis, R. W., Proc. Natl. Acad. Sci. USA 80: 1194–1198 (1983).
23. Hugh, T., et al., In DNA Cloning: A Practical Approach (D. Glover, ed.), IRL Press, Oxford (1984).
24. Vog l, et al., Proc. Natl. Acad. Sci. USA 69: 3180–3184 (1972).
25. Bagly, D., et al., Methods in Enzymol. 45: 669–678 (1976).
26. Wagner and Hynes, J. Biol. Chem. 25: 6746–6754 (1979).
27. McDonagh, R. P., et al., FEBS Lett. 127: 174–178 (1981).
28. Mosher, et al., J. Biol. Chem. 255: 1181–1188 (1980).
29. Russel, P. B., et al., J. Clin. Micro. 25: 1083–1087 (1987).
30. Bolton, A. E. and Hunter, W. M., Biochem. J. 133: 529 (1973).
31. Obara, et al., Cell 53: 649–657 (1988).
32. Fritzberg, A. R., et al., Proc. Natl. Acad. Sci. 85: 4025–4029 (1988).
33. Knight, L. C., et al., Radiology 173: 163–169 (–1989).
34. Wasser, M. N. J. M., et al., Blood 74: 708–714 (1989).
35. Burger, J. J., et al., Methods in Enzymology 112: 43–56 (1985).
36. Yamamoto, K., et al., Eur. J. Nucl. Med. 14: 60–64 (1988).

What is claimed is:

1. An imaging agent which comprises a polypeptide labeled with an imageable marker, such polypeptide having an amino acid sequence which comprises at least one fifth of the amino acid sequence of the N-terminal fibrin binding domain of naturally occurring fibronectin, commencing from the fourth amino acid shown in SEQ ID NO: 15, wherein the N-terminal fibrin binding domain comprises 262 amino acids commencing from the fourth amino acid shown in SEQ ID NO: 15, and wherein the polypeptide optionally has a methionine at its N-terminus, and wherein the polypeptide has a molecular weight less than 31 kD.

2. The agent of claim 1, wherein the marker is a radioactive isotope, an element which is opaque to X-rays, or a paramagnetic ion.

3. The agent of claim 2, wherein the marker is a radioactive isotope.

4. A purified polypeptide having an amino acid sequence which comprises at least one fifth of the amino acid sequence of the N-terminal fibrin binding domain of naturally-occurring fibronectin commencing from the fourth amino acid shown in SEQ ID NO: 15, wherein the N-terminal fibrin binding domain comprises 262 amino acids commencing from the fourth amino acid show in SEQ ID NO:15, and wherein the polypeptide optionally has a methionine at its N-terminus, and wherein the polypeptide has a molecular weight less than 31 kD.

* * * * *